US012806212B2

(12) United States Patent
Pietras et al.

(10) Patent No.: US 12,806,212 B2
(45) Date of Patent: Nov. 24, 2026

(54) ESTROGEN RECEPTOR INHIBITORS AND USES THEREOF

(71) Applicant: The Regents of the University of California, Oakland, CA (US)

(72) Inventors: Richard J. Pietras, Sherman Oaks, CA (US); Michael E. Jung, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1116 days.

(21) Appl. No.: 15/734,199

(22) PCT Filed: Jun. 6, 2019

(86) PCT No.: PCT/US2019/035862
§ 371 (c)(1),
(2) Date: Dec. 1, 2020

(87) PCT Pub. No.: WO2019/236901
PCT Pub. Date: Dec. 12, 2019

(65) Prior Publication Data

US 2022/0133747 A1 May 5, 2022

Related U.S. Application Data

(60) Provisional application No. 62/681,423, filed on Jun. 6, 2018.

(51) Int. Cl.

| | |
|---|---|
| ***A61K 31/58*** | (2006.01) |
| ***A61K 31/565*** | (2006.01) |
| ***A61K 45/06*** | (2006.01) |
| ***A61P 35/00*** | (2006.01) |

(52) U.S. Cl.
CPC ............ *A61K 31/58* (2013.01); *A61K 31/565* (2013.01); *A61K 45/06* (2013.01); *A61P 35/00* (2018.01)

(58) Field of Classification Search
CPC ...... A61K 31/58; A61K 31/565; A61K 45/06; A61P 35/00
See application file for complete search history.

(56) References Cited

U.S. PATENT DOCUMENTS

| | | | |
|---|---|---|---|
| 7,528,123 B1 | 5/2009 | Loozen et al. | |
| 10,400,006 B2 | 9/2019 | Pietras et al. | |
| 10,918,648 B2 | 2/2021 | Pietras et al. | |
| 2004/0142915 A1 | 7/2004 | Hochberg | |
| 2017/0037132 A1 | 2/2017 | Manekas et al. | |
| 2018/0086787 A1 | 3/2018 | Pietras et al. | |
| 2019/0216923 A1* | 7/2019 | Lee .................... | C07K 16/2818 |

FOREIGN PATENT DOCUMENTS

| | | | |
|---|---|---|---|
| WO | WO-2016085825 A1 * | 6/2016 | ........... A61K 31/085 |
| WO | WO-2017/205611 A1 | 11/2017 | |

OTHER PUBLICATIONS

Chou, T. C. Cancer research 70.2 (2010): 440-446. (Year: 2010).*
Berenbaum, M. C. Clin. Exp. Immunol., 1977, 28, 1-18. (Year: 1977).*
International Search Report mailed on Oct. 23, 2019, for PCT Application No. PCT/US2019/035862, filed Jun. 6, 2019, 4 pages.
Written Opinion mailed on Oct. 23, 2019, for PCT Application No. PCT/US2019/035862, filed Jun. 6, 2019, 5 pages.
Ashton JC. Drug combination studies and their synergy quantification using the Chou-Talalay method. Cancer Res. 75(11):2400 (2015).
Berthoud HR. Synergy: a concept in search of a definition. Endocrinology. 154(11):3974-7 (2013).
Calzetta L, Page C, Matera MG, Cazzola M, Rogliani P. Drug-Drug Interactions and Synergy: From Pharmacological Models to Clinical Application. Pharmacol Rev. 76(6):1159-1220 (2024).
Chou, T.C. and Talalay P., Quantitative Analysis of Dose-Effect Relationships: The Combined Effects of Multiple Drugs or Enzyme Inhibitors, Adv Enzyme Regul, 22:27-55 (1984).
Geary N. Understanding synergy. Am J Physiol Endocrinol Metab. 304(3):E237-53 (2013).
Márquez-Garbán DC, Deng G, Comin-Anduix B, Garcia AJ, Xing Y, Chen HW, Cheung-Lau G, Hamilton N, Jung ME, Pietras RJ. Antiestrogens in combination with immune checkpoint inhibitors in breast cancer immunotherapy. J Steroid Biochem Mol Biol. 193:105415 (2019).
Meyer CT, Wooten DJ, Lopez CF, Quaranta V. Charting the Fragmented Landscape of Drug Synergy. Trends Pharmacol Sci. 41(4):266-280 (2020).
Pegram, M., Hsu, S., Lewis, G., Pietras, R., Beryt, M., Sliwkowski, M., Coombs, D., Baly, D., Kabbinavar F., and Slamon, D. Inhibitory effects of combinations of HER-2/neu antibody and chemotherapeutic agents used for treatment of human breast cancers. *Oncogene*, 18 : 2241-2251 (1999).
Pietras RJ, Fendly BM, Chazin VR, Pegram MD, Howell SB, Slamon DJ. Antibody to HER-2/neu receptor blocks DNA repair after cisplatin in human breast and ovarian cancer cells. Oncogene, 9(7):1829-38 (1994).
Svoronos N., et al., Tumor Cell-Independent Estrogen Signaling Drives Disease Progression Through Mobilization of Myeloid-Derived Suppressor Cells, Cancer Discover, 7(1):72-85 (2017).

* cited by examiner

*Primary Examiner* — Kamal A Saeed
*Assistant Examiner* — Quincy Mckoy
(74) *Attorney, Agent, or Firm* — Mintz, Levin, Cohn, Ferris, Glovsky and Popeo, P.C.

(57) ABSTRACT

Described herein, inter alia, are compositions and methods for treating or preventing hyperproliferative disorders, including cancer.

20 Claims, 31 Drawing Sheets

1′

2′

11d SERD109

22 SERD128

20a SERD140

25a SERD160

6

11a-d a $R_2 = (CH_2)_5$ b $R_2 = (CH_2)_4$
c $R_2 = (CH_2CH_2)_2O$ d $R_2 = Me_2$

6

12a-d a $R_2 = (CH_2)_5$ b $R_2 = (CH_2)_4$
c $R_2 = (CH_2CH_2)_2O$ d $R_2 = Me_2$

6

13a-d a $R_2 = (CH_2)_5$ b $R_2 = (CH_2)_4$
c $R_2 = (CH_2CH_2)_2O$ d $R_2 = Me_2$

6

14a-d a $R_2 = (CH_2)_5$ b $R_2 = (CH_2)_4$
c $R_2 = (CH_2CH_2)_2O$ d $R_2 = Me_2$ 17a-d to 20a-d 17 n = 1
18 n = 2
19 n = 3
20 n = 4
a $R_2$ = $(CH_2)_5$
b $R_2$ = $(CH_2)_4$
c $R_2$ = $(CH_2CH_2)_2O$
d $R_2$ = $Me_2$ 23a-d to 26a-d 23 n = 1
24 n = 2
25 n = 3
26 n = 4
a $R_2$ = $(CH_2)_5$
b $R_2$ = $(CH_2)_4$
c $R_2$ = $(CH_2CH_2)_2O$
d $R_2$ = $Me_2$

15 X = F
21 X = $CF_3$

16 X = F
22 X = $CF_3$ 90877582v.1

ESTROGEN RECEPTOR INHIBITORS AND USES THEREOF

CROSS-REFERENCES TO RELATED APPLICATIONS

This application is a Section 371 US national phase of International Application No. PCT/US19/35862 filed Jun. 6, 2019, which claims the benefit of priority to U.S. Provisional Patent Application No. 62/681,423 filed Jun. 6, 2018, which is incorporated herein in its entirety and for all purposes.

STATEMENT AS TO RIGHTS TO INVENTIONS MADE UNDER FEDERALLY SPONSORED RESEARCH AND DEVELOPMENT

This invention was made with government support under Grant Number CA143930, awarded by the National Institutes of Health. The government has certain rights in the invention.

BACKGROUND

Breast cancer is the most common malignancy in women in North America. Each year more than 210,000 new cases of breast cancer are diagnosed in the US (1-3). In the clinic, endocrine therapy is an important intervention for cancers that express estrogen receptor (ER), and it has proven to be one of the most effective treatment strategies for breast cancer (3,4). At diagnosis, about 70% of breast cancers contain estrogen receptors and depend on estrogen for growth and progression. Expression of ER in a tumor is predictive of a clinical response to hormonal therapy. Such observations have led to current use of antiestrogens (such as fulvestrant, tamoxifen and its relatives, raloxifene, toremifene, lasofoxifene, etc.) and aromatase inhibitors in treating ER-positive breast cancer (2,3). Tamoxifen and its analogues are among the most highly prescribed drugs for initial estrogen-dependent breast cancer. However, they are not without their drawbacks since they bind to the estrogen receptor in many tissues (bone, uterus, etc.) and can have harmful effects. A substantial proportion of patients presenting with localized disease, and all of the patients with metastatic breast cancer, become resistant to current endocrine therapies (5, 6). Thus, there is an urgent need to develop alternative therapeutics to overcome endocrine resistance and to improve the long-term survival of afflicted patients. Despite remarkable improvements in treatment options, development of endocrine resistance is one reason that breast cancer is the second most frequent cause of cancer death in women (5-7). In most cases, the ER is present in resistant tumors, and in many of these its activity continues to regulate tumor growth.

Classical and nonclassical mechanisms of estrogen action in breast malignancy. Estrogen modulates gene transcription in breast cancers through its receptors using different signaling pathways (2,8). The classical pathway involves direct DNA binding of liganded receptor to estrogen response elements (EREs) in the promoter regions of responsive genes.

The proliferation and survival of breast cancers is closely regulated by growth factor receptors as well as estrogens (E2) and their receptors, estrogen receptor (ER)-α and -β, with ERα generally considered most important in tumor progression (5,6,9). ERα has 6 major functional domains including an N-terminal transactivation domain, an adjacent DNA-binding domain and a C-terminal portion involved in hormone-binding, receptor dimerization and activity of a second transactivation region. In classical models of E2 action, E2 binds ER to promote dimerization and phosphorylation of the receptor. This allows direct binding of the ligand-ER complex with steroid receptor coactivators (CoReg) and E2-responsive elements (ERE) in DNA, leading to changes in gene transcription that regulate growth, differentiation, apoptosis and angiogenesis. In addition, there are alternate pathways of E2 action that involve protein-protein interactions and do not require direct ER binding to DNA. A subset of ER associate with extranuclear sites and interact there with membrane growth factor receptors (EGFR, HER2) and other signaling molecules (components of the ras-MAPK and PI3K/AKT pathways, Shc, src kinases, JAK/STAT, nitric oxide synthase (NOS), G-proteins). Of special note, growth factor and extranuclear estrogen receptors appear to form a structured complex for signal transduction to MAPK and/or PI3K/AKT kinase that interacts, in turn, with nuclear ER and CoReg. Signaling for cell growth involves phosphorylation (P) of nuclear ER and CoReg, and such phosphorylation can occur in ligand-dependent as well as ligand-independent modes. ERE-dependent and alternate transcription sites may be activated. Further, E2 is produced locally in supporting cells by the action of aromatase (ARO), and ARO is regulated by both nulcear and extranuclear ER and growth factor-mediated signaling. In addition, estrogens may regulate tumor-associated angiogenesis by direct interactions with vascular endothelial cells or by indirect stimulation of VEGF secretion from tumors.

However, it is now clear that the ERa can regulate genes that lack a canonical ERE, suggesting additional pathways for estrogen action that may be of paramount importance in modulating tumor progression. Alternate, nonclassical pathways involve indirect modulation of transcription by ER interaction with components of other transcription complexes (AP-1, nuclear factor-kB) or kinase signaling complexes (MAPK, PI3K/AKT kinase) via protein-protein interactions. Emerging data suggest that interactions of ER with growth factor receptor-kinase signaling pathways may play a critical role in promoting estrogen signaling for tumor progression (9). Based on current data in estrogen target cells, nonclassical ER signaling is associated with epithelial proliferation but not other estrogen-responsive events such as fluid accumulation in uterus (8), while classical ER signaling appears more essential for skeletal development, bone health and other differentiated cell functions (10).

ER often continues to play a major role in controlling growth of hormone-resistant cancers. In treatment with aromatase inhibitors (AI's), ER activation by alternate ligands, local E2 production and development of ER hypersensitivity are especially problematic (2, 6). In addition, ligand-independent activation of ER occurs in tumors overexpressing growth factor receptors such as HER2, with growth factor receptors promoting ER phosphorylation even in the absence of estrogen (5, 9, 11). Such ligand-independent mechanisms likely contribute to resistance to AI's as well as antiestrogens (12, 13). These nonclassical events are mediated by ER or adaptor proteins that impact gene expression indirectly by activating growth-promoting kinase cascades to regulate transcription. In breast tumors, significant evidence suggests that regulation of both proliferation and cell death pathways occurs, in part, by the action of nonclassical kinase-mediated pathways (9, 11, 14-19). Better understanding and targeting of these complex signaling pathways in tumors with endocrine resistance to both antiestrogens and AI's will help in development of individualized and improved treatments in the clinic.

Current antiestrogens are competitive antagonists of estrogen and disrupt ER-induced transcription. However, some antagonists display partial estrogenic activity in a tissue- and gene-dependent manner, hence their description as selective estrogen receptor modulators (SERMs). Tamoxifen, a partial agonist that limits effects of E2 in breast, has been the most widely used hormone therapy for the past 20 years, achieving a 39% reduction in disease recurrence and a 31% reduction in mortality in ER+ early breast cancer (6, 20, 21). Although effective, tamoxifen has an important drawback—the limited period of activity before resistance develops (7, 20). Further, prolonged treatment with tamoxifen is associated with an increased risk for endometrial cancer due to significant agonist activity of the drug in uterus. As long as the ER is present in tumors, growth may still be stimulated by small amounts of estrogens or antiestrogens or by ligand-independent actions. The introduction of AI's for postmenopausal patients, either initially, or sequentially after tamoxifen, may produce better outcomes than the standard treatment of 5 years of tamoxifen (22-24). Nonetheless, in patients with advanced disease, only about ⅓ of HR+ tumors respond to AI's as first-line treatments (6). Further, resistance to AI's also develops due, in part, to E2-independent mechanisms (6, 12, 13). The drug, fulvestrant (25) is a pure ER antagonist that also exhibits a unique mechanism of action—downregulation of ER due in part to induced hyperubiquitination of ER (26, 27). As fulvestrant has no agonistic activity but instead destabilizes ER, the drug elicits marked disruption of ER-mediated growth. However, fulvestrant has a major drawback—very low bioavailability—which is problematic in the clinic. Although fulvestrant has activity in treating ER+ metastatic breast cancer in postmenopausal women with disease progression after tamoxifen or AI therapy (7, 28, 29), discovery of new ER antagonists with improved bioavailability and antitumor activity remains an important goal.

ER degradation limits hormone action. Ligand-induced down-regulation of ER is a pivotal step in halting E2 stimulation of growth, and the ubiquitin-proteasome pathway is the major system for selective degradation of such regulatory proteins (30). ERα was among the first of the nuclear receptors identified as substrates for this pathway (31-34). A common feature of proteasome-mediated protein degradation is covalent attachment of ubiquitin to lysine residues of proteins targeted for degradation followed by formation of polyubiquitin chains attached covalently to the protein. Ubiquitinated ERα is recognized and degraded by the multisubunit protease complex, the 26S proteasome (35). ER is degraded in a hormone-dependent manner, with this process contributing to regulation of hormone action; and the proteasome inhibitor, MG132, is well known to promote in vivo accumulation of ER and to block ligand-induced ER degradation (33). As noted above, the proteasome pathway also plays a critical role in interaction of ER with antagonists, such as SERMs and fulvestrant (27, 34).

Therefore it would be useful to test new novel ER antagonists to find compounds which inhibit the growth of hyperproliferative cells, including breast cancer. Disclosed herein, inter alia, are solutions to these and other problems in the art.

SUMMARY

In an aspect there is provided a pharmaceutical composition for increasing immune recognition of cancer, including a compound, or a pharmaceutically acceptable salt thereof, having the formula (I):

(I)

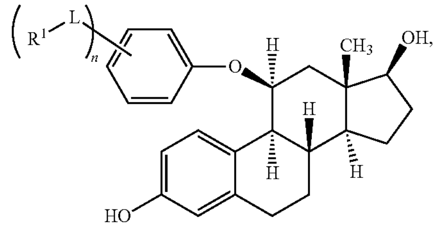

or a pharmaceutically acceptable salt thereof and a pharmaceutically acceptable excipient.

$R^1$ is independently a hydrogen, halogen, $-NR^2R^3$, $-CX^a_3$, $-CN$, $-SO_{n1}R^{10}$, $-SO_{v1}NR^2R^3$, $-NHNR^2R^3$, $-ONR^2R^3$, $-NHC(O)NHNR^2R^3$, $-NHC(O)NR^2R^3$, $-N(O)_{m1}$, $-C(O)R^9$, $-C(O)-OR^9$, $-C(O)NR^2R^3$, $-OR^{10}$, $-NR^2SO_2R^{10}$, $-NR^2C(O)R^9$, $-NR^2C(O)-OR^9$, $-NR^2OR^9$, $-OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently a hydrogen, halogen, $-CX^b_3$, $-CN$, $-SO_2R^{14}$, $-SO_{v2}NR^{11}R^{12}$, $-NHNH_2$, $-ONR^{11}R^{12}$, $-NHC(O)NHNH_2$, $-NHC(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C(O)R^{13}$, $-NR^{11}(O)-OR^{13}$, $-NR^{11}OR^{13}$, $-OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, $-OX^c_3$, $-CN$, $-SO_{n3}R^{18}$, $-SO_{v3}NR^{15}R^{16}$, $-NHNH_2$, $-ONR^{15}R^{16}$, $-NHC(O)NHNH_2$, $-NHC(O)NR^{15}R^{16}$, $-N(O)_{m3}$, $-NR^{15}R^{16}$, $-C(O)R^{17}$, $-C(O)-OR^{17}$, $-C(O)NR^{15}R^{16}$, $-OR^{18}$, $-NR^{15}SO_2R^{18}$, $-NR^{15}C(O)R^{17}$, $-NR^{15}C(O)-OR^{17}$, $-NR^{15}OR^{17}$, $-OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ and $R^3$ substituents may optionally be joined to form a substituted or unsubstituted heterocycloalkyl, or substituted or unsubstituted heteroaryl.

L is independently a bond, $-NR^4-$, $-NR^4C(O)-$, $-C(O)NR^4-$, $-O-$, $-S-$, $-C(O)-$, $-S(O)-$, $-S(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker. $R^4$ is independently a hydrogen, halogen, $-CX^d_3$, $-CN$, $-SO_{n4}R^{22}$, $-SO_{v4}NR^{19}R^{20}$, $-NHNH_2$, $-ONR^{19}R^{20}$, $-NHC(O)NHNH_2$, $-NHC(O)NR^{19}R^{20}$, $-N(O)_{m4}$, $-NR^{19}R^{20}$, $-C(O)R^{21}$, $-C(O)-OR^{21}$, $-C(O)NR^{19}R^{20}$, $-OR^{22}$, $-NR^{19}SO_2R^{22}$, $-NR^{19}C(O)R^{21}$, $-NR^{19}C(O)-OR^{21}$, $-NR^{19}OR^{21}$, $-OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $—CX_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)—OH, —NHOH, $—OCX_3$, $—OCHX_2$, $—CF_3$, $—OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl.

The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, $X^a$, $X^b$, $X^c$ and $X^d$ are independently —Cl, —Br, —I, or —F.

In an aspect there is provided a pharmaceutical composition including a compound, or a pharmaceutically acceptable salt thereof, having the formula (I):

(I)

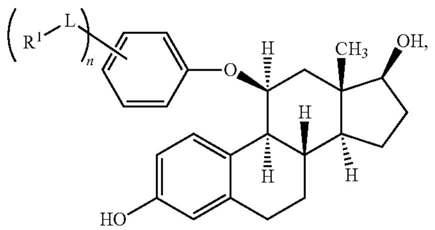

or a pharmaceutically acceptable salt thereof; an immune checkpoint inhibitor; and a pharmaceutically acceptable excipient.

$R^1$ is independently a hydrogen, halogen, $—NR^2R^3$, $—CX^a_3$, —CN, $—SO_{n1}R^{10}$, $—SO_{v1}NR^2R^3$, $—NHNR^2R^3$, $—ONR^2R^3$, $—NHC(O)NHNR^2R^3$, $—NHC(O)NR^2R^3$, $—N(O)_{m1}$, $—C(O)R^9$, $—C(O)—OR^9$, $—C(O)NR^2R^3$, $—OR^{10}$, $—NR^2SO_2R^{10}$), $—NR^2C(O)R^9$, $—NR^2C(O)—OR^9$, $—NR^2OR^9$, $—OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently a hydrogen, halogen, $—CX^b_3$, —CN, $—SO_{n2}R^{14}$, $—SO_{v2}NR^{11}R^{12}$, $—NHNH_2$, $—ONR^{11}R^{12}$, $—NHC(O)NHNH_2$, $—NHC(O)NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^{14}$, $—NR^{11}C(O)R^{13}$, $—NR^{11}C(O)—OR^{13}$, $—NR^{11}OR^{13}$, $—OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, $—CX^c_3$, —CN, $—SO_{n3}R^{18}$, $—SO_{v3}NR^{15}R^{16}$, $—NHNH_2$, $—ONR^{15}R^{16}$, $—NHC(O)NHNH_2$, $—NHC(O)NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C(O)R^{17}$, $—NR^{15}C(O)—OR^{17}$, $—NR^{15}OR^{17}$, $—OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ and $R^3$ substituents may optionally be joined to form a substituted or unsubstituted heterocycloalkyl, or substituted or unsubstituted heteroaryl.

L is independently a bond, $—NR^4—$, $—NR^4C(O)—$, $—C(O)NR^4—$, —O—, —S—, —C(O)—, —S(O)—, $—S(O)_2—$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker. $R^4$ is independently a hydrogen, halogen, $—CX^d_3$, —CN, $—SO_{n4}R^{22}$, $—SO_{v4}NR^{19}R^{20}$, $NHNH_2$, $—ONR^{19}R^{20}$, $—NHC(O)NHNH_2$, $—NHC(O)NR^{19}R^{20}$, $—N(O)_{m4}$, $—NR^{19}R^{20}$, $—C(O)R^{21}$, $—C(O)—OR^{21}$, $—C(O)NR^{19}R^{20}$, $—OR^{22}$, $—NR^{19}SO_2R^{22}$, $—NR^{19}C(O)R^{21}$, $—NR^{19}C(O)—OR^{21}$, $—NR^{19}OR^{21}$, $—OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $—CX_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)—OH, —NHOH, $—OCX_3$, $—OCHX_2$, $—CF_3$, $—OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{11}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl.

The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, $X^a$, $X^b$, $X^c$ and $X^d$ are independently —Cl, —Br, —I, or —F.

In an aspect there is provided a kit for increasing immune recognition of cancer, including an estrogen receptor inhibitor (e.g., a compound described herein, or pharmaceutically acceptable salt thereof). The term, "immune recognition," is used herein according to its plain and ordinary meaning and includes increasing the immune response in a subject (e.g. increasing the immune response to cancer (e.g. TNBC cells, melanoma cells, small cell lung cancer cells, etc.). In an aspect there is provided a kit including an estrogen receptor inhibitor (e.g., a compound described herein, or pharmaceutically acceptable salt thereof), and an immune checkpoint inhibitor.

In an aspect there is provided a method of treating a hyperproliferative disorder in a subject in need thereof, the method including administering to the subject an effective amount of a composition as disclosed herein (e.g., an estrogen receptor inhibitor (e.g., a compound having the structure of Formula X, Xa, I', I, Ia, Ib, II, IIa, IIb, or pharmaceutically acceptable salt thereof)), or a kit as disclosed herein. In an aspect thereis provided a method of treating a hyperproliferative disorder in a subject in need thereof, the method including administering to the subject an effective amount of a composition as disclosed herein (e.g., an estrogen receptor inhibitor (e.g., a compound having the structure of Formula X, Xa, I', I, Ia, Ib, II, IIa, IIb, or pharmaceutically acceptable salt thereof) and an immune checkpoint inhibitor), or a kit, as disclosed herein.

In an aspect there is provided a method of inhibiting estrogen receptor activity in a subject in need thereof, including administering to the subject an effective amount of a composition as disclosed herein (e.g., an estrogen receptor inhibitor (e.g., a compound having the structure of Formula X, Xa, I', I, Ia, Ib, II, IIa, IIb, or pharmaceutically acceptable salt thereof)), or a kit as disclosed herein. In an aspect there is provided a method of inhibiting estrogen receptor activity in a subject in need thereof, including administering to the subject an effective amount of a composition as disclosed herein (e.g., an estrogen receptor inhibitor (e.g., a compound having the structure of Formula X, Xa, I', I, Ia, Ib, II, IIa, IIb, or pharmaceutically acceptable salt thereof) and an immune checkpoint inhibitor), or a kit as disclosed herein.

BRIEF DESCRIPTION OF THE DRAWINGS

FIG. 5A shows that single cell suspensions prepared from 4T1 tumors grown in BALC/c mice treated for 12 days with control (CON), 100 sg of anti-PD-L1 antibody Q3 days (PD-L1), 50 mg/kg SERD128 via oral gavage (S128) or combined (S128+PD-L1). Cells were labeled with specific antibodies and analyzed by mass cytometry (CyTOF). Graph shows representative example of G-MDSC (CDI Ib+Ly6GhiLy6Clow) and M-MDSC (CD11b+ Ly6GlowLy6Chi) subsets present in the tumor bed as % $CD45^+$ cells. FIG. 5B shows quantification of G-MDSC and M-MDSC in tumors from 4T1 bearing mice shown as events/$CD45^+$ cells (*P<0.05, n=5).

FIG. 7A-7F shows increased expression of biomarkers for $CD8^+$-TIL population activation. Single cell suspensions were isolated from 4T1 tumors grown in BALB/c mice and stained with 28 different antibodies against cell surface, nuclear and secreted proteins. After staining, cell suspensions were fixed, processed and subjected to mass cytometry. Figure panels show $CD8^+$ cells that are positive for expression of different activation markers. FIG. 7A: shows interferon gamma (IFNγ); FIG. 7B: Tumor Necrosis Factor alpha (TNFα); FIG. 7C: CD69high expressing cells; FIG. 7D: proliferation marker Ki-67; FIG. 7E: Interleukin 4 (IL-4); FIG. 7F: Interleukin 2 (IL-2). *P<0.05, P<0.01, P<0.001. n=5.

Figure 8:
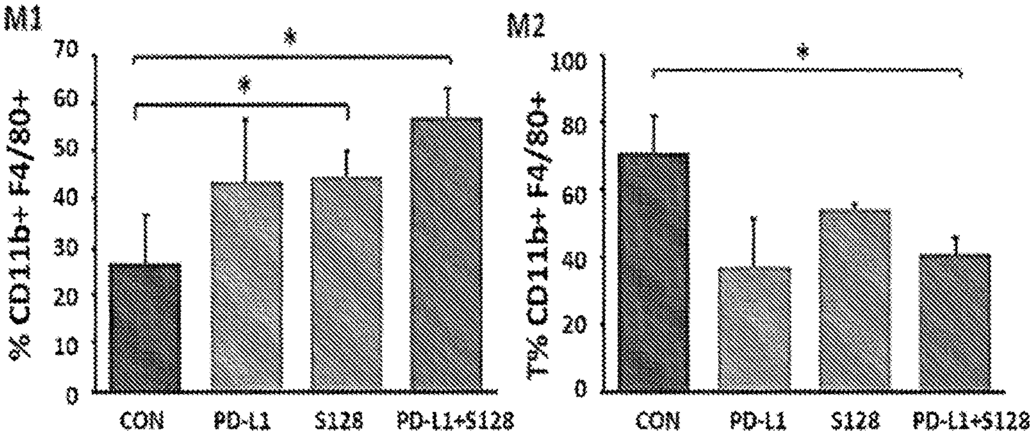

FIG. 8 shows expression of M1 and M2 macrophages from murine 4T1 tumors. Cells were stained and analyzed by mass cytometry as described above (FIG. 4). M1 (left panel, MHCIIhigh) and M2 (right panel, MHCIIlow) macrophages are expressed as % of CD11b+F4/80+ cells. Statistical significance determined by Student's t test where *P<0.05. n=5.

Figure 9:
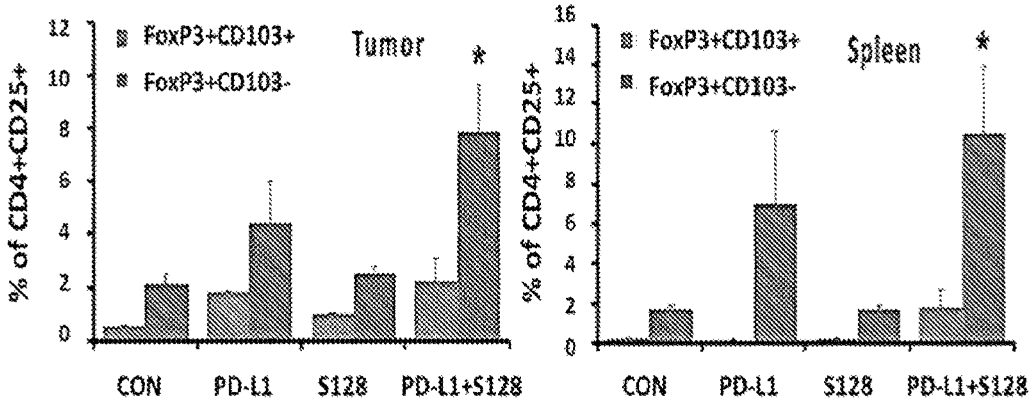

FIG. 9 shows graph shows Treg populations gated on CD4+$CD25^+$ T cells that are CD103+ and CD103−. Single cell suspensions derived from in vivo experiments as shown above (FIG. 4) were analyzed for CD4, CD25, FoxP3 and CD103 expression by CyTOF. Panel shows expression of FoxP3+CD103+ and FoxP3+CD103-populations in tumors (left panel) and spleens (right panel). *P<0.05, n=5.

Figure 10:
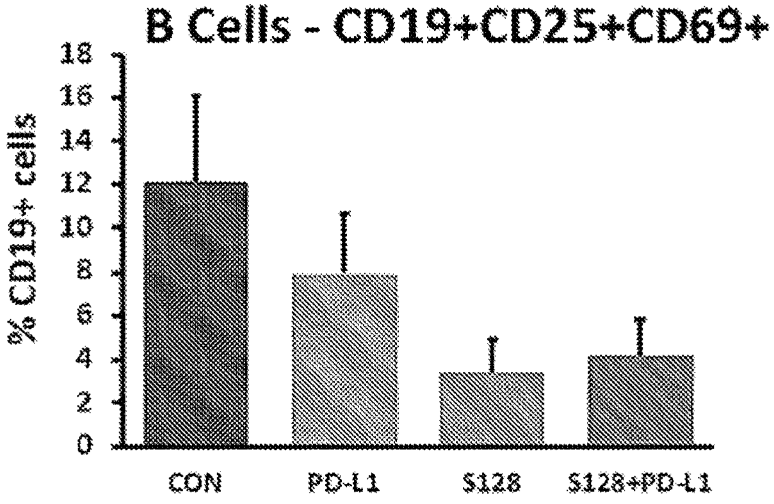

FIG. 10 shows that SERD128 decreases expression of B regulatory cells present in 4T1 tumors grown in BALB/c mice. Graph shows subpopulation of B cells that are $CD19^+$ $CD25^+CD69^+$ gated on $CD19^+$ cells from experiment described in FIG. 4.

Figure 11:
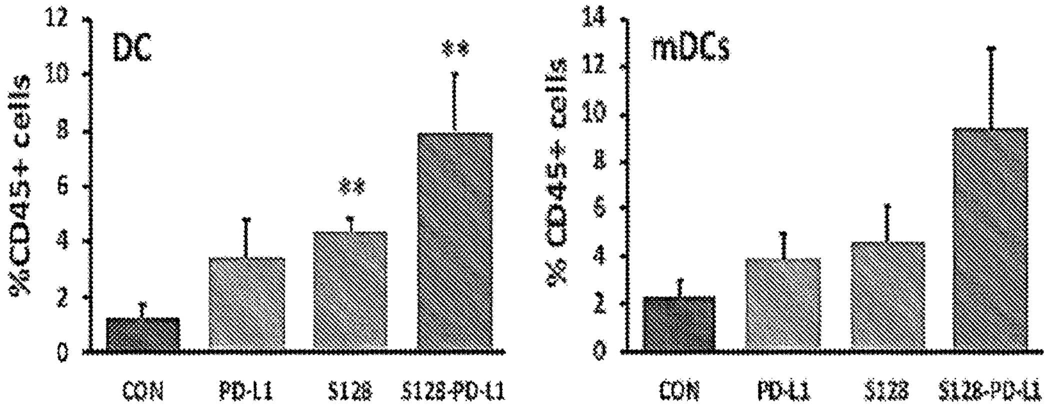

FIG. 11 shows that SERD128 increase expression of total dendritic cells (DC) and their stimulatory/myeloid subgroup. Single cell suspension purified from 4T1 tumors from mice were stained and analyzed by mass cytometry as described above (FIG. 4). Total dendritic cells CD11c+ MHCII+ (DC) left panel are increased by S128 single treatment and combination with PD-L1. Likewise, the stimulatory/myeloid subgroup of DCs was increased (right panel). Statistical significance determined by Student's t test where **P<0.05. n=5.

Figure 12:
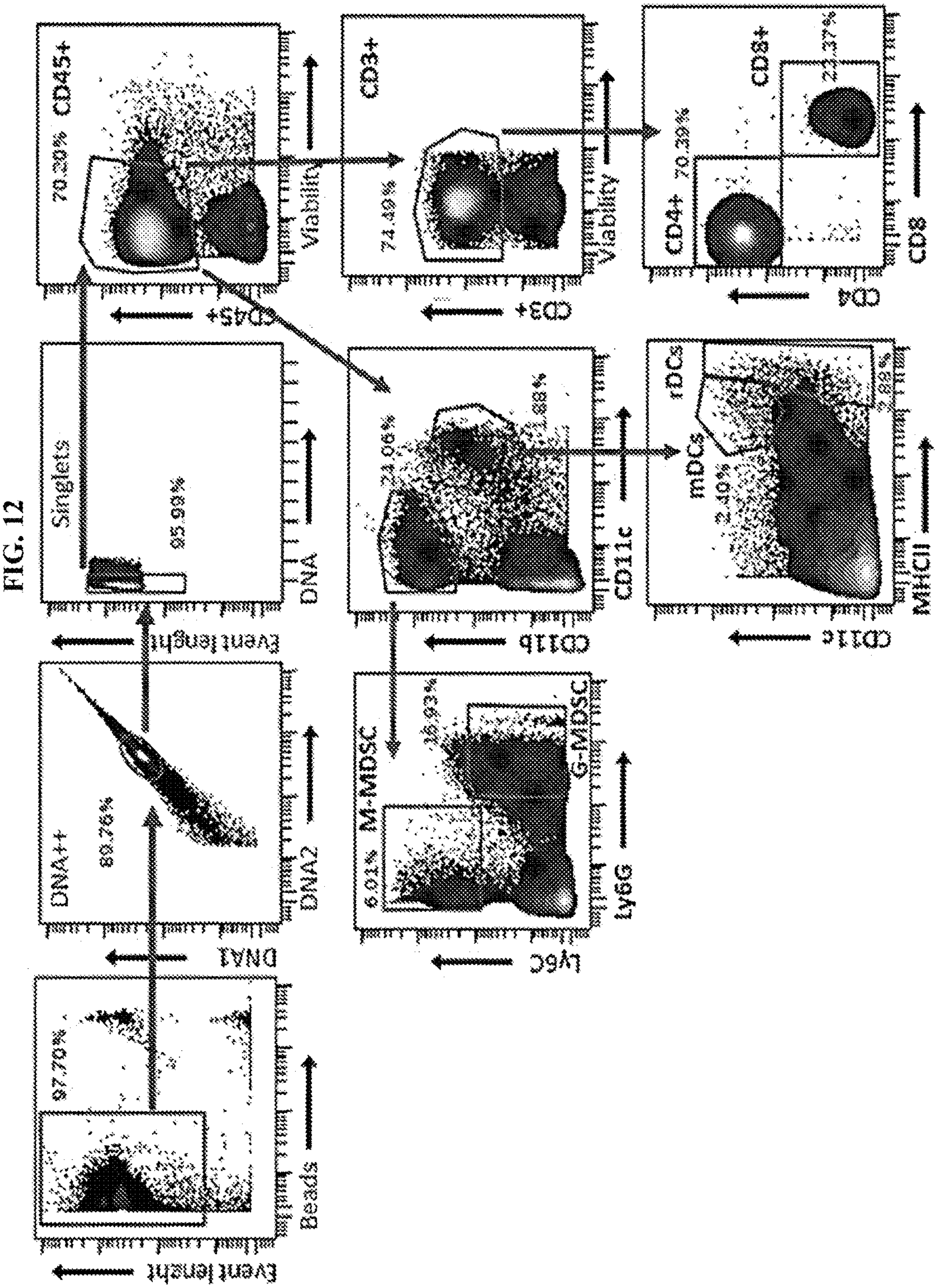

FIG. 12 schematically shows mass cytometry gating strategy using a Helios cyTOF platform (representative example). Sequential gating strategy for analysis of spleen and tumor cell subsets. Dead cell events and CyTOF calibration beads were excluded before gating on $CD45^+$ leukocytes. Single cell events were identified using Iridium-Intercalator according to manufacturer's protocol. Distinct immune cell subsets were further analyzed for differences in functional marker expression, $CD3^+$CD4 and $CD3^+CD8^+$ lymphocytes, granulocytic myeloid suppressor cells (G-MDSC, CD11b+Ly6$G^{hi}$Ly6$G^{low}$), monocytic myeloid suppressor cells (M-MDSC CD11b+Ly6$C^{hi}$Ly6$G^{low}$), regulatory dendritic cells (rDCs−CD11c+CD11c− MHCII+), myeloid dendritic cells (mDCs−CD11c+ MHCII+). Panel shows cyTOF data from one spleen sample. Plots include concatenated data from one experiment (n=5 mice).

Figure 13:
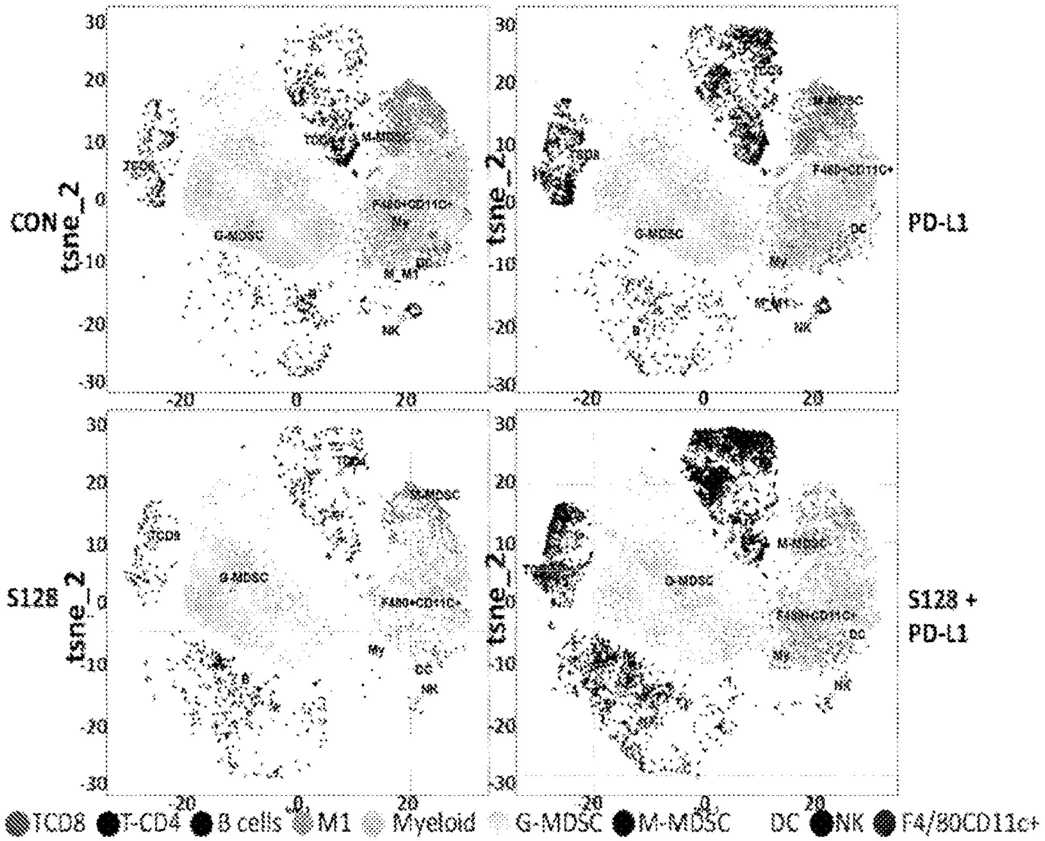

FIG. 13 shows PhenoGraph analysis of different cell populations present in spleens and tumors. CyTOF analysis of tumors and spleens from BALB/c mice bearing 4T1 tumors treated for 12 days as described above (cf. FIG. 4). Single cell suspensions were stained with 28 different intracellular and cell surface markers and then analyzed by CyTOF. Data show all viable single cells, subjected to PhenoGraph in cytofkit, which calculates the optimal amount of clusters (right panel) with data from one control tumor plotted on a tSNE plot. Defined populations include $CD4^+$ and $CD8^+$ T lymphocytes, B lymphocytes, G-MDSC, M-MDSC, dendritic cells (DC), natural killer cells (NK), M1 macrophages, CD11b+ myeloid cells (Myeloid) and F4/80+CD11c+ cells.

Figure 14:
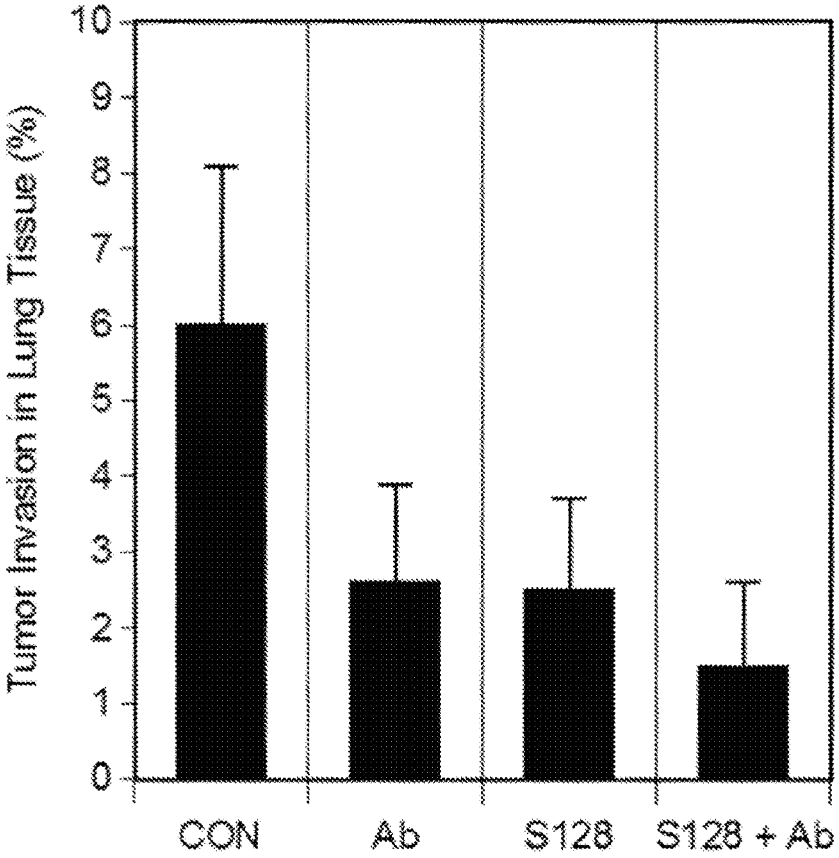

FIG. 14 shows TNBC invasion in lung tissue at 12 days after control (CON), anti-PD-L 1 antibody (Ab), S128 or combination of S128+Ab treatments. Mice were treated as detailed in FIG. 4 above. At the end of day 12 treatments, mice were sacrificed and lung tissues were harvested and then processed for staining using standard H & E. Lung specimens were then assessed to determine the proportion of lung tissue with evidence of early tumor invasion. The lung is known to be a primary site of metastasis for 4T1 TNBC tumors, with most reports focusing on treatments for 28 days or longer. The results suggest an early trend toward reduced metastasis to the lung in mice with 4T1 implants in mice treated with S128 when combined with anti-PD-L1 antibody.

Figure 15:
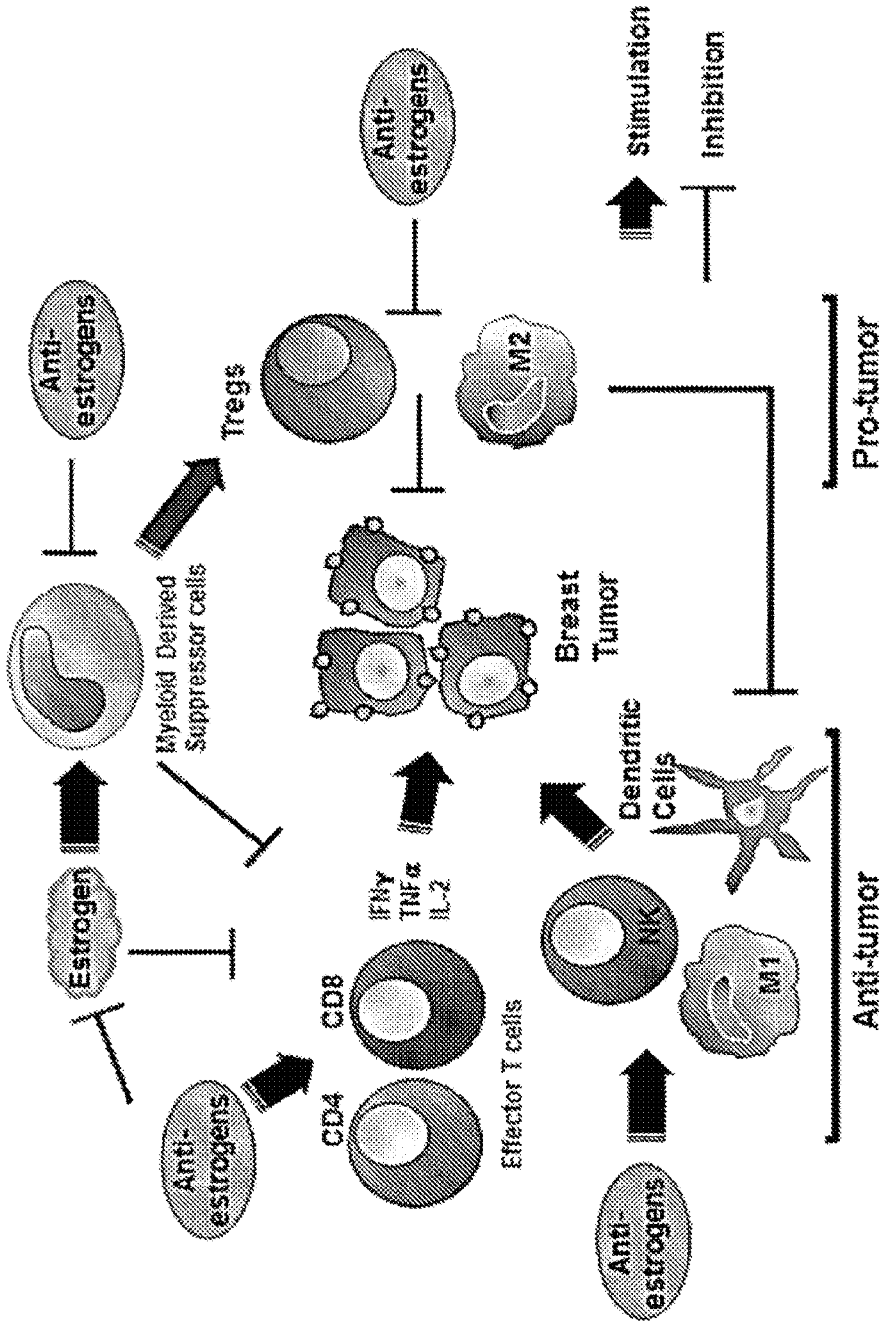

FIG. 15 shows Estrogen (E2) orchestrates a number of effects on immune cells in the tumor microenvironment.

Figure 16:
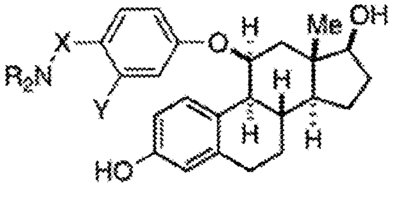
Figure 16:
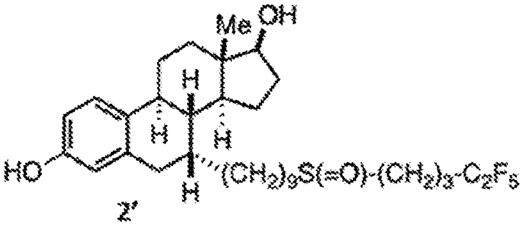
Figure 16:
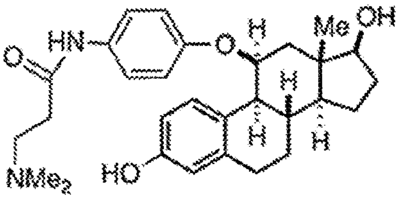
Figure 16:
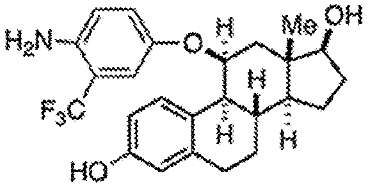
Figure 16:
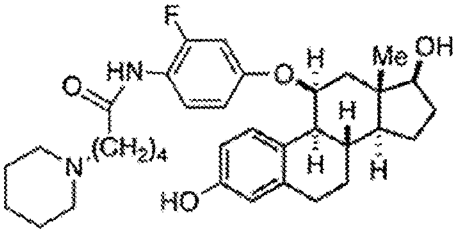
Figure 16:
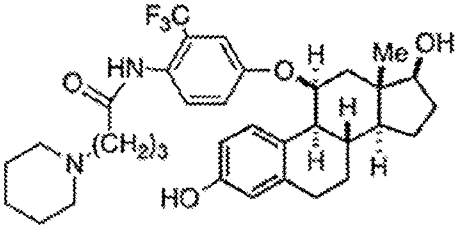

FIG. 16 shows exemplary substituted estradiols in Example 6.

Figure 17:
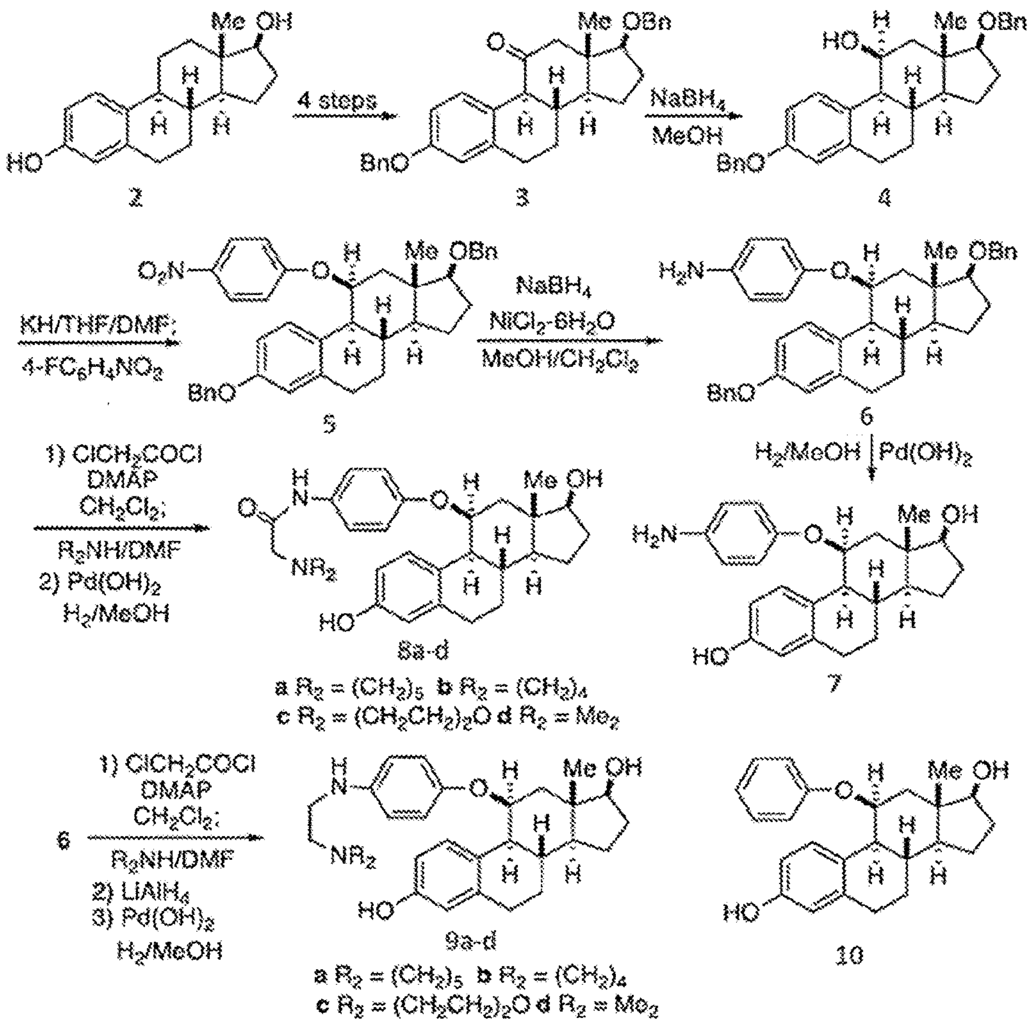

FIG. 17 shows exemplary synthesis pathways for exemplary analogues in Example 6.

Figure 18:
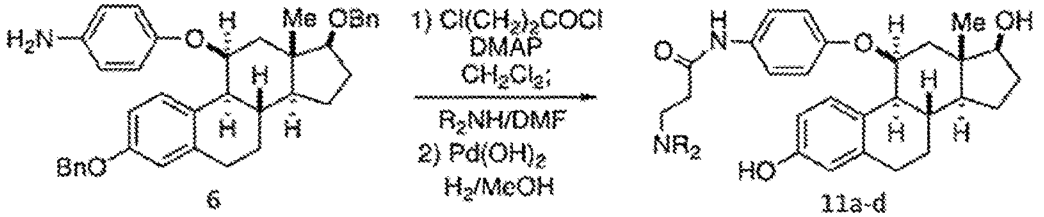
Figure 18:
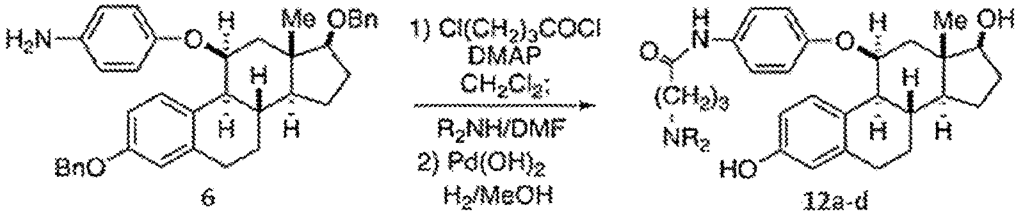
Figure 18:
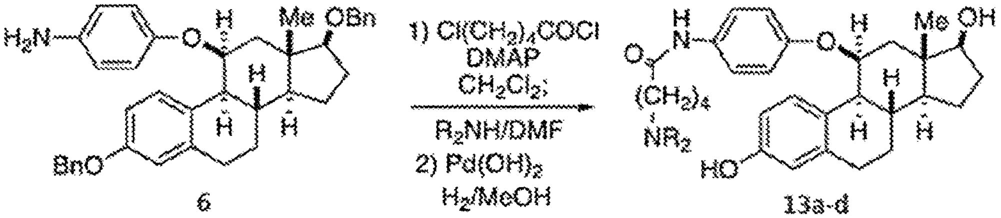
Figure 18:
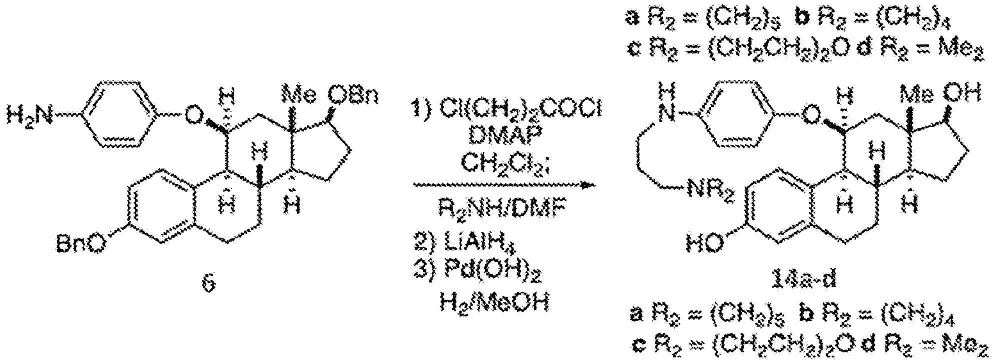

FIG. 18 shows exemplary synthesis pathways for another exemplary analogues in Example 6.

Figure 19:
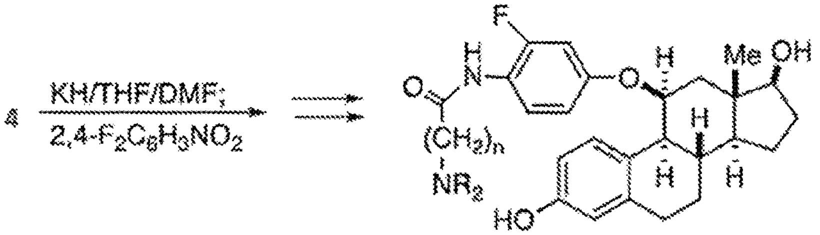
Figure 19:
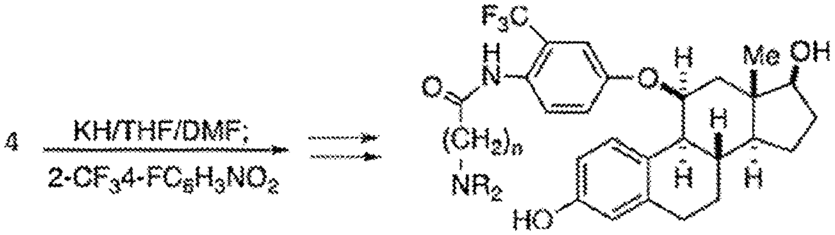
Figure 19:
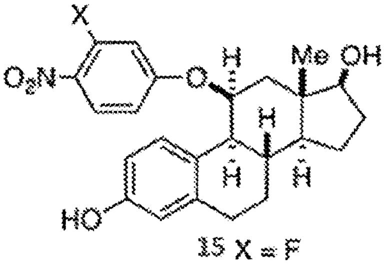
Figure 19:
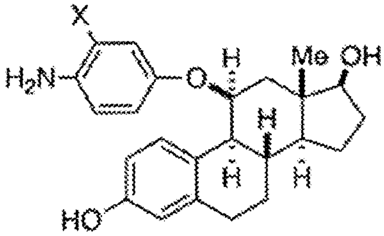

FIG. 19 shows exemplary synthesis pathways for another exemplary analogues in Example 6.

Figure 20A:
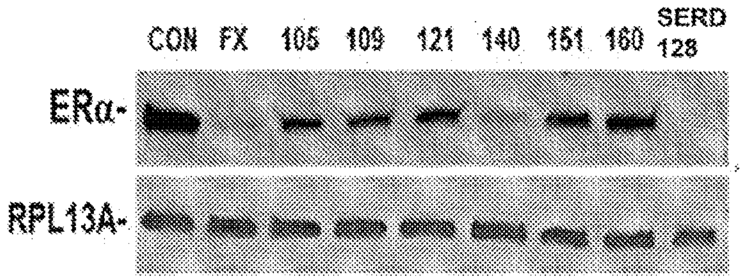
Figure 20B:
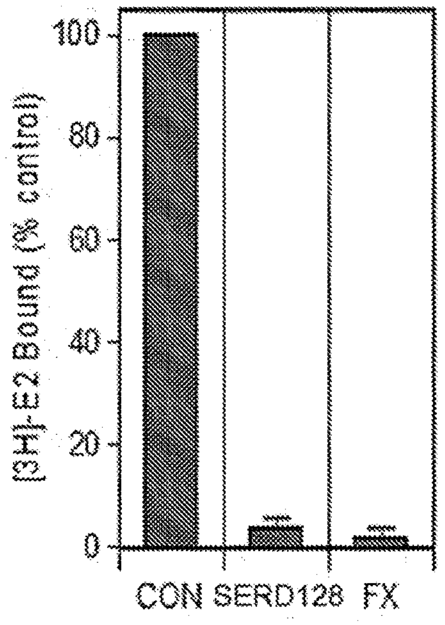
Figure 20C:
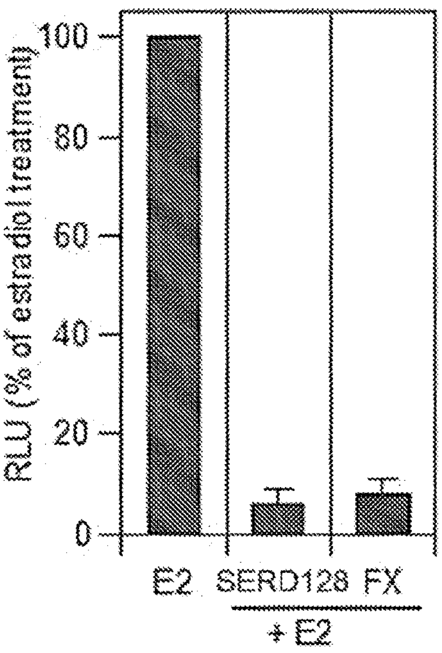

FIGS. 20A-20C show biologic activity of selected SERD candidates. FIG. 20A shows downregulation of ER protein. ER-positive MCF-7 cells were treated in phenol-red free RPMI 1640 without FBS and containing vehicle control (CON) or 100 nM concentrations of either fulvestrant (FX) or antiestrogens 105, 109, 121, 140, 151, 160 or SERD128 in vitro. After 4 hours, cells were harvested and processed for PAGE and Western immunoblots using ERα antibody (1D5, Thermofisher Scientific). RPL13A was used as a loading control. FIG. 20B shows that specific [3H]estradiol-17β (E2) binding and competition for binding by antiestrogen SERD128 or fulvestrant (FX) at 10 nM was assessed in human MCF-7 breast cancer cells using methods as described before [36, 40]. FIG. 20C shows response of the ERE-luciferase T47D reporter construct to estrogen antagonists fulvestrant (10 nM) or SERD128 (10 nM) in combination with 2 nM 17β-estradiol as compared to treatment with 17β-estradiol alone (E2; 2 nM). Cells were dosed with either E2 alone or with SERDs combined with E2 in phenol redfree medium with 0.1% dextran-coated charcoal-treated FBS in luminometer plates. Data are presented as relative light units (RLU) relative to that of E2 alone in three replicate assays (4 wells per replicate) f SEM. Treatment with E2 alone induced a 12-fold induction of ER-dependent luciferase activity quantified as RLU relative to vehicle control-treated samples.

Figure 21A:
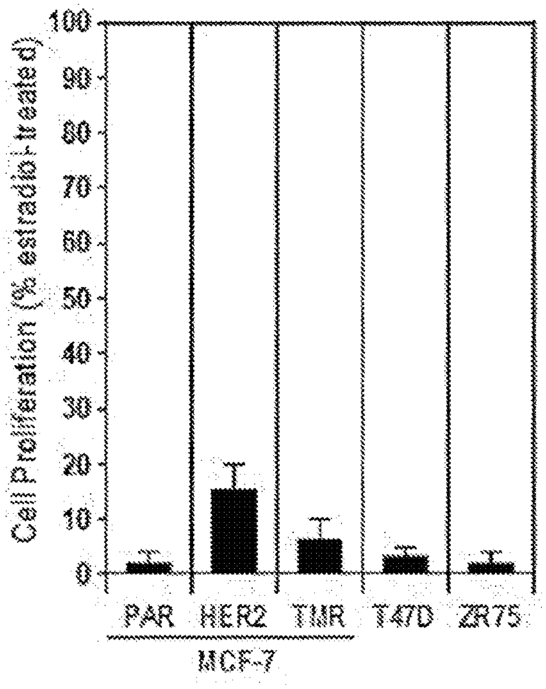
Figure 21B:
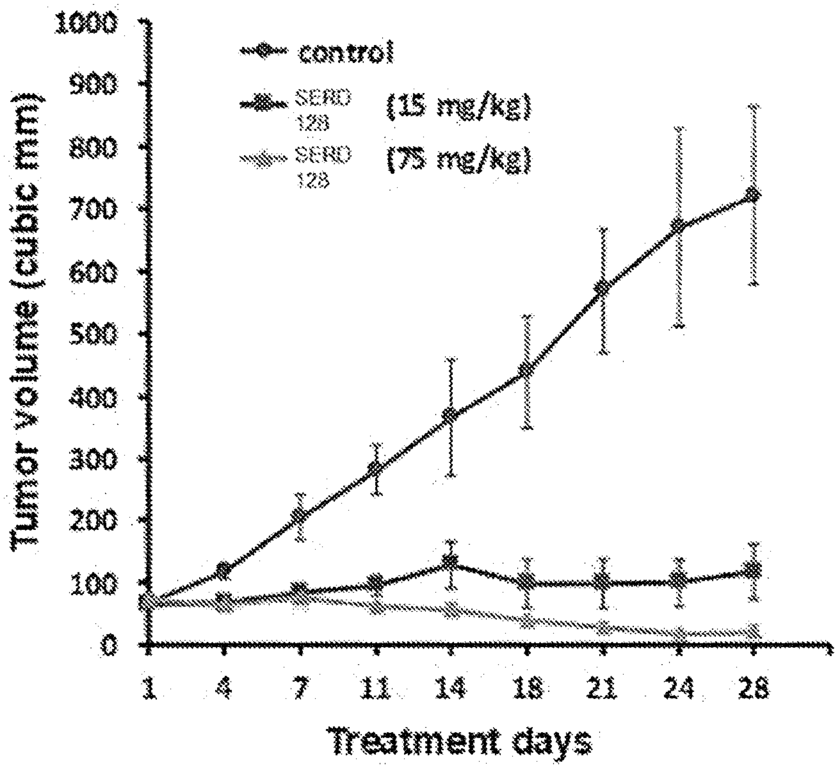

FIGS. 21A-B show steroid-like SERD128 inhibits estrogen-induced BC cell proliferation in vitro and in vivo. FIG. 21A shows that ER-positive MCF-7, T47D and ZR75 cells were grown in phenol red-free media with 1% DCC-FBS for 48 hr., then treated 48 hr. with 2 nM estradiol-17β alone (control) or in combination with 10 nM doses of SERD128. Note that MCF-7 cell populations included cells with no HER2-overexpression (MCF-7/PAR), cells with HER2-overexpression (MCF-7/HER2) and MCF-7 cells with tamoxifen resistance (MCF-7/TMR). Cell proliferation is shown as % of that in estradiol-treated controls (n=3 experiments). SERD128 significantly blocked proliferation in all BC cell models in vitro (P<0.001). Of note, E2 alone stimulated cell proliferation several-fold in each cell line as compared to cells treated only with vehicle (not shown). FIG. 21B shows SERD128 inhibits growth of human breast tumor xenografts in vivo. MCF-7 human breast cancer cells were subcutaneously inoculated in nude mice previously primed with estradiol pellets. When animals developed tumors of comparable size they were randomized to treatment with vehicle control (control) or SERD128 at 15 and 75 mg/kg once a day by oral gavage for 28 days. Tumors were measured every 3 days, and tumor volume was calculated as V=(l×w×w)/2). Results are expressed as mean±SEM. ***P<0.001 as compared to control group.

Figure 22A:
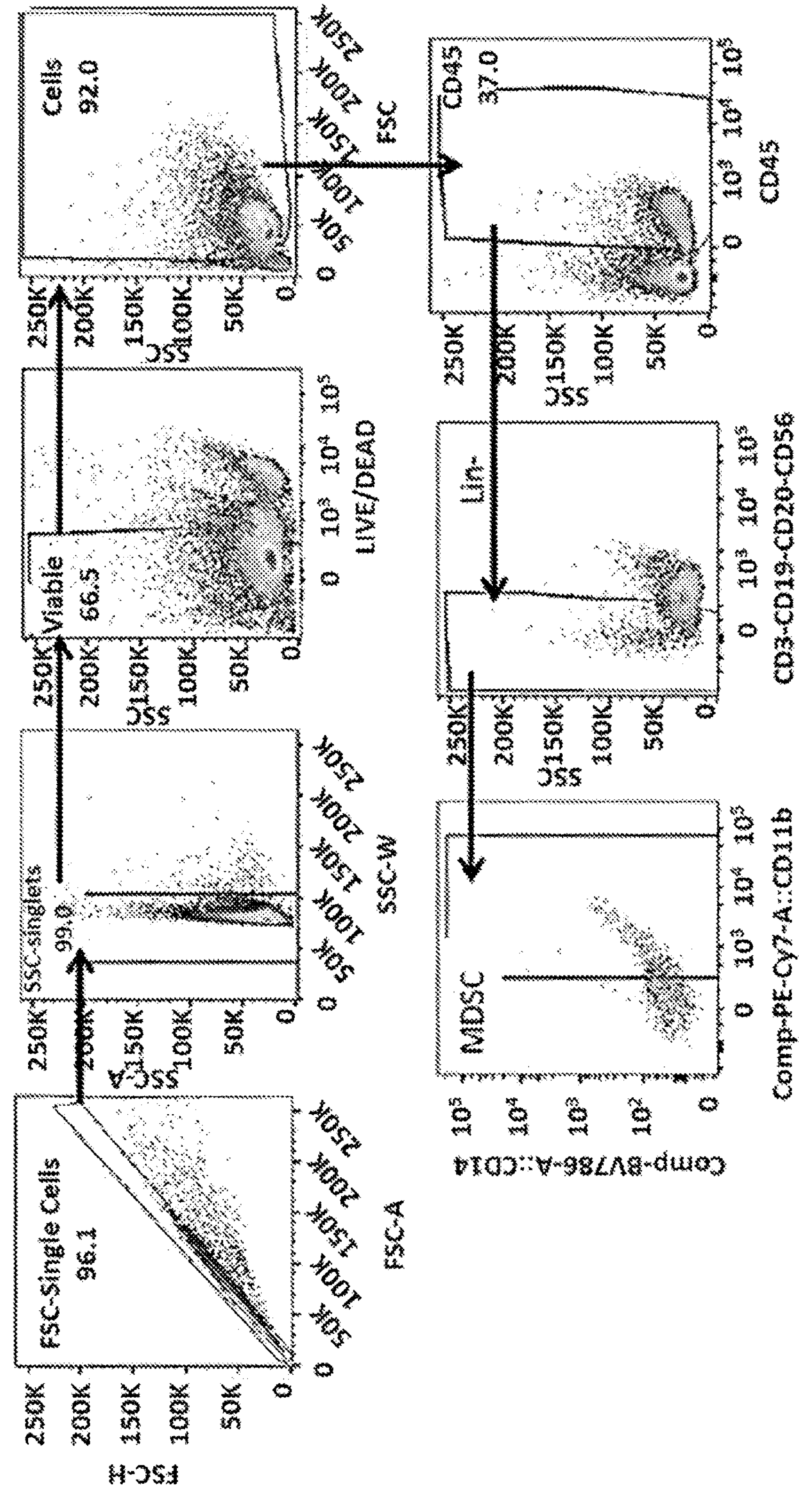
Figure 22B:
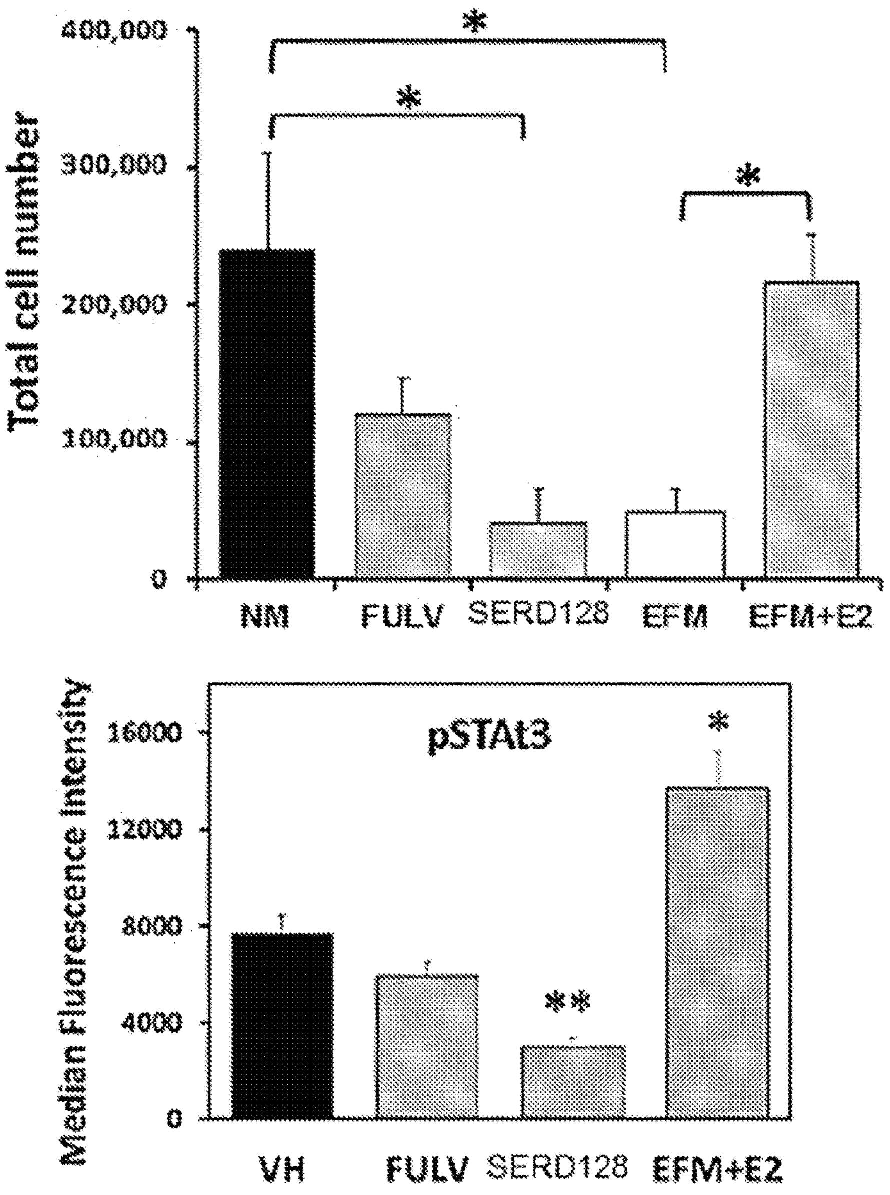

FIGS. 22A-22B show expansion of MDSCs is dependent on estrogen signaling and reversed by antiestrogens. E2 increases total numbers of MDSCs, with total numbers of human MDSCs derived from bone marrow (BM) of BC patients. Retrospectively-collected BM cells from de-identified BC patients were purified by established methods including red blood cell lysis and Ficoll gradients and then incubated with GM-CSF and IL-6 for 6 days in either regular RPMI medium+15% FBS (NM) (contains estrogens), NM with antiestrogens (FULV or SERD128) or in phenol red-free medium with 15% charcoal coated-dextran treated FBS (EFM) (estrogen-depleted) with or without the addition of 100 nM estradiol-17β (EFM+E2). Normal cell culture medium (NM) drives E2-dependent signaling due to the presence of various estrogens in FBS as well as estrogenic properties of phenol red. These effects were significantly inhibited by fulvestrant (FULV) and SERD128 at 1 μM concentrations in normal medium. FIG. 22A shows that the gating strategy used to identify MDSCs is shown. The figure shows total MDSC populations ($CD45^+CD3^-CD19^-CD20^-CD56^-CD11b^+$) identified by following the gating strategy of Ruffell et al. [16] and modified by Svoronos et al. [7]. FIG. 22B shows graphs showing quantification of total MDSC cultivated as described (top panel) and SERD128 blocks phosphorylation/activation of STAT3 in G-MDSC subpopulations under the same conditions described in FIG. 22A (low panel). Results show median fluorescence intensity for p-STAT3 in G-MDSC subsets ($CD45+HLA^-DR^-CD11b^+CD14^-CD15^+$) after expansion of human total MDSC.

Figure 23A:
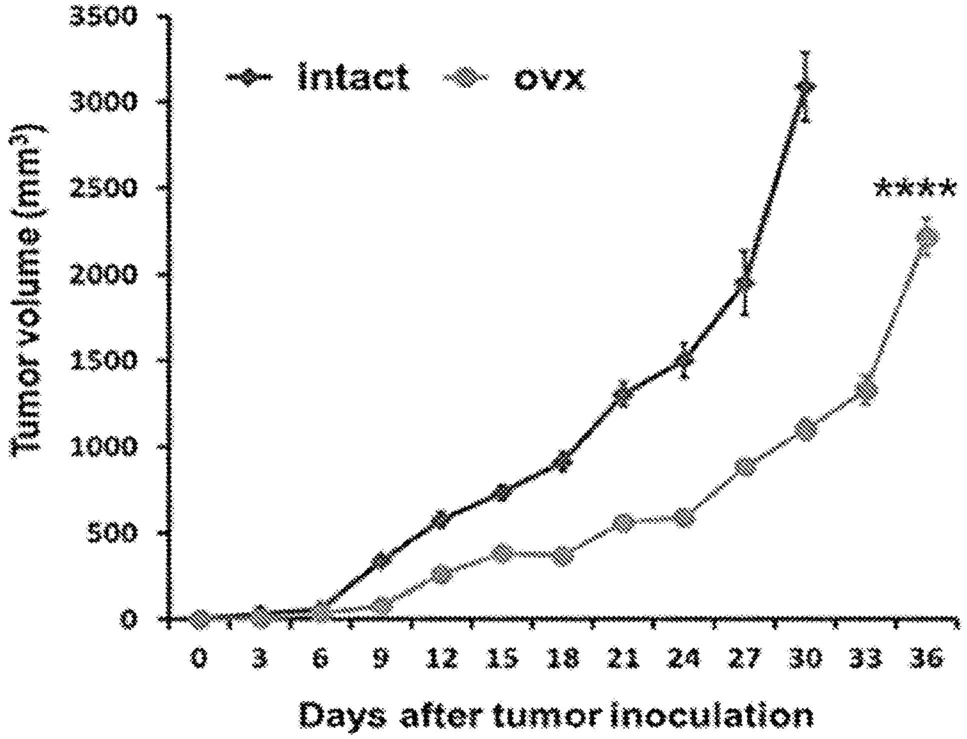
Figure 23B:
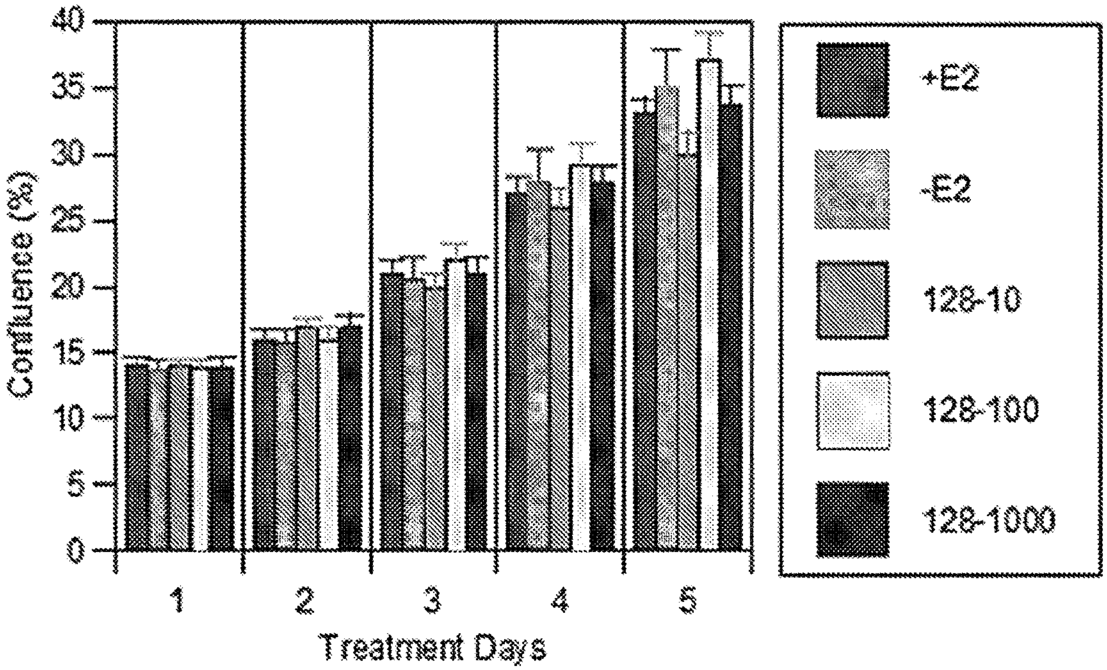
Figure 23C:
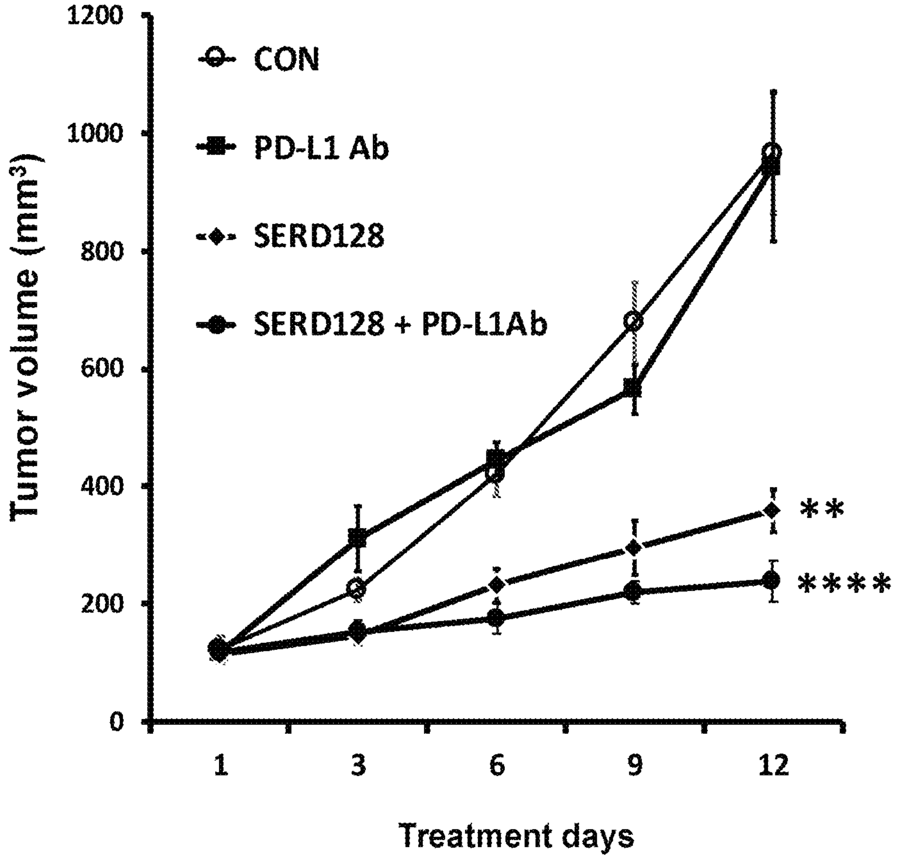

FIGS. 23A-23C show estrogen effects on ERα negative tumor growth in vitro and in vivo. FIG. 23A shows ovariectomy reduces progression of 4T1 TNBC in syngeneic mice in vivo. Female 6-wk-old BALB/c mice, either ovariectomized (ovx) or sham-operated (intact), were inoculated s.c. with 2×105 4T1 TNBC cells. Tumor growth was then assessed every 3 days, with tumor volume calculated as V=(l×w×w)/2. **P≤0.0001. FIG. 23B shows that 4T1 triple negative breast cancer cells do not respond to estrogen or antiestrogens in vitro. 4T1 cells were grown in the presence (+E2) or absence (−E2) of estradiol-17β and increasing concentrations of SERD128 at 10 nM (128-10), 100 nM (128-100) or 1000 nM (128-1000). Cell proliferation was assessed using the Incucyte S3 Live-Cell Analysis system with pictures obtained every 4-6 hours. Graph shows average cell proliferation expressed as phase object confluence measured for 5 days. No significant differences were observed in cell proliferation. FIG. 23C shows that selective estrogen receptor downregulator, SERD128, alone and combined with anti-PD-L1 checkpoint antibody inhibits breast cancer growth in vivo. Ovariectomized 6-week-old female syngeneic BALB/c mice were primed with estradiol-17β slow-release pellets prior to tumor cell inoculation. After three days, 4T1 cells were injected in the $4^{th}$ mammary fat pad ($2\times10^5$ cells). After tumors reached ~200 $mm^3$ mice were randomized and treated with control vehicle (CON), 100 mg of anti-PD-L1 antibody every $3^{rd}$ day (PD-L1 Ab), 50 mg/kg SERD128 via oral gavage (SERD128), and combinations of antibody and SERD128 (SERD128+PD-L1 Ab). Tumors were measured every 3 days, and tumor volume was calculated as V=(W(2)×L)/2). P<0,01, ****P<0.0001 as compared to control group. n=11-12.

Figures 24A, 24B, 24C:
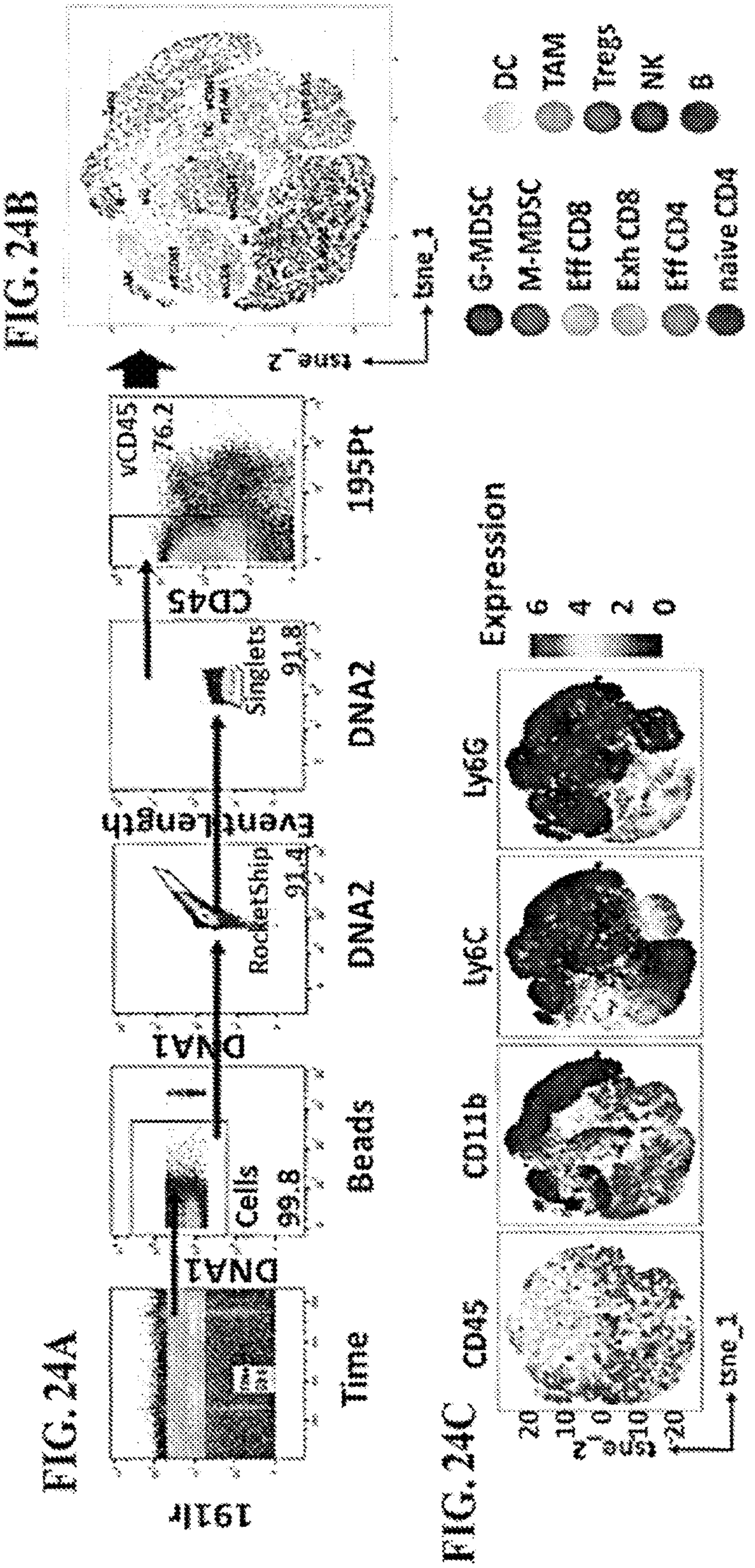
Figure 24D:
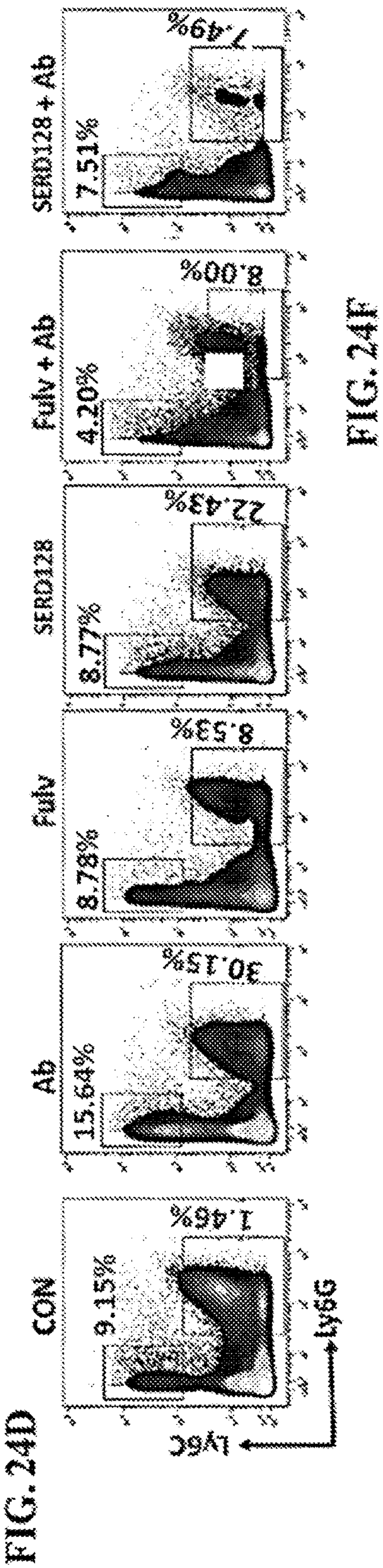
Figure 24E:
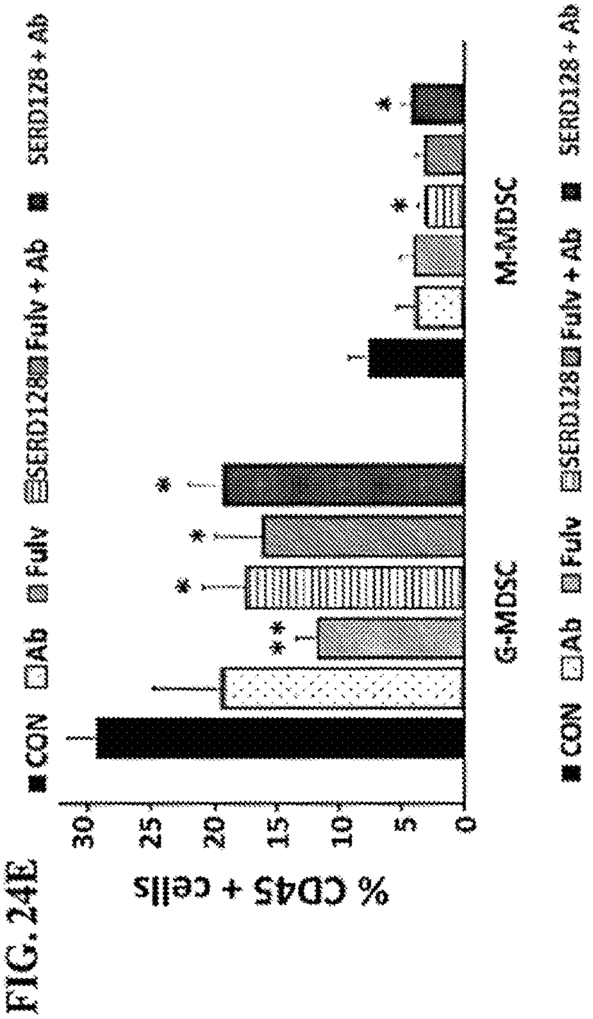

FIGS. 24A-24E show high-dimensional analysis of mass cytometry data indicating antiestrogens decrease the amount of myeloid derived suppressor cells present in 4T1 tumors. Single cells were purified from 4T1 tumors grown in BALB/c mice, stained with a panel of 28 markers by mass cytometry. FIG. 24A shows sequential gating strategy to analyze tumor CD45+ cell subsets present in the TME. FIG. 24B shows phenograph example of different cell populations identified by single cell analysis using Cytofkit. FIG. 24C shows tSNE plots indicating cluster expression of markers for both populations of myeloid cells G-MDSC and M-MDSC. FIG. 24D shows representative plots of G-MDSC ($CD11b^+Ly6G^{hi}$, $Ly6C^{lo}$) and M-MDSC ($CD11b^+Ly6C^{hi}Ly6G^{low}$) as percentage of CD45+ cells. FIG. 24E shows quantification of G-MDSC and M-MDSC present in the tumor bed of BALB/c mice bearing 4T1 tumors. *P<0.05, P<0.01. FIG. 24**F shows ERα expression in total MDSC, G-MDSC and M-MDSC.

Figures 25A, 25B, 25C:
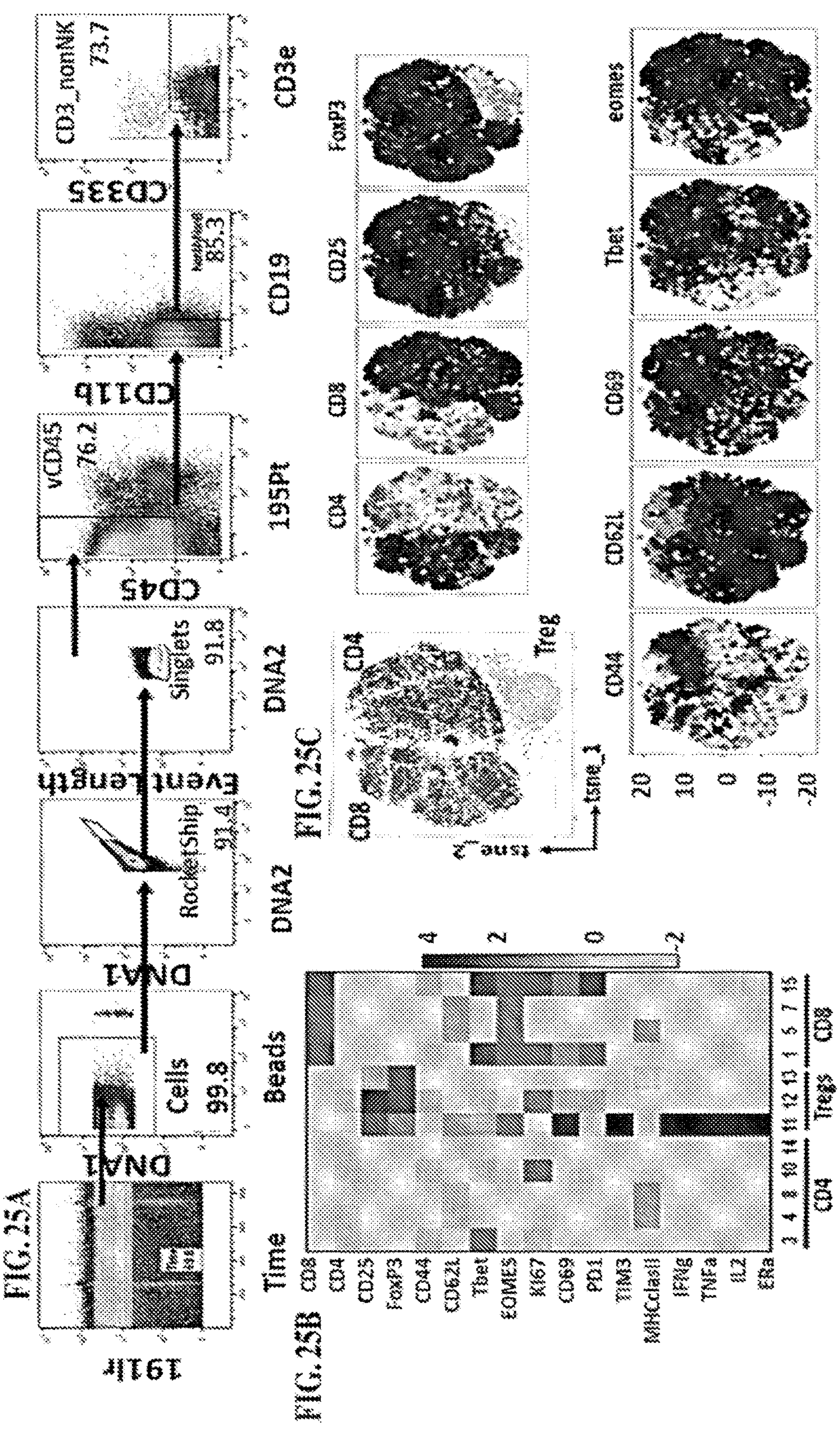
Figure 25D:
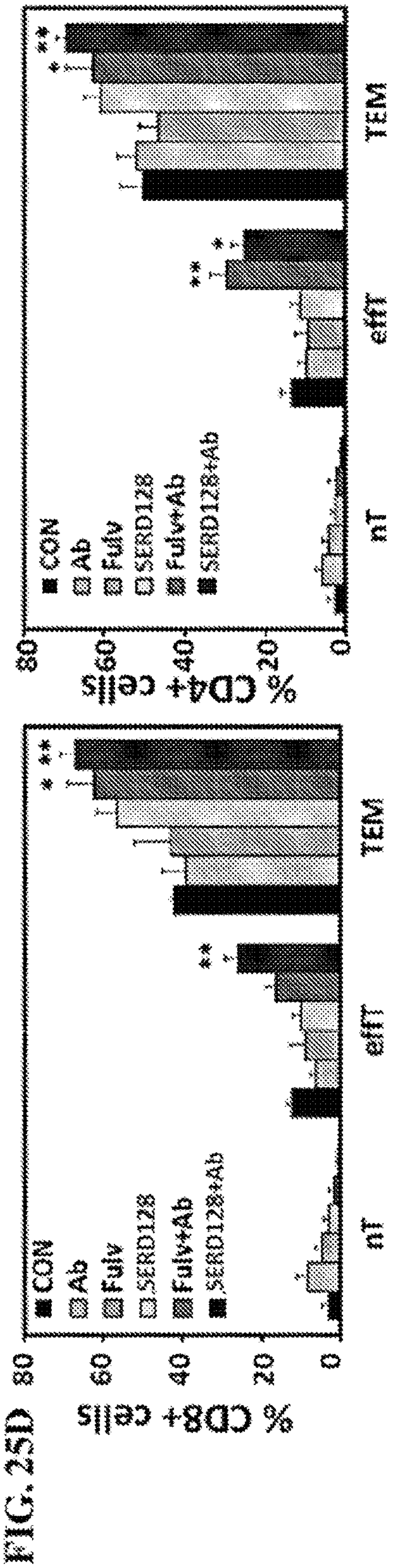
Figure 25E:
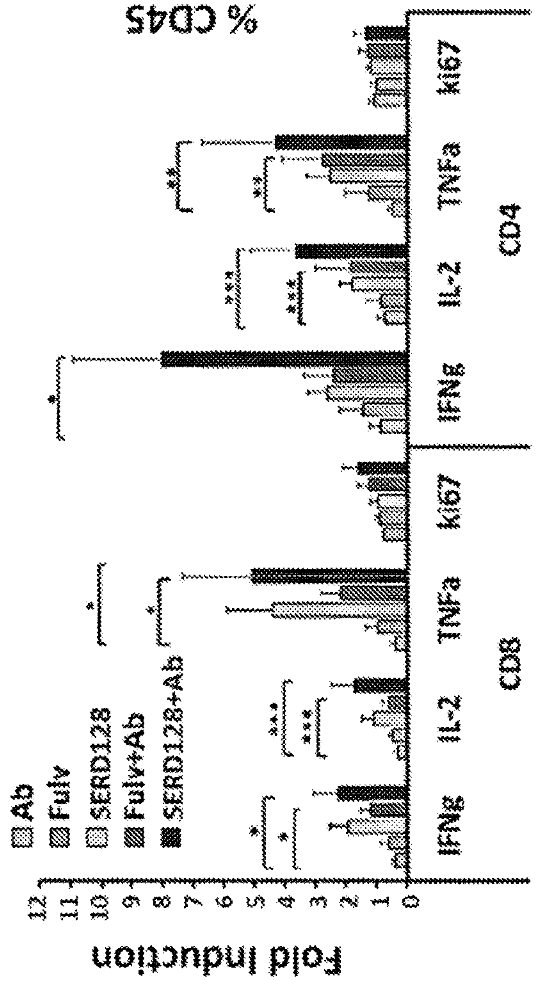
Figure 25F:
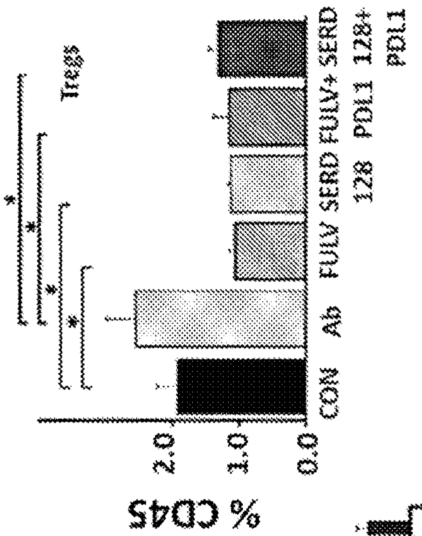

FIGS. 25A-25F show tumor infiltrating lymphocytes (TILs) in 4T1 tumors from BALB/c mice, with $CD8^+$ and $CD4^+$ TILs shown. Single cell suspensions were purified, stained and analyzed by cyTOF. Groups include mice treated with control vehicle (CON), anti-PD-L1 antibody (Ab), fulvestrant (Fulv), SERD128 or the combination of fulvestrant with anti-PD L1 antibody (Fulv+Ab) or SERD128 and anti-PD-L1 antibody (SERD128+Ab). FIG. 25A shows sequential gating strategy to analyze tumor CD3+ cell subsets. FIG. 25B shows Z-scores of median intensity of distinct protein markers shown in heatmap for all clusters analyzed by Cytofkit. FIG. 25C shows tSNE scatter plot visualization of $CD3^+$ cells showing clusters of $CD8^+$, $CD4^+$ and Tregs ($CD4^+CD25^+FoxP3^+$) cells (upper left); and t-SNE plots with arcsinh transformed signal intensity of different activation markers (right). FIG. 25D shows percentage of different type of $CD8_+$ and $CD4_+$ T cells, naïve (nT) ($CD44^-CD62L^+CD69^-$), effector (effT) ($CD44^+CD69^+Tbet^{hi}eomes^-$) and effector memory (TEM) ($CD44^+CD62L^-$). FIG. 25E shows increased expression of activation cytokines in $CD8^+$ and $CD4^+$TIL population. FIG. 25F shows that $CD4^+CD25^+FoxP3^+$Tregs are significantly decreased by antiestrogen therapy. *P<0.05, P<0.01, *P<0.001. n=6.

Figure 26A:
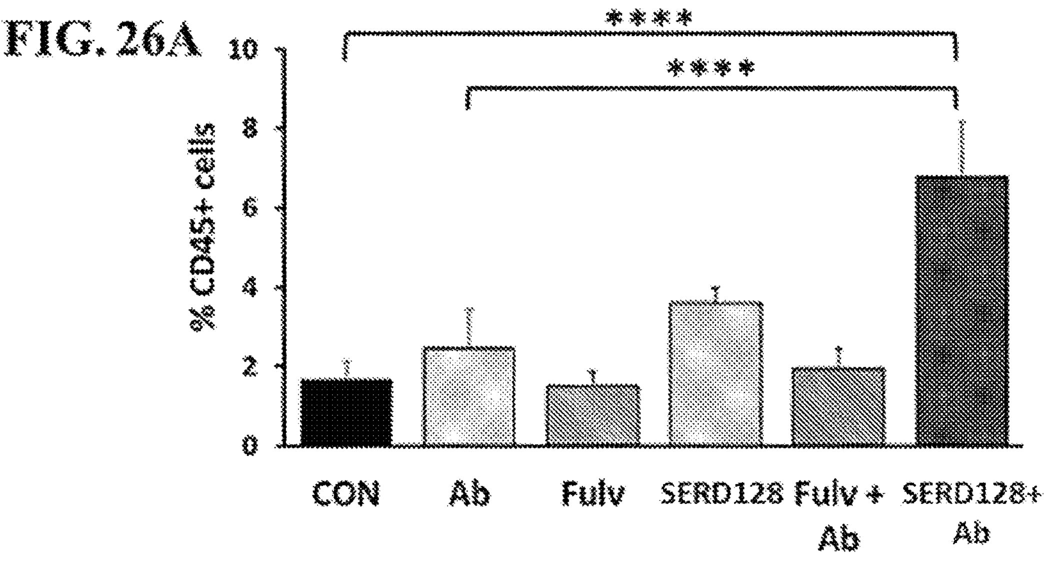
Figure 26B:
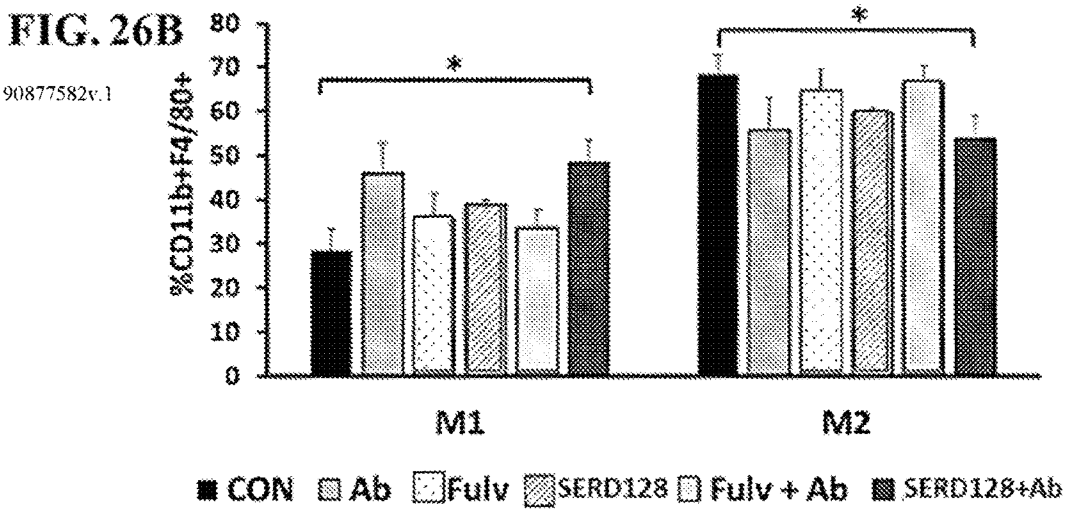

FIGS. 26A-26B show combined therapy with SERD128 and anti-PD-L1 antibody enhance tumor infiltrating dendritic cells and M1 macrophages. Single cell suspensions were purified, stained and analyzed by cyTOF as described above. Groups include mice treated with control vehicle (CON), anti-PD-L1 antibody (Ab), fulvestrant (Fulv), SERD128 or the combination of fulvestrant with anti-PD-L1 antibody (Fulv+Ab) or SERD128 and anti-PD-L1 antibody (SERD128+Ab). FIG. 26A shows subset of dendritic cells present in the tumor bed indicating a significant increase in the total number of DC gated as ($CD45^+CD11c^+MHCII^+$) when SERD128 was added to ICI therapy. FIG. 26B shows that M1 tumor infiltrating macrophages were significantly increased by combination therapy of SERD128 and anti- PD-L1 antibody. Macrophages were gated as ($CD45^+$ $CD11b^+F4/80^+$M1: $MHCII^{hi}$ M2: $MHCII^{lo}$). *P≤0.05, ****P<0.0001, n=6-10.

DETAILED DESCRIPTION

Provided herein, inter alia, is a novel composition including a selective estrogen receptor inhibitor or downregulator for cancer treatment or cancer immunotherapy. Also provided herein, inter alia, is a novel composition including a selective estrogen receptor inhibitor or downregulator and an immune checkpoint inhibitor for cancer treatment or cancer immunotherapy.

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbomenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-O-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol “ ” denotes the point of attachment of a chemical moiety to the remainder of a molecule or chemical formula.

The term “oxo,” as used herein, means an oxygen that is double bonded to a carbon atom.

The term “alkylsulfonyl,” as used herein, means a moiety having the formula —$S(O_2)$—R', where R' is a substituted or unsubstituted alkyl group as defined above. R' may have a specified number of carbons (e.g., “$C_1$-$C_4$ alkylsulfonyl”).

The term “alkylarylene” as an arylene moiety covalently bonded to an alkylene moiety (also referred to herein as an alkylene linker). In embodiments, the alkylarylene group has the formula:

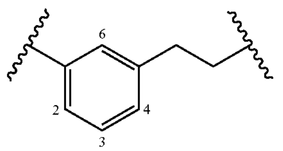

or

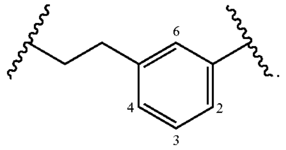

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., “alkyl,” “heteroalkyl,” “cycloalkyl,” “heterocycloalkyl,” “aryl,” and “heteroaryl”) includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —$NR^{11}$C(O)R', —NR'—C(O)$NR^{11}$R'", —$NR^{11}C(O)_2$R', —NR—C(NR'RR'")=NR"", —NR—C(NR'R")=NR'", —S(O)R', —$S(O)_2$R', —$S(O)_2$NR'R", —$NRSO_2$R', —NR'$NR^{11}$R'", —ONR'R", —NR'C(O)NR"NR'"R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R and R are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —$NR^{11}$C(O)R', —NR'—C(O)$NR^{11}$R'", —$NR^{11}C(O)_2$R', —NR—C(NR'R"R'")=NR"", —NR—C(NR'R")=NR'", —S(O)R', —$S(O)_2$R', —$S(O)_2$NR'R", —$NRSO_2$R', —NR'$NR^{11}$R'", —ONR'R", —NR'C(O)NR"NR'"R"", —CN, —$NO_2$, —R', —$N_3$, —CH$(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)-(CRR')_q-U-$, wherein T and U are independently $-NR-$, $-O-$, $-CRR'-$, or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently $-CRR'-$, $-O-$, $-NR-$, $-S-$, $-S(O)-$, $-S(O)_2-$, $-S(O)_2NR'-$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR')_s-X'-(C''R''R''')_d-$, where s and d are independently integers of from 0 to 3, and X' is $-O-$, $-NR'-$, $-S-$, $-S(O)-$, $-S(O)_2-$, or $-S(O)_2NR'-$. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OC Br_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-O CBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_5$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_5$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "~" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with estrogen receptor activity. Certain methods described herein may treat diseases associated with estrogen receptor activity (e.g., breast cancer, lung cancer, a gynecological cancer, ovarian cancer, endometrial cancer, or prostate cancer, lymphangioleiomyomatosis (LAM)) by inhibiting estrogen receptor activity. Certain methods described herein may treat diseases associated with estrogen receptor activity by inhibiting ligand binding to estrogen receptor. Certain methods described herein may treat diseases associated with estrogen receptor activity by inducing the degradation of estrogen receptor. Certain methods described herein may treat diseases associated with estrogen receptor activity by inducing a non-active conformation of estrogen receptor. Certain methods described herein may treat diseases associated with hyperproliferation (e.g., of cells). For example, certain methods herein treat cancer. For example certain methods herein treat cancer by decreasing a symptom of cancer. Symptoms of cancer would be known or may be determined by a person of ordinary skill in the art. The term "treating" and conjugations thereof, include prevention of injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art. Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. hyperproliferative disease, cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with estrogen receptor activity may be treated with an agent (e.g. compound as described herein) effective for decreasing the level of estrogen receptor activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term “contacting” may include allowing two species to react, interact, or physically touch, wherein the two species may be a compound as described herein and a protein or enzyme. In some embodiments contacting includes allowing a compound described herein to interact with a protein or enzyme.

As defined herein, the term “inhibition”, “inhibit”, “inhibiting” and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term “CDK4 inhibitor” or “cyclin dependent kinase 4 inhibitor” is a compound (e.g., synthetic or natural compound) or a biological molecule (e.g., protein, nucleic acid, or antibody) which may reduce, suppress or negatively affect (e.g. decrease) the level of activity (e.g., enzyme activity), expression (e.g., protein expression, or mRNA expression), or function of cyclin dependent kinase 4 (CDK4) relative to the level of activity (e.g., enzyme activity), expression (e.g., protein expression, or mRNA expression) or function of the CDK4 in the absence of the inhibitor.

As defined herein, the term “CDK6 inhibitor” or “cyclin dependent kinase 6 inhibitor” is a compound (e.g., synthetic or natural compound) or a biological molecule (e.g., protein, nucleic acid, or antibody) which may reduce, suppress or negatively affect (e.g. decrease) the level of activity (e.g., enzyme activity), expression (e.g., protein expression, or mRNA expression), or function of cyclin dependent kinase 6 (CDK6) relative to the level of activity (e.g., enzyme activity), expression (e.g., protein expression, or mRNA expression) or function of the CDK6 in the absence of the inhibitor.

As defined herein, the term “activation”, “activate”, “activating” and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term “modulator” refers to a composition that increases or decreases the level of a target molecule or the function of a target molecule. In embodiments, a modulator is an anti-cancer agent. In embodiments, a modulator is an estrogen receptor antagonist. In embodiments, a modulator is a hormone receptor antagonist. In embodiments, a modulator is an estrogen receptor inhibitor. In embodiments, a modulator is an estrogen receptor covalent modifier. In some embodiments, the estrogen receptor antagonist or estrogen receptor inhibitor includes tamoxifen, fulvestrant, clomifene, femarelle, ormeloxifene, raloxifene, toremifene, lasofoxifene, ospemifene, anastrazole, letrozole, exemestane, vorozole, formestane, fadrozole, aminoglutethimide, or testolactone. An estrogen receptor inhibitor is a composition, compound, or substance capable of reducing the activity or function of an estrogen receptor, including reducing the activity or function of a downstream component of a signal transduction pathway activated by estrogen receptor (e.g., reducing relative to ER activity or function in the presence of estrogen or another activating ligand or agonist or relative to unliganded activity of ER).

An “additional agent” or “further agent”, as used herein, refer to a compound for use in conjunction with the compounds provided herein (the compounds of Formula I and embodiments thereof). An additional agent or further agent may be an anti-cancer agent. In embodiments, the additional agent or further agent is an agent for treating a hyperproliferative disorder. In embodiments, the further agent is a chemotherapeutic. In embodiments, the further agent is an agent for treating breast cancer. In embodiments, the further agent is an agent for treating lung cancer. In embodiments, the further agent is an agent for treating a gynecological cancer. In embodiments, the further agent is an agent for treating ovarian cancer. In embodiments, the further agent is an agent for treating endometrial cancer. In embodiments, the further agent is an agent for treating prostate cancer. In embodiments, the further agent is an agent for treating lymphangioleiomyomatosis. In embodiments, the further agent is a HER-2 inhibitor. In embodiments, the further agent is Herceptin. In embodiments, the further agent is an EGFR inhibitor (e.g. gefitinib (Iressa™), erlotinib (Tarceva™), cetuximab (Erbitux™), lapatinib (TYKERB™), panitumumab (VECTIBIX™), vandetanib (CAPRELSA™), afatinib/BIBW2992, CI-1033/canertinib, neratinib/HKI-272, pelitinib/EKB-569, BMS-599626, TAK-285, CUDC-101, OSI-420/desmethyl erlotinib, CP-724714, dacomitinib/PF299804, AG-490, AG-1478, AST-1306, WZ3146, AZD8931, sapitinib, PD153035, icotinib, ARRY334543/varlitinib, ARRY-380, AEE788, WZ8040, WZ4002, or XL647). In embodiments, the further agent is a mammalian target of rapamycin (mTOR) inhibitor (such as everolimus) for use in treating cancer (e.g. in breast and NSCLC tumors); HER2-targeted therapeutics (such as trastuzumab, lapatinib, trastuzumab-emtansine) for use in treating cancer (e.g. ER-positive breast cancers with over-expression of HER-2 receptors); HER3-targeted agents (e.g. pertuzumab); EGFR-targeted therapeutics (such as erlotinib, gefitinib, afitinib) for treating cancer (e.g. NSCLC expressing mutant EGFR or having EGFR-positivity); tamoxifen or aromatase inhibitors in treating cancer (e.g. ovarian suppression).

“Anti-cancer agent” or “anti-cancer drug” is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (GLEEVEC@), geldanamycin, 17-N-Allylamino-17-Demethoxygeldanamycin (17-AAG), bortezomib, trastuzumab, anastrazole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras famesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Gudrin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (TYKERB™), panitumumab (VECTIBIX™), vandetanib (CAPRELSA™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: e.g., monomethyl auristatin E), anthracycline antibiotics (such as doxorubicin, daunorubicin, etc.), duocarmycins and duocarmycin analogs, enediynes (such as neocarzinostatin and calicheamicins), leptomycin derivatives, maytansinoids and maytansinoid analogs (e.g. mertansine), methotrexate, mitomycin C, taxoids, vinca alkaloids (such as vinblastine and vincristine), epothilones (e.g. epothilone B), fluvestrant, camptothecin and its clinical analogs topotecan and irinotecan, SERMS (e.g., clomifene, femarelle, ormeloxifene, raloxifene, tamoxifen, toremifene, lasofoxifene, ospemifene), aromatase inhibitors (e.g., anastrazole, letrozole, exemestane, vorozole, formestane, fadrozole, aminoglutethimide, testolactone), or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a disease having the symptom of an aberrant level of estrogen receptor activity. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is breast cancer. In embodiments, the disease is hormone sensitive breast cancer. In embodiments, the disease is hormone refractory (insensitive) breast cancer. In embodiments, the disease is ER positive breast cancer. In embodiments, the disease is ER negative breast cancer. In embodiments, the disease is breast cancer expressing HER-2. In embodiments, the disease is a hyperproliferative disorder.

The term "hyperproliferative disorder" as used herein refers to a disorder or disease associated with abnormally high rate of proliferation of cells or tissues by rapid division and/or substantial overproliferation. The term "hyperproliferation" as used herein refers to an increased proliferation from the expected proliferation for the specific cells or tissues in their normal development and function. Exemplary hyperproliferative disorder that may be treated with a compound or method provided herein include psoriasis, cancer, and wound healing, disorders of keratinization and keratosis, diabetic retinopathy, endometriosis, benign prostatic hypertrophy, macular degenerative disorders, keloids, warts, cirrhosis, chronic inflammatory-related disorders, proliferative vitreoretinopathy, retinopathy of prematurity, granulomatosis, immune hyperproliferation associated with organ or tissue transplantation, and an immunoproliferative disease or disorder. In embodiments, the hyperproliferative disorder is psoriasis. In embodiments, the hyperproliferative disorder is a cancer. In embodiments, the hyperproliferative disorder is immune hyperproliferation associated with organ or tissue transplantation. In embodiments, the hyperproliferative disorder is an immunoproliferative disease or disorder.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "breast cancer" refers to a cancer that develops from breast tissue. In embodiments, the breast cancer may be associated or linked to proteins (e.g., hormones) in female reproductive system. In embodiments, the breast cancer cells may be associated with receptors, for example, an estrogen receptor (ER) such as G-protein coupled estrogen receptors, progesterone receptor (PR), and HER2, which locate on a cell surface and/or in the cytoplasm (cytosol) and/or nucleus. In embodiments, the breast cancer may be linked to estrogen exposure (e.g. estrogen receptor (ER)-positive breast cancers with overexpression of HER-2 receptors), or estrogen receptor (ER) negative breast cancers. In embodiments, the breast cancer may be a triple-negative (TNBC), in which the cancer does not express the genes for these three receptor types (estrogen receptors (e.g., estrogen receptor-alpha), progesterone receptors, or HER2).

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

The terms "synergy", "synergism", "synergistic", "combined synergistic amount", "synergistic therapeutic effect", and "synergy in dual therapy", which are used herein interchangeably, refer to a measured effect of compounds administered in combination where the measured effect is greater than the sum of the individual effects of each of the compounds administered alone as a single agent. For example, a "combined synergistic amount" as used herein refers to the sum of a first amount (e.g., an amount of a compound described herein) and a second amount (e.g., an amount of a second agent) that results in a synergistic effect (i.e. an effect greater than an additive effect).

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount (e.g., effective amount or therapeutically effective amount) of an estrogen receptor inhibitor (e.g., compound of Formula (I') or embodiments thereof) provided herein when used separately from an immune checkpoint inhibitor (e.g., for achieving the same or similar effect). In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount (e.g., effective amount or therapeutically effective amount) of an immune checkpoint inhibitor when used separately from an estrogen receptor inhibitor (e.g., compound of Formula (I') or embodiments thereof) provided herein (e.g., for achieving the same or similar effect).

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer or aberrant androgen receptor activity). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

A "drug-resistant estrogen receptor" is a modified (relative to wildtype) estrogen receptor that is inhibited less effectively by the drug than a wildtype estrogen receptor. A "drug-resistant human estrogen receptor" is a modified (relative to wildtype) human estrogen receptor that is inhibited less effectively by the drug than a wildtype human estrogen receptor.

A "drug-resistant cancer" is a cancer that is inhibited less effectively by the drug than a non-drug resistant cancer. An "antiestrogen-resistant cancer" is a cancer that is inhibited less effectively by the antiestrogen than a non-antiestrogren resistant cancer. An "endocrine therapeutic-resistant cancer" is a cancer that is inhibited less effectively by the endocrine therapeutic than a non-endocrine therapeutic resistant cancer.

The term "antiestrogen" refers to a compound that binds estrogen receptor without one or more of the estrogen receptor activities associated with the binding of estrogen to the estrogen receptor. In embodiments an antiestrogen is a compound that inhibits one or more effects of estrogen (e.g., on ER, on a cell, on a tissue, or on an organism). Examples of an antiestrogen include fluvestrant, clomifene, femarelle, ormeloxifene, raloxifene, tamoxifen, toremifene, lasofoxifene, and ospemifene.

The term "endocrine therapeutic" refers to a compound that is effective for modulating hormone activity in a subject. Use of an endocrine therapeutic in treatment of a subject is "endocrine therapy". Modulation of hormone activity by an endocrine therapeutic may include increasing, decreasing, blocking, removing, or otherwise changing the level of a hormone or the level of activity of a hormone. Examples of endocrine therapeutics include antiestrogens, aromatase inhibitors, SERMs, fluvestrant, clomifene, femarelle, ormeloxifene, raloxifene, tamoxifen, toremifene, lasofoxifene, ospemifene, anastrazole, letrozole, exemestane, vorozole, formestane, fadrozole, aminoglutethimide, and testolactone.

The term "estrogen receptor" or "ER" refers to an established member of the nuclear receptor family of receptors which is a transcription factor activated by binding ligands such as the hormones 17β-estradiol, estriol, estrone, etc. In embodiments, "estrogen receptor" or "ER" refers to a nuclear receptor which is a transcription factor activated by binding ligands such as the hormones 17β-estradiol, estriol, and/or estrone. In embodiments, "estrogen receptor" or "ER" refers to a nuclear receptor which is a transcription factor activated by binding the hormone 17β-estradiol. The term "estrogen receptor" may refer to the nucleotide sequence or protein sequence of human estrogen receptor. The term "estrogen receptor" may refer to the nucleotide sequence or protein sequence of human estrogen receptor 1 (a.k.a. ER-alpha, ERα lpha, or ERG) (e.g., Entrez 2099, Uniprot P03372, RefSeq NM_000125, OMIM 133430, NP_000116, NP_000116.2, NM_000125.3, GI:62821794, and/or GI: 170295798). The term "estrogen receptor" may refer to the nucleotide sequence or protein sequence of human estrogen receptor 2 (a.k.a. ER-beta, ERbeta, or ERO) (e.g., Entrez 2100, Uniprot Q92731, RefSeq NM_001040275, OMIM 601663, and/or GI: 94538324). The term "estrogen receptor" includes both the wild-type form of the nucleotide sequences or proteins as well as any mutants thereof. In some embodiments, "estrogen receptor" is wild-type estrogen receptor. In some embodiments, "estrogen receptor" is one or more mutant forms. In embodiments, an estrogen receptor is the wildtype human ERα. In embodiments, an estrogen receptor is the wildtype human ER. In embodiments, an estrogen receptor is the wildtype human ERα or ERβ. In embodiments, an estrogen receptor is the wildtype human ERα and ERβ. In embodiments, the estrogen receptor is a mutant estrogen receptor. In embodiments, the mutant estrogen receptor is associated with a disease that is not associated with wildtype estrogen receptor (e.g., drug resistant cancer). In embodiments, the estrogen receptor includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above.

The terms "dose," "dosage" and like refer, in the usual and customary sense, to the amount of active ingredient given to an individual at each administration. For the methods and compositions provided herein, the dose may generally refer to the amount of disease treatment. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the composition, active compound, pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection. A composition can contain a plurality of active ingredients (e.g., two active ingredients) in a plurality of separate dosage forms (e.g., a separate dosage form for each of two active ingredients). A composition can contain a single dosage form (e.g., a single pill, tablet injection aliquot or the like) which single dosage form includes a plurality of active ingredients (e.g., two active ingredients). The dosage form is preferably in unit dosage form. In embodiments, such unit dosage form of the composition is subdivided into unit doses containing appropriate quantities of the active components. In embodiments, such unit dosage form of the composition is subdivided into unit doses containing appropriate quantities of the active components, each component contained within a separate unit dosage form. The unit dosage form can be a packaged preparation, the package containing discrete quantities of composition or separate active ingredients of the composition, such as packeted tablets, capsules, and powders in vials or ampoules. Also, the unit dosage form can be a capsule, tablet, cachet, or lozenge itself, or it can be the appropriate number of any of these in packaged form.

The term "immune checkpoint" refers, in the usual and customary sense, to a molecule or agent that regulates signal or regulates antigen recognition of immune cells (e.g., T cell receptor) in the process of immune response. The immune checkpoint may act as stimulatory checkpoint molecules or inhibitory checkpoint molecules and such immune checkpoint and signaling molecules and ligands include PD-1, PD-L1, PD-L2, CTLA-4, CD28, CD80, CD86, B7-H3, B7-H4, B7-H5, ICOS-L, ICOS, BTLA, CD137L, CD137, HVEM, KIR, 4-1BB, $OX_{40}L$, CD70, CD27, CD47, CIS, $OX_{40}$, GITR, IDO, TIM3, GAL9, VISTA, CD155, TIGIT, LIGHT, LAIR-1, Siglecs and A2aR (Pardoll D M. 2012. Nature Rev Cancer 12:252-264, Thaventhiran T, et al. 2012. J Clin Cell Immunol S12:004). The term "immune checkpoint inhibitor" and the like refer, in the usual and customary sense, to a compound or an agent which inhibits or suppresses the function of an immune checkpoint or its related signaling molecule (e.g., protein). For example, the immune checkpoint inhibitor is specific to an immune checkpoint or its ligand and acts as an inhibitor of immune checkpoint suppressive activity or as an agonist of immune stimulatory activity. Exemplary antibody domains may include ipilimumab and/or tremelimumab (anti-CTLA4), nivolumab, pembrolizumab, pidilizumab, TSR-042, ANBO11, AMP-514 and AMP-224 (a ligand-Fc fusion) (anti-PDI), atezolizumab (MPDL3280A), avelumab (MSB0010718C), durvalumab (MEDI4736), MEDIO680, and BMS-9365569 (anti-PDL 1), MEDI6469 (anti-$OX_{40}$ agonist), BMS-986016, IMP701, IMP731, IMP321 (anti-LAG3) and GITR ligand. In some embodiments, the immune checkpoint inhibitors include an anti-PD-1 antibody, an anti-PD-L1 antibody, anti-CTLA4 antibody, nivolumab (e.g., OPDIVO, CAS Number 946414-94-4), pembrolizumab (e.g., MK-3475, lambrolizumab, or KEYTRUDA, CAS Number 1374853-91-4), atezolizumab (e.g., TECENTRIQ, CAS Number 1380723-44-3), avelumab (e.g., BAVENCIO, CAS Number 1537032-82-8), durvalumab (e.g., IMFINZI, CAS Number 1428935-60-7).

The term "selective ER downregulators" is abbreviated as "SERD", which is used together with compound numbering (e.g., SERD128). In embodiments, the compound name of "SERD" with numbering is interchangeably used with a letter "S", for example, SERD128 refers to the same compound named S128. In embodiments, the compound name of "SERD" with numbering is interchangeably used with a denote "JD", for example, SERD128 refers to the same compound named JD128.

Compositions

In an aspect, there is provided a pharmaceutical composition which includes an estrogen receptor inhibitor (e.g. compound as described herein), and a pharmaceutically acceptable excipient. In another aspect, there is provided a pharmaceutical composition which includes an estrogen receptor inhibitor (e.g. compound as described herein), an immune checkpoint inhibitor, and a pharmaceutically acceptable excipient. Further provided is a pharmaceutical composition which includes an estrogen receptor inhibitor (e.g. compound as described herein), an immune checkpoint inhibitor, a further agent (e.g., a CDK4 inhibitor and/or CDK6 inhibitor) and a pharmaceutically acceptable excipient.

In embodiments, an estrogen receptor inhibitor may be a molecule (e.g., small molecule, hormome, antibody, peptide, nucleic acid, polymer, and the like) in the composition that decreases or downregulates the level of an estrogen receptor (ER) as described herein, including embodiments thereof or the function thereof. In embodiments, an estrogen receptor inhibitor (e.g. an estrogen receptor antagonist) may interact with an estrogen receptor and negatively affect (e.g. decrease) the level of activity or function of ER relative to the level of activity or function of the ER in the absence of the inhibitor. In embodiments, the estrogen receptor inhibitor may, at least in part, partially or totally block stimulation; decrease, prevent, or delay activation; or inactivate, desensitize, or down-regulate signal transduction or ER activity or the amount of ER In some embodiments, the estrogen receptor inhibitor is an antiestrogen. In embodiments, the estrogen receptor inhibitor is an aromatase inhibitor. In some embodiments, the estrogen receptor inhibitor includes, but is not limited to, tamoxifen, fulvestrant, clomifene, femarelle, ormeloxifene, raloxifene, toremifene, lasofoxifene, ospemifene, anastrazole, letrozole, exemestane, vorozole, formestane, fadrozole, aminoglutethimide, or testolactone. In some embodiments, the estrogen receptor inhibitor may include RAD1901 (CAS No: 1349723-93-8 (HCl)), H3B-6545, endoxifen (CAS Numbers: 110025-28-0; 114828-90-9 (E-isomer); 15917-65-4 (HCl)), AZD9496 (CAS No: 1639042-08-2), GDC-0810 (CAS No: 1365888-06-7) or derivatives thereof. In embodiments, the estrogen receptor inhibitor is a compound described herein (e.g., compound of formula (I') or an embodiment thereof).

In an aspect, there is provided a compound, or a pharmaceutically acceptable salt thereof, having the formula (I')

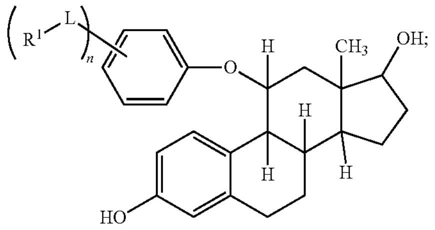

and a pharmaceutically acceptable excipient.

$R^1$ is independently a hydrogen, halogen, —$NR^2R^3$, —$CX^a_3$, —CN, —$SO_{n1}R^{10}$, —$SO_{v1}NR^2R^3$, —$NHNR^2R^3$, —$ONR^2R^3$, —$NHC(O)NHNR^2R^3$, —$NHC(O)NR^2R^3$, —$N(O)_{m1}$, —$C(O)R^9$, —C(O)—$OR^9$, —$C(O)NR^2R^3$, —$OR^{10}$, —$NR^2SO_2R^{10}$, —$NR^2C(O)R^9$, —$NR^2C(O)$—$OR^9$, —$NR^2OR^9$, —$OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently a hydrogen, halogen, —$CX^b_3$, —CN, —$SO_{n2}R^{14}$, —$SO_{v2}NR^{11}R^{12}$, —$NHNH_2$, —$ONR^{11}R^{12}$, —$NHC(O)NHNH_2$, —$NHC(O)NR^{11}R^{12}$, —$N(O)_{m2}$, —$NR^{11}R^{12}$, —$C(O)R^{13}$, —C(O)—$OR^{13}$, —$C(O)NR^{11}R^{12}$, —$OR^{14}$, —$NR^{11}SO_2R^{14}$, —$NR^{11}C(O)R^{13}$, —$NR^{11}C(O)$—$OR^{13}$, —$NR^{11}OR^{13}$, —$OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently a hydrogen, halogen, —$CX^c_3$, —CN, —$SO_{n3}R^{18}$, —$SO_{v3}NR^{15}R^{16}$,
—$NHNH_2$, —$ONR^{15}R^{16}$, —$NHC(O)NHNH_2$, —$NHC(O)NR^{15}R^{16}$, —$N(O)_{m3}$, —$NR^{15}R^{16}$, —$C(O)R^{17}$, —C(O)—$OR^{17}$, —$C(O)NR^{15}R^{16}$, —$OR^{18}$, —$NR^{15}SO_2R^{18}$, —$NR^{15}C(O)R^{17}$, —$NR^{15}C(O)$—$OR^{17}$, —$NR^{15}OR^{17}$, —$OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^3$ substituents may optionally be joined to form a substituted or unsubstituted heterocycloalkyl, or substituted or unsubstituted heteroaryl. L is independently a bond, —$NR^4$—, —$NR^4C(O)$—, —$C(O)NR^4$—, —O—, —S—, —C(O)—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker.

$R^4$ is independently a hydrogen, halogen, —$CX^d_3$, —CN, —$SO_{n4}R^{22}$, —$SO_{V4}NR^{19}R^{20}$, —$NHNH_2$, —$ONR^{19}R^{20}$, —$NHC(O)NHNH_2$,
—$NHC(O)NR^{19}R^{20}$, —$N(O)_{m4}$, —$NR^{19}R^{20}$, —$C(O)R^{21}$, —C(O)—$OR^{21}$, —$C(O)NR^{19}R^{20}$, —$OR^{22}$, —$NR^{19}SO_2R^{22}$, —$NR^{19}C(O)R^{21}$, —$NR^{19}C(O)$—$OR^{21}$, —$NR^9OR^{21}$, —$OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl.

The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, $X^a$, $X^b$, $X^c$ and $X^d$ are independently —Cl, —Br, —I, or —F.

In an aspect, there is provided a pharmaceutical composition for increasing immune recognition of cancer, which includes a compound as described herein, or a pharmaceutically acceptable salt thereof, having the formula (I')

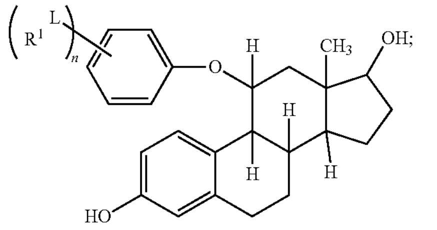

and a pharmaceutically acceptable excipient.

$R^1$ is independently a hydrogen, halogen, —$NR^2R^3$, —$CX^a_3$, —CN, —$SO_{n1}R^{10}$, —$SO_{v1}NR^2R^3$, —$NHNR^2R^3$, —$ONR^2R^3$, —$NHC(O)NHNR^2R^3$,
—$NHC(O)NR^2R^3$, —$N(O)_{m1}$, —$C(O)R^9$, —C(O)—$OR^9$, —$C(O)NR^2R^3$, —$OR^{10}$, —$NR^2SO_2R^{10}$, —$NR^2C(O)R^9$, —$NR^2C(O)$—$OR^9$, —$NR^2OR^9$, —$OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently a hydrogen, halogen, —$CX^b_3$, —CN, —$SO_{n2}R^{14}$, —$SO_{v2}NR^{11}R^{12}$, —$NHNH_2$, —$ONR^{11}R^{12}$, —$NHC(O)NHNH_2$, —$NHC(O)NR^{11}R^{12}$, —$N(O)_{m2}$, —$NR^{11}R^{12}$, —$C(O)R^{13}$, —C(O)—$OR^{13}$, —$C(O)NR^{11}R^{12}$, —$OR^{14}$, —$NR^{11}SO_2R^{14}$, —$NR^{11}C(O)R^{13}$, —$NR^{11}C(O)$—$OR^{13}$, —$NR^{11}OR^{13}$, —$OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently a hydrogen, halogen, —$CX^c_3$, —CN, —$SO_{n3}R^{18}$, —$SO_{v3}NR^{15}R^{16}$, —$NHNH_2$, —$ONR^{15}R^{16}$, —$NHC(O)NHNH_2$, —$NHC(O)NR^{15}R^{16}$, —$N(O)_{m3}$, —$NR^{15}R^{16}$, —$C(O)R^{17}$, —C(O)—$OR^{17}$, —$C(O)NR^{15}R^{16}$, —$OR^{18}$, —$NR^{15}SO_2R^{18}$, —$NR^{15}C(O)R^{17}$, —$NR^{15}C(O)$—$OR^{17}$, —$NR^{15}OR^{17}$, —$OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^3$ substituents may optionally be joined to form a substituted or unsubstituted heterocycloalkyl, or substituted or unsubstituted heteroaryl. L is independently a bond, —$NR^4$—, —$NR^4C(O)$—, —$C(O)NR^4$—, —O—, —S—, —C(O)—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker.

$R^4$ is independently a hydrogen, halogen, —$CX^d_3$, —CN, —$SO_{n4}R^{22}$, —$SO_{v4}NR^{19}R^{21}$, —$NHNH_2$, —$ONR^{19}R^{20}$, —$NHC(O)NHNH_2$, —$NHC(O)NR^{19}R^{20}$, —$N(O)_{m4}$, —$NR^{19}R^{20}$, —$C(O)R^{21}$, —C(O)—$OR^{21}$, —$C(O)NR^{19}R^{20}$, —$OR^{22}$, —$NR^{19}SO_2R^{22}$, —$NR^{19}C(O)R^{21}$, —$NR^{19}C(O)$—$OR^{21}$, —$NR^9OR^{21}$, —$OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl.

The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, $X^a$, $X^b$, $X^c$ and $X^d$ are independently —Cl, —Br, —I, or —F.

In an aspect, there is provided a pharmaceutical composition which includes an immune checkpoint inhibitor as defined herein, and a compound as described herein, or a pharmaceutically acceptable salt thereof, having the formula (I')

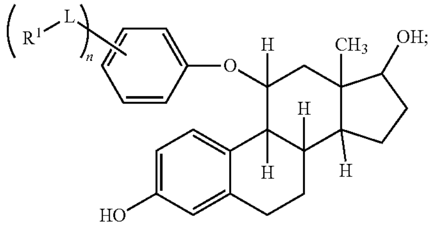

and a pharmaceutically acceptable excipient. The symbols n, $R^1$, and L are as described herein.

In embodiments, the pharmaceutical composition is provided as a single dosage form including a compound as described herein (e.g., compound of Formula (I') or embodiments thereof). In embodiments, the composition is provided as a plurality of dosage forms of a compound described herein (e.g., compound of Formula (I') or embodiments thereof).

In embodiments, the pharmaceutical composition is provided as a single dosage form including both an immune checkpoint inhibitor in combination with a compound as described herein (e.g., compound of Formula (I') or embodiments thereof). In embodiments, the composition is provided as a plurality of dosage forms, each dosage form including an immune checkpoint inhibitor, and a compound described herein (e.g., compound of Formula (I') or embodiments thereof).

In an embodiment, the compound has the structure of formula (I):

(I)

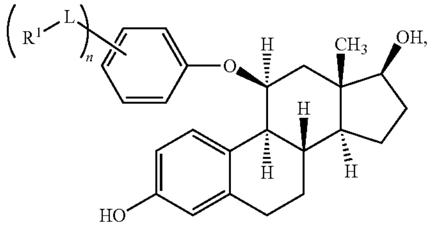

or a pharmaceutically acceptable salt thereof. Also provided herein are compounds of formula (I) provided as a racemic mixture, including all embodiments thereof. Also provided herein are stereoisomers of the compounds of formula (I), including all embodiments thereof. Thus, also provided herein is a population of compounds comprising the compound of formula (I) and additional compounds that are stereoisomers of the compound of formula (I).

$R^1$ is independently a hydrogen, halogen, —$NR^2R^3$, —$CX^a_3$, —CN, —$SO_{n1}R^{10}$, —$SO_{v1}NR^2R^3$, —$NHNR^2R^3$, —$ONR^2R^3$, —$NHC(O)NHNR^2R^3$, —$NHC(O)NR^2R^3$, —$N(O)_{m1}$, —$C(O)R^9$, —$C(O)OR^9$, —$C(O)NR^2R^3$, —$OR^{10}$, —$NR^2SO_2R^{10}$, —$NR^2C(O)R^9$, —$NR^2C(O)$—$OR^9$, —$NR^2OR^9$, —$OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently a hydrogen, halogen, —$CX^b_3$, —CN, —$SO_{n2}R^4$, —$SO_{v2}NR^{11}R^{12}$, —$NHNH_2$, —$ONR^{11}R^{12}$, —$NHC(O)NHNH_2$, —$NHC(O)NR^{11}R^{12}$, —$N(O)_{m2}$, $—NR^{11}R^{12}$, —C(O)$R^{13}$, —C(O)—$OR^{13}$, —C(O)$NR^{11}R^{12}$, $—OR^{14}$, $—NR^{11}SO_2R^{12}$, $—NR^{11}C(O)R^{13}$, $—NR^{11}C(O)—OR^{13}$, $—NR^{11}OR^{13}$, $—OCX^{b}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently a hydrogen, halogen, $—CX^{c}_3$, —CN, $—SO_{n3}R^{14}$, $—SO_{v3}NR^{15}R^{16}$, $—NHNH_2$, $—ONR^{15}R^{16}$, $—NHC(O)NHNH_2$, $—NHC(O)NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C(O)R^{17}$, $—NR^{15}C(O)—OR^{17}$, $—NR^{15}OR^{17}$, $—OCX^{c}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^3$ substituents may optionally be joined to form a substituted or unsubstituted heterocycloalkyl, or substituted or unsubstituted heteroaryl. L is independently a bond, $—NR^4—$, $—NR^4C(O)—$, $—C(O)NR^4—$, —O—, —S—, —C(O)—, —S(O)—, $—S(O)_2—$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker.

$R^4$ is independently a hydrogen, halogen, $—CX^{d}_3$, —CN, $—SO_4R^{22}$, $—SO_{n4}NR^{19}R^{20}$, $—NHNH_2$, $—ONR^{19}R^{20}$, $—NHC(O)NHNH_2$, $—NHC(O)NR^{19}R^{20}$, $—N(O)_{m4}$, $—NR^{19}R^{20}$, $—C(O)R^{21}$, $—C(O)—OR^{21}$, $—C(O)NR^{19}R^{20}$, $—OR^{22}$, $—NR^{19}SO_2R^{2}$, $—NR^{19}C(O)R^{21}$, $—NR^{19}C(O)—OR^{21}$, $—NR^{19}OR^{21}$, $—OCX^{d}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $—CX_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)—OH, —NHOH, $—OCX_3$, $—OCHX_2$, $—CF_3$, $—OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{13}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl.

The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, $X^a$, $X^b$, $X^c$ and $X^d$ are independently —Cl, —Br, —I, or —F.

For compounds described herein, the $—CH_3$ as indicated by an asterisk in the structures below, may be replaced with an unsubstituted $C_1$-$C_{10}$ alkyl:

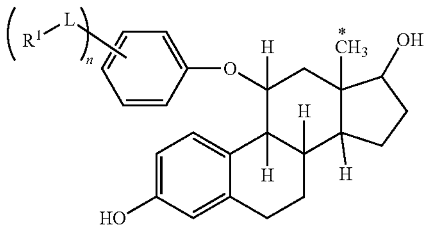

or

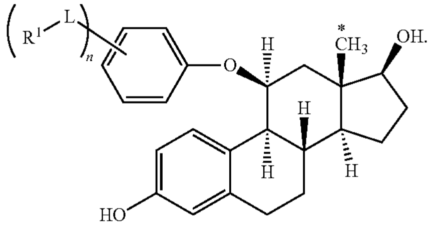

In embodiments, the $—CH_3$ as indicated by the asterisk in these structures may be replaced with an unsubstituted $C_1$-$C_8$ alkyl.

In an aspect, there is provided a compound, or a pharmaceutically acceptable salt thereof, having the formula (X)

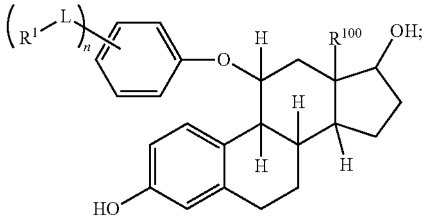

and a pharmaceutically acceptable excipient.

$R^{100}$ is independently an unsubstituted $C_1$-$C_{10}$ alkyl (e.g., methyl).

$R^1$ is independently a hydrogen, halogen, $—NR^2R^3$, $—CX^{a}_3$, —CN, $—SO_{n1}R^{10}$, $—SO_{v1}NR^2R^3$, $—NHNR^2R^3$, $—ONR^2R^3$, $—NHC(O)NHNR^2R^3$, $—NHC(O)NR^2R^3$, $—N(O)_{m1}$, $—C(O)R^9$, $—C(O)—OR^9$, $—C(O)NR^2R^3$, $—OR^{10}$, $—NR^2SO_2R^{10}$, $—NR^2C(O)R^9$, $—NR^2C(O)—OR^9$, $—NR^2OR^9$, $—OCX^{a}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is independently a hydrogen, halogen, $—CX^{b}_3$, —CN, $—SO_{n2}R^1$, $—SO_{v2}NR^{11}R^{12}$, $—NHNH_2$, $—ONR^{11}R^{12}$, $—NHC(O)NHNH_2$, $—NHC(O)NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^4$, $—NR^{11}C(O)R^{13}$, $—NR^{11}C(O)—OR^{13}$, $—NR^{11}OR^{13}$, $—OCX^{b}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is independently a hydrogen, halogen, $—CX^{c}_3$, —CN, $—SO_{n3}R^{18}$, $—SO_{v3}NR^{15}R^{16}$, $—NHNH_2$, $—ONR^{15}R^{16}$, $—NHC(O)NHNH_2$,
$—NHC(O)NR^{15}R^{16}$, $—N(O)_{m3}$, $—NR^{15}R^{16}$, $—C(O)R^{17}$, $—C(O)OR^7$,
$—C(O)NR^{15}R^{16}$, $—OR^{18}$, $—NR^{15}SO_2R^{18}$, $—NR^{13}C(O)R^{17}$, $—NR^{15}C(O)—OR^{17}$, $—NR^{15}OR^{17}$, $—OCX^{c}_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^3$ substituents may optionally be joined to form a substituted or unsubstituted heterocycloalkyl, or substituted or unsubstituted heteroaryl. L is independently a bond, —$NR^4$—, —$NR^4C(O)$—, —$C(O)NR^4$—, —O—, —S—, —C(O)—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker.

$R^4$ is independently a hydrogen, halogen, —$CX^d_3$, —CN, —$SO_{n4}R^{22}$, —$SO_{v4}NR^{19}R^{20}$, —$NHNH_2$, —$ONR^{19}R^{20}$, —$NHC(O)NHNH_2$,
—$NHC(O)NR^{19}R^{20}$, —$N(O)_{m4}$, —$NR^{19}R^{20}$, —$C(O)R^{21}$, —C(O)—$OR^{21}$, —$C(O)NR^{19}R^{20}$, —$OR^{22}$, —$NR^{19}SO_2R^{22}$, —$NR^{19}C(O)R^{21}$, —$NR^{19}C(O)$—$OR^{21}$, —$NR^{19}OR^{21}$, —$OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{11}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl.

The symbol n is an integer from 0 to 5. The symbols m1, m2, m3, m4, v1, v2, v3, and v4 are independently 1 or 2. The symbols n1, n2, n3, and n4 are independently an integer from 0 to 4. The symbols X, $X^a$, $X^b$, $X^c$ and $X^d$ are independently —Cl, —Br, —I, or —F.

In an embodiment, the compound has the structure of formula (X):

(Xa)

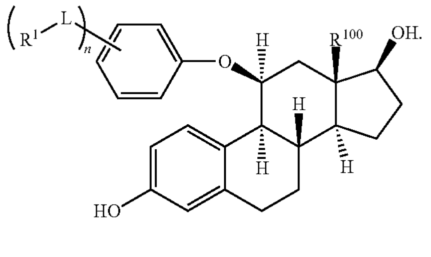

$R^1$, L, n, $R^{100}$ are as described herein.

In an aspect a method described herein, includes a compound of formula (X) or formula (Xa). In an aspect a use described herein, includes a compound of formula (X) or formula (Xa). In an aspect a pharmaceutical composition described herein, includes a compound of formula (X) or formula (Xa).

In embodiments, the compound has the formula (Ia):

(Ia)

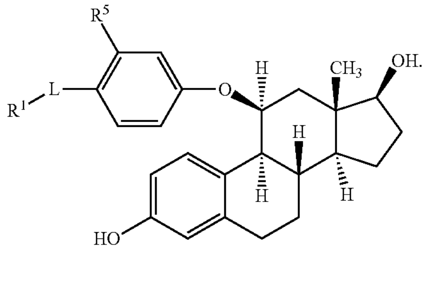

The variables L and $R^1$ are as described herexein.

$R^3$ is independently a hydrogen, halogen, —$CX^c_3$, —CN, —$SO_{n5}R^{26}$, —$SO_{v5}NR^{23}R^{24}$,
—$NHNH_2$, —$ONR^{23}R^{24}$,
—$NHC(O)NHNH_2$, —$NHC(O)NR^{23}R^{24}$, —$N(O)_{m5}$, —$NR^{23}R^{24}$, —$C(O)R^{25}$, —C(O)—$OR^{25}$, —$C(O)NR^{23}R^{24}$, —$OR^{26}$, —$NR^{23}SO_2R^{26}$, —$NR^{23}C(O)R^{25}$, —$NR^{23}C(O)$—$OR^{25}$, —$NR^{23}OR^{21}$, —$OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{23}$, $R^{24}$, $R^{23}$, and $R^{26}$ are independently hydrogen,
halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{23}$ and $R^{24}$ substituents bonded to the same nitrogen atom may optionally be joined to form a substituted or unsubstituted heterocycloalkyl or substituted or unsubstituted heteroaryl. The symbols m5 and v5 are independently 1 or 2. The symbol n5 is independently an integer from 0 to 4. The symbol $X^e$ is independently —Cl, —Br, —I, or —F.

In embodiments, the compound has the formula (Ib):

(Ib)

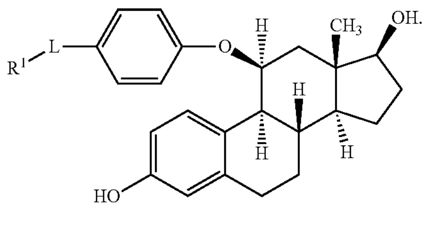

The variables L and $R^1$ are as described herein.

In embodiments, the compound has the formula (II):

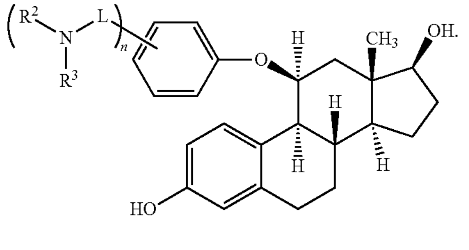

(II)

The variables L, n, $R^2$, and $R^3$ are as described herein.

In embodiments, the compound has the formula (IIa):

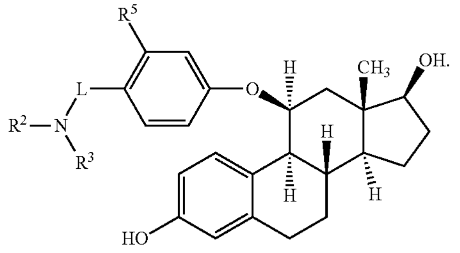

(IIa)

The variables L, $R^2$, $R^3$, and $R^3$ are as described herein.

In embodiments, the compound has the formula (IIb):

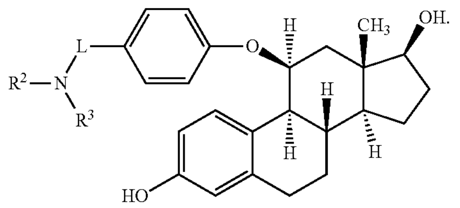

(IIb)

The variables L, $R^2$, and $R^3$ are as described herein.

In embodiments, $R^1$ is independently halogen, $-NR^2R^3$, $-CX^a_3$, —CN, $-SO_{n1}R^{10}$, $-SO_{v1}NR^2R^3$, $-NHNR^2R^3$, $-ONR^2R^3$, $-NHC(O)NHNR^2R^3$, $-NHC(O)NR^2R^3$, $-N(O)_{m1}$, $-C(O)R^9$, $-C(O)-OR^9$, $-C(O)NR^2R^3$, $-OR^{10}$, $-NR^2SO_2R^{10}$, $-NR^2C(O)R^9$, $-NR^2C(O)-OR^9$, $-NR^2OR^9$, $-OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is independently hydrogen. In embodiments, $R^1$ is independently $-NR^2R^3$. In embodiments, $R^1$ is independently $-NH_2$. In embodiments, $R^1$ is independently $-CF_3$. In embodiments, $R^1$ is independently $-CCl_3$. In embodiments, $R^1$ is independently $-N(O)_2$. In embodiments, $R^1$ is independently halogen. In embodiments, $R^1$ is independently —F. In embodiments, $R^1$ is independently —Cl. In embodiments, $R^1$ is independently —Br. In embodiments, $R^1$ is independently —I. In embodiments, $R^1$ is independently substituted or unsubstituted cycloalkyl, substituted or unsubstituted heterocycloalkyl, substituted or unsubstituted aryl, or substituted or unsubstituted heteroaryl. In embodiments, $R^1$ is independently unsubstituted cycloalkyl, unsubstituted heterocycloalkyl, unsubstituted aryl, or unsubstituted heteroaryl.

In embodiments, $L-R^1$ is not hydrogen. In embodiments, L is not a bond and $R^1$ is not a hydrogen.

In embodiments, $R^1$ is independently substituted or unsubstituted $C_3$-$C_8$ cycloalkyl. In embodiments, $R^1$ is independently unsubstituted $C_3$-$C_8$ cycloalkyl. In embodiments, $R^1$ is independently substituted or unsubstituted $C_3$-$C_7$ cycloalkyl. In embodiments, $R^1$ is independently unsubstituted $C_3$-$C_7$ cycloalkyl. In embodiments, $R^1$ is independently substituted or unsubstituted 3 to 8 membered heterocycloalkyl. In embodiments, $R^1$ is independently unsubstituted 3 to 8 membered heterocycloalkyl. In embodiments, $R^1$ is independently substituted or unsubstituted 3 to 7 membered heterocycloalkyl. In embodiments, $R^1$ is independently unsubstituted 3 to 7 membered heterocycloalkyl. In embodiments, $R^1$ is independently substituted or unsubstituted $C_6$-$C_{12}$ aryl. In embodiments, $R^1$ is independently unsubstituted $C_6$-$C_{12}$ aryl. In embodiments, $R^1$ is independently substituted or unsubstituted $C_6$-$C_{10}$ aryl. In embodiments, $R^1$ is independently unsubstituted $C_6$-$C_{10}$ aryl. In embodiments, $R^1$ is independently substituted or unsubstituted phenyl. In embodiments, $R^1$ is independently unsubstituted phenyl. In embodiments, $R^1$ is independently substituted or unsubstituted 5 to 10 membered heteroaryl. In embodiments, $R^1$ is independently unsubstituted 5 to 10 membered heteroaryl. In embodiments, $R^1$ is independently substituted or unsubstituted 5 to 9 membered heteroaryl. In embodiments, $R^1$ is independently unsubstituted 5 to 9 membered heteroaryl. In embodiments, $R^1$ is independently substituted or unsubstituted 5 to 6 membered heteroaryl. In embodiments, $R^1$ is independently unsubstituted 5 to 6 membered heteroaryl. In embodiments, $R^1$ is independently unsubstituted piperidinyl. In embodiments, $R^1$ is independently unsubstituted piperazinyl. In embodiments, $R^1$ is independently unsubstituted pyridinyl. In embodiments, $R^1$ is independently unsubstituted pyrazinyl. In embodiments, $R^1$ is independently dimethylamino. In embodiments, $R^1$ is independently dimethylaminoethyl. In embodiments, $R^1$ is independently dimethylaminopropyl. In embodiments, $R^1$ is independently ethylmorpholinyl. In embodiments, $R^1$ is independently unsubstituted morpholinyl.

In embodiments, $R^2$ is independently halogen, $-CX^b_3$, —CN, $-SO_{n2}R^4$, $-SO_{v2}NR^{11}R^{12}$, $-NHNH_2$, $-ONR^{11}R^{12}$, $-NHC(O)NHNH_2$, $-NHC(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^4$, $-NR^{11}C(O)R^{13}$, $-NR^{11}C(O)-OR^{13}$, $-NR^{11}OR^{13}$, $-OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is independently hydrogen. In embodiments, $R^2$ is independently halogen. In embodiments, $R^2$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is independently substituted or unsubstituted $C_1$-$C_{12}$ alkyl. In embodiments, $R^2$ is independently unsubstituted $C_1$-$C_{12}$ alkyl. In embodiments, $R^2$ is independently substituted or unsubstituted $C_1$-$C_8$ alkyl. In embodiments, $R^2$ is independently unsubstituted $C_1$-$C_8$ alkyl. In embodiments, $R^2$ is independently substituted or unsubstituted $C_1$-$C_4$ alkyl. In embodiments, $R^2$ is independently unsubstituted $C_1$-$C_4$ alkyl. In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently substituted or unsubstituted 2 to 12 membered heteroalkyl. In embodiments, $R^2$ is independently unsubstituted 2 to 12 membered heteroalkyl. In embodiments, $R^2$ is independently substituted or unsubstituted 2 to 8 membered heteroalkyl. In embodiments, $R^2$ is independently unsubstituted 2 to 8 membered heteroalkyl. In embodiments, $R^2$ is independently substituted or unsubstituted 2 to 4 membered heteroalkyl. In embodiments, $R^2$ is independently unsubstituted 2 to 4 membered heteroalkyl. In embodiments, $R^2$ is independently substituted or unsubstituted alkyl or substituted or unsubstituted heteroalkyl. In embodiments, $R^2$ is independently substituted or unsubstituted $C_1$-$C_{10}$ alkyl or substituted or unsubstituted 2 to 10 membered heteroalkyl.

In embodiments, $R^3$ is independently a halogen, $—CX^c_3$, —CN, $—SO_3R^{18}$, $—SO_{v3}NR^{11}R^{16}$, $—NHNH_2$, $—ONR^{15}R^{16}$, $—NHC(O)NHNH_2$, $—NHC(O)NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C(O)R^{17}$, $—NR^{15}C(O)—OR^{17}$, $—NR^{15}OR^{17}$, $—OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently hydrogen. In embodiments, $R^3$ is independently halogen. In embodiments, $R^3$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is independently substituted or unsubstituted $C_1$-$C_{12}$ alkyl. In embodiments, $R^3$ is independently unsubstituted $C_1$-$C_{12}$ alkyl. In embodiments, $R^3$ is independently substituted or unsubstituted $C_1$-$C_8$ alkyl. In embodiments, $R^3$ is independently unsubstituted $C_1$-$C_8$ alkyl. In embodiments, $R^3$ is independently substituted or unsubstituted $C_1$-$C_4$ alkyl. In embodiments, $R^3$ is independently unsubstituted $C_1$-$C_4$ alkyl. In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently substituted or unsubstituted 2 to 12 membered heteroalkyl. In embodiments, $R^3$ is independently unsubstituted 2 to 12 membered heteroalkyl. In embodiments, $R^3$ is independently substituted or unsubstituted 2 to 8 membered heteroalkyl. In embodiments, $R^3$ is independently unsubstituted 2 to 8 membered heteroalkyl. In embodiments, $R^3$ is independently substituted or unsubstituted 2 to 4 membered heteroalkyl. In embodiments, $R^3$ is independently unsubstituted 2 to 4 membered heteroalkyl. In embodiments, $R^3$ is independently substituted or unsubstituted alkyl or substituted or unsubstituted heteroalkyl. In embodiments, $R^3$ is independently substituted or unsubstituted $C_1$-$C_{10}$ alkyl or substituted or unsubstituted 2 to 10 membered heteroalkyl.

In embodiments, $R^2$ and $R^3$ substituents may optionally be joined to form a substituted or unsubstituted heterocycloalkyl, or substituted or unsubstituted heteroaryl. In embodiments, $R^2$ and $R^3$ substituents are joined to form a substituted or unsubstituted heterocycloalkyl. In embodiments, $R^2$ and $R^3$ substituents are joined to form an unsubstituted heterocycloalkyl. In embodiments, $R^2$ and $R^3$ substituents are joined to form a substituted or unsubstituted 3 to 8 membered heterocycloalkyl. In embodiments, $R^2$ and $R^3$ substituents are joined to form an unsubstituted 3 to 8 membered heterocycloalkyl. In embodiments, $R^2$ and $R^3$ substituents are joined to form a substituted or unsubstituted 3 to 7 membered heterocycloalkyl. In embodiments, $R^2$ and $R^3$ substituents are joined to form an unsubstituted 3 to 7 membered heterocycloalkyl. In embodiments, $R^2$ and $R^3$ substituents are joined to form a substituted or unsubstituted 3 to 6 membered heterocycloalkyl. In embodiments, $R^2$ and $R^3$ substituents are joined to form an unsubstituted 3 to 6 membered heterocycloalkyl.

In embodiments, $R^2$ and $R^3$ substituents are joined to form a substituted or unsubstituted heteroaryl. In embodiments, $R^2$ and $R^3$ substituents are joined to form an unsubstituted heteroaryl. In embodiments, $R^2$ and $R^3$ substituents are joined to form a substituted or unsubstituted 5 to 10 membered heteroaryl. In embodiments, $R^2$ and $R^3$ substituents are joined to form an unsubstituted 5 to 10 membered heteroaryl. In embodiments, $R^2$ and $R^3$ substituents are joined to form a substituted or unsubstituted 5 to 9 membered heteroaryl. In embodiments, $R^2$ and $R^3$ substituents are joined to form an unsubstituted 5 to 9 membered heteroaryl. In embodiments, $R^2$ and $R^3$ substituents are joined to form a substituted or unsubstituted 5 to 6 membered heteroaryl. In embodiments, $R^2$ and $R^3$ substituents are joined to form an unsubstituted 5 to 6 membered heteroaryl. In embodiments, $R^2$ and $R^3$ substituents are joined to form

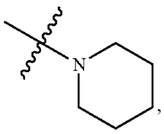,
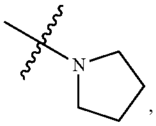, or
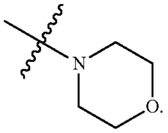

In embodiments, L is independently a bond, $—NR^4—$, $—NR^4C(O)—$, $—C(O)NR^4—$, —O—, —S—, —C(O)—, —S(O)—, $—S(O)_2—$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L is independently a bond. In embodiments, L is independently $—NR^4—$. In embodiments, L is independently $—NR^4C(O)—$. In embodiments, L is independently $—C(O)NR^4—$. In embodiments, L is independently —O—. In embodiments, L is independently —S—. In embodiments, L is independently —C(O)—. In embodiments, L is independently —S(O)—. In embodiments, L is independently $—S(O)_2—$. In embodiments, L is independently substituted or unsubstituted alkylene. In embodiments, L is independently unsubstituted alkylene.

In embodiments, L is independently substituted or unsubstituted $C_1$-$C_{12}$ alkylene. In embodiments, L is independently unsubstituted $C_1$-$C_{12}$ alkylene. In embodiments, L is independently substituted or unsubstituted $C_1$-$C_8$ alkylene. In embodiments, L is independently unsubstituted $C_1$-$C_8$ alkylene. In embodiments, L is independently substituted or unsubstituted $C_1$-$C_6$ alkylene. In embodiments, L is independently unsubstituted $C_1$-$C_6$ alkylene. In embodiments, L is independently substituted or unsubstituted $C_1$-$C_4$ alkylene. In embodiments, L is independently unsubstituted $C_1$-$C_4$ alkylene. In embodiments, L is independently unsubstituted methylene. In embodiments, L is independently unsubstituted ethylene. In embodiments, L is independently unsubstituted propylene. In embodiments, L is independently unsubstituted butylene. In embodiments, L is independently substituted or unsubstituted heteroalkylene. In embodiments, L is independently unsubstituted heteroalkylene. In embodiments, L is independently substituted or unsubstituted 2 to 12 membered heteroalkylene. In embodiments, L is independently unsubstituted 2 to 12 membered heteroalkylene. In embodiments, L is independently substituted or unsubstituted 2 to 8 membered heteroalkylene. In embodiments, L is independently unsubstituted 2 to 8 membered heteroalkylene. In embodiments, L is independently substituted or unsubstituted 2 to 6 membered heteroalkylene. In embodiments, L is independently unsubstituted 2 to 6 membered heteroalkylene. In embodiments, L is independently substituted or unsubstituted 2 to 4 membered heteroalkylene. In embodiments, L is independently unsubstituted 2 to 4 membered heteroalkylene. In embodiments, L is independently substituted or unsubstituted cycloalkylene. In embodiments, L is independently unsubstituted cycloalkylene. In embodiments, L is independently substituted or unsubstituted $C_3$-$C_8$ cycloalkylene. In embodiments, L is independently unsubstituted $C_3$-$C_8$ cycloalkylene. In embodiments, L is independently substituted or unsubstituted heterocycloalkylene. In embodiments, L is independently unsubstituted heterocycloalkylene. In embodiments, L is independently substituted or unsubstituted 3 to 8 membered heterocycloalkylene. In embodiments, L is independently unsubstituted 3 to 8 membered heterocycloalkylene. In embodiments, L is independently substituted or unsubstituted arylene. In embodiments, L is independently unsubstituted arylene. In embodiments, L is independently substituted or unsubstituted $C_6$-$C_{10}$ arylene. In embodiments, L is independently unsubstituted $C_6$-$C_{10}$ arylene. In embodiments, L is independently substituted or unsubstituted heteroarylene. In embodiments, L is independently unsubstituted heteroarylene. In embodiments, L is independently substituted or unsubstituted 5 to 10 membered heteroarylene. In embodiments, L is independently unsubstituted 5 to 10 membered heteroarylene.

In embodiments, L is independently —NH-(substituted or unsubstituted alkylene). In embodiments, L is independently —NH-(unsubstituted alkylene). In embodiments, L is independently —NH-(substituted or unsubstituted ($C_1$-$C_5$) alkylene). In embodiments, L is independently —NH-(unsubstituted ($C_1$-$C_5$) alkylene). In embodiments, L is independently —NH-(substituted or unsubstituted ($C_1$-$C_4$) alkylene). In embodiments, L is independently —NH-(unsubstituted ($C_1$-$C_4$) alkylene). In embodiments, L is independently —NH-(unsubstituted methylene). In embodiments, L is independently —NH-(unsubstituted ethylene). In embodiments, L is independently —NH-(unsubstituted propylene). In embodiments, L is independently —NH-(unsubstituted butylene). In embodiments, L is independently —NH-(unsubstituted n-propylene). In embodiments, L is independently —NH-(unsubstituted n-butylene). In embodiments, L is independently —NHC(O)-(substituted or unsubstituted alkylene). In embodiments, L is independently —NHC(O)-(unsubstituted alkylene). In embodiments, L is independently —NHC(O)-(substituted or unsubstituted ($C_1$-$C_5$) alkylene). In embodiments, L is independently —NHC(O)-(unsubstituted ($C_1$-$C_5$) alkylene). In embodiments, L is independently —NHC(O)-(substituted or unsubstituted ($C_1$-$C_4$) alkylene). In embodiments, L is independently —NHC(O)-(unsubstituted ($C_1$-$C_4$) alkylene). In embodiments, L is independently —NHC(O)-(unsubstituted methylene). In embodiments, L is independently —NHC(O)-(unsubstituted ethylene). In embodiments, L is independently —NHC(O)-(unsubstituted propylene). In embodiments, L is independently —NHC(O)-(unsubstituted butylene). In embodiments, L is independently —NHC(O)-(unsubstituted n-propylene). In embodiments, L is independently —NHC(O)-(unsubstituted n-butylene).

In embodiments, $R^4$ is independently a hydrogen, halogen, $—CX^d_3$, —CN, $—SO_{n4}R^{22}$, $—SO_{v4}NR^{19}R^{20}$, $—NHNH_2$, $—ONR^{19}R^{20}$, $—NHC(O)NHNH_2$, $—NHC(O)NR^{19}R^{20}$, $—N(O)_{m4}$, $—NR^{19}R^{20}$, $—C(O)R^{21}$, $—C(O)—OR^{21}$, $—C(O)NR^{19}R^{20}$, $—OR^{22}$, $—NR^{19}SO_2R^{22}$, $—NR^{19}C(O)R^{2'}$, $—NR^{19}C(O)—OR^{21}$, $—NR^{19}OR^{21}$, $—OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is independently hydrogen. In embodiments, $R^4$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is independently substituted or unsubstituted $C_1$-$C_{12}$ alkyl. In embodiments, $R^4$ is independently unsubstituted $C_1$-$C_{12}$ alkyl. In embodiments, $R^4$ is independently substituted or unsubstituted $C_1$-$C_8$ alkyl. In embodiments, $R^4$ is independently unsubstituted $C_1$-$C_8$ alkyl. In embodiments, $R^4$ is independently substituted or unsubstituted $C_1$-$C_4$ alkyl. In embodiments, $R^4$ is independently unsubstituted $C_1$-$C_4$ alkyl. In embodiments, $R^4$ is independently unsubstituted methyl. In embodiments, $R^4$ is independently unsubstituted ethyl. In embodiments, $R^4$ is independently unsubstituted propyl. In embodiments, $R^4$ is independently substituted or unsubstituted 2 to 12 membered heteroalkyl. In embodiments, $R^4$ is independently unsubstituted 2 to 12 membered heteroalkyl. In embodiments, $R^4$ is independently substituted or unsubstituted 2 to 8 membered heteroalkyl. In embodiments, $R^4$ is independently unsubstituted 2 to 8 membered heteroalkyl. In embodiments, $R^4$ is independently substituted or unsubstituted 2 to 4 membered heteroalkyl. In embodiments, $R^4$ is independently unsubstituted 2 to 4 membered heteroalkyl. In embodiments, $R^4$ is independently substituted or unsubstituted alkyl or substituted or unsubstituted heteroalkyl. In embodiments, $R^4$ is independently substituted or unsubstituted ($C_1$-$C_{10}$) alkyl or substituted or unsubstituted 2 to 10 membered heteroalkyl. In embodiments, $R^4$ is independently unsubstituted methyl. In embodiments, $R^4$ is independently unsubstituted cycloalkyl, unsubstituted heterocycloalkyl, unsubstituted aryl, or unsubstituted heteroaryl. In embodiments, $R^4$ is independently substituted or unsubstituted $C_3$-$C_8$ cycloalkyl. In embodiments, $R^4$ is independently unsubstituted $C_3$-$C_8$ cycloalkyl. In embodiments, $R^4$ is independently substituted or unsubstituted $C_3$-$C_7$ cycloalkyl. In embodiments, $R^4$ is independently unsubstituted $C_3$-$C_7$ cycloalkyl.

In embodiments, $R^4$ is independently substituted or unsubstituted 3 to 8 membered heterocycloalkyl. In embodiments, $R^4$ is independently unsubstituted 3 to 8 membered heterocycloalkyl. In embodiments, $R^4$ is independently substituted or unsubstituted 3 to 7 membered heterocycloalkyl.

In embodiments, $R^4$ is independently unsubstituted 3 to 7 membered heterocycloalkyl. In embodiments, $R^4$ is independently substituted or unsubstituted $C_6$-$C_{12}$ aryl. In embodiments, $R^4$ is independently unsubstituted $C_6$-$C_{12}$ aryl. In embodiments, $R^4$ is independently substituted or unsubstituted $C_6$-$C_{10}$ aryl. In embodiments, $R^4$ is independently unsubstituted $C_6$-$C_{10}$ aryl. In embodiments, $R^4$ is independently substituted or unsubstituted phenyl. In embodiments, $R^4$ is independently unsubstituted phenyl. In embodiments, $R^4$ is independently substituted or unsubstituted 5 to 10 membered heteroaryl. In embodiments, $R^4$ is independently unsubstituted 5 to 10 membered heteroaryl. In embodiments, $R^4$ is independently substituted or unsubstituted 5 to 9 membered heteroaryl. In embodiments, $R^4$ is independently unsubstituted 5 to 9 membered heteroaryl. In embodiments, $R^4$ is independently substituted or unsubstituted 5 to 6 membered heteroaryl. In embodiments, $R^4$ is independently unsubstituted 5 to 6 membered heteroaryl.

In embodiments, $R^3$ is independently a halogen, —$CX^e_3$, —CN, —$SO_{n5}R^{26}$, —$SO_{v5}NR^{23}R^{24}$, —$NHNH_2$, —$ONR^{23}R^{24}$, —$NHC(O)NHNH_2$, —$NHC(O)NR^{23}R^{24}$, —$N(O)_{m5}$, —$NR^{23}R^{24}$, —$C(O)R^{25}$, —C(O)—$OR^{25}$, —$C(O)NR^{23}R^{24}$, —$OR^{26}$, —$NR^{23}SO_2R^{26}$, —$NR^{23}C(O)R^{25}$, —$NR^{23}C(O)$—$OR^{25}$, —$NR^{23}OR^{25}$, —$OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is independently hydrogen. In embodiments, $R^3$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is independently —$NH_2$. In embodiments, $R^5$ is independently —$CF_3$. In embodiments, $R^5$ is independently —$CCl_3$. In embodiments, $R^5$ is independently —$N(O)_2$. In embodiments, $R^5$ is independently halogen. In embodiments, $R^5$ is independently —F. In embodiments, $R^5$ is independently —Cl. In embodiments, $R^5$ is independently —Br. In embodiments, $R^5$ is independently —I. In embodiments, $R^5$ is independently substituted or unsubstituted cycloalkyl, substituted or unsubstituted heterocycloalkyl, substituted or unsubstituted aryl, or substituted or unsubstituted heteroaryl.

In embodiments, $R^3$ is independently substituted or unsubstituted $C_1$-$C_{12}$ alkyl. In embodiments, $R^5$ is independently unsubstituted $C_1$-$C_{12}$ alkyl. In embodiments, $R^5$ is independently substituted or unsubstituted $C_1$-$C_8$ alkyl. In embodiments, $R^3$ is independently unsubstituted $C_1$-$C_8$ alkyl. In embodiments, $R^3$ is independently substituted or unsubstituted $C_1$-$C_4$ alkyl. In embodiments, $R^3$ is independently unsubstituted $C_1$-$C_4$ alkyl. In embodiments, $R^3$ is independently unsubstituted methyl. In embodiments, $R^3$ is independently unsubstituted ethyl. In embodiments, $R^5$ is independently unsubstituted propyl. In embodiments, $R^3$ is independently substituted or unsubstituted 2 to 12 membered heteroalkyl. In embodiments, $R^5$ is independently unsubstituted 2 to 12 membered heteroalkyl. In embodiments, $R^5$ is independently substituted or unsubstituted 2 to 8 membered heteroalkyl. In embodiments, $R^3$ is independently unsubstituted 2 to 8 membered heteroalkyl. In embodiments, $R^3$ is independently substituted or unsubstituted 2 to 4 membered heteroalkyl. In embodiments, $R^3$ is independently unsubstituted 2 to 4 membered heteroalkyl. In embodiments, $R^3$ is independently substituted or unsubstituted alkyl or substituted or unsubstituted heteroalkyl. In embodiments, $R^3$ is independently substituted or unsubstituted ($C_1$-$C_{10}$) alkyl or substituted or unsubstituted 2 to 10 membered heteroalkyl.

In embodiments, $R^3$ is independently unsubstituted cycloalkyl, unsubstituted heterocycloalkyl, unsubstituted aryl, or unsubstituted heteroaryl. In embodiments, $R^5$ is independently substituted or unsubstituted $C_3$-$C_8$ cycloalkyl. In embodiments, $R^5$ is independently unsubstituted $C_3$-$C_8$ cycloalkyl. In embodiments, $R^5$ is independently substituted or unsubstituted $C_3$-$C_7$ cycloalkyl. In embodiments, $R^5$ is independently unsubstituted $C_3$-$C_7$ cycloalkyl. In embodiments, $R^3$ is independently substituted or unsubstituted 3 to 8 membered heterocycloalkyl. In embodiments, $R^5$ is independently unsubstituted 3 to 8 membered heterocycloalkyl. In embodiments, $R^3$ is independently substituted or unsubstituted 3 to 7 membered heterocycloalkyl. In embodiments, $R^3$ is independently unsubstituted 3 to 7 membered heterocycloalkyl.

In embodiments, $R^3$ is independently substituted or unsubstituted $C_6$-$C_{12}$ aryl. In embodiments, $R^5$ is independently unsubstituted $C_6$-$C_{12}$ aryl. In embodiments, $R^5$ is independently substituted or unsubstituted $C_6$-$C_{10}$ aryl. In embodiments, $R^3$ is independently unsubstituted $C_6$-$C_{10}$ aryl. In embodiments, $R^5$ is independently substituted or unsubstituted phenyl. In embodiments, $R^3$ is independently unsubstituted phenyl. In embodiments, $R^3$ is independently substituted or unsubstituted 5 to 10 membered heteroaryl. In embodiments, $R^5$ is independently unsubstituted 5 to 10 membered heteroaryl. In embodiments, $R^5$ is independently substituted or unsubstituted 5 to 9 membered heteroaryl. In embodiments, $R^5$ is independently unsubstituted 5 to 9 membered heteroaryl. In embodiments, $R^5$ is independently substituted or unsubstituted 5 to 6 membered heteroaryl. In embodiments, $R^3$ is independently unsubstituted 5 to 6 membered heteroaryl.

In embodiments, $R^3$ is independently —$CX^e_3$. In embodiments, $R^3$ is independently —CN. In embodiments, $R^3$ is independently —$SO_2Cl$. In embodiments, $R^3$ is independently —$SO_{n5}R^{26}$. In embodiments, $R^3$ is independently —$SO_{v5}NR^{23}R^{24}$. In embodiments, $R^3$ is independently —$NHNH_2$. In embodiments, $R^3$ is independently —$ONR^{23}R^{24}$. In embodiments, $R^3$ is independently —NHC(O)$NHNH_2$. In embodiments, $R^3$ is independently —NHC(O)$NR^{23}R^{24}$. In embodiments, $R^5$ is independently —$N(O)_{m5}$. In embodiments, $R^3$ is independently —$NR^{23}R^{24}$. In embodiments, $R^3$ is independently —$C(O)R^{25}$. In embodiments, $R^3$ is independently —C(O)—$OR^{25}$. In embodiments, $R^3$ is independently —$C(O)NR^{23}R^{24}$. In embodiments, $R^3$ is independently —$OR^E$. In embodiments, $R^3$ is independently —$NR^{23}SO_2R^1$. In embodiments, $R^3$ is independently —$NR^{23}C(O)R^{21}$. In embodiments, $R^3$ is independently —$NR^{23}C(O)$—$OR^{21}$. In embodiments, $R^3$ is independently —$NR^{23}OR^{25}$. In embodiments, $R^5$ is independently —$OCX^e_3$. In embodiments, $R^3$ is independently a hydrogen, halogen, —$CX^e_3$, or unsubstituted alkyl. In embodiments, $R^3$ is independently a hydrogen, —F, —$CF_3$, or unsubstituted methyl.

In embodiments, each $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ are independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_1$-$C_{12}$ alkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_1$-$C_{12}$ alkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_1$-$C_8$ alkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_1$-$C_8$ alkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_1$-$C_4$ alkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_1$-$C_4$ alkyl.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 2 to 12 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 2 to 12 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^6$ is independently substituted or unsubstituted 2 to 8 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 2 to 8 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 2 to 4 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 2 to 4 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted alkyl or substituted or unsubstituted heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted ($C_1$-$C_{10}$) alkyl or substituted or unsubstituted 2 to 10 membered heteroalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted methyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently H.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted cycloalkyl, unsubstituted heterocycloalkyl, unsubstituted aryl, or unsubstituted heteroaryl. In embodiments, $R^9$, $R^{10}$, $R^{11}$, $R^{12}$, $R^{13}$, $R^{14}$, $R^{13}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_3$-$C_8$ cycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_3$-$C_8$ cycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_3$-$C_7$ cycloalkyl. In embodiments, $R^9$, $R^{10}$, $R^{11}$, $R^{12}$, $R^{13}$, $R^{14}$, $R^{13}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_3$-$C_7$ cycloalkyl.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 3 to 8 membered heterocycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 3 to 8 membered heterocycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 3 to 7 membered heterocycloalkyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 3 to 7 membered heterocycloalkyl.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_6$-$C_{12}$ aryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_6$-$C_{12}$ aryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted $C_6$-$C_{10}$ aryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted $C_6$-$C_{10}$ aryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted phenyl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted phenyl.

In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 5 to 10 membered heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 5 to 10 membered heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 5 to 9 membered heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 5 to 9 membered heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently substituted or unsubstituted 5 to 6 membered heteroaryl. In embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, or $R^{26}$ is independently unsubstituted 5 to 6 membered heteroaryl.

In embodiments, $R^{11}$ and $R^{12}$ substituents may optionally be joined to form a substituted or unsubstituted heterocycloalkyl, or substituted or unsubstituted heteroaryl. In embodiments, $R^{11}$ and $R^{12}$ substituents are joined to form a substituted or unsubstituted heterocycloalkyl. In embodiments, $R^{11}$ and $R^{12}$ substituents are joined to form an unsubstituted heterocycloalkyl. In embodiments, $R^{11}$ and $R^{12}$ substituents are joined to form a substituted or unsubstituted 3 to 8 membered heterocycloalkyl. In embodiments, $R^{11}$ and $R^{12}$ substituents are joined to form an unsubstituted 3 to 8 membered heterocycloalkyl. In embodiments, $R^{11}$ and $R^{12}$ substituents are joined to form a substituted or unsubstituted 3 to 7 membered heterocycloalkyl. In embodiments, $R^{11}$ and $R^{12}$ substituents are joined to form an unsubstituted 3 to 7 membered heterocycloalkyl. In embodiments, $R^{11}$ and $R^{12}$ substituents are joined to form a substituted or unsubstituted 3 to 6 membered heterocycloalkyl. In embodiments, $R^{11}$ and $R^{12}$ substituents are joined to form an unsubstituted 3 to 6 membered heterocycloalkyl.

In embodiments, $R^{11}$ and $R^{12}$ substituents are joined to form a substituted or unsubstituted heteroaryl. In embodiments, $R^{11}$ and $R^{12}$ substituents are joined to form an unsubstituted heteroaryl. In embodiments, $R^{11}$ and $R^{12}$ substituents are joined to form a substituted or unsubstituted 5 to 10 membered heteroaryl. In embodiments, $R^{11}$ and $R^{12}$ substituents are joined to form an unsubstituted 5 to 10 membered heteroaryl. In embodiments, $R^{11}$ and $R^{12}$ substituents are joined to form a substituted or unsubstituted 5 to 9 membered heteroaryl. In embodiments, $R^{11}$ and $R^{12}$ substituents are joined to form an unsubstituted 5 to 9 membered heteroaryl. In embodiments, $R^{11}$ and $R^{12}$ substituents are joined to form a substituted or unsubstituted 5 to 6 membered heteroaryl. In embodiments, $R^{11}$ and $R^{12}$ substituents are joined to form unsubstituted 5 to 6 membered heteroaryl.

In embodiments, $R^{15}$ and $R^{16}$ substituents may optionally be joined to form a substituted or unsubstituted heterocycloalkyl, or substituted or unsubstituted heteroaryl. In embodiments, $R^{15}$ and $R^{16}$ substituents are joined to form a substituted or unsubstituted heterocycloalkyl. In embodiments, $R^{15}$ and $R^{16}$ substituents are joined to form an unsubstituted heterocycloalkyl. In embodiments, $R^{15}$ and $R^{16}$ substituents are joined to form a substituted or unsubstituted 3 to 8 membered heterocycloalkyl. In embodiments, $R^{15}$ and $R^{16}$ substituents are joined to form an unsubstituted 3 to 8 membered heterocycloalkyl. In embodiments, $R^{15}$ and $R^{16}$ substituents are joined to form a substituted or unsubstituted 3 to 7 membered heterocycloalkyl. In embodiments, $R^{15}$ and $R^{16}$ substituents are joined to form an unsubstituted 3 to 7 membered heterocycloalkyl. In embodiments, $R^{15}$ and $R^{16}$ substituents are joined to form a substituted or unsubstituted 3 to 6 membered heterocycloalkyl. In embodiments, $R^{15}$ and $R^{16}$ substituents are joined to form an unsubstituted 3 to 6 membered heterocycloalkyl.

In embodiments, $R^{15}$ and $R^{16}$ substituents are joined to form a substituted or unsubstituted heteroaryl. In embodiments, $R^{15}$ and $R^{16}$ substituents are joined to form an unsubstituted heteroaryl. In embodiments, $R^{15}$ and $R^{16}$ substituents are joined to form a substituted or unsubstituted 5 to 10 membered heteroaryl. In embodiments, $R^{15}$ and $R^{16}$ substituents are joined to form an unsubstituted 5 to 10 membered heteroaryl. In embodiments, $R^{15}$ and $R^{16}$ substituents are joined to form a substituted or unsubstituted 5 to 9 membered heteroaryl. In embodiments, $R^{15}$ and $R^{16}$ substituents are joined to form an unsubstituted 5 to 9 membered heteroaryl. In embodiments, $R^{15}$ and $R^{16}$ substituents are joined to form a substituted or unsubstituted 5 to 6 membered heteroaryl. In embodiments, $R^{13}$ and $R^{16}$ substituents are joined to form unsubstituted 5 to 6 membered heteroaryl.

In embodiments, $R^{19}$ and $R^{20}$ substituents may optionally be joined to form a substituted or unsubstituted heterocycloalkyl, or substituted or unsubstituted heteroaryl. In embodiments, $R^{19}$ and $R^{20}$ substituents are joined to form a substituted or unsubstituted heterocycloalkyl. In embodiments, $R^{19}$ and $R^{20}$ substituents are joined to form an unsubstituted heterocycloalkyl. In embodiments, $R^{19}$ and $R^{20}$ substituents are joined to form a substituted or unsubstituted 3 to 8 membered heterocycloalkyl. In embodiments, $R^{19}$ and $R^{20}$ substituents are joined to form an unsubstituted 3 to 8 membered heterocycloalkyl. In embodiments, $R^{19}$ and $R^{20}$ substituents are joined to form a substituted or unsubstituted 3 to 7 membered heterocycloalkyl. In embodiments, $R^{19}$ and $R^{20}$ substituents are joined to form an unsubstituted 3 to 7 membered heterocycloalkyl. In embodiments, $R^{19}$ and $R^{20}$ substituents are joined to form a substituted or unsubstituted 3 to 6 membered heterocycloalkyl. In embodiments, $R^{19}$ and $R^{20}$ substituents are joined to form an unsubstituted 3 to 6 membered heterocycloalkyl.

In embodiments, $R^{19}$ and $R^{20}$ substituents are joined to form a substituted or unsubstituted heteroaryl. In embodiments, $R^{19}$ and $R^{20}$ substituents are joined to form an unsubstituted heteroaryl. In embodiments, $R^{19}$ and $R^{20}$ substituents are joined to form a substituted or unsubstituted 5 to 10 membered heteroaryl. In embodiments, $R^{19}$ and $R^{20}$ substituents are joined to form an unsubstituted 5 to 10 membered heteroaryl. In embodiments, $R^{19}$ and $R^{20}$ substituents are joined to form a substituted or unsubstituted 5 to 9 membered heteroaryl. In embodiments, $R^{19}$ and $R^{20}$ substituents are joined to form an unsubstituted 5 to 9 membered heteroaryl. In embodiments, $R^{19}$ and $R^{20}$ substituents are joined to form a substituted or unsubstituted 5 to 6 membered heteroaryl. In embodiments, $R^{19}$ and $R^{20}$ substituents are joined to form unsubstituted 5 to 6 membered heteroaryl.

In embodiments, $R^{23}$ and $R^{24}$ substituents may optionally be joined to form a substituted or unsubstituted heterocycloalkyl, or substituted or unsubstituted heteroaryl. In embodiments, $R^{23}$ and $R^{24}$ substituents are joined to form a substituted or unsubstituted heterocycloalkyl. In embodiments, $R^{23}$ and $R^{24}$ substituents are joined to form an unsubstituted heterocycloalkyl. In embodiments, $R^{23}$ and $R^{24}$ substituents are joined to form a substituted or unsubstituted 3 to 8 membered heterocycloalkyl. In embodiments, $R^{23}$ and $R^{24}$ substituents are joined to form an unsubstituted 3 to 8 membered heterocycloalkyl. In embodiments, $R^{23}$ and $R^{24}$ substituents are joined to form a substituted or unsubstituted 3 to 7 membered heterocycloalkyl. In embodiments, $R^{23}$ and $R^{24}$ substituents are joined to form an unsubstituted 3 to 7 membered heterocycloalkyl. In embodiments, $R^{23}$ and $R^{24}$ substituents are joined to form a substituted or unsubstituted 3 to 6 membered heterocycloalkyl. In embodiments, $R^{23}$ and $R^{24}$ substituents are joined to form an unsubstituted 3 to 6 membered heterocycloalkyl.

In embodiments, $R^{23}$ and $R^{24}$ substituents are joined to form a substituted or unsubstituted heteroaryl. In embodiments, $R^{23}$ and $R^{24}$ substituents are joined to form an unsubstituted heteroaryl. In embodiments, $R^{23}$ and $R^{24}$ substituents are joined to form a substituted or unsubstituted 5 to 10 membered heteroaryl. In embodiments, $R^{23}$ and $R^{24}$ substituents are joined to form an unsubstituted 5 to 10 membered heteroaryl. In embodiments, $R^{23}$ and $R^{24}$ substituents are joined to form a substituted or unsubstituted 5 to 9 membered heteroaryl. In embodiments, $R^{23}$ and $R^{24}$ substituents are joined to form an unsubstituted 5 to 9 membered heteroaryl. In embodiments, $R^{23}$ and $R^{24}$ substituents are joined to form a substituted or unsubstituted 5 to 6 membered heteroaryl. In embodiments, $R^{23}$ and $R^{24}$ substituents are joined to form unsubstituted 5 to 6 membered heteroaryl.

In embodiments, n is 0. In embodiments, n is 1. In embodiments, n is 2. In embodiments, n is 3. In embodiments, n is 4. In embodiments, n is 5. In embodiments, m1 is 1. In embodiments, m1 is 2. In embodiments, m2 is 1. In embodiments, m2 is 2. In embodiments, m3 is 1. In embodiments, m3 is 2. In embodiments, m4 is 1. In embodiments, m4 is 2. In embodiments, m5 is 1. In embodiments, m5 is 2. In embodiments, v1 is 1. In embodiments, v1 is 2. In embodiments, v2 is 1. In embodiments, v2 is 2. In embodiments, v3 is 1. In embodiments, v3 is 2. In embodiments, v4 is 1. In embodiments, v4 is 2. In embodiments, v5 is 1. In embodiments, v5 is 2. In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n3 is 0. In embodiments, n3 is 1. In embodiments, n3 is 2. In embodiments, n3 is 3. In embodiments, n3 is 4. In embodiments, n4 is 0. In embodiments, n4 is 1. In embodiments, n4 is 2. In embodiments, n4 is 3. In embodiments, n4 is 4. In embodiments, n5 is 0. In embodiments, n5 is 1. In embodiments, n5 is 2. In embodiments, n5 is 3. In embodiments, n5 is 4.

In embodiments, X is independently —Cl. In embodiments, X is independently —Br. In embodiments, X is independently —I. In embodiments, X is independently —F. In embodiments, X is independently —Cl. In embodiments, $X^a$ is independently —Br. In embodiments, $X^a$ is independently —I. In embodiments, $X^a$ is independently —F. In embodiments, $X^b$ is independently —Cl. In embodiments, $X^b$ is independently —Br. In embodiments, $X^b$ is independently —I. In embodiments, $X^b$ is independently —F. In embodiments, $X^c$ is independently —Cl. In embodiments, $X^c$ is independently —Br. In embodiments, $X^c$ is independently —I. In embodiments, $X^c$ is independently —F. In embodiments, $X^d$ is independently —Cl. In embodiments, $X^d$ is independently —Br. In embodiments, $X^d$ is independently —I. In embodiments, $X^d$ is independently —F. In embodiments, $X^c$ is independently —Cl. In embodiments, $X^c$ is independently —Br. In embodiments, $X^c$ is independently —I. In embodiments, $X^c$ is independently —F.

In embodiments, $R^1$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{27}$-substituted or unsubstituted alkyl (e.g. $C_1$-$C_8$ alkyl, $C_1$-$C_6$ alkyl, or $C_1$-$C_4$ alkyl), $R^{27}$-substituted or unsubstituted heteroalkyl (e.g. 2 to 8 membered heteroalkyl, 2 to 6 membered heteroalkyl, or 2 to 4 membered heteroalkyl), $R^{27}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{27}$-substituted or unsubstituted heterocycloalkyl (e.g. 3 to 8 membered heterocycloalkyl, 4 to 8 membered heterocycloalkyl, or 5 to 6 membered heterocycloalkyl), $R^{27}$-substituted or unsubstituted aryl (e.g. $C_6$-$C_{10}$ aryl, $C_{10}$ aryl or phenyl), or $R^{27}$-substituted or unsubstituted heteroaryl (e.g. 5 to 10 membered heteroaryl, 5 to 9 membered heteroaryl, or 5 to 6 membered heteroaryl). In embodiments, $R^1$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{27}$-substituted alkyl (e.g. $C_1$-$C_8$ alkyl, $C_1$-$C_6$ alkyl, or $C_1$-$C_4$ alkyl), $R^{27}$-substituted heteroalkyl (e.g. 2 to 8 membered heteroalkyl, 2 to 6 membered heteroalkyl, or 2 to 4 membered heteroalkyl), $R^{27}$-substituted cycloalkyl (e.g. $C_3$-$C_8$ cycloalkyl, $C_4$-$C_8$ cycloalkyl, or $C_5$-$C_6$ cycloalkyl), $R^{27}$-substituted heterocycloalkyl (e.g. 3 to 8 membered heterocycloalkyl, 4 to 8 membered heterocycloalkyl, or 5 to 6 membered heterocycloalkyl), $R^{27}$-substituted aryl (e.g. $C_6$-$C_{10}$ aryl, $C_{10}$ aryl or phenyl), or $R^{27}$-substituted heteroaryl (e.g. 5 to 10 membered heteroaryl, 5 to 9 membered heteroaryl, or 5 to 6 membered heteroaryl). In embodiments, $R^1$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{27}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{28}$-substituted or unsubstituted alkyl (e.g. $C_1$-$C_8$ alkyl, $C_1$-$C_6$ alkyl, or $C_1$-$C_4$ alkyl), $R^{28}$-substituted or unsubstituted heteroalkyl (e.g. 2 to 8 membered heteroalkyl, 2 to 6 membered heteroalkyl, or 2 to 4 membered heteroalkyl), $R^{28}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{28}$-substituted or unsubstituted heterocycloalkyl (e.g. 3 to 8 membered heterocycloalkyl, 4 to 8 membered heterocycloalkyl, or 5 to 6 membered heterocycloalkyl), $R^{28}$-substituted or unsubstituted aryl (e.g. $C_6$-$C_{10}$ aryl, $C_{10}$ aryl or phenyl), or $R^{28}$-substituted or unsubstituted heteroaryl (e.g. 5 to 10 membered heteroaryl, 5 to 9 membered heteroaryl, or 5 to 6 membered heteroaryl). In embodiments, $R^{27}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O) $NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl). In embodiments, $R^{27}$ is unsubstituted piperidinyl. In embodiments, $R^{27}$ is unsubstituted piperazinyl. In embodiments, $R^{27}$ is unsubstituted pyridinyl. In embodiments, $R^{27}$ is unsubstituted pyrazinyl. In embodiments, $R^{27}$ is dimethylamino. In embodiments, $R^{27}$ is dimethylaminoethyl. In embodiments, $R^{27}$ is dimethylaminopropyl. In embodiments, $R^{27}$ is ethylmorpholinyl. In embodiments, $R^{27}$ is unsubstituted morpholinyl.

$R^{28}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{29}$-substituted or unsubstituted alkyl (e.g. $C_1$-$C_8$ alkyl, $C_1$-$C_6$ alkyl, or $C_1$-$C_4$ alkyl), $R^{29}$-substituted or unsubstituted heteroalkyl (e.g. 2 to 8 membered heteroalkyl, 2 to 6 membered heteroalkyl, or 2 to 4 membered heteroalkyl), $R^{29}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{29}$-substituted or unsubstituted heterocycloalkyl (e.g. 3 to 8 membered heterocycloalkyl, 4 to 8 membered heterocycloalkyl, or 5 to 6 membered heterocycloalkyl), $R^{29}$-substituted or unsubstituted aryl (e.g. $C_6$-$C_{10}$ aryl, $C_{10}$ aryl or phenyl), or $R^{29}$-substituted or unsubstituted heteroaryl (e.g. 5 to 10 membered heteroaryl, 5 to 9 membered heteroaryl, or 5 to 6 membered heteroaryl). In embodiments, $R^{28}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{29}$-substituted alkyl (e.g. $C_1$-$C_8$ alkyl, $C_1$-$C_6$ alkyl, or $C_1$-$C_4$ alkyl), $R^{29}$-substituted heteroalkyl (e.g. 2 to 8 membered heteroalkyl, 2 to 6 membered heteroalkyl, or 2 to 4 membered heteroalkyl), $R^{29}$-substituted cycloalkyl (e.g. $C_3$-$C_8$ cycloalkyl, $C_4$-$C_8$ cycloalkyl, or $C_5$-$C_6$ cycloalkyl), $R^{29}$-substituted heterocycloalkyl (e.g. 3 to 8 membered heterocycloalkyl, 4 to 8 membered heterocycloalkyl, or 5 to 6 membered heterocycloalkyl), $R^{29}$-substituted aryl (e.g. $C_6$-$C_{10}$ aryl, $C_{10}$ aryl or phenyl), or $R^{29}$-substituted heteroaryl (e.g. 5 to 10 membered heteroaryl, 5 to 9 membered heteroaryl, or 5 to 6 membered heteroaryl). In embodiments, $R^{28}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl). In embodiments, $R^{28}$ is unsubstituted piperidinyl. In embodiments, $R^{28}$ is unsubstituted piperazinyl. In embodiments, $R^{28}$ is unsubstituted pyridinyl. In embodiments, $R^{28}$ is unsubstituted pyrazinyl. In embodiments, $R^{28}$ is dimethylamino. In embodiments, $R^{28}$ is dimethylaminoethyl. In embodiments, $R^{28}$ is dimethylaminopropyl. In embodiments, $R^{28}$ is ethylmorpholinyl. In embodiments, $R^{28}$ is unsubstituted morpholinyl.

In embodiments, $R^2$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{30}$-substituted or unsubstituted alkyl (e.g. $C_1$-$C_8$ alkyl, $C_1$-$C_6$ alkyl, or $C_1$-$C_4$ alkyl), $R^{30}$-substituted or unsubstituted heteroalkyl (e.g. 2 to 8 membered heteroalkyl, 2 to 6 membered heteroalkyl, or 2 to 4 membered heteroalkyl), $R^{30}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{30}$-substituted or unsubstituted heterocycloalkyl (e.g. 3 to 8 membered heterocycloalkyl, 4 to 8 membered heterocycloalkyl, or 5 to 6 membered heterocycloalkyl), $R^{30}$-substituted or unsubstituted aryl (e.g. $C_6$-$C_{10}$ aryl, $C_{10}$ aryl or phenyl), or $R^{30}$-substituted or unsubstituted heteroaryl (e.g. 5 to 10 membered heteroaryl, 5 to 9 membered heteroaryl, or 5 to 6 membered heteroaryl). In embodiments, $R^2$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{30}$-substituted or unsubstituted alkyl (e.g. $C_1$-$C_8$ alkyl, $C_1$-$C_6$ alkyl, or $C_1$-$C_4$ alkyl), $R^{30}$-substituted or unsubstituted heteroalkyl (e.g. 2 to 8 membered heteroalkyl, 2 to 6 membered heteroalkyl, or 2 to 4 membered heteroalkyl), $R^{30}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{30}$-substituted or unsubstituted heterocycloalkyl (e.g. 3 to 8 membered heterocycloalkyl, 4 to 8 membered heterocycloalkyl, or 5 to 6 membered heterocycloalkyl), $R^{30}$-substituted or unsubstituted aryl (e.g. $C_6$-$C_{10}$ aryl, $C_{10}$ aryl or phenyl), or $R^{30}$-substituted or unsubstituted heteroaryl (e.g. 5 to 10 membered heteroaryl, 5 to 9 membered heteroaryl, or 5 to 6 membered heteroaryl). In embodiments, $R^2$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{30}$-substituted alkyl (e.g. $C_1$-$C_8$ alkyl, $C_1$-$C_6$ alkyl, or $C_1$-$C_4$ alkyl), $R^{30}$-substituted heteroalkyl (e.g. 2 to 8 membered heteroalkyl, 2 to 6 membered heteroalkyl, or 2 to 4 membered heteroalkyl), $R^{30}$-substituted cycloalkyl (e.g. $C_3$-$C_8$ cycloalkyl, $C_4$-$C_5$ cycloalkyl, or $C_5$-$C_6$ cycloalkyl), $R^{30}$-substituted heterocycloalkyl (e.g. 3 to 8 membered heterocycloalkyl, 4 to 8 membered heterocycloalkyl, or 5 to 6 membered heterocycloalkyl), $R^{30}$-substituted aryl (e.g. $C_6$-$C_{10}$ aryl, $C_{10}$ aryl or phenyl), or $R^{30}$-substituted heteroaryl (e.g. 5 to 10 membered heteroaryl, 5 to 9 membered heteroaryl, or 5 to 6 membered heteroaryl). In embodiments, $R^2$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{30}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{31}$-substituted or unsubstituted alkyl (e.g. $C_1$-$C_8$ alkyl, $C_1$-$C_6$ alkyl, or $C_1$-$C_4$ alkyl), $R^{31}$-substituted or unsubstituted heteroalkyl (e.g. 2 to 8 membered heteroalkyl, 2 to 6 membered heteroalkyl, or 2 to 4 membered heteroalkyl), $R^{31}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{31}$-substituted or unsubstituted heterocycloalkyl (e.g. 3 to 8 membered heterocycloalkyl, 4 to 8 membered heterocycloalkyl, or 5 to 6 membered heterocycloalkyl), $R^{31}$-substituted or unsubstituted aryl (e.g. $C_6$-$C_{10}$ aryl, $C_{10}$ aryl or phenyl), or $R^{31}$-substituted or unsubstituted heteroaryl (e.g. 5 to 10 membered heteroaryl, 5 to 9 membered heteroaryl, or 5 to 6 membered heteroaryl). In embodiments, $R^{30}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{31}$-substituted alkyl (e.g. $C_1$-$C_8$ alkyl, $C_1$-$C_6$ alkyl, or $C_1$-$C_4$ alkyl), $R^{31}$-substituted heteroalkyl (e.g. 2 to 8 membered heteroalkyl, 2 to 6 membered heteroalkyl, or 2 to 4 membered heteroalkyl), $R^{31}$-substituted cycloalkyl (e.g. $C_3$-$C_8$ cycloalkyl, $C_4$-$C_8$ cycloalkyl, or $C_5$-$C_6$ cycloalkyl), $R^{31}$-substituted heterocycloalkyl (e.g. 3 to 8 membered heterocycloalkyl, 4 to 8 membered heterocycloalkyl, or 5 to 6 membered heterocycloalkyl), $R^{31}$-substituted aryl (e.g. $C_6$-$C_{10}$ aryl, $C_{10}$ aryl or phenyl), or $R^3$-substituted heteroaryl (e.g. 5 to 10 membered heteroaryl, 5 to 9 membered heteroaryl, or 5 to 6 membered heteroaryl). In embodiments, $R^{30}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{31}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{32}$-substituted or unsubstituted alkyl (e.g. $C_1$-$C_8$ alkyl, $C_1$-$C_6$ alkyl, or $C_1$-$C_4$ alkyl), $R^{32}$-substituted or unsubstituted heteroalkyl (e.g. 2 to 8 membered heteroalkyl, 2 to 6 membered heteroalkyl, or 2 to 4 membered heteroalkyl), $R^{32}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{32}$-substituted or unsubstituted heterocycloalkyl (e.g. 3 to 8 membered heterocycloalkyl, 4 to 8 membered heterocycloalkyl, or 5 to 6 membered heterocycloalkyl), $R^{32}$-substituted or unsubstituted aryl (e.g. $C_6$-$C_{10}$ aryl, $C_{10}$ aryl or phenyl), or $R^{32}$-substituted or unsubstituted heteroaryl (e.g. 5 to 10 membered heteroaryl, 5 to 9 membered heteroaryl, or 5 to 6 membered heteroaryl). In embodiments, $R^{31}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{32}$-substituted alkyl (e.g. $C_1$-$C_8$ alkyl, $C_1$-$C_6$ alkyl, or $C_1$-$C_4$ alkyl), $R^{32}$-substituted heteroalkyl (e.g. 2 to 8 membered heteroalkyl, 2 to 6 membered heteroalkyl, or 2 to 4 membered heteroalkyl), $R^{32}$-substituted cycloalkyl (e.g. $C_3$-$C_8$ cycloalkyl, $C_4$-$C_8$ cycloalkyl, or $C_5$-$C_6$ cycloalkyl), $R^{32}$-substituted heterocycloalkyl (e.g. 3 to 8 membered heterocycloalkyl, 4 to 8 membered heterocycloalkyl, or 5 to 6 membered heterocycloalkyl), $R^{32}$-substituted aryl (e.g. $C_6$-$C_{10}$ aryl, $C_{10}$ aryl or phenyl), or $R^{32}$-substituted heteroaryl (e.g. 5 to 10 membered heteroaryl, 5 to 9 membered heteroaryl, or 5 to 6 membered heteroaryl). In embodiments, $R^{31}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^3$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{33}$-substituted or unsubstituted alkyl (e.g. $C_1$-$C_8$ alkyl, $C_1$-$C_6$ alkyl, or $C_1$-$C_4$ alkyl), $R^{33}$-substituted or unsubstituted heteroalkyl (e.g. 2 to 8 membered heteroalkyl, 2 to 6 membered heteroalkyl, or 2 to 4 membered heteroalkyl), $R^{33}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{33}$-substituted or unsubstituted heterocycloalkyl (e.g. 3 to 8 membered heterocycloalkyl, 4 to 8 membered heterocycloalkyl, or 5 to 6 membered heterocycloalkyl), $R^{33}$-substituted or unsubstituted aryl (e.g. 6 to 12 membered aryl or 6 membered aryl), or $R^3$-substituted or unsubstituted heteroaryl (e.g. 5 to 10 membered heteroaryl, 5 to 9 membered heteroaryl, or 5 to 6 membered heteroaryl). In embodiments, $R^3$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{33}$-substituted or unsubstituted alkyl (e.g. $C_1$-$C_8$ alkyl, $C_1$-$C_6$ alkyl, or $C_1$-$C_4$ alkyl), $R^{33}$-substituted or unsubstituted heteroalkyl (e.g. 2 to 8 membered heteroalkyl, 2 to 6 membered heteroalkyl, or 2 to 4 membered heteroalkyl), $R^{33}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{33}$-substituted or unsubstituted heterocycloalkyl (e.g. 3 to 8 membered heterocycloalkyl, 4 to 8 membered heterocycloalkyl, or 5 to 6 membered heterocycloalkyl), $R^{33}$-substituted or unsubstituted aryl (e.g. $C_6$-$C_{10}$ aryl, $C_{10}$ aryl or phenyl), or $R^{33}$-substituted or unsubstituted heteroaryl (e.g. 5 to 10 membered heteroaryl, 5 to 9 membered heteroaryl, or 5 to 6 membered heteroaryl). In embodiments, $R^3$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{33}$-substituted alkyl (e.g. $C_1$-$C_8$ alkyl, $C_1$-$C_6$ alkyl, or $C_1$-$C_4$ alkyl), $R^{33}$-substituted heteroalkyl (e.g. 2 to 8 membered heteroalkyl, 2 to 6 membered heteroalkyl, or 2 to 4 membered heteroalkyl), $R^{33}$-substituted cycloalkyl (e.g. $C_3$-$C_8$ cycloalkyl, $C_4$-$C_5$ cycloalkyl, or $C_5$-$C_6$ cycloalkyl), $R^{33}$-substituted heterocycloalkyl (e.g. 3 to 8 membered heterocycloalkyl, 4 to 8 membered heterocycloalkyl, or 5 to 6 membered heterocycloalkyl), $R^{33}$-substituted aryl (e.g. $C_6$-$C_{10}$ aryl, $C_{10}$ aryl or phenyl), or $R^3$-substituted heteroaryl (e.g. 5 to 10 membered heteroaryl, 5 to 9 membered heteroaryl, or 5 to 6 membered heteroaryl). In embodiments, $R^3$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{33}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{34}$-substituted or unsubstituted alkyl (e.g. $C_1$-$C_8$ alkyl, $C_1$-$C_6$ alkyl, or $C_1$-$C_4$ alkyl), $R^{34}$-substituted or unsubstituted heteroalkyl (e.g. 2 to 8 membered heteroalkyl, 2 to 6 membered heteroalkyl, or 2 to 4 membered heteroalkyl), $R^{34}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{34}$-substituted or unsubstituted heterocycloalkyl (e.g. 3 to 8 membered heterocycloalkyl, 4 to 8 membered heterocycloalkyl, or 5 to 6 membered heterocycloalkyl), $R^{34}$-substituted or unsubstituted aryl (e.g. $C_6$-$C_{10}$ aryl, $C_{10}$ aryl or phenyl), or $R^{34}$-substituted or unsubstituted heteroaryl (e.g. 5 to 10 membered heteroaryl, 5 to 9 membered heteroaryl, or 5 to 6 membered heteroaryl). In embodiments, $R^{33}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{34}$-substituted alkyl (e.g. $C_1$-$C_8$ alkyl, $C_1$-$C_6$ alkyl, or $C_1$-$C_4$ alkyl), $R^{34}$-substituted heteroalkyl (e.g. 2 to 8 membered heteroalkyl, 2 to 6 membered heteroalkyl, or 2 to 4 membered heteroalkyl), $R^{34}$-substituted cycloalkyl (e.g. $C_3$-$C_8$ cycloalkyl, $C_4$-$C_8$ cycloalkyl, or $C_5$-$C_6$ cycloalkyl), $R^{34}$-substituted heterocycloalkyl (e.g. 3 to 8 membered heterocycloalkyl, 4 to 8 membered heterocycloalkyl, or 5 to 6 membered heterocycloalkyl), $R^{34}$-substituted aryl (e.g. $C_6$-$C_{10}$ aryl, $C_{10}$ aryl or phenyl), or $R^{34}$-substituted heteroaryl (e.g. 5 to 10 membered heteroaryl, 5 to 9 membered heteroaryl, or 5 to 6 membered heteroaryl). In embodiments, $R^{33}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{34}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{35}$-substituted or unsubstituted alkyl (e.g. $C_1$-$C_8$ alkyl, $C_1$-$C_6$ alkyl, or $C_1$-$C_4$ alkyl), $R^{35}$-substituted or unsubstituted heteroalkyl (e.g. 2 to 8 membered heteroalkyl, 2 to 6 membered heteroalkyl, or 2 to 4 membered heteroalkyl), $R^{35}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{35}$-substituted or unsubstituted heterocycloalkyl (e.g. 3 to 8 membered heterocycloalkyl, 4 to 8 membered heterocycloalkyl, or 5 to 6 membered heterocycloalkyl), $R^{35}$-substituted or unsubstituted aryl (e.g. $C_6$-$C_{10}$ aryl, $C_{10}$ aryl or phenyl), or $R^{35}$-substituted or unsubstituted heteroaryl (e.g. 5 to 10 membered heteroaryl, 5 to 9 membered heteroaryl, or 5 to 6 membered heteroaryl). In embodiments, $R^{34}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{35}$-substituted alkyl (e.g. $C_1$-$C_8$ alkyl, $C_1$-$C_6$ alkyl, or $C_1$-$C_4$ alkyl), $R^{35}$-substituted heteroalkyl (e.g. 2 to 8 membered heteroalkyl, 2 to 6 membered heteroalkyl, or 2 to 4 membered heteroalkyl), $R^{35}$-substituted cycloalkyl (e.g. $C_3$-$C_8$ cycloalkyl, $C_4$-$C_8$ cycloalkyl, or $C_5$-$C_6$ cycloalkyl), $R^{35}$-substituted heterocycloalkyl (e.g. 3 to 8 membered heterocycloalkyl, 4 to 8 membered heterocycloalkyl, or 5 to 6 membered heterocycloalkyl), $R^{35}$-substituted aryl (e.g. $C_6$-$C_{10}$ aryl, $C_{10}$ aryl or phenyl), or $R^{35}$-substituted heteroaryl (e.g. 5 to 10 membered heteroaryl, 5 to 9 membered heteroaryl, or 5 to 6 membered heteroaryl). In embodiments, $R^{34}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^4$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{36}$-substituted or unsubstituted alkyl (e.g. $C_1$-$C_8$ alkyl, $C_1$-$C_6$ alkyl, or $C_1$-$C_4$ alkyl), $R^{36}$-substituted or unsubstituted heteroalkyl (e.g. 2 to 8 membered heteroalkyl, 2 to 6 membered heteroalkyl, or 2 to 4 membered heteroalkyl), $R^{36}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{36}$-substituted or unsubstituted heterocycloalkyl (e.g. 3 to 8 membered heterocycloalkyl, 4 to 8 membered heterocycloalkyl, or 5 to 6 membered heterocycloalkyl), $R^{36}$-substituted or unsubstituted aryl (e.g. $C_6$-$C_{10}$ aryl, $C_{10}$ aryl or phenyl), or $R^{36}$-substituted or unsubstituted heteroaryl (e.g. 5 to 10 membered heteroaryl, 5 to 9 membered heteroaryl, or 5 to 6 membered heteroaryl). In embodiments, $R^4$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{36}$-substituted or unsubstituted alkyl (e.g. $C_1$-$C_8$ alkyl, $C_1$-$C_6$ alkyl, or $C_1$-$C_4$ alkyl), $R^6$-substituted or unsubstituted heteroalkyl (e.g. 2 to 8 membered heteroalkyl, 2 to 6 membered heteroalkyl, or 2 to 4 membered heteroalkyl), $R^{36}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{36}$-substituted or unsubstituted heterocycloalkyl (e.g. 3 to 8 membered heterocycloalkyl, 4 to 8 membered heterocycloalkyl, or 5 to 6 membered heterocycloalkyl), $R^{36}$-substituted or unsubstituted aryl (e.g. $C_6$-$C_{10}$ aryl, $C_{10}$ aryl or phenyl), or $R^{36}$-substituted or unsubstituted heteroaryl (e.g. 5 to 10 membered heteroaryl, 5 to 9 membered heteroaryl, or 5 to 6 membered heteroaryl). In embodiments, $R^4$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{36}$-substituted alkyl (e.g. $C_1$-$C_8$ alkyl, $C_1$-$C_6$ alkyl, or $C_1$-$C_4$ alkyl), $R^{36}$-substituted heteroalkyl (e.g. 2 to 8 membered heteroalkyl, 2 to 6 membered heteroalkyl, or 2 to 4 membered heteroalkyl), $R^{36}$-substituted cycloalkyl (e.g. $C_3$-$C_8$ cycloalkyl, $C_4$-$C_5$ cycloalkyl, or $C_5$-$C_6$ cycloalkyl), $R^{36}$-substituted heterocycloalkyl (e.g. 3 to 8 membered heterocycloalkyl, 4 to 8 membered heterocycloalkyl, or 5 to 6 membered heterocycloalkyl), $R^{36}$-substituted aryl (e.g. $C_6$-$C_{10}$ aryl, $C_{10}$ aryl or phenyl), or $R^3$-substituted heteroaryl (e.g. 5 to 10 membered heteroaryl, 5 to 9 membered heteroaryl, or 5 to 6 membered heteroaryl). In embodiments, $R^4$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{36}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{37}$-substituted or unsubstituted alkyl (e.g. $C_1$-$C_8$ alkyl, $C_1$-$C_6$ alkyl, or $C_1$-$C_4$ alkyl), $R^{37}$-substituted or unsubstituted heteroalkyl (e.g. 2 to 8 membered heteroalkyl, 2 to 6 membered heteroalkyl, or 2 to 4 membered heteroalkyl), $R^{37}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{37}$-substituted or unsubstituted heterocycloalkyl (e.g. 3 to 8 membered heterocycloalkyl, 4 to 8 membered heterocycloalkyl, or 5 to 6 membered heterocycloalkyl), $R^{37}$-substituted or unsubstituted aryl (e.g. $C_6$-$C_{10}$ aryl, $C_{10}$ aryl or phenyl), or $R^{37}$-substituted or unsubstituted heteroaryl (e.g. 5 to 10 membered heteroaryl, 5 to 9 membered heteroaryl, or 5 to 6 membered heteroaryl). In embodiments, $R^{36}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{37}$-substituted alkyl (e.g. $C_1$-$C_8$ alkyl, $C_1$-$C_6$ alkyl, or $C_1$-$C_4$ alkyl), $R^{37}$-substituted heteroalkyl (e.g. 2 to 8 membered heteroalkyl, 2 to 6 membered heteroalkyl, or 2 to 4 membered heteroalkyl), $R^{37}$-substituted cycloalkyl (e.g. $C_3$-$C_8$ cycloalkyl, $C_4$-$C_8$ cycloalkyl, or $C_5$-$C_6$ cycloalkyl), $R^{37}$-substituted heterocycloalkyl (e.g. 3 to 8 membered heterocycloalkyl, 4 to 8 membered heterocycloalkyl, or 5 to 6 membered heterocycloalkyl), $R^{37}$-substituted aryl (e.g. $C_6$-$C_{10}$ aryl, $C_{10}$ aryl or phenyl), or $R^{37}$-substituted heteroaryl (e.g. 5 to 10 membered heteroaryl, 5 to 9 membered heteroaryl, or 5 to 6 membered heteroaryl). In embodiments, $R^{36}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{37}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{38}$-substituted or unsubstituted alkyl (e.g. $C_1$-$C_8$ alkyl, $C_1$-$C_6$ alkyl, or $C_1$-$C_4$ alkyl), $R^{38}$-substituted or unsubstituted heteroalkyl (e.g. 2 to 8 membered heteroalkyl, 2 to 6 membered heteroalkyl, or 2 to 4 membered heteroalkyl), $R^{38}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{38}$-substituted or unsubstituted heterocycloalkyl (e.g. 3 to 8 membered heterocycloalkyl, 4 to 8 membered heterocycloalkyl, or 5 to 6 membered heterocycloalkyl), $R^{38}$-substituted or unsubstituted aryl (e.g. $C_6$-$C_{10}$ aryl, $C_{10}$ aryl or phenyl), or $R^{38}$-substituted or unsubstituted heteroaryl (e.g. 5 to 10 membered heteroaryl, 5 to 9 membered heteroaryl, or 5 to 6 membered heteroaryl). In embodiments, $R^{37}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{38}$-substituted alkyl (e.g. $C_1$-$C_8$ alkyl, $C_1$-$C_6$ alkyl, or $C_1$-$C_4$ alkyl), $R^{38}$-substituted heteroalkyl (e.g. 2 to 8 membered heteroalkyl, 2 to 6 membered heteroalkyl, or 2 to 4 membered heteroalkyl), $R^{38}$-substituted cycloalkyl (e.g. $C_3$-$C_8$ cycloalkyl, $C_4$-$C_8$ cycloalkyl, or $C_5$-$C_6$ cycloalkyl), $R^{38}$-substituted heterocycloalkyl (e.g. 3 to 8 membered heterocycloalkyl, 4 to 8 membered heterocycloalkyl, or 5 to 6 membered heterocycloalkyl), $R^{38}$-substituted aryl (e.g. $C_6$-$C_{10}$ aryl, $C_{10}$ aryl or phenyl), or $R^{38}$-substituted heteroaryl (e.g. 5 to 10 membered heteroaryl, 5 to 9 membered heteroaryl, or 5 to 6 membered heteroaryl). In embodiments, $R^{37}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^5$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{39}$-substituted or unsubstituted alkyl (e.g. $C_1$-$C_8$ alkyl, $C_1$-$C_6$ alkyl, or $C_1$-$C_4$ alkyl), $R^{39}$-substituted or unsubstituted heteroalkyl (e.g. 2 to 8 membered heteroalkyl, 2 to 6 membered heteroalkyl, or 2 to 4 membered heteroalkyl), $R^{39}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{39}$-substituted or unsubstituted heterocycloalkyl (e.g. 3 to 8 membered heterocycloalkyl, 4 to 8 membered heterocycloalkyl, or 5 to 6 membered heterocycloalkyl), $R^{39}$-substituted or unsubstituted aryl (e.g. $C_6$-$C_{10}$ aryl, $C_{10}$ aryl or phenyl), or $R^{39}$-substituted or unsubstituted heteroaryl (e.g. 5 to 10 membered heteroaryl, 5 to 9 membered heteroaryl, or 5 to 6 membered heteroaryl). In embodiments, $R^3$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{39}$-substituted alkyl (e.g. $C_1$-$C_8$ alkyl, $C_1$-$C_6$ alkyl, or $C_1$-$C_4$ alkyl), $R^{39}$-substituted heteroalkyl (e.g. 2 to 8 membered heteroalkyl, 2 to 6 membered heteroalkyl, or 2 to 4 membered heteroalkyl), $R^{39}$-substituted cycloalkyl (e.g. $C_3$-$C_8$ cycloalkyl, $C_4$-$C_8$ cycloalkyl, or $C_5$-$C_6$ cycloalkyl), $R^{39}$-substituted heterocycloalkyl (e.g. 3 to 8 membered heterocycloalkyl, 4 to 8 membered heterocycloalkyl, or 5 to 6 membered heterocycloalkyl), $R^{39}$-substituted aryl (e.g. $C_6$-$C_{10}$ aryl, $C_{10}$ aryl or phenyl), or $R^{39}$-substituted heteroaryl (e.g. 5 to 10 membered heteroaryl, 5 to 9 membered heteroaryl, or 5 to 6 membered heteroaryl). In embodiments, $R^5$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{39}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, Ru-substituted or unsubstituted alkyl (e.g. $C_1$-$C_8$ alkyl, $C_1$-$C_6$ alkyl, or $C_1$-$C_4$ alkyl), $R^{40}$-substituted or unsubstituted heteroalkyl (e.g. 2 to 8 membered heteroalkyl, 2 to 6 membered heteroalkyl, or 2 to 4 membered heteroalkyl), $R^{40}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{40}$-substituted or unsubstituted heterocycloalkyl (e.g. 3 to 8 membered heterocycloalkyl, 4 to 8 membered heterocycloalkyl, or 5 to 6 membered heterocycloalkyl), $R^{40}$-substituted or unsubstituted aryl (e.g. $C_6$-$C_{10}$ aryl, $C_{10}$ aryl or phenyl), or $R^{40}$-substituted or unsubstituted heteroaryl (e.g. 5 to 10 membered heteroaryl, 5 to 9 membered heteroaryl, or 5 to 6 membered heteroaryl). In embodiments, $R^{39}$ is independently oxo, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, Ru-substituted alkyl (e.g. $C_1$-$C_8$ alkyl, $C_1$-$C_6$ alkyl, or $C_1$-$C_4$ alkyl), $R^{40}$-substituted heteroalkyl (e.g. 2 to 8 membered heteroalkyl, 2 to 6 membered heteroalkyl, or 2 to 4 membered heteroalkyl), $R^{40}$-substituted cycloalkyl (e.g. $C_3$-$C_8$ cycloalkyl, $C_4$-$C_5$ cycloalkyl, or $C_5$-$C_6$ cycloalkyl), $R^{40}$-substituted heterocycloalkyl (e.g. 3 to 8 membered heterocycloalkyl, 4 to 8 membered heterocycloalkyl, or 5 to 6 membered heterocycloalkyl), $R^{40}$-substituted aryl (e.g. $C_6$-$C_{10}$ aryl, $C_{10}$ aryl or phenyl), or $R^4$-substituted heteroaryl (e.g. 5 to 10 membered heteroaryl, 5 to 9 membered heteroaryl, or 5 to 6 membered heteroaryl). In embodiments, $R^{39}$ is independently oxo, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{40}$ is independently oxo, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $R^{41}$-substituted or unsubstituted alkyl (e.g. $C_1$-$C_8$ alkyl, $C_1$-$C_6$ alkyl, or $C_1$-$C_4$ alkyl), $R^{41}$-substituted or unsubstituted heteroalkyl (e.g. 2 to 8 membered heteroalkyl, 2 to 6 membered heteroalkyl, or 2 to 4 membered heteroalkyl), $R^{41}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{41}$-substituted or unsubstituted heterocycloalkyl (e.g. 3 to 8 membered heterocycloalkyl, 4 to 8 membered heterocycloalkyl, or 5 to 6 membered heterocycloalkyl), $R^{41}$-substituted or unsubstituted aryl (e.g. $C_6$-$C_{10}$ aryl, $C_{10}$ aryl or phenyl), or $R^{41}$-substituted or unsubstituted heteroaryl (e.g. 5 to 10 membered heteroaryl, 5 to 9 membered heteroaryl, or 5 to 6 membered heteroaryl). In embodiments, $R^{40}$ is independently oxo, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $R^{41}$-substituted alkyl (e.g. $C_1$-$C_8$ alkyl, $C_1$-$C_6$ alkyl, or $C_1$-$C_4$ alkyl), $R^{41}$-substituted heteroalkyl (e.g. 2 to 8 membered heteroalkyl, 2 to 6 membered heteroalkyl, or 2 to 4 membered heteroalkyl), $R^{41}$-substituted cycloalkyl (e.g. $C_3$-$C_8$ cycloalkyl, $C_4$-$C_5$ cycloalkyl, or $C_5$-$C_6$ cycloalkyl), $R^{41}$-substituted heterocycloalkyl (e.g. 3 to 8 membered heterocycloalkyl, 4 to 8 membered heterocycloalkyl, or 5 to 6 membered heterocycloalkyl), $R^{41}$-substituted aryl (e.g. $C_6$-$C_{10}$ aryl, $C_{10}$ aryl or phenyl), or $R^{41}$-substituted heteroaryl (e.g. 5 to 10 membered heteroaryl, 5 to 9 membered heteroaryl, or 5 to 6 membered heteroaryl). In embodiments, $R^{40}$ is independently oxo, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^9$ is independently hydrogen, oxo, halogen, $-CF_3$, $-CCl_3$, $-CBr_3$, $-CI_3$, $-CHF_2$, $-CHCl_2$, $-CHBr_2$, $-CHI_2$, $-CH_2F$, $-CH_2Cl$, $-CH_2Br$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-N_3$, $R^{42}$-substituted or unsubstituted alkyl (e.g. $C_1$-$C_8$ alkyl, $C_1$-$C_6$ alkyl, or $C_1$-$C_4$ alkyl), $R^{42}$-substituted or unsubstituted heteroalkyl (e.g. 2 to 8 membered heteroalkyl, 2 to 6 membered heteroalkyl, or 2 to 4 membered heteroalkyl), $R^{42}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{42}$-substituted or unsubstituted heterocycloalkyl (e.g. 3 to 8 membered heterocycloalkyl, 4 to 8 membered heterocycloalkyl, or 5 to 6 membered heterocycloalkyl), $R^{42}$-substituted or unsubstituted aryl (e.g. $C_6$-$C_{10}$ aryl, $C_{10}$ aryl or phenyl), or $R^{42}$-substituted or unsubstituted heteroaryl (e.g. 5 to 10 membered heteroaryl, 5 to 9 membered heteroaryl, or 5 to 6 membered heteroaryl). In embodiments, $R^9$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{42}$-substituted alkyl (e.g. $C_1$-$C_8$ alkyl, $C_1$-$C_6$ alkyl, or $C_1$-$C_4$ alkyl), $R^{42}$-substituted heteroalkyl (e.g. 2 to 8 membered heteroalkyl, 2 to 6 membered heteroalkyl, or 2 to 4 membered heteroalkyl), $R^{42}$-substituted cycloalkyl (e.g. $C_3$-$C_8$ cycloalkyl, $C_4$-$C_5$ cycloalkyl, or $C_5$-$C_6$ cycloalkyl), $R^{42}$-substituted heterocycloalkyl (e.g. 3 to 8 membered heterocycloalkyl, 4 to 8 membered heterocycloalkyl, or 5 to 6 membered heterocycloalkyl), $R^{42}$-substituted aryl (e.g. $C_6$-$C_{10}$ aryl, $C_{10}$ aryl or phenyl), or $R^{42}$-substituted heteroaryl (e.g. 5 to 10 membered heteroaryl, 5 to 9 membered heteroaryl, or 5 to 6 membered heteroaryl). In embodiments, $R^9$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{42}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{43}$-substituted or unsubstituted alkyl (e.g. $C_1$-$C_8$ alkyl, $C_1$-$C_6$ alkyl, or $C_1$-$C_4$ alkyl), $R^{43}$-substituted or unsubstituted heteroalkyl (e.g. 2 to 8 membered heteroalkyl, 2 to 6 membered heteroalkyl, or 2 to 4 membered heteroalkyl), $R^{43}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{43}$-substituted or unsubstituted heterocycloalkyl (e.g. 3 to 8 membered heterocycloalkyl, 4 to 8 membered heterocycloalkyl, or 5 to 6 membered heterocycloalkyl), $R^{43}$-substituted or unsubstituted aryl (e.g. $C_6$-$C_{10}$ aryl, $C_{10}$ aryl or phenyl), or $R^{43}$-substituted or unsubstituted heteroaryl (e.g. 5 to 10 membered heteroaryl, 5 to 9 membered heteroaryl, or 5 to 6 membered heteroaryl). In embodiments, $R^{42}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{43}$-substituted alkyl (e.g. $C_1$-$C_8$ alkyl, $C_1$-$C_6$ alkyl, or $C_1$-$C_4$ alkyl), $R^{43}$-substituted heteroalkyl (e.g. 2 to 8 membered heteroalkyl, 2 to 6 membered heteroalkyl, or 2 to 4 membered heteroalkyl), $R^{43}$-substituted cycloalkyl (e.g. $C_3$-$C_8$ cycloalkyl, $C_4$-$C_5$ cycloalkyl, or $C_5$-$C_6$ cycloalkyl), $R^{43}$-substituted heterocycloalkyl (e.g. 3 to 8 membered heterocycloalkyl, 4 to 8 membered heterocycloalkyl, or 5 to 6 membered heterocycloalkyl), $R^{43}$-substituted aryl (e.g. $C_6$-$C_{10}$ aryl, $C_{10}$ aryl or phenyl), or $R^{4}$-substituted heteroaryl (e.g. 5 to 10 membered heteroaryl, 5 to 9 membered heteroaryl, or 5 to 6 membered heteroaryl). In embodiments, $R^{42}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{43}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{44}$-substituted or unsubstituted alkyl (e.g. $C_1$-$C_8$ alkyl, $C_1$-$C_6$ alkyl, or $C_1$-$C_4$ alkyl), $R^{44}$-substituted or unsubstituted heteroalkyl (e.g. 2 to 8 membered heteroalkyl, 2 to 6 membered heteroalkyl, or 2 to 4 membered heteroalkyl), $R^{44}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{44}$-substituted or unsubstituted heterocycloalkyl (e.g. 3 to 8 membered heterocycloalkyl, 4 to 8 membered heterocycloalkyl, or 5 to 6 membered heterocycloalkyl), $R^{44}$-substituted or unsubstituted aryl (e.g. $C_6$-$C_{10}$ aryl, $C_{10}$ aryl or phenyl), or $R^{44}$-substituted or unsubstituted heteroaryl (e.g. 5 to 10 membered heteroaryl, 5 to 9 membered heteroaryl, or 5 to 6 membered heteroaryl). In embodiments, $R^{43}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{44}$-substituted alkyl (e.g. $C_1$-$C_8$ alkyl, $C_1$-$C_6$ alkyl, or $C_1$-$C_4$ alkyl), $R^{44}$-substituted heteroalkyl (e.g. 2 to 8 membered heteroalkyl, 2 to 6 membered heteroalkyl, or 2 to 4 membered heteroalkyl), $R^{44}$-substituted cycloalkyl (e.g. $C_3$-$C_8$ cycloalkyl, $C_4$-$C_5$ cycloalkyl, or $C_5$-$C_6$ cycloalkyl), $R^{44}$-substituted heterocycloalkyl (e.g. 3 to 8 membered heterocycloalkyl, 4 to 8 membered heterocycloalkyl, or 5 to 6 membered heterocycloalkyl), $R^{44}$-substituted aryl (e.g. $C_6$-$C_{10}$ aryl, $C_{10}$ aryl or phenyl), or $R^{44}$-substituted heteroaryl (e.g. 5 to 10 membered heteroaryl, 5 to 9 membered heteroaryl, or 5 to 6 membered heteroaryl). In embodiments, $R^{43}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{10}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{45}$-substituted or unsubstituted alkyl (e.g. $C_1$-$C_8$ alkyl, $C_1$-$C_6$ alkyl, or $C_1$-$C_4$ alkyl), $R^{45}$-substituted or unsubstituted heteroalkyl (e.g. 2 to 8 membered heteroalkyl, 2 to 6 membered heteroalkyl, or 2 to 4 membered heteroalkyl), $R^{45}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{45}$-substituted or unsubstituted heterocycloalkyl (e.g. 3 to 8 membered heterocycloalkyl, 4 to 8 membered heterocycloalkyl, or 5 to 6 membered heterocycloalkyl), $R^{45}$-substituted or unsubstituted aryl (e.g. $C_6$-$C_{10}$ aryl, $C_{10}$ aryl or phenyl), or $R^{45}$-substituted or unsubstituted heteroaryl (e.g. 5 to 10 membered heteroaryl, 5 to 9 membered heteroaryl, or 5 to 6 membered heteroaryl). In embodiments, $R^{10}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{45}$-substituted alkyl (e.g. $C_1$-$C_8$ alkyl, $C_1$-$C_6$ alkyl, or $C_1$-$C_4$ alkyl), $R^{45}$-substituted heteroalkyl (e.g. 2 to 8 membered heteroalkyl, 2 to 6 membered heteroalkyl, or 2 to 4 membered heteroalkyl), $R^{45}$-substituted cycloalkyl (e.g. $C_3$-$C_8$ cycloalkyl, $C_4$-$C_8$ cycloalkyl, or $C_5$-$C_6$ cycloalkyl), $R^{45}$-substituted heterocycloalkyl (e.g. 3 to 8 membered heterocycloalkyl, 4 to 8 membered heterocycloalkyl, or 5 to 6 membered heterocycloalkyl), $R^{45}$-substituted aryl (e.g. $C_6$-$C_{10}$ aryl, $C_{10}$ aryl or phenyl), or $R^{4}$-substituted heteroaryl (e.g. 5 to 10 membered heteroaryl, 5 to 9 membered heteroaryl, or 5 to 6 membered heteroaryl). In embodiments, $R^{10}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{45}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC (O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{46}$-substituted or unsubstituted alkyl (e.g. $C_1$-$C_8$ alkyl, $C_1$-$C_6$ alkyl, or $C_1$-$C_4$ alkyl), $R^{46}$-substituted or unsubstituted heteroalkyl (e.g. 2 to 8 membered heteroalkyl, 2 to 6 membered heteroalkyl, or 2 to 4 membered heteroalkyl), $R^{46}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{46}$-substituted or unsubstituted heterocycloalkyl (e.g. 3 to 8 membered heterocycloalkyl, 4 to 8 membered heterocycloalkyl, or 5 to 6 membered heterocycloalkyl), $R^{46}$-substituted or unsubstituted aryl (e.g. $C_6$-$C_{10}$ aryl, $C_{10}$ aryl or phenyl), or $R^{46}$-substituted or unsubstituted heteroaryl (e.g. 5 to 10 membered heteroaryl, 5 to 9 membered heteroaryl, or 5 to 6 membered heteroaryl). In embodiments, $R^{45}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{46}$-substituted alkyl (e.g. $C_1$-$C_8$ alkyl, $C_1$-$C_6$ alkyl, or $C_1$-$C_4$ alkyl), $R^{46}$-substituted heteroalkyl (e.g. 2 to 8 membered heteroalkyl, 2 to 6 membered heteroalkyl, or 2 to 4 membered heteroalkyl), $R^{46}$-substituted cycloalkyl (e.g. $C_3$-$C_8$ cycloalkyl, $C_4$-$C_8$ cycloalkyl, or $C_5$-$C_6$ cycloalkyl), $R^{46}$-substituted heterocycloalkyl (e.g. 3 to 8 membered heterocycloalkyl, 4 to 8 membered heterocycloalkyl, or 5 to 6 membered heterocycloalkyl), $R^{46}$-substituted aryl (e.g. $C_6$-$C_{10}$ aryl, $C_{10}$ aryl or phenyl), or $R^{46}$-substituted heteroaryl (e.g. 5 to 10 membered heteroaryl, 5 to 9 membered heteroaryl, or 5 to 6 membered heteroaryl). In embodiments, $R^{45}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{46}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, $R^{47}$-substituted or unsubstituted alkyl (e.g. $C_1$-$C_8$ alkyl, $C_1$-$C_6$ alkyl, or $C_1$-$C_4$ alkyl), $R^{47}$-substituted or unsubstituted heteroalkyl (e.g. 2 to 8 membered heteroalkyl, 2 to 6 membered heteroalkyl, or 2 to 4 membered heteroalkyl), $R^{47}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{47}$-substituted or unsubstituted heterocycloalkyl (e.g. 3 to 8 membered heterocycloalkyl, 4 to 8 membered heterocycloalkyl, or 5 to 6 membered heterocycloalkyl), $R^{47}$-substituted or unsubstituted aryl (e.g. $C_6$-$C_{10}$ aryl, $C_{10}$ aryl or phenyl), or $R^{47}$-substituted or unsubstituted heteroaryl (e.g. 5 to 10 membered heteroaryl, 5 to 9 membered heteroaryl, or 5 to 6 membered heteroaryl). In embodiments, $R^6$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, $R^{47}$-substituted alkyl (e.g. $C_1$-$C_8$ alkyl, $C_1$-$C_6$ alkyl, or $C_1$-$C_4$ alkyl), $R^{47}$-substituted heteroalkyl (e.g. 2 to 8 membered heteroalkyl, 2 to 6 membered heteroalkyl, or 2 to 4 membered heteroalkyl), $R^{47}$-substituted cycloalkyl (e.g. $C_3$-$C_8$ cycloalkyl, $C_4$-$C_5$ cycloalkyl, or $C_5$-$C_6$ cycloalkyl), $R^{47}$-substituted heterocycloalkyl (e.g. 3 to 8 membered heterocycloalkyl, 4 to 8 membered heterocycloalkyl, or 5 to 6 membered heterocycloalkyl), $R^{47}$-substituted aryl (e.g. $C_6$-$C_{10}$ aryl, $C_{10}$ aryl or phenyl), or $R^{47}$-substituted heteroaryl (e.g. 5 to 10 membered heteroaryl, 5 to 9 membered heteroaryl, or 5 to 6 membered heteroaryl). In embodiments, $R^6$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{11}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{48}$-substituted or unsubstituted alkyl (e.g. $C_1$-$C_8$ alkyl, $C_1$-$C_6$ alkyl, or $C_1$-$C_4$ alkyl), $R^{48}$-substituted or unsubstituted heteroalkyl (e.g. 2 to 8 membered heteroalkyl, 2 to 6 membered heteroalkyl, or 2 to 4 membered heteroalkyl), $R^{48}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{48}$-substituted or unsubstituted heterocycloalkyl (e.g. 3 to 8 membered heterocycloalkyl, 4 to 8 membered heterocycloalkyl, or 5 to 6 membered heterocycloalkyl), $R^{48}$-substituted or unsubstituted aryl (e.g. $C_6$-$C_{10}$ aryl, $C_{10}$ aryl or phenyl), or $R^{48}$-substituted or unsubstituted heteroaryl (e.g. 5 to 10 membered heteroaryl, 5 to 9 membered heteroaryl, or 5 to 6 membered heteroaryl). In embodiments, $R^{48}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{48}$-substituted or unsubstituted alkyl (e.g. $C_1$-$C_8$ alkyl, $C_1$-$C_6$ alkyl, or $C_1$-$C_4$ alkyl), $R^{48}$-substituted or unsubstituted heteroalkyl (e.g. 2 to 8 membered heteroalkyl, 2 to 6 membered heteroalkyl, or 2 to 4 membered heteroalkyl), $R^{48}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{48}$-substituted or unsubstituted heterocycloalkyl (e.g. 3 to 8 membered heterocycloalkyl, 4 to 8 membered heterocycloalkyl, or 5 to 6 membered heterocycloalkyl), $R^{48}$-substituted or unsubstituted aryl (e.g. $C_6$-$C_{10}$ aryl or $C_6$ aryl), or $R^{48}$-substituted or unsubstituted heteroaryl (e.g. 5 to 10 membered heteroaryl, 5 to 9 membered heteroaryl, or 5 to 6 membered heteroaryl). In embodiments, $R^{11}$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, $R^{48}$-substituted alkyl (e.g. $C_1$-$C_8$ alkyl, $C_1$-$C_6$ alkyl, or $C_1$-$C_4$ alkyl), $R^{48}$-substituted heteroalkyl (e.g. 2 to 8 membered heteroalkyl, 2 to 6 membered heteroalkyl, or 2 to 4 membered heteroalkyl), $R^{48}$-substituted cycloalkyl (e.g. $C_3$-$C_8$ cycloalkyl, $C_4$-$C_8$ cycloalkyl, or $C_5$-$C_6$ cycloalkyl), $R^{48}$-substituted heterocycloalkyl (e.g. 3 to 8 membered heterocycloalkyl, 4 to 8 membered heterocycloalkyl, or 5 to 6 membered heterocycloalkyl), $R^{48}$-substituted aryl (e.g. $C_6$-$C_{10}$ aryl, $C_{10}$ aryl or phenyl), or $R^{48}$-substituted heteroaryl (e.g. 5 to 10 membered heteroaryl, 5 to 9 membered heteroaryl, or 5 to 6 membered heteroaryl). In embodiments, $R^{11}$ is independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCHF_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{48}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{49}$-substituted or unsubstituted alkyl (e.g. $C_1$-$C_8$ alkyl, $C_1$-$C_6$ alkyl, or $C_1$-$C_4$ alkyl), $R^{49}$-substituted or unsubstituted heteroalkyl (e.g. 2 to 8 membered heteroalkyl, 2 to 6 membered heteroalkyl, or 2 to 4 membered heteroalkyl), $R^{49}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{49}$-substituted or unsubstituted heterocycloalkyl (e.g. 3 to 8 membered heterocycloalkyl, 4 to 8 membered heterocycloalkyl, or 5 to 6 membered heterocycloalkyl), $R^{49}$-substituted or unsubstituted aryl (e.g. $C_6$-$C_{10}$ aryl, $C_{10}$ aryl or phenyl), or $R^{49}$-substituted or unsubstituted heteroaryl (e.g. 5 to 10 membered heteroaryl, 5 to 9 membered heteroaryl, or 5 to 6 membered heteroaryl). In embodiments, $R^{48}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{49}$-substituted alkyl (e.g. $C_1$-$C_8$ alkyl, $C_1$-$C_6$ alkyl, or $C_1$-$C_4$ alkyl), $R^{49}$-substituted heteroalkyl (e.g. 2 to 8 membered heteroalkyl, 2 to 6 membered heteroalkyl, or 2 to 4 membered heteroalkyl), $R^{49}$-substituted cycloalkyl (e.g. $C_3$-$C_8$ cycloalkyl, $C_4$-$C_5$ cycloalkyl, or $C_5$-$C_6$ cycloalkyl), $R^{49}$-substituted heterocycloalkyl (e.g. 3 to 8 membered heterocycloalkyl, 4 to 8 membered heterocycloalkyl, or 5 to 6 membered heterocycloalkyl), $R^{49}$-substituted aryl (e.g. $C_6$-$C_{10}$ aryl, $C_{10}$ aryl or phenyl), or $R^9$-substituted heteroaryl (e.g. 5 to 10 membered heteroaryl, 5 to 9 membered heteroaryl, or 5 to 6 membered heteroaryl). In embodiments, $R^{48}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{49}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, $R^{50}$-substituted or unsubstituted alkyl (e.g. $C_1$-$C_8$ alkyl, $C_1$-$C_6$ alkyl, or $C_1$-$C_4$ alkyl), $R^{50}$-substituted or unsubstituted heteroalkyl (e.g. 2 to 8 membered heteroalkyl, 2 to 6 membered heteroalkyl, or 2 to 4 membered heteroalkyl), $R^{50}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{50}$-substituted or unsubstituted heterocycloalkyl (e.g. 3 to 8 membered heterocycloalkyl, 4 to 8 membered heterocycloalkyl, or 5 to 6 membered heterocycloalkyl), $R^{50}$-substituted or unsubstituted aryl (e.g. $C_6$-$C_{10}$ aryl, $C_{10}$ aryl or phenyl), or $R^{50}$-substituted or unsubstituted heteroaryl (e.g. 5 to 10 membered heteroaryl, 5 to 9 membered heteroaryl, or 5 to 6 membered heteroaryl). In embodiments, $R^{49}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, $R^{50}$-substituted alkyl (e.g. $C_1$-$C_8$ alkyl, $C_1$-$C_6$ alkyl, or $C_1$-$C_4$ alkyl), $R^{50}$-substituted heteroalkyl (e.g. 2 to 8 membered heteroalkyl, 2 to 6 membered heteroalkyl, or 2 to 4 membered heteroalkyl), $R^{50}$-substituted cycloalkyl (e.g. $C_3$-$C_8$ cycloalkyl, $C_4$-$C_5$ cycloalkyl, or $C_5$-$C_6$ cycloalkyl), $R^{50}$-substituted heterocycloalkyl (e.g. 3 to 8 membered heterocycloalkyl, 4 to 8 membered heterocycloalkyl, or 5 to 6 membered heterocycloalkyl), $R^{50}$-substituted aryl (e.g. $C_6$-$C_{10}$ aryl, $C_{10}$ aryl or phenyl), or $R^{50}$-substituted heteroaryl (e.g. 5 to 10 membered heteroaryl, 5 to 9 membered heteroaryl, or 5 to 6 membered heteroaryl). In embodiments, $R^{49}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{12}$ is independently hydrogen, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, $R^{31}$-substituted or unsubstituted alkyl (e.g. $C_1$-$C_8$ alkyl, $C_1$-$C_6$ alkyl, or $C_1$-$C_4$ alkyl), $R^{51}$-substituted or unsubstituted heteroalkyl (e.g. 2 to 8 membered heteroalkyl, 2 to 6 membered heteroalkyl, or 2 to 4 membered heteroalkyl), $R^{31}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{31}$-substituted or unsubstituted heterocycloalkyl (e.g. 3 to 8 membered heterocycloalkyl, 4 to 8 membered heterocycloalkyl, or 5 to 6 membered heterocycloalkyl), $R^{51}$-substituted or unsubstituted aryl (e.g. $C_6$-$C_{10}$ aryl, $C_{10}$ aryl or phenyl), or $R^{51}$-substituted or unsubstituted heteroaryl (e.g. 5 to 10 membered heteroaryl, 5 to 9 membered heteroaryl, or 5 to 6 membered heteroaryl). In embodiments, $R^{12}$ is independently hydrogen, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —COOH, —CONH$_2$, $R^{11}$-substituted or unsubstituted alkyl (e.g. $C_1$-$C_8$ alkyl, $C_1$-$C_6$ alkyl, or $C_1$-$C_4$ alkyl), $R^{51}$-substituted or unsubstituted heteroalkyl (e.g. 2 to 8 membered heteroalkyl, 2 to 6 membered heteroalkyl, or 2 to 4 membered heteroalkyl), $R^{51}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{51}$-substituted or unsubstituted heterocycloalkyl (e.g. 3 to 8 membered heterocycloalkyl, 4 to 8 membered heterocycloalkyl, or 5 to 6 membered heterocycloalkyl), $R^{51}$-substituted or unsubstituted aryl (e.g. $C_6$-$C_{10}$ aryl, $C_{10}$ aryl or phenyl), or $R^{51}$-substituted or unsubstituted heteroaryl (e.g. 5 to 10 membered heteroaryl, 5 to 9 membered heteroaryl, or 5 to 6 membered heteroaryl). In embodiments, $R^{12}$ is independently hydrogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —COOH, —CONH$_2$, $R^{51}$-substituted alkyl (e.g. $C_1$-$C_8$ alkyl, $C_1$-$C_6$ alkyl, or $C_1$-$C_4$ alkyl), $R^{51}$-substituted heteroalkyl (e.g. 2 to 8 membered heteroalkyl, 2 to 6 membered heteroalkyl, or 2 to 4 membered heteroalkyl), $R^{51}$-substituted cycloalkyl (e.g. $C_3$-$C_8$ cycloalkyl, $C_4$-$C_5$ cycloalkyl, or $C_5$-$C_6$ cycloalkyl), $R^{51}$-substituted heterocycloalkyl (e.g. 3 to 8 membered heterocycloalkyl, 4 to 8 membered heterocycloalkyl, or 5 to 6 membered heterocycloalkyl), $R^{51}$-substituted aryl (e.g. $C_6$-$C_{10}$ aryl, $C_{10}$ aryl or phenyl), or $R^5$-substituted heteroaryl (e.g. 5 to 10 membered heteroaryl, 5 to 9 membered heteroaryl, or 5 to 6 membered heteroaryl). In embodiments, $R^{12}$ is independently hydrogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —COOH, —CONH$_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{51}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{52}$-substituted or unsubstituted alkyl (e.g. $C_1$-$C_8$ alkyl, $C_1$-$C_6$ alkyl, or $C_1$-$C_4$ alkyl), $R^{52}$-substituted or unsubstituted heteroalkyl (e.g. 2 to 8 membered heteroalkyl, 2 to 6 membered heteroalkyl, or 2 to 4 membered heteroalkyl), $R^{52}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{52}$-substituted or unsubstituted heterocycloalkyl (e.g. 3 to 8 membered heterocycloalkyl, 4 to 8 membered heterocycloalkyl, or 5 to 6 membered heterocycloalkyl), $R^{52}$-substituted or unsubstituted aryl (e.g. $C_6$-$C_{10}$ aryl, $C_{10}$ aryl or phenyl), or $R^{52}$-substituted or unsubstituted heteroaryl (e.g. 5 to 10 membered heteroaryl, 5 to 9 membered heteroaryl, or 5 to 6 membered heteroaryl). In embodiments, $R^{50}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{12}$-substituted alkyl (e.g. $C_1$-$C_8$ alkyl, $C_1$-$C_6$ alkyl, or $C_1$-$C_4$ alkyl), $R^{52}$-substituted heteroalkyl (e.g. 2 to 8 membered heteroalkyl, 2 to 6 membered heteroalkyl, or 2 to 4 membered heteroalkyl), $R^{52}$-substituted cycloalkyl (e.g. $C_3$-$C_8$ cycloalkyl, $C_4$-$C_8$ cycloalkyl, or $C_5$-$C_6$ cycloalkyl), $R^{52}$-substituted heterocycloalkyl (e.g. 3 to 8 membered heterocycloalkyl, 4 to 8 membered heterocycloalkyl, or 5 to 6 membered heterocycloalkyl), $R^{52}$-substituted aryl (e.g. $C_6$-$C_{10}$ aryl, $C_{10}$ aryl or phenyl), or $R^2$-substituted heteroaryl (e.g. 5 to 10 membered heteroaryl, 5 to 9 membered heteroaryl, or 5 to 6 membered heteroaryl). In embodiments, $R^{51}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{52}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{53}$-substituted or unsubstituted alkyl (e.g. $C_1$-$C_8$ alkyl, $C_1$-$C_6$ alkyl, or $C_1$-$C_4$ alkyl), $R^{53}$-substituted or unsubstituted heteroalkyl (e.g. 2 to 8 membered heteroalkyl, 2 to 6 membered heteroalkyl, or 2 to 4 membered heteroalkyl), $R^{53}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{53}$-substituted or unsubstituted heterocycloalkyl (e.g. 3 to 8 membered heterocycloalkyl, 4 to 8 membered heterocycloalkyl, or 5 to 6 membered heterocycloalkyl), $R^{53}$-substituted or unsubstituted aryl (e.g. $C_6$-$C_{10}$ aryl, $C_{10}$ aryl or phenyl), or $R^{53}$-substituted or unsubstituted heteroaryl (e.g. 5 to 10 membered heteroaryl, 5 to 9 membered heteroaryl, or 5 to 6 membered heteroaryl). In embodiments, $R^{52}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{53}$-substituted alkyl (e.g. $C_1$-$C_8$ alkyl, $C_1$-$C_6$ alkyl, or $C_1$-$C_4$ alkyl), $R^{53}$-substituted heteroalkyl (e.g. 2 to 8 membered heteroalkyl, 2 to 6 membered heteroalkyl, or 2 to 4 membered heteroalkyl), $R^{53}$-substituted cycloalkyl (e.g. $C_3$-$C_8$ cycloalkyl, $C_4$-$C_5$ cycloalkyl, or $C_5$-$C_6$ cycloalkyl), $R^{53}$-substituted heterocycloalkyl (e.g. 3 to 8 membered heterocycloalkyl, 4 to 8 membered heterocycloalkyl, or 5 to 6 membered heterocycloalkyl), $R^{53}$-substituted aryl (e.g. $C_6$-$C_{10}$ aryl, $C_{10}$ aryl or phenyl), or $R^5$-substituted heteroaryl (e.g. 5 to 10 membered heteroaryl, 5 to 9 membered heteroaryl, or 5 to 6 membered heteroaryl). In embodiments, $R^{52}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{13}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{54}$-substituted or unsubstituted alkyl (e.g. $C_1$-$C_8$ alkyl, $C_1$-$C_6$ alkyl, or $C_1$-$C_4$ alkyl), $R^{54}$-substituted or unsubstituted heteroalkyl (e.g. 2 to 8 membered heteroalkyl, 2 to 6 membered heteroalkyl, or 2 to 4 membered heteroalkyl), $R^{54}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{54}$-substituted or unsubstituted heterocycloalkyl (e.g. 3 to 8 membered heterocycloalkyl, 4 to 8 membered heterocycloalkyl, or 5 to 6 membered heterocycloalkyl), $R^{54}$-substituted or unsubstituted aryl (e.g. $C_6$-$C_{10}$ aryl, $C_{10}$ aryl or phenyl), or $R^{54}$-substituted or unsubstituted heteroaryl (e.g. 5 to 10 membered heteroaryl, 5 to 9 membered heteroaryl, or 5 to 6 membered heteroaryl). In embodiments, $R^{13}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{54}$-substituted alkyl (e.g. $C_1$-$C_8$ alkyl, $C_1$-$C_6$ alkyl, or $C_1$-$C_4$ alkyl), $R^{54}$-substituted heteroalkyl (e.g. 2 to 8 membered heteroalkyl, 2 to 6 membered heteroalkyl, or 2 to 4 membered heteroalkyl), $R^{54}$-substituted cycloalkyl (e.g. $C_3$-$C_8$ cycloalkyl, $C_4$-$C_8$ cycloalkyl, or $C_5$-$C_6$ cycloalkyl), $R^{54}$-substituted heterocycloalkyl (e.g. 3 to 8 membered heterocycloalkyl, 4 to 8 membered heterocycloalkyl, or 5 to 6 membered heterocycloalkyl), $R^{54}$-substituted aryl (e.g. $C_6$-$C_{10}$ aryl, $C_{10}$ aryl or phenyl), or $R^{54}$-substituted heteroaryl (e.g. 5 to 10 membered heteroaryl, 5 to 9 membered heteroaryl, or 5 to 6 membered heteroaryl). In embodiments, $R^{13}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^1$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{11}$-substituted or unsubstituted alkyl (e.g. $C_1$-$C_8$ alkyl, $C_1$-$C_6$ alkyl, or $C_1$-$C_4$ alkyl), $R^{55}$-substituted or unsubstituted heteroalkyl (e.g. 2 to 8 membered heteroalkyl, 2 to 6 membered heteroalkyl, or 2 to 4 membered heteroalkyl), $R^{15}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{15}$-substituted or unsubstituted heterocycloalkyl (e.g. 3 to 8 membered heterocycloalkyl, 4 to 8 membered heterocycloalkyl, or 5 to 6 membered heterocycloalkyl), $R^{55}$-substituted or unsubstituted aryl (e.g. $C_6$-$C_{10}$ aryl, $C_{10}$ aryl or phenyl), or $R^{55}$-substituted or unsubstituted heteroaryl (e.g. 5 to 10 membered heteroaryl, 5 to 9 membered heteroaryl, or 5 to 6 membered heteroaryl). In embodiments, $R^{54}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{15}$-substituted alkyl (e.g. $C_1$-$C_8$ alkyl, $C_1$-$C_6$ alkyl, or $C_1$-$C_4$ alkyl), $R^{55}$-substituted heteroalkyl (e.g. 2 to 8 membered heteroalkyl, 2 to 6 membered heteroalkyl, or 2 to 4 membered heteroalkyl), $R^{55}$-substituted cycloalkyl (e.g. $C_3$-$C_8$ cycloalkyl, $C_4$-$C_5$ cycloalkyl, or $C_5$-$C_6$ cycloalkyl), $R^{55}$-substituted heterocycloalkyl (e.g. 3 to 8 membered heterocycloalkyl, 4 to 8 membered heterocycloalkyl, or 5 to 6 membered heterocycloalkyl), $R^{55}$-substituted aryl (e.g. $C_6$-$C_{10}$ aryl, $C_{10}$ aryl or phenyl), or $R^{55}$-substituted heteroaryl (e.g. 5 to 10 membered heteroaryl, 5 to 9 membered heteroaryl, or 5 to 6 membered heteroaryl). In embodiments, $R^{54}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{55}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{56}$-substituted or unsubstituted alkyl (e.g. $C_1$-$C_8$ alkyl, $C_1$-$C_6$ alkyl, or $C_1$-$C_4$ alkyl), $R^{56}$-substituted or unsubstituted heteroalkyl (e.g. 2 to 8 membered heteroalkyl, 2 to 6 membered heteroalkyl, or 2 to 4 membered heteroalkyl), $R^{M}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{56}$-substituted or unsubstituted heterocycloalkyl (e.g. 3 to 8 membered heterocycloalkyl, 4 to 8 membered heterocycloalkyl, or 5 to 6 membered heterocycloalkyl), $R^{56}$-substituted or unsubstituted aryl (e.g. $C_6$-$C_{10}$ aryl, $C_{10}$ aryl or phenyl), or $R^{56}$-substituted or unsubstituted heteroaryl (e.g. 5 to 10 membered heteroaryl, 5 to 9 membered heteroaryl, or 5 to 6 membered heteroaryl). In embodiments, $R^{55}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{56}$-substituted alkyl (e.g. $C_1$-$C_8$ alkyl, $C_1$-$C_6$ alkyl, or $C_1$-$C_4$ alkyl), $R^{56}$-substituted heteroalkyl (e.g. 2 to 8 membered heteroalkyl, 2 to 6 membered heteroalkyl, or 2 to 4 membered heteroalkyl), $R^{56}$-substituted cycloalkyl (e.g. $C_3$-$C_8$ cycloalkyl, $C_4$-$C_5$ cycloalkyl, or $C_5$-$C_6$ cycloalkyl), $R^{56}$-substituted heterocycloalkyl (e.g. 3 to 8 membered heterocycloalkyl, 4 to 8 membered heterocycloalkyl, or 5 to 6 membered heterocycloalkyl), $R^{56}$-substituted aryl (e.g. $C_6$-$C_{10}$ aryl, $C_{10}$ aryl or phenyl), or R-substituted heteroaryl (e.g. 5 to 10 membered heteroaryl, 5 to 9 membered heteroaryl, or 5 to 6 membered heteroaryl). In embodiments, $R^{55}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{14}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{17}$-substituted or unsubstituted alkyl (e.g. $C_1$-$C_8$ alkyl, $C_1$-$C_6$ alkyl, or $C_1$-$C_4$ alkyl), $R^{17}$-substituted or unsubstituted heteroalkyl (e.g. 2 to 8 membered heteroalkyl, 2 to 6 membered heteroalkyl, or 2 to 4 membered heteroalkyl), $R^{57}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{17}$-substituted or unsubstituted heterocycloalkyl (e.g. 3 to 8 membered heterocycloalkyl, 4 to 8 membered heterocycloalkyl, or 5 to 6 membered heterocycloalkyl), $R^{57}$-substituted or unsubstituted aryl (e.g. $C_6$-$C_{10}$ aryl, $C_{10}$ aryl or phenyl), or $R^{57}$-substituted or unsubstituted heteroaryl (e.g. 5 to 10 membered heteroaryl, 5 to 9 membered heteroaryl, or 5 to 6 membered heteroaryl). In embodiments, $R^4$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{17}$-substituted alkyl (e.g. $C_1$-$C_8$ alkyl, $C_1$-$C_6$ alkyl, or $C_1$-$C_4$ alkyl), $R^{17}$-substituted heteroalkyl (e.g. 2 to 8 membered heteroalkyl, 2 to 6 membered heteroalkyl, or 2 to 4 membered heteroalkyl), $R^{17}$-substituted cycloalkyl (e.g. $C_3$-$C_8$ cycloalkyl, $C_4$-$C_8$ cycloalkyl, or $C_5$-$C_6$ cycloalkyl), $R^{17}$-substituted heterocycloalkyl (e.g. 3 to 8 membered heterocycloalkyl, 4 to 8 membered heterocycloalkyl, or 5 to 6 membered heterocycloalkyl), $R^{17}$-substituted aryl (e.g. $C_6$-$C_{10}$ aryl, $C_{10}$ aryl or phenyl), or $R^{57}$-substituted heteroaryl (e.g. 5 to 10 membered heteroaryl, 5 to 9 membered heteroaryl, or 5 to 6 membered heteroaryl). In embodiments, $R^4$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^7$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{38}$-substituted or unsubstituted alkyl (e.g. $C_1$-$C_8$ alkyl, $C_1$-$C_6$ alkyl, or $C_1$-$C_4$ alkyl), $R^{18}$-substituted or unsubstituted heteroalkyl (e.g. 2 to 8 membered heteroalkyl, 2 to 6 membered heteroalkyl, or 2 to 4 membered heteroalkyl), $R^{35}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{58}$-substituted or unsubstituted heterocycloalkyl (e.g. 3 to 8 membered heterocycloalkyl, 4 to 8 membered heterocycloalkyl, or 5 to 6 membered heterocycloalkyl), $R^{58}$-substituted or unsubstituted aryl (e.g. $C_6$-$C_{10}$ aryl, $C_{10}$ aryl or phenyl), or $R^{58}$-substituted or unsubstituted heteroaryl (e.g. 5 to 10 membered heteroaryl, 5 to 9 membered heteroaryl, or 5 to 6 membered heteroaryl). In embodiments, $R^{57}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{58}$-substituted alkyl (e.g. $C_1$-$C_8$ alkyl, $C_1$-$C_6$ alkyl, or $C_1$-$C_4$ alkyl), $R^{58}$-substituted heteroalkyl (e.g. 2 to 8 membered heteroalkyl, 2 to 6 membered heteroalkyl, or 2 to 4 membered heteroalkyl), $R^{58}$-substituted cycloalkyl (e.g. $C_3$-$C_8$ cycloalkyl, $C_4$-$C_5$ cycloalkyl, or $C_5$-$C_6$ cycloalkyl), $R^{58}$-substituted heterocycloalkyl (e.g. 3 to 8 membered heterocycloalkyl, 4 to 8 membered heterocycloalkyl, or 5 to 6 membered heterocycloalkyl), $R^{58}$-substituted aryl (e.g. $C_6$-$C_{10}$ aryl, $C_{10}$ aryl or phenyl), or $R^5$-substituted heteroaryl (e.g. 5 to 10 membered heteroaryl, 5 to 9 membered heteroaryl, or 5 to 6 membered heteroaryl). In embodiments, $R^{11}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{58}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{19}$-substituted or unsubstituted alkyl (e.g. $C_1$-$C_8$ alkyl, $C_1$-$C_6$ alkyl, or $C_1$-$C_4$ alkyl), $R^{19}$-substituted or unsubstituted heteroalkyl (e.g. 2 to 8 membered heteroalkyl, 2 to 6 membered heteroalkyl, or 2 to 4 membered heteroalkyl), $R^9$-substituted or unsubstituted cycloalkyl (e.g. $C_3$-$C_8$ cycloalkyl, $C_4$-$C_8$ cycloalkyl, or $C_5$-$C_6$ cycloalkyl), $R^{19}$-substituted or unsubstituted heterocycloalkyl (e.g. 3 to 8 membered heterocycloalkyl, 4 to 8 membered heterocycloalkyl, or 5 to 6 membered heterocycloalkyl), $R^{59}$-substituted or unsubstituted aryl (e.g. $C_6$-$C_{10}$ aryl, $C_{10}$ aryl or phenyl), or $R^{59}$-substituted or unsubstituted heteroaryl (e.g. 5 to 10 membered heteroaryl, 5 to 9 membered heteroaryl, or 5 to 6 membered heteroaryl). In embodiments, $R^3$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{19}$-substituted alkyl (e.g. $C_1$-$C_8$ alkyl, $C_1$-$C_6$ alkyl, or $C_1$-$C_4$ alkyl), $R^{19}$-substituted heteroalkyl (e.g. 2 to 8 membered heteroalkyl, 2 to 6 membered heteroalkyl, or 2 to 4 membered heteroalkyl), $R^{19}$-substituted cycloalkyl (e.g. $C_3$-$C_8$ cycloalkyl, $C_4$-$C_5$ cycloalkyl, or $C_5$-$C_6$ cycloalkyl), $R^{19}$-substituted heterocycloalkyl (e.g. 3 to 8 membered heterocycloalkyl, 4 to 8 membered heterocycloalkyl, or 5 to 6 membered heterocycloalkyl), $R^{19}$-substituted aryl (e.g. $C_6$-$C_{10}$ aryl, $C_{10}$ aryl or phenyl), or $R^9$-substituted heteroaryl (e.g. 5 to 10 membered heteroaryl, 5 to 9 membered heteroaryl, or 5 to 6 membered heteroaryl). In embodiments, $R^{35}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{15}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{60}$-substituted or unsubstituted alkyl (e.g. $C_1$-$C_8$ alkyl, $C_1$-$C_6$ alkyl, or $C_1$-$C_4$ alkyl), $R^{60}$-substituted or unsubstituted heteroalkyl (e.g. 2 to 8 membered heteroalkyl, 2 to 6 membered heteroalkyl, or 2 to 4 membered heteroalkyl), $R^{60}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{60}$-substituted or unsubstituted heterocycloalkyl (e.g. 3 to 8 membered heterocycloalkyl, 4 to 8 membered heterocycloalkyl, or 5 to 6 membered heterocycloalkyl), $R^{60}$-substituted or unsubstituted aryl (e.g. $C_6$-$C_{10}$ aryl, $C_{10}$ aryl or phenyl), or $R^{60}$-substituted or unsubstituted heteroaryl (e.g. 5 to 10 membered heteroaryl, 5 to 9 membered heteroaryl, or 5 to 6 membered heteroaryl). In embodiments, $R^{15}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{60}$-substituted or unsubstituted alkyl (e.g. $C_1$-$C_8$ alkyl, $C_1$-$C_6$ alkyl, or $C_1$-$C_4$ alkyl), $R^{60}$-substituted or unsubstituted heteroalkyl (e.g. 2 to 8 membered heteroalkyl, 2 to 6 membered heteroalkyl, or 2 to 4 membered heteroalkyl), $R^{60}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{60}$-substituted or unsubstituted heterocycloalkyl (e.g. 3 to 8 membered heterocycloalkyl, 4 to 8 membered heterocycloalkyl, or 5 to 6 membered heterocycloalkyl), $R^{60}$-substituted or unsubstituted aryl (e.g. $C_6$-$C_{10}$ aryl, $C_{10}$ aryl or phenyl), or $R^{60}$-substituted or unsubstituted heteroaryl (e.g. 5 to 10 membered heteroaryl, 5 to 9 membered heteroaryl, or 5 to 6 membered heteroaryl). In embodiments, $R^{15}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{60}$-substituted alkyl (e.g. $C_1$-$C_8$ alkyl, $C_1$-$C_6$ alkyl, or $C_1$-$C_4$ alkyl), $R^{60}$-substituted heteroalkyl (e.g. 2 to 8 membered heteroalkyl, 2 to 6 membered heteroalkyl, or 2 to 4 membered heteroalkyl), $R^{60}$-substituted cycloalkyl (e.g. $C_3$-$C_8$ cycloalkyl, $C_4$-$C_5$ cycloalkyl, or $C_5$-$C_6$ cycloalkyl), $R^{60}$-substituted heterocycloalkyl (e.g. 3 to 8 membered heterocycloalkyl, 4 to 8 membered heterocycloalkyl, or 5 to 6 membered heterocycloalkyl), $R^{60}$-substituted aryl (e.g. $C_6$-$C_{10}$ aryl, $C_{10}$ aryl or phenyl), or $R^{60}$-substituted heteroaryl (e.g. 5 to 10 membered heteroaryl, 5 to 9 membered heteroaryl, or 5 to 6 membered heteroaryl). In embodiments, $R^{15}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{60}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{61}$-substituted or unsubstituted alkyl (e.g. $C_1$-$C_8$ alkyl, $C_1$-$C_6$ alkyl, or $C_1$-$C_4$ alkyl), $R^{61}$-substituted or unsubstituted heteroalkyl (e.g. 2 to 8 membered heteroalkyl, 2 to 6 membered heteroalkyl, or 2 to 4 membered heteroalkyl), $R^{61}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{61}$-substituted or unsubstituted heterocycloalkyl (e.g. 3 to 8 membered heterocycloalkyl, 4 to 8 membered heterocycloalkyl, or 5 to 6 membered heterocycloalkyl), $R^{61}$-substituted or unsubstituted aryl (e.g. $C_6$-$C_{10}$ aryl, $C_{10}$ aryl or phenyl), or $R^{61}$-substituted or unsubstituted heteroaryl (e.g. 5 to 10 membered heteroaryl, 5 to 9 membered heteroaryl, or 5 to 6 membered heteroaryl). In embodiments, $R^6$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{61}$-substituted alkyl (e.g. $C_1$-$C_8$ alkyl, $C_1$-$C_6$ alkyl, or $C_1$-$C_4$ alkyl), $R^{61}$-substituted heteroalkyl (e.g. 2 to 8 membered heteroalkyl, 2 to 6 membered heteroalkyl, or 2 to 4 membered heteroalkyl), $R^{61}$-substituted cycloalkyl (e.g. $C_3$-$C_8$ cycloalkyl, $C_4$-$C_5$ cycloalkyl, or $C_5$-$C_6$ cycloalkyl), $R^{61}$-substituted heterocycloalkyl (e.g. 3 to 8 membered heterocycloalkyl, 4 to 8 membered heterocycloalkyl, or 5 to 6 membered heterocycloalkyl), $R^{61}$-substituted aryl (e.g. $C_6$-$C_{10}$ aryl, $C_{10}$ aryl or phenyl), or $R^{61}$-substituted heteroaryl (e.g. 5 to 10 membered heteroaryl, 5 to 9 membered heteroaryl, or 5 to 6 membered heteroaryl). In embodiments, $R^6$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{61}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{62}$-substituted or unsubstituted alkyl (e.g. $C_1$-$C_8$ alkyl, $C_1$-$C_6$ alkyl, or $C_1$-$C_4$ alkyl), $R^{62}$-substituted or unsubstituted heteroalkyl (e.g. 2 to 8 membered heteroalkyl, 2 to 6 membered heteroalkyl, or 2 to 4 membered heteroalkyl), $R^{62}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{62}$-substituted or unsubstituted heterocycloalkyl (e.g. 3 to 8 membered heterocycloalkyl, 4 to 8 membered heterocycloalkyl, or 5 to 6 membered heterocycloalkyl), $R^{62}$-substituted or unsubstituted aryl (e.g. $C_6$-$C_{10}$ aryl, $C_{10}$ aryl or phenyl), or $R^{62}$-substituted or unsubstituted heteroaryl (e.g. 5 to 10 membered heteroaryl, 5 to 9 membered heteroaryl, or 5 to 6 membered heteroaryl). In embodiments, $R^{61}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{62}$-substituted alkyl (e.g. $C_1$-$C_8$ alkyl, $C_1$-$C_6$ alkyl, or $C_1$-$C_4$ alkyl), $R^{62}$-substituted heteroalkyl (e.g. 2 to 8 membered heteroalkyl, 2 to 6 membered heteroalkyl, or 2 to 4 membered heteroalkyl), $R^{62}$-substituted cycloalkyl (e.g. $C_3$-$C_8$ cycloalkyl, $C_4$-$C_8$ cycloalkyl, or $C_5$-$C_6$ cycloalkyl), $R^{62}$-substituted heterocycloalkyl (e.g. 3 to 8 membered heterocycloalkyl, 4 to 8 membered heterocycloalkyl, or 5 to 6 membered heterocycloalkyl), $R^{62}$-substituted aryl (e.g. $C_6$-$C_{10}$ aryl, $C_{10}$ aryl or phenyl), or $R^{62}$-substituted heteroaryl (e.g. 5 to 10 membered heteroaryl, 5 to 9 membered heteroaryl, or 5 to 6 membered heteroaryl). In embodiments, $R^{61}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{16}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{63}$-substituted or unsubstituted alkyl (e.g. $C_1$-$C_8$ alkyl, $C_1$-$C_6$ alkyl, or $C_1$-$C_4$ alkyl), $R^{63}$-substituted or unsubstituted heteroalkyl (e.g. 2 to 8 membered heteroalkyl, 2 to 6 membered heteroalkyl, or 2 to 4 membered heteroalkyl), $R^{63}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{63}$-substituted or unsubstituted heterocycloalkyl (e.g. 3 to 8 membered heterocycloalkyl, 4 to 8 membered heterocycloalkyl, or 5 to 6 membered heterocycloalkyl), $R^{63}$-substituted or unsubstituted aryl (e.g. $C_6$-$C_{10}$ aryl, $C_{10}$ aryl or phenyl), or $R^{63}$-substituted or unsubstituted heteroaryl (e.g. 5 to 10 membered heteroaryl, 5 to 9 membered heteroaryl, or 5 to 6 membered heteroaryl). In embodiments, $R^{16}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{63}$-substituted or unsubstituted alkyl (e.g. $C_1$-$C_8$ alkyl, $C_1$-$C_6$ alkyl, or $C_1$-$C_4$ alkyl), $R^{63}$-substituted or unsubstituted heteroalkyl (e.g. 2 to 8 membered heteroalkyl, 2 to 6 membered heteroalkyl, or 2 to 4 membered heteroalkyl), $R^{63}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{63}$-substituted or unsubstituted heterocycloalkyl (e.g. 3 to 8 membered heterocycloalkyl, 4 to 8 membered heterocycloalkyl, or 5 to 6 membered heterocycloalkyl), $R^{63}$-substituted or unsubstituted aryl (e.g. $C_6$-$C_{10}$ aryl, $C_{10}$ aryl or phenyl), or $R^{63}$-substituted or unsubstituted heteroaryl (e.g. 5 to 10 membered heteroaryl, 5 to 9 membered heteroaryl, or 5 to 6 membered heteroaryl). In embodiments, $R^{16}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{63}$-substituted alkyl (e.g. $C_1$-$C_8$ alkyl, $C_1$-$C_6$ alkyl, or $C_1$-$C_4$ alkyl), $R^{63}$-substituted heteroalkyl (e.g. 2 to 8 membered heteroalkyl, 2 to 6 membered heteroalkyl, or 2 to 4 membered heteroalkyl), $R^{63}$-substituted cycloalkyl (e.g. $C_3$-$C_8$ cycloalkyl, $C_4$-$C_5$ cycloalkyl, or $C_5$-$C_6$ cycloalkyl), $R^{63}$-substituted heterocycloalkyl (e.g. 3 to 8 membered heterocycloalkyl, 4 to 8 membered heterocycloalkyl, or 5 to 6 membered heterocycloalkyl), $R^{63}$-substituted aryl (e.g. $C_6$-$C_{10}$ aryl, $C_{10}$ aryl or phenyl), or $R^{63}$-substituted heteroaryl (e.g. 5 to 10 membered heteroaryl, 5 to 9 membered heteroaryl, or 5 to 6 membered heteroaryl). In embodiments, $R^{16}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{63}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{64}$-substituted or unsubstituted alkyl (e.g. $C_1$-$C_8$ alkyl, $C_1$-$C_6$ alkyl, or $C_1$-$C_4$ alkyl), $R^{64}$-substituted or unsubstituted heteroalkyl (e.g. 2 to 8 membered heteroalkyl, 2 to 6 membered heteroalkyl, or 2 to 4 membered heteroalkyl), $R^{64}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{64}$-substituted or unsubstituted heterocycloalkyl (e.g. 3 to 8 membered heterocycloalkyl, 4 to 8 membered heterocycloalkyl, or 5 to 6 membered heterocycloalkyl), $R^{64}$-substituted or unsubstituted aryl (e.g. $C_6$-$C_{10}$ aryl, $C_{10}$ aryl or phenyl), or $R^{64}$-substituted or unsubstituted heteroaryl (e.g. 5 to 10 membered heteroaryl, 5 to 9 membered heteroaryl, or 5 to 6 membered heteroaryl). In embodiments, $R^{63}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{64}$-substituted alkyl (e.g. $C_1$-$C_8$ alkyl, $C_1$-$C_6$ alkyl, or $C_1$-$C_4$ alkyl), $R^{64}$-substituted heteroalkyl (e.g. 2 to 8 membered heteroalkyl, 2 to 6 membered heteroalkyl, or 2 to 4 membered heteroalkyl), $R^{64}$-substituted cycloalkyl (e.g. $C_3$-$C_8$ cycloalkyl, $C_4$-$C_8$ cycloalkyl, or $C_5$-$C_6$ cycloalkyl), $R^{64}$-substituted heterocycloalkyl (e.g. 3 to 8 membered heterocycloalkyl, 4 to 8 membered heterocycloalkyl, or 5 to 6 membered heterocycloalkyl), $R^{64}$-substituted aryl (e.g. $C_6$-$C_{10}$ aryl, $C_{10}$ aryl or phenyl), or $R^{64}$-substituted heteroaryl (e.g. 5 to 10 membered heteroaryl, 5 to 9 membered heteroaryl, or 5 to 6 membered heteroaryl). In embodiments, $R^{63}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{64}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{61}$-substituted or unsubstituted alkyl (e.g. $C_1$-$C_8$ alkyl, $C_1$-$C_6$ alkyl, or $C_1$-$C_4$ alkyl), $R^{65}$-substituted or unsubstituted heteroalkyl (e.g. 2 to 8 membered heteroalkyl, 2 to 6 membered heteroalkyl, or 2 to 4 membered heteroalkyl), $R^{65}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{65}$-substituted or unsubstituted heterocycloalkyl (e.g. 3 to 8 membered heterocycloalkyl, 4 to 8 membered heterocycloalkyl, or 5 to 6 membered heterocycloalkyl), $R^{65}$-substituted or unsubstituted aryl (e.g. $C_6$-$C_{10}$ aryl, $C_{10}$ aryl or phenyl), or $R^{65}$-substituted or unsubstituted heteroaryl (e.g. 5 to 10 membered heteroaryl, 5 to 9 membered heteroaryl, or 5 to 6 membered heteroaryl). In embodiments, $R^{64}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{65}$-substituted alkyl (e.g. $C_1$-$C_8$ alkyl, $C_1$-$C_6$ alkyl, or $C_1$-$C_4$ alkyl), $R^{65}$-substituted heteroalkyl (e.g. 2 to 8 membered heteroalkyl, 2 to 6 membered heteroalkyl, or 2 to 4 membered heteroalkyl), $R^{65}$-substituted cycloalkyl (e.g. $C_3$-$C_8$ cycloalkyl, $C_4$-$C_5$ cycloalkyl, or $C_5$-$C_6$ cycloalkyl), $R^{65}$-substituted heterocycloalkyl (e.g. 3 to 8 membered heterocycloalkyl, 4 to 8 membered heterocycloalkyl, or 5 to 6 membered heterocycloalkyl), $R^{65}$-substituted aryl (e.g. $C_6$-$C_{10}$ aryl, $C_{10}$ aryl or phenyl), or $R^{65}$-substituted heteroaryl (e.g. 5 to 10 membered heteroaryl, 5 to 9 membered heteroaryl, or 5 to 6 membered heteroaryl). In embodiments, $R^{64}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^7$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{66}$-substituted or unsubstituted alkyl (e.g. $C_1$-$C_8$ alkyl, $C_1$-$C_6$ alkyl, or $C_1$-$C_4$ alkyl), $R^{66}$-substituted or unsubstituted heteroalkyl (e.g. 2 to 8 membered heteroalkyl, 2 to 6 membered heteroalkyl, or 2 to 4 membered heteroalkyl), $R^{66}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{66}$-substituted or unsubstituted heterocycloalkyl (e.g. 3 to 8 membered heterocycloalkyl, 4 to 8 membered heterocycloalkyl, or 5 to 6 membered heterocycloalkyl), $R^{66}$-substituted or unsubstituted aryl (e.g. $C_6$-$C_{10}$ aryl, $C_{10}$ aryl or phenyl), or $R^{66}$-substituted or unsubstituted heteroaryl (e.g. 5 to 10 membered heteroaryl, 5 to 9 membered heteroaryl, or 5 to 6 membered heteroaryl). In embodiments, $R^7$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{66}$-substituted or unsubstituted alkyl (e.g. $C_1$-$C_8$ alkyl, $C_1$-$C_6$ alkyl, or $C_1$-$C_4$ alkyl), $R^{66}$-substituted or unsubstituted heteroalkyl (e.g. 2 to 8 membered heteroalkyl, 2 to 6 membered heteroalkyl, or 2 to 4 membered heteroalkyl), $R^{66}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{66}$-substituted or unsubstituted heterocycloalkyl (e.g. 3 to 8 membered heterocycloalkyl, 4 to 8 membered heterocycloalkyl, or 5 to 6 membered heterocycloalkyl), $R^{66}$-substituted or unsubstituted aryl (e.g. $C_6$-$C_{10}$ aryl, $C_{10}$ aryl or phenyl), or $R^{66}$-substituted or unsubstituted heteroaryl (e.g. 5 to 10 membered heteroaryl, 5 to 9 membered heteroaryl, or 5 to 6 membered heteroaryl). In embodiments, $R^7$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{66}$-substituted alkyl (e.g. $C_1$-$C_8$ alkyl, $C_1$-$C_6$ alkyl, or $C_1$-$C_4$ alkyl), $R^{66}$-substituted heteroalkyl (e.g. 2 to 8 membered heteroalkyl, 2 to 6 membered heteroalkyl, or 2 to 4 membered heteroalkyl), $R^{66}$-substituted cycloalkyl (e.g. $C_3$-$C_8$ cycloalkyl, $C_4$-$C_8$ cycloalkyl, or $C_5$-$C_6$ cycloalkyl), $R^{66}$-substituted heterocycloalkyl (e.g. 3 to 8 membered heterocycloalkyl, 4 to 8 membered heterocycloalkyl, or 5 to 6 membered heterocycloalkyl), $R^{66}$-substituted aryl (e.g. $C_6$-$C_{10}$ aryl, $C_{10}$ aryl or phenyl), or $R^{66}$-substituted heteroaryl (e.g. 5 to 10 membered heteroaryl, 5 to 9 membered heteroaryl, or 5 to 6 membered heteroaryl). In embodiments, $R^{17}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{66}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{67}$-substituted or unsubstituted alkyl (e.g. $C_1$-$C_8$ alkyl, $C_1$-$C_6$ alkyl, or $C_1$-$C_4$ alkyl), $R^{67}$-substituted or unsubstituted heteroalkyl (e.g. 2 to 8 membered heteroalkyl, 2 to 6 membered heteroalkyl, or 2 to 4 membered heteroalkyl), $R^{67}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{67}$-substituted or unsubstituted heterocycloalkyl (e.g. 3 to 8 membered heterocycloalkyl, 4 to 8 membered heterocycloalkyl, or 5 to 6 membered heterocycloalkyl), $R^{67}$-substituted or unsubstituted aryl (e.g. $C_6$-$C_{10}$ aryl, $C_{10}$ aryl or phenyl), or $R^{67}$-substituted or unsubstituted heteroaryl (e.g. 5 to 10 membered heteroaryl, 5 to 9 membered heteroaryl, or 5 to 6 membered heteroaryl). In embodiments, $R^{66}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{67}$-substituted alkyl (e.g. $C_1$-$C_8$ alkyl, $C_1$-$C_6$ alkyl, or $C_1$-$C_4$ alkyl), $R^{67}$-substituted heteroalkyl (e.g. 2 to 8 membered heteroalkyl, 2 to 6 membered heteroalkyl, or 2 to 4 membered heteroalkyl), $R^{67}$-substituted cycloalkyl (e.g. $C_3$-$C_8$ cycloalkyl, $C_4$-$C_5$ cycloalkyl, or $C_5$-$C_6$ cycloalkyl), $R^{67}$-substituted heterocycloalkyl (e.g. 3 to 8 membered heterocycloalkyl, 4 to 8 membered heterocycloalkyl, or 5 to 6 membered heterocycloalkyl), $R^{67}$-substituted aryl (e.g. $C_6$-$C_{10}$ aryl, $C_{10}$ aryl or phenyl), or $R^{67}$-substituted heteroaryl (e.g. 5 to 10 membered heteroaryl, 5 to 9 membered heteroaryl, or 5 to 6 membered heteroaryl). In embodiments, $R^{66}$ is independently oxo, halogen, $—CF_3$, $—CCl_3$, $—CBr_3$, $—CI_3$, $—CHF_2$, $—CHCl_2$, $—CHBr_2$, $—CHI_2$, $—CH_2F$, $—CH_2Cl$, $—CH_2Br$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)—OH, —NHOH, $—OCF_3$, $—OCCl_3$, $—OCBr_3$, $—OCI_3$, $—OCHF_2$, $—OCHCl_2$, $—OCHBr_2$, $—OCHI_2$, $—OCH_2F$, $—OCH_2Cl$, $—OCH_2Br$, $—OCH_2I$, $—N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{67}$ is independently oxo, halogen, $—CF_3$, $—CCl_3$, $—CBr_3$, $—CI_3$, $—CHF_2$, $—CHCl_2$, $—CHBr_2$, $—CHI_2$, $—CH_2F$, $—CH_2Cl$, $—CH_2Br$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)—OH, —NHOH, $—OCF_3$, $—OCCl_3$, $—OCBr_3$, $—OCI_3$, $—OCHF_2$, $—OCHCl_2$, $—OCHBr_2$, $—OCHI_2$, $—OCH_2F$, $—OCH_2Cl$, $—OCH_2Br$, $—OCH_2I$, $—N_3$, $R^{68}$-substituted or unsubstituted alkyl (e.g. $C_1$-$C_8$ alkyl, $C_1$-$C_6$ alkyl, or $C_1$-$C_4$ alkyl), $R^{68}$-substituted or unsubstituted heteroalkyl (e.g. 2 to 8 membered heteroalkyl, 2 to 6 membered heteroalkyl, or 2 to 4 membered heteroalkyl), $R^{68}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{68}$-substituted or unsubstituted heterocycloalkyl (e.g. 3 to 8 membered heterocycloalkyl, 4 to 8 membered heterocycloalkyl, or 5 to 6 membered heterocycloalkyl), $R^{68}$-substituted or unsubstituted aryl (e.g. $C_6$-$C_{10}$ aryl, $C_{10}$ aryl or phenyl), or $R^{68}$-substituted or unsubstituted heteroaryl (e.g. 5 to 10 membered heteroaryl, 5 to 9 membered heteroaryl, or 5 to 6 membered heteroaryl). In embodiments, $R^{67}$ is independently oxo, halogen, $—CF_3$, $—CCl_3$, $—CBr_3$, $—CI_3$, $—CHF_2$, $—CHCl_2$, $—CHBr_2$, $—CHI_2$, $—CH_2F$, $—CH_2Cl$, $—CH_2Br$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)—OH, —NHOH, $—OCF_3$, $—OCCl_3$, $—OCBr_3$, $—OCI_3$, $—OCHF_2$, $—OCHCl_2$, $—OCHBr_2$, $—OCHI_2$, $—OCH_2F$, $—OCH_2Cl$, $—OCH_2Br$, $—OCH_2I$, $—N_3$, $R^{61}$-substituted alkyl (e.g. $C_1$-$C_8$ alkyl, $C_1$-$C_6$ alkyl, or $C_1$-$C_4$ alkyl), $R^{68}$-substituted heteroalkyl (e.g. 2 to 8 membered heteroalkyl, 2 to 6 membered heteroalkyl, or 2 to 4 membered heteroalkyl), $R^{68}$-substituted cycloalkyl (e.g. $C_3$-$C_8$ cycloalkyl, $C_4$-$C_8$ cycloalkyl, or $C_5$-$C_6$ cycloalkyl), $R^{68}$-substituted heterocycloalkyl (e.g. 3 to 8 membered heterocycloalkyl, 4 to 8 membered heterocycloalkyl, or 5 to 6 membered heterocycloalkyl), $R^{68}$-substituted aryl (e.g. $C_6$-$C_{10}$ aryl, $C_{10}$ aryl or phenyl), or $R^{68}$-substituted heteroaryl (e.g. 5 to 10 membered heteroaryl, 5 to 9 membered heteroaryl, or 5 to 6 membered heteroaryl). In embodiments, $R^{67}$ is independently oxo, halogen, $—CF_3$, $—CCl_3$, $—CBr_3$, $—CI_3$, $—CHF_2$, $—CHCl_2$, $—CHBr_2$, $—CHI_2$, $—CH_2F$, $—CH_2Cl$, $—CH_2Br$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)—OH, —NHOH, $—OCF_3$, $—OCCl_3$, $—OCBr_3$, $—OCI_3$, $—OCHF_2$, $—OCHCl_2$, $—OCHBr_2$, $—OCHI_2$, $—OCH_2F$, $—OCH_2Cl$, $—OCH_2Br$, $—OCH_2I$, $—N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{18}$ is independently hydrogen, oxo, halogen, $—CF_3$, $—CCl_3$, $—CBr_3$, $—CI_3$, $—CHF_2$, $—CHCl_2$, $—CHBr_2$, $—CHI_2$, $—CH_2F$, $—CH_2Cl$, $—CH_2Br$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)—OH, —NHOH, $—OCF_3$, $—OCCl_3$, $—OCBr_3$, $—OCI_3$, $—OCHF_2$, $—OCHCl_2$, $—OCHBr_2$, $—OCHI_2$, $—OCH_2F$, $—OCH_2Cl$, $—OCH_2Br$, $—OCH_2I$, $—N_3$, $R^{69}$-substituted or unsubstituted alkyl (e.g. $C_1$-$C_8$alkyl, $C_1$-$C_6$ alkyl, or $C_1$-$C_4$ alkyl), $R^{69}$-substituted or unsubstituted heteroalkyl (e.g. 2 to 8 membered heteroalkyl, 2 to 6 membered heteroalkyl, or 2 to 4 membered heteroalkyl), $R^{69}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{69}$-substituted or unsubstituted heterocycloalkyl (e.g. 3 to 8 membered heterocycloalkyl, 4 to 8 membered heterocycloalkyl, or 5 to 6 membered heterocycloalkyl), $R^{69}$-substituted or unsubstituted aryl (e.g. $C_6$-$C_{10}$ aryl, $C_{10}$ aryl or phenyl), or $R^{69}$-substituted or unsubstituted heteroaryl (e.g. 5 to 10 membered heteroaryl, 5 to 9 membered heteroaryl, or 5 to 6 membered heteroaryl). In embodiments, $R^{18}$ is independently hydrogen, $—CF_3$, $—CCl_3$, $—CBr_3$, $—CI_3$, $—CHF_2$, $—CHCl_2$, $—CHBr_2$, $—CHI_2$, $—CH_2F$, $—CH_2Cl$, $—CH_2Br$, $—CH_2I$, —CN, —OH, —COOH, $—CONH_2$, $R^{69}$-substituted or unsubstituted alkyl (e.g. $C_1$-$C_8$ alkyl, $C_1$-$C_6$ alkyl, or $C_1$-$C_4$ alkyl), $R^{69}$-substituted or unsubstituted heteroalkyl (e.g. 2 to 8 membered heteroalkyl, 2 to 6 membered heteroalkyl, or 2 to 4 membered heteroalkyl), $R^{69}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{69}$-substituted or unsubstituted heterocycloalkyl (e.g. 3 to 8 membered heterocycloalkyl, 4 to 8 membered heterocycloalkyl, or 5 to 6 membered heterocycloalkyl), $R^{69}$-substituted or unsubstituted aryl (e.g. $C_6$-$C_{10}$ aryl, $C_{10}$ aryl or phenyl), or $R^{69}$-substituted or unsubstituted heteroaryl (e.g. 5 to 10 membered heteroaryl, 5 to 9 membered heteroaryl, or 5 to 6 membered heteroaryl). In embodiments, $R^{18}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{69}$-substituted alkyl (e.g. $C_1$-$C_8$ alkyl, $C_1$-$C_6$ alkyl, or $C_1$-$C_4$ alkyl), $R^{69}$-substituted heteroalkyl (e.g. 2 to 8 membered heteroalkyl, 2 to 6 membered heteroalkyl, or 2 to 4 membered heteroalkyl), $R^{69}$-substituted cycloalkyl (e.g. $C_3$-$C_8$ cycloalkyl, $C_4$-$C_5$ cycloalkyl, or $C_5$-$C_6$ cycloalkyl), $R^{69}$-substituted heterocycloalkyl (e.g. 3 to 8 membered heterocycloalkyl, 4 to 8 membered heterocycloalkyl, or 5 to 6 membered heterocycloalkyl), $R^{69}$-substituted aryl (e.g. $C_6$-$C_{10}$ aryl, $C_{10}$ aryl or phenyl), or $R^{69}$-substituted heteroaryl (e.g. 5 to 10 membered heteroaryl, 5 to 9 membered heteroaryl, or 5 to 6 membered heteroaryl). In embodiments, $R^{18}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{69}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{70}$-substituted or unsubstituted alkyl (e.g. $C_1$-$C_8$ alkyl, $C_1$-$C_6$ alkyl, or $C_1$-$C_4$ alkyl), $R^{70}$-substituted or unsubstituted heteroalkyl (e.g. 2 to 8 membered heteroalkyl, 2 to 6 membered heteroalkyl, or 2 to 4 membered heteroalkyl), $R^{70}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{70}$-substituted or unsubstituted heterocycloalkyl (e.g. 3 to 8 membered heterocycloalkyl, 4 to 8 membered heterocycloalkyl, or 5 to 6 membered heterocycloalkyl), $R^{70}$-substituted or unsubstituted aryl (e.g. $C_6$-$C_{10}$ aryl, $C_{10}$ aryl or phenyl), or $R^{70}$-substituted or unsubstituted heteroaryl (e.g. 5 to 10 membered heteroaryl, 5 to 9 membered heteroaryl, or 5 to 6 membered heteroaryl). In embodiments, $R^{69}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{70}$-substituted alkyl (e.g. $C_1$-$C_8$ alkyl, $C_1$-$C_6$ alkyl, or $C_1$-$C_4$ alkyl), $R^{70}$-substituted heteroalkyl (e.g. 2 to 8 membered heteroalkyl, 2 to 6 membered heteroalkyl, or 2 to 4 membered heteroalkyl), $R^{70}$-substituted cycloalkyl (e.g. $C_3$-$C_8$ cycloalkyl, $C_4$-$C_5$ cycloalkyl, or $C_5$-$C_6$ cycloalkyl), $R^{70}$-substituted heterocycloalkyl (e.g. 3 to 8 membered heterocycloalkyl, 4 to 8 membered heterocycloalkyl, or 5 to 6 membered heterocycloalkyl), $R^{70}$-substituted aryl (e.g. $C_6$-$C_{10}$ aryl, $C_{10}$ aryl or phenyl), or $R^{70}$-substituted heteroaryl (e.g. 5 to 10 membered heteroaryl, 5 to 9 membered heteroaryl, or 5 to 6 membered heteroaryl). In embodiments, $R^{69}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

$R^{70}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{71}$-substituted or unsubstituted alkyl (e.g. $C_1$-$C_8$ alkyl, $C_1$-$C_6$ alkyl, or $C_1$-$C_4$ alkyl), $R^{71}$-substituted or unsubstituted heteroalkyl (e.g. 2 to 8 membered heteroalkyl, 2 to 6 membered heteroalkyl, or 2 to 4 membered heteroalkyl), $R^{71}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{71}$-substituted or unsubstituted heterocycloalkyl (e.g. 3 to 8 membered heterocycloalkyl, 4 to 8 membered heterocycloalkyl, or 5 to 6 membered heterocycloalkyl), $R^{71}$-substituted or unsubstituted aryl (e.g. $C_6$-$C_{10}$ aryl, $C_{10}$ aryl or phenyl), or $R^{71}$-substituted or unsubstituted heteroaryl (e.g. 5 to 10 membered heteroaryl, 5 to 9 membered heteroaryl, or 5 to 6 membered heteroaryl). In embodiments, $R^{70}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{71}$-substituted alkyl (e.g. $C_1$-$C_8$ alkyl, $C_1$-$C_6$ alkyl, or $C_1$-$C_4$ alkyl), $R^{71}$-substituted heteroalkyl (e.g. 2 to 8 membered heteroalkyl, 2 to 6 membered heteroalkyl, or 2 to 4 membered heteroalkyl), $R^{71}$-substituted cycloalkyl (e.g. $C_3$-$C_8$ cycloalkyl, $C_4$-$C_8$ cycloalkyl, or $C_5$-$C_6$ cycloalkyl), $R^{71}$-substituted heterocycloalkyl (e.g. 3 to 8 membered heterocycloalkyl, 4 to 8 membered heterocycloalkyl, or 5 to 6 membered heterocycloalkyl), $R^{71}$-substituted aryl (e.g. $C_6$-$C_{10}$ aryl, $C_{10}$ aryl or phenyl), or $R^{71}$-substituted heteroaryl (e.g. 5 to 10 membered heteroaryl, 5 to 9 membered heteroaryl, or 5 to 6 membered heteroaryl). In embodiments, $R^{70}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{19}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{72}$-substituted or unsubstituted alkyl (e.g. $C_1$-$C_8$ alkyl, $C_1$-$C_6$ alkyl, or $C_1$-$C_4$ alkyl), $R^{72}$-substituted or unsubstituted heteroalkyl (e.g. 2 to 8 membered heteroalkyl, 2 to 6 membered heteroalkyl, or 2 to 4 membered heteroalkyl), $R^{72}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{72}$-substituted or unsubstituted heterocycloalkyl (e.g. 3 to 8 membered heterocycloalkyl, 4 to 8 membered heterocycloalkyl, or 5 to 6 membered heterocycloalkyl), $R^{72}$-substituted or unsubstituted aryl (e.g. $C_6$-$C_{10}$ aryl, $C_{10}$ aryl or phenyl), or $R^{72}$-substituted or unsubstituted heteroaryl (e.g. 5 to 10 membered heteroaryl, 5 to 9 membered heteroaryl, or 5 to 6 membered heteroaryl). In embodiments, $R^{19}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{72}$-substituted or unsubstituted alkyl (e.g. $C_1$-$C_8$ alkyl, $C_1$-$C_6$ alkyl, or $C_1$-$C_4$ alkyl), $R^{72}$-substituted or unsubstituted heteroalkyl (e.g. 2 to 8 membered heteroalkyl, 2 to 6 membered heteroalkyl, or 2 to 4 membered heteroalkyl), $R^{72}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{72}$-substituted or unsubstituted heterocycloalkyl (e.g. 3 to 8 membered heterocycloalkyl, 4 to 8 membered heterocycloalkyl, or 5 to 6 membered heterocycloalkyl), $R^{72}$-substituted or unsubstituted aryl (e.g. $C_6$-$C_{10}$ aryl, $C_{10}$ aryl or phenyl), or $R^{72}$-substituted or unsubstituted heteroaryl (e.g. 5 to 10 membered heteroaryl, 5 to 9 membered heteroaryl, or 5 to 6 membered heteroaryl). In embodiments, $R^{19}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{72}$-substituted alkyl (e.g. $C_1$-$C_8$ alkyl, $C_1$-$C_6$ alkyl, or $C_1$-$C_4$ alkyl), $R^{72}$-substituted heteroalkyl (e.g. 2 to 8 membered heteroalkyl, 2 to 6 membered heteroalkyl, or 2 to 4 membered heteroalkyl), $R^{72}$-substituted cycloalkyl (e.g. $C_3$-$C_8$ cycloalkyl, $C_4$-$C_5$ cycloalkyl, or $C_5$-$C_6$ cycloalkyl), $R^{72}$-substituted heterocycloalkyl (e.g. 3 to 8 membered heterocycloalkyl, 4 to 8 membered heterocycloalkyl, or 5 to 6 membered heterocycloalkyl), $R^{72}$-substituted aryl (e.g. $C_6$-$C_{10}$ aryl, $C_{10}$ aryl or phenyl), or $R^{72}$-substituted heteroaryl (e.g. 5 to 10 membered heteroaryl, 5 to 9 membered heteroaryl, or 5 to 6 membered heteroaryl). In embodiments, $R^{19}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{20}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{73}$-substituted or unsubstituted alkyl (e.g. $C_1$-$C_8$ alkyl, $C_1$-$C_6$ alkyl, or $C_1$-$C_4$ alkyl), $R^{73}$-substituted or unsubstituted heteroalkyl (e.g. 2 to 8 membered heteroalkyl, 2 to 6 membered heteroalkyl, or 2 to 4 membered heteroalkyl), $R^{73}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{73}$-substituted or unsubstituted heterocycloalkyl (e.g. 3 to 8 membered heterocycloalkyl, 4 to 8 membered heterocycloalkyl, or 5 to 6 membered heterocycloalkyl), $R^{73}$-substituted or unsubstituted aryl (e.g. $C_6$-$C_{10}$ aryl, $C_{10}$ aryl or phenyl), or $R^{73}$-substituted or unsubstituted heteroaryl (e.g. 5 to 10 membered heteroaryl, 5 to 9 membered heteroaryl, or 5 to 6 membered heteroaryl). In embodiments, $R^{20}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{73}$-substituted or unsubstituted alkyl (e.g. $C_1$-$C_8$ alkyl, $C_1$-$C_6$ alkyl, or $C_1$-$C_4$ alkyl), $R^{73}$-substituted or unsubstituted heteroalkyl (e.g. 2 to 8 membered heteroalkyl, 2 to 6 membered heteroalkyl, or 2 to 4 membered heteroalkyl), $R^{73}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{73}$-substituted or unsubstituted heterocycloalkyl (e.g. 3 to 8 membered heterocycloalkyl, 4 to 8 membered heterocycloalkyl, or 5 to 6 membered heterocycloalkyl), $R^{73}$-substituted or unsubstituted aryl (e.g. $C_6$-$C_{10}$ aryl, $C_{10}$ aryl or phenyl), or $R^{73}$-substituted or unsubstituted heteroaryl (e.g. 5 to 10 membered heteroaryl, 5 to 9 membered heteroaryl, or 5 to 6 membered heteroaryl). In embodiments, $R^{20}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{73}$-substituted alkyl (e.g. $C_1$-$C_8$ alkyl, $C_1$-$C_6$ alkyl, or $C_1$-$C_4$ alkyl), $R^{73}$-substituted heteroalkyl (e.g. 2 to 8 membered heteroalkyl, 2 to 6 membered heteroalkyl, or 2 to 4 membered heteroalkyl), $R^{73}$-substituted cycloalkyl (e.g. $C_3$-$C_8$ cycloalkyl, $C_4$-$C_5$ cycloalkyl, or $C_5$-$C_6$ cycloalkyl), $R^{73}$-substituted heterocycloalkyl (e.g. 3 to 8 membered heterocycloalkyl, 4 to 8 membered heterocycloalkyl, or 5 to 6 membered heterocycloalkyl), $R^{73}$-substituted aryl (e.g. $C_6$-$C_{10}$ aryl, $C_{10}$ aryl or phenyl), or $R^{73}$-substituted heteroaryl (e.g. 5 to 10 membered heteroaryl, 5 to 9 membered heteroaryl, or 5 to 6 membered heteroaryl). In embodiments, $R^{20}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{21}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{74}$-substituted or unsubstituted alkyl (e.g. $C_1$-$C_8$ alkyl, $C_1$-$C_6$ alkyl, or $C_1$-$C_4$ alkyl), $R^{74}$-substituted or unsubstituted heteroalkyl (e.g. 2 to 8 membered heteroalkyl, 2 to 6 membered heteroalkyl, or 2 to 4 membered heteroalkyl), $R^{74}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{74}$-substituted or unsubstituted heterocycloalkyl (e.g. 3 to 8 membered heterocycloalkyl, 4 to 8 membered heterocycloalkyl, or 5 to 6 membered heterocycloalkyl), $R^{74}$-substituted or unsubstituted aryl (e.g. $C_6$-$C_{10}$ aryl, $C_{10}$ aryl or phenyl), or $R^{74}$-substituted or unsubstituted heteroaryl (e.g. 5 to 10 membered heteroaryl, 5 to 9 membered heteroaryl, or 5 to 6 membered heteroaryl). In embodiments, $R^{21}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{74}$-substituted alkyl (e.g. $C_1$-$C_8$ alkyl, $C_1$-$C_6$ alkyl, or $C_1$-$C_4$ alkyl), $R^{74}$-substituted heteroalkyl (e.g. 2 to 8 membered heteroalkyl, 2 to 6 membered heteroalkyl, or 2 to 4 membered heteroalkyl), $R^{74}$-substituted cycloalkyl (e.g. $C_3$-$C_8$ cycloalkyl, $C_4$-$C_8$ cycloalkyl, or $C_5$-$C_6$ cycloalkyl), $R^{74}$-substituted heterocycloalkyl (e.g. 3 to 8 membered heterocycloalkyl, 4 to 8 membered heterocycloalkyl, or 5 to 6 membered heterocycloalkyl), $R^{74}$-substituted aryl (e.g. $C_6$-$C_{10}$ aryl, $C_{10}$ aryl or phenyl), or $R^{74}$-substituted heteroaryl (e.g. 5 to 10 membered heteroaryl, 5 to 9 membered heteroaryl, or 5 to 6 membered heteroaryl). In embodiments, $R^{21}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{22}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{75}$-substituted or unsubstituted alkyl (e.g. $C_1$-$C_8$ alkyl, $C_1$-$C_6$ alkyl, or $C_1$-$C_4$ alkyl), $R^{75}$-substituted or unsubstituted heteroalkyl (e.g. 2 to 8 membered heteroalkyl, 2 to 6 membered heteroalkyl, or 2 to 4 membered heteroalkyl), $R^{75}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{75}$-substituted or unsubstituted heterocycloalkyl (e.g. 3 to 8 membered heterocycloalkyl, 4 to 8 membered heterocycloalkyl, or 5 to 6 membered heterocycloalkyl), $R^{75}$-substituted or unsubstituted aryl (e.g. $C_6$-$C_{10}$ aryl, $C_{10}$ aryl or phenyl), or $R^{75}$-substituted or unsubstituted heteroaryl (e.g. 5 to 10 membered heteroaryl, 5 to 9 membered heteroaryl, or 5 to 6 membered heteroaryl). In embodiments, $R^{22}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{75}$-substituted alkyl (e.g. $C_1$-$C_8$ alkyl, $C_1$-$C_6$ alkyl, or $C_1$-$C_4$ alkyl), $R^{75}$-substituted heteroalkyl (e.g. 2 to 8 membered heteroalkyl, 2 to 6 membered heteroalkyl, or 2 to 4 membered heteroalkyl), $R^{75}$-substituted cycloalkyl (e.g. $C_3$-$C_8$ cycloalkyl, $C_4$-$C_8$ cycloalkyl, or $C_5$-$C_6$ cycloalkyl), $R^{75}$-substituted heterocycloalkyl (e.g. 3 to 8 membered heterocycloalkyl, 4 to 8 membered heterocycloalkyl, or 5 to 6 membered heterocycloalkyl), $R^{75}$-substituted aryl (e.g. $C_6$-$C_{10}$ aryl, $C_{10}$ aryl or phenyl), or $R^5$-substituted heteroaryl (e.g. 5 to 10 membered heteroaryl, 5 to 9 membered heteroaryl, or 5 to 6 membered heteroaryl). In embodiments, $R^{22}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{23}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{76}$-substituted or unsubstituted alkyl (e.g. $C_1$-$C_8$ alkyl, $C_1$-$C_6$ alkyl, or $C_1$-$C_4$ alkyl), $R^{76}$-substituted or unsubstituted heteroalkyl (e.g. 2 to 8 membered heteroalkyl, 2 to 6 membered heteroalkyl, or 2 to 4 membered heteroalkyl), $R^{76}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{76}$-substituted or unsubstituted heterocycloalkyl (e.g. 3 to 8 membered heterocycloalkyl, 4 to 8 membered heterocycloalkyl, or 5 to 6 membered heterocycloalkyl), $R^{76}$-substituted or unsubstituted aryl (e.g. $C_6$-$C_{10}$ aryl, $C_{10}$ aryl or phenyl), or $R^{76}$-substituted or unsubstituted heteroaryl (e.g. 5 to 10 membered heteroaryl, 5 to 9 membered heteroaryl, or 5 to 6 membered heteroaryl). In embodiments, $R^{23}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{76}$-substituted or unsubstituted alkyl (e.g. $C_1$-$C_8$ alkyl, $C_1$-$C_6$ alkyl, or $C_1$-$C_4$ alkyl), $R^{76}$-substituted or unsubstituted heteroalkyl (e.g. 2 to 8 membered heteroalkyl, 2 to 6 membered heteroalkyl, or 2 to 4 membered heteroalkyl), $R^{76}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{76}$-substituted or unsubstituted heterocycloalkyl (e.g. 3 to 8 membered heterocycloalkyl, 4 to 8 membered heterocycloalkyl, or 5 to 6 membered heterocycloalkyl), $R^{76}$-substituted or unsubstituted aryl (e.g. $C_6$-$C_{10}$ aryl, $C_{10}$ aryl or phenyl), or $R^{76}$-substituted or unsubstituted heteroaryl (e.g. 5 to 10 membered heteroaryl, 5 to 9 membered heteroaryl, or 5 to 6 membered heteroaryl). In embodiments, $R^{23}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{76}$-substituted alkyl (e.g. $C_1$-$C_8$ alkyl, $C_1$-$C_6$ alkyl, or $C_1$-$C_4$ alkyl), $R^{76}$-substituted heteroalkyl (e.g. 2 to 8 membered heteroalkyl, 2 to 6 membered heteroalkyl, or 2 to 4 membered heteroalkyl), $R^{76}$-substituted cycloalkyl (e.g. $C_3$-$C_8$ cycloalkyl, $C_4$-$C_5$ cycloalkyl, or $C_5$-$C_6$ cycloalkyl), $R^{76}$-substituted heterocycloalkyl (e.g. 3 to 8 membered heterocycloalkyl, 4 to 8 membered heterocycloalkyl, or 5 to 6 membered heterocycloalkyl), $R^{76}$-substituted aryl (e.g. $C_6$-$C_{10}$ aryl, $C_{10}$ aryl or phenyl), or $R^{76}$-substituted heteroaryl (e.g. 5 to 10 membered heteroaryl, 5 to 9 membered heteroaryl, or 5 to 6 membered heteroaryl). In embodiments, $R^{23}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$—$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{24}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{77}$-substituted or unsubstituted alkyl (e.g. $C_1$-$C_8$ alkyl, $C_1$-$C_6$ alkyl, or $C_1$-$C_4$ alkyl), $R^{77}$-substituted or unsubstituted heteroalkyl (e.g. 2 to 8 membered heteroalkyl, 2 to 6 membered heteroalkyl, or 2 to 4 membered heteroalkyl), $R^{77}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{77}$-substituted or unsubstituted heterocycloalkyl (e.g. 3 to 8 membered heterocycloalkyl, 4 to 8 membered heterocycloalkyl, or 5 to 6 membered heterocycloalkyl), $R^{77}$-substituted or unsubstituted aryl (e.g. $C_6$-$C_{10}$ aryl, $C_{10}$ aryl or phenyl), or $R^{77}$-substituted or unsubstituted heteroaryl (e.g. 5 to 10 membered heteroaryl, 5 to 9 membered heteroaryl, or 5 to 6 membered heteroaryl). In embodiments, $R^{24}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{77}$-substituted or unsubstituted alkyl (e.g. $C_1$-$C_8$ alkyl, $C_1$-$C_6$ alkyl, or $C_1$-$C_4$ alkyl), $R^{77}$-substituted or unsubstituted heteroalkyl (e.g. 2 to 8 membered heteroalkyl, 2 to 6 membered heteroalkyl, or 2 to 4 membered heteroalkyl), $R^{77}$-substituted or unsubstituted cycloalkyl (e.g. $C_3$-$C_8$ cycloalkyl, $C_4$-$C_5$ cycloalkyl, or $C_5$-$C_6$ cycloalkyl), $R^{77}$-substituted or unsubstituted heterocycloalkyl (e.g. 3 to 8 membered heterocycloalkyl, 4 to 8 membered heterocycloalkyl, or 5 to 6 membered heterocycloalkyl), $R^{77}$-substituted or unsubstituted aryl (e.g. $C_6$-$C_{10}$ aryl, $C_{10}$ aryl or phenyl), or $R^{77}$-substituted or unsubstituted heteroaryl (e.g. 5 to 10 membered heteroaryl, 5 to 9 membered heteroaryl, or 5 to 6 membered heteroaryl). In embodiments, $R^{24}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, $R^{77}$-substituted alkyl (e.g. $C_1$-$C_8$ alkyl, $C_1$-$C_6$ alkyl, or $C_1$-$C_4$ alkyl), $R^{77}$-substituted heteroalkyl (e.g. 2 to 8 membered heteroalkyl, 2 to 6 membered heteroalkyl, or 2 to 4 membered heteroalkyl), $R^{77}$-substituted cycloalkyl (e.g. $C_3$-$C_8$ cycloalkyl, $C_4$-$C_8$ cycloalkyl, or $C_5$-$C_6$ cycloalkyl), $R^{77}$-substituted heterocycloalkyl (e.g. 3 to 8 membered heterocycloalkyl, 4 to 8 membered heterocycloalkyl, or 5 to 6 membered heterocycloalkyl), $R^{77}$-substituted aryl (e.g. $C_6$-$C_{10}$ aryl, $C_{10}$ aryl or phenyl), or $R^{77}$-substituted heteroaryl (e.g. 5 to 10 membered heteroaryl, 5 to 9 membered heteroaryl, or 5 to 6 membered heteroaryl). In embodiments, $R^{24}$ is independently hydrogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —COOH, —$CONH_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^{25}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{78}$-substituted or unsubstituted alkyl (e.g. $C_1$-$C_8$ alkyl, $C_1$-$C_6$ alkyl, or $C_1$-$C_4$ alkyl), $R^{78}$-substituted or unsubstituted heteroalkyl (e.g. 2 to 8 membered heteroalkyl, 2 to 6 membered heteroalkyl, or 2 to 4 membered heteroalkyl), $R^{71}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{78}$-substituted or unsubstituted heterocycloalkyl (e.g. 3 to 8 membered heterocycloalkyl, 4 to 8 membered heterocycloalkyl, or 5 to 6 membered heterocycloalkyl), $R^{78}$-substituted or unsubstituted aryl (e.g. $C_6$-$C_{10}$ aryl, $C_{10}$ aryl or phenyl), or $R^{78}$-substituted or unsubstituted heteroaryl (e.g. 5 to 10 membered heteroaryl, 5 to 9 membered heteroaryl, or 5 to 6 membered heteroaryl). In embodiments, $R^{25}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{78}$-substituted alkyl (e.g. $C_1$-$C_8$ alkyl, $C_1$-$C_6$ alkyl, or $C_1$-$C_4$ alkyl), $R^{78}$-substituted heteroalkyl (e.g. 2 to 8 membered heteroalkyl, 2 to 6 membered heteroalkyl, or 2 to 4 membered heteroalkyl), $R^{78}$-substituted cycloalkyl (e.g. $C_3$-$C_8$ cycloalkyl, $C_4$-$C_5$ cycloalkyl, or $C_5$-$C_6$ cycloalkyl), $R^{78}$-substituted heterocycloalkyl (e.g. 3 to 8 membered heterocycloalkyl, 4 to 8 membered heterocycloalkyl, or 5 to 6 membered heterocycloalkyl), $R^{78}$-substituted aryl (e.g. $C_6$-$C_{10}$ aryl, $C_{10}$ aryl or phenyl), or $R^{78}$-substituted heteroaryl (e.g. 5 to 10 membered heteroaryl, 5 to 9 membered heteroaryl, or 5 to 6 membered heteroaryl). In embodiments, $R^{25}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, $R^2$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{79}$-substituted or unsubstituted alkyl (e.g. $C_1$-$C_8$ alkyl, $C_1$-$C_6$ alkyl, or $C_1$-$C_4$ alkyl), $R^{79}$-substituted or unsubstituted heteroalkyl (e.g. 2 to 8 membered heteroalkyl, 2 to 6 membered heteroalkyl, or 2 to 4 membered heteroalkyl), $R^{79}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{79}$-substituted or unsubstituted heterocycloalkyl (e.g. 3 to 8 membered heterocycloalkyl, 4 to 8 membered heterocycloalkyl, or 5 to 6 membered heterocycloalkyl), $R^{79}$-substituted or unsubstituted aryl (e.g. $C_6$-$C_{10}$ aryl, $C_{10}$ aryl or phenyl), or $R^{79}$-substituted or unsubstituted heteroaryl (e.g. 5 to 10 membered heteroaryl, 5 to 9 membered heteroaryl, or 5 to 6 membered heteroaryl). In embodiments, $R^{26}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, $R^{79}$-substituted alkyl (e.g. $C_1$-$C_8$ alkyl, $C_1$-$C_6$ alkyl, or $C_1$-$C_4$ alkyl), $R^{79}$-substituted heteroalkyl (e.g. 2 to 8 membered heteroalkyl, 2 to 6 membered heteroalkyl, or 2 to 4 membered heteroalkyl), $R^{79}$-substituted cycloalkyl (e.g. $C_3$-$C_8$ cycloalkyl, $C_4$-$C_5$ cycloalkyl, or $C_5$-$C_6$ cycloalkyl), $R^{79}$-substituted heterocycloalkyl (e.g. 3 to 8 membered heterocycloalkyl, 4 to 8 membered heterocycloalkyl, or 5 to 6 membered heterocycloalkyl), $R^{79}$-substituted aryl (e.g. $C_6$-$C_{10}$ aryl, $C_{10}$ aryl or phenyl), or $R^{79}$-substituted heteroaryl (e.g. 5 to 10 membered heteroaryl, 5 to 9 membered heteroaryl, or 5 to 6 membered heteroaryl). In embodiments, $R^{26}$ is independently hydrogen, oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, L is independently a bond, $R^{80}$-substituted or unsubstituted alkylene, $R^{80}$-substituted or unsubstituted heteroalkylene, $R^{80}$-substituted or unsubstituted cycloalkylene, $R^{80}$-substituted or unsubstituted heterocycloalkylene, $R^{80}$-substituted or unsubstituted arylene, or $R^{80}$-substituted or unsubstituted heteroarylene. In embodiments, L is independently a bond, $R^{80}$-substituted alkylene, $R^{80}$-substituted heteroalkylene, $R^{80}$-substituted cycloalkylene, $R^{80}$-substituted heterocycloalkylene, $R^{80}$-substituted arylene, or $R^{80}$-substituted heteroarylene. In embodiments, L is independently a bond, unsubstituted alkylene, unsubstituted heteroalkylene, unsubstituted cycloalkylene, unsubstituted heterocycloalkylene, unsubstituted arylene, or unsubstituted heteroarylene.

$R^{29}$, $R^{32}$, $R^{35}$, $R^{38}$, $R^{41}$, $R^{44}$, $R^{47}$, $R^{50}$, $R^{53}$, $R^{56}$, $R^{59}$, $R^{62}$, $R^{61}$, $R^{68}$, $R^{71}$, $R^{72}$, $R^{73}$, $R^{74}$, $R^{75}$, $R^{76}$, $R^{77}$, $R^{78}$, $R^{79}$, and $R^{80}$ are independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_5$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl, $C_{10}$ aryl or phenyl), or unsubstituted heteroaryl (e.g. 5 to 10 membered heteroaryl, 5 to 9 membered heteroaryl, or 5 to 6 membered heteroaryl).

In embodiments, the compound is (SERD119 or S119)

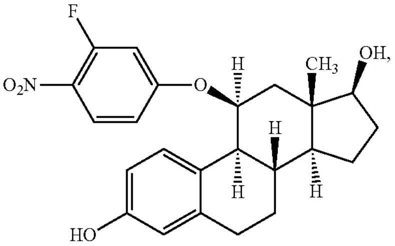

(SERD128 or S128)

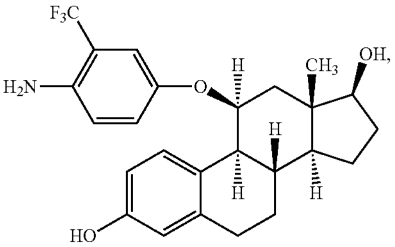

(SERD140 or S140)

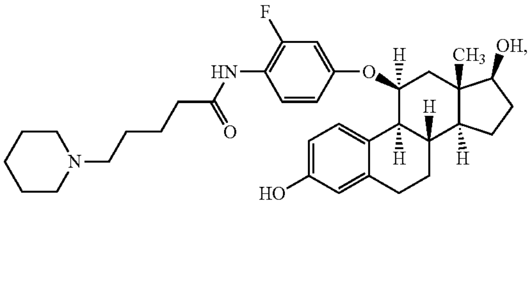

-continued (SERD160 or S160)

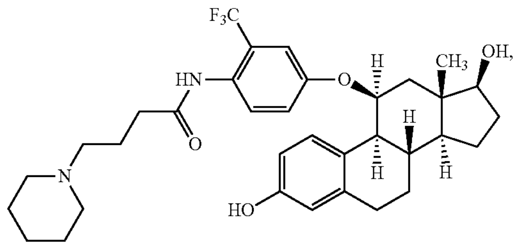

(SERD121 or S121)

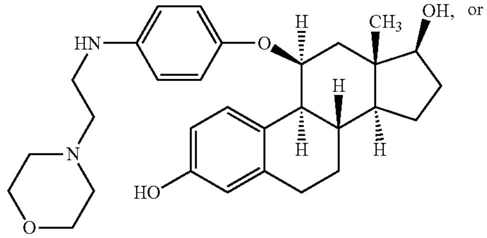

or (SERD109 or S109)

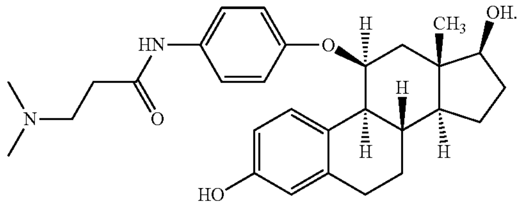

In embodiments, the compound is a compound described herein. In some embodiments, the compound is a compound selected from SERD101 to SERD160 (e.g., SERD101, SERD102, SERD103, SERD104, SERD105, SERD106, SERD107, SERD108, SERD109, SERD110, SERD111, SERD112, SERD113, SERD114, SERD115, SERD116, SERD117, SERD118, SERD119, SERD120, SERD121, SERD122, SERD123, SERD124, SERD125, SERD126, SERD127, SERD128, SERD129, SERD130, SERD131, SERD132, SERD133, SERD134, SERD135, SERD136, SERD137, SERD138, SERD139, SERD140, SERD141, SERD142, SERD143, SERD144, SERD145, SERD146, SERD147, SERD148, SERD149, SERD150, SERD151, SERD152, SERD153, SERD154, SERD155, SERD156, SERD157, SERD158, SERD159, or SERD160). In embodiments, the compound is not a compound selected from SERD101 to SERD160 (e.g., SERD101, SERD102, SERD103, SERD104, SERD105, SERD106, SERD107, SERD108, SERD109, SERD110, SERD111, SERD112, SERD113, SERD114, SERD115, SERD116, SERD117, SERD118, SERD119, SERD120, SERD121, SERD122, SERD123, SERD124, SERD125, SERD126, SERD127, SERD128, SERD129, SERD130, SERD131, SERD132, SERD133, SERD134, SERD135, SERD136, SERD137, SERD138, SERD139, SERD140, SERD141, SERD142, SERD143, SERD144, SERD145, SERD146, SERD147, SERD148, SERD149, SERD150, SERD151, SERD152, SERD153, SERD154, SERD155, SERD156, SERD157, SERD158, SERD159, or SERD160).

In embodiments, a compound as described herein may include multiple instances of $R^1$, $R^2$, $R^3$, $R^4$, $R^5$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, m1, m2, m3, m4, m5, v1, v2, v3, v4, v5, n1, n2, n3, n4, n5, X, $X^a$, $X^b$, $X^c$, $X^d$ and $X^e$, and/or other variables. In such embodiments, each variable may optional be different and be appropriately labeled to distinguish each group for greater clarity. For example, where each $R^1$, $R^2$, $R^3$, $R^4$, $R^1$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, m1, m2, m3, m4, m5, v1, v2, v3, v4, v5, n1, n2, n3, n4, n5, X, $X^a$, $X^b$, $X^c$, $X^d$ and $X^e$, is different, they may be referred to, for example, as $R^{1.1}$, $R^{1.2}$, $R^{1.3}$, $R^{1.4}$, $R^{1.5}$, $R^{2.1}$, $R^{2.2}$, $R^{2.3}$, $R^{2.4}$, $R^{2.5}$, $R^{3.1}$, $R^{3.2}$, $R^{3.3}$, $R^{3.4}$, $R^{3.5}$, $R^{4.1}$, $R^{4.2}$, $R^{4.3}$, $R^{4.4}$, $R^{4.5}$, $R^{5.1}$, $R^{5.2}$, $R^{5.3}$, $R^{5.4}$, $R^{5.5}$, $R^{9.1}$, $R^{9.2}$, $R^{9.3}$, $R^{9.4}$, $R^{9.5}$, $R^{10.1}$, $R^{10.2}$, $R^{10.3}$, $R^{10.4}$, $R^{10.5}$, $R^{11.1}$, $R^{11.2}$, $R^{11.3}$, $R^{11.4}$, $R^{11.5}$, $R^{12.1}$, $R^{12.2}$, $R^{12.3}$, $R^{12.4}$, $R^{12.5}$, $R^{13.1}$, $R^{13.2}$, $R^{13.3}$, $R^{13.4}$, $R^{13.5}$, $R^{14.1}$, $R^{14.2}$, $R^{14.3}$, $R^{14.4}$, $R^{14.5}$, $R^{15.1}$, $R^{15.2}$, $R^{15.3}$, $R^{15.4}$, $R^{15.5}$, $R^{16.1}$, $R^{16.2}$, $R^{16.3}$, $R^{16.4}$, $R^{16.5}$, $R^{17.1}$, $R^{17.2}$, $R^{17.3}$, $R^{17.4}$, $R^{17.5}$, $R^{18.1}$, $R^{18.2}$, $R^{18.3}$, $R^{18.4}$, $R^{18.5}$, $R^{19.1}$, $R^{19.2}$, $R^{19.3}$, $R^{19.4}$, $R^{19.5}$, $R^{20.1}$, $R^{20.2}$, $R^{20.3}$, $R^{20.4}$, $R^{20.5}$, $R^{21.1}$, $R^{21.2}$, $R^{21.3}$, $R^{21.4}$, $R^{21.5}$, $R^{22.1}$, $R^{22.2}$, $R^{22.3}$, $R^{22.4}$, $R^{22.5}$, $R^{23.1}$, $R^{23.2}$, $R^{23.3}$, $R^{23.4}$, $R^{23.5}$, $R^{24.1}$, $R^{24.2}$, $R^{24.3}$, $R^{24.4}$, $R^{24.5}$, $R^{25.1}$, $R^{25.2}$, $R^{25.3}$, $R^{25.4}$, $R^{25.5}$, $R^{26.1}$, $R^{26.2}$, $R^{26.3}$, $R^{26.4}$, $R^{26.5}$, $m1^1$, $m1^2$, $m1^3$, m14, $m1^5$, $m2^1$, $m2^2$, $m2^3$, $m2^4$, $m2^5$, $m3^1$, $m3^2$, $m3^3$, $m3^4$, $m3^5$, $m4^1$, $m4^2$, $m4^3$, $m4^4$, $m4^5$, $m5^1$, $m5^2$, $m5^3$, $m5^4$, $m5^5$, $v1^1$, $v1^2$, $v1^3$, $v1^4$, $v1^5$, $v2^1$, $v2^2$, $v2^3$, $v2^4$, $v2^5$, $v3^1$, $v3^2$, $v3^3$, $v3^4$, $v3^5$, $v4^1$, $v4^2$, $v4^3$, $v4^4$, $v4^5$, $v5^1$, $v5^2$, $v5^3$, $v5^4$, $v5^5$, $n1^1$, $n1^2$, $n1^3$, $n1^4$, $n1^5$, $n2^1$, $n2^2$, $n2^3$, $n2^4$, $n2^5$, $n3^1$, $n3^2$, $n3^3$, $n3^4$, $n3^5$, $n4^1$, $n4^2$, $n4^3$, $n4^4$, $n4^5$, $n5^1$, $n5^2$, $n5^3$, $n5^4$, $n5^5$, $X^1$, $X^2$, $X^3$, $X^4$, $X^5$, $X^{a1}$, $X^aX^2$, $X^{a3}$, $X^{a4}$, $X^{a5}$, $X^{b1}$, $X^{b2}$, $X^{b3}$, $X^{b4}$, $X^{b5}$, $X^{c1}$, $X^{c2}$, $X^{c3}$, $X^{c4}$, $X^{c5}$, $X^{d1}$, $X^{d2}$, $X^{d3}$, $X^{d4}$, $X^{d5}$, $X^{e1}$, $X^{e2}$, $X^{e3}$, $X^{e4}$, and/or $X^{e5}$, respectively, wherein the definition of $R^1$ is assumed by $R^{1.1}$, $R^{1.2}$, $R^{1.3}$, $R^{1.4}$, and/or $R^{1.5}$, wherein the definition of $R^2$ is assumed by $R^{2.1}$, $R^{2.2}$, $R^{2.3}$, $R^{2.4}$, and/or $R^{2.5}$, wherein the definition of $R^3$ is assumed by $R^{3.1}$, $R^{3.2}$, $R^{3.3}$, $R^{3.4}$, and/or $R^{3.5}$, wherein the definition of $R^4$ is assumed by $R^{4.1}$, $R^{4.2}$, $R^{4.3}$, $R^{4.4}$, and/or $R^{4.5}$, wherein the definition of $R^5$ is assumed by $R^{5.1}$, $R^{5.2}$, $R^{5.3}$, $R^{5.4}$, and/or $R^{5.5}$, wherein the definition of $R^9$ is assumed by $R^{9.1}$, $R^{9.2}$, $R^{9.3}$, $R^{9.4}$, and/or $R^{9.5}$, wherein the definition of $R^{10}$ is assumed by $R^{10.1}$, $R^{10.2}$, $R^{10.3}$, $R^{10.4}$, and/or $R^{10.5}$, wherein the definition of $R^{11}$ is assumed by $R^{11.1}$, $R^{11.2}$, $R^{11.3}$, $R^{11.4}$, and/or $R^{11.5}$, wherein the definition of $R^{12}$ is assumed by $R^{12.1}$, $R^{12.2}$, $R^{12.3}$, $R^{1.4}$, and/or $R^{12.5}$, wherein the definition of $R^{13}$ is assumed by $R^{13.1}$, $R^{13.2}$, $R^{13.3}$, $R^{13.4}$, and/or $R^{13.5}$, wherein the definition of $R^{14}$ is assumed by $R^{14.1}$, $R^{14.2}$, $R^{14.3}$, $R^{14.4}$, and/or $R^{14.5}$, wherein the definition of $R^{15}$ is assumed by $R^{15.1}$, $R^{15.2}$, $R^{15.3}$, $R^{15.4}$, and/or $R^{15.5}$, wherein the definition of $R^{16}$ is assumed by $R^{16.1}$, $R^{16.2}$, $R^{16.3}$, $R^{16.4}$, and/or $R^{16.5}$, wherein the definition of $R^{17}$ is assumed by $R^{17.1}$, $R^{17.2}$, $R^{17.3}$, $R^{17.4}$, and/or $R^{17.5}$, wherein the definition of $R^{18}$ is assumed by $R^{18.1}$, $R^{18.2}$, $R^{18.3}$, $R^{18.4}$, and/or $R^{18.5}$, wherein the definition of $R^{19}$ is assumed by $R^{19.1}$, $R^{19.2}$, $R^{19.3}$, $R^{19.4}$, and/or $R^{19.5}$, wherein the definition of $R^{20}$ is assumed by $R^{20.1}$, $R^{20.2}$, $R^{20.3}$, $R^{20.4}$, and/or $R^{21.4}$, wherein the definition of $R^{21}$ is assumed by $R^{21.1}$, $R^{21.2}$, $R^{21.3}$, $R^{21.4}$, and/or $R^{21.5}$, wherein the definition of $R^{22}$ is assumed by $R^{22.1}$, $R^{22.2}$, $R^{22.3}$, $R^{22.4}$, and/or $R^{22.5}$, wherein the definition of $R^{23}$ is assumed by $R^{23.1}$, $R^{23.2}$, $R^{23.3}$, $R^{23.4}$, and/or $R^{23.5}$, wherein the definition of $R^{24}$ is assumed by $R^{24.1}$, $R^{24.2}$, $R^{24.3}$, $R^{24.4}$, and/or $R^{24.5}$, wherein the definition of $R^{25}$ is assumed by $R^{25.1}$, $R^{25.2}$, $R^{25.3}$, $R^{25.4}$, and/or $R^{25.5}$, wherein the definition of $R^{26}$ is assumed by $R^{26.1}$, $R^{26.2}$, $R^{26.3}$, $R^{26.4}$, and/or $R^{26.5}$, wherein the definition of m1 is assumed by $m1^1$, $m1^2$, $m1^3$, m14, and/or $m1^5$, wherein the definition of m2 is assumed by $m2^1$, $m2^2$, $m2^3$, $m2^4$, and/or $m2^5$, wherein the definition of m3 is assumed by $m3^1$, $m3^2$, $m3^3$, $m3^4$, and/or $m3^5$, wherein the definition of m4 is assumed by $m4^1$, $m4^2$, $m4^3$, $m4^4$, and/or $m4^5$, wherein the definition of m5 is assumed by $m5^1$, $m5^2$, $m5^3$, $m5^4$, and/or $m5^5$, wherein the definition of v1 is assumed by $v1^1$, $v1^2$, $v1^3$, $v1^4$, and/or $v1^5$, wherein the definition of v2 is assumed by $v2^1$, $v2^2$, $v2^3$, $v2^4$, and/or $v2^5$, wherein the definition of v3 is assumed by $v3^1$, $v3^2$, $v3^3$, $v3^4$, and/or $v3^5$, wherein the definition of v4 is assumed by $v4^1$, $v4^2$, $v4^3$, $v4^4$, and/or $v4^5$, wherein the definition of v5 is assumed by $v5^1$, $v5^2$, $v5^3$, $v5^4$, and/or $v5^5$, wherein the definition of n1 is assumed by $n1^1$, $n1^2$, $n1^3$, $n1^4$, and/or $n1^5$, wherein the definition of n2 is assumed by $n2^1$, $n2^2$, $n2^3$, $n2^4$, and/or $n2^5$, wherein the definition of n3 is assumed by $n3^1$, $n3^2$, $n3^3$, $n3^4$, and/or $n3^5$, wherein the definition of n4 is assumed by $n4^1$, $n4^2$, $n4^3$, $n4^4$, and/or $n4^5$, wherein the definition of n5 is assumed by $n5^1$, $n5^2$, $n5^3$, $n5^4$, and/or $n5^5$, wherein the definition of X is assumed by $X^1$, $X^2$, $X^3$, $X^4$, and/or $X^5$, wherein the definition of $X^a$ is assumed by $X^{a1}$, $X^aX^2$, $X^3$, $X^{a4}$, and/or $X^{a5}$, wherein the definition of $X^b$ is assumed by $X^{b1}$, $X^{b2}$, $X^{b3}$, $X^{b4}$, and/or $X^{b5}$, wherein the definition of $X^c$ is assumed by $X^{c1}$, $X^{c2}$, $X^{c3}$, $X^{c4}$, and/or $X^{c5}$, wherein the definition of $X^d$ is assumed by $X^{d1}$, $X^{d2}$, $X^{d3}$, $X^{d4}$, and/or $X^{d5}$, wherein the definition of $X^e$ is assumed by $X^{e1}$, $X^{e2}$, $X^{e3}$, $X^{e4}$, and/or $X^{e5}$. The variables used within a definition of $R^1$, $R^2$, $R^3$, $R^4$, $R^5$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, m1, m2, m3, m4, m5, v1, v2, v3, v4, v5, n1, n2, n3, n4, n5, X, $X^a$, $X^b$, $X^c$, $X^d$ and $X^e$, and/or other variables that appear at multiple instances and are different may similarly be appropriately labeled to distinguish each group for greater clarity.

In embodiments, the compound competes with estrogen for binding to estrogen receptor (ER). In embodiments, the compound competes with 4-hydroxy tamoxifen for binding to ER. In embodiments, the compound binds the ligand binding domain of ER. In embodiments, the compound modulates the conformation of helix 12 of ER relative to the conformation of helix 12 when estrogen is bound to ER. In embodiments, the compound modulates (e.g., reduces relative to estrogen bound ER) the binding of ER to estrogen response elements. In embodiments, the compound modulates (e.g., reduces relative to estrogen bound ER) the phosphorylation of ER. In embodiments, the compound modulates (e.g., reduces relative to estrogen bound ER) the activity of a cellular pathway (e.g., ras-MAPK containing pathway, PI3K/AKT containing pathway, Shc containing pathway, Src kinase containing pathway, JAK/STAT containing pathway, nitric oxide synthase pathway, VEGF secretion pathway). In embodiments, the compound modulates (e.g., reduces relative to estrogen bound ER) DNA synthesis. In embodiments, the compound modulates (e.g., reduces relative to estrogen bound ER) cell growth. In embodiments, the compound modulates (e.g., reduces relative to estrogen bound ER) cell proliferation. In embodiments, the compound modulates (e.g., reduces relative to estrogen bound ER) epithelial cell proliferation. In embodiments, the compound modulates (e.g., increases relative to estrogen bound ER) the degradation of ER. In embodiments, the compound modulates (e.g., increases relative to estrogen bound ER) the ubiquitination of ER. In embodiments, the compound modulates (e.g., increases relative to estrogen bound ER) the degradation of ER by the proteasome.

In embodiments, the composition includes an immune checkpoint inhibitor. In embodiments, the composition does not include an immune checkpoint inhibitor. In embodiments, the composition includes an immune checkpoint inhibitor (e.g., an anti-PD-1 antibody, an anti-PD-L1 antibody, anti-CTLA4 antibody, nivolumab, pembrolizumab, atezolizumab, avelumab, durvalumab, and the like). In embodiments, the composition does not include an immune checkpoint inhibitor (e.g., an anti-PD-1 antibody, an anti-PD-L1 antibody, anti-CTLA4 antibody, nivolumab, pembrolizumab, atezolizumab, avelumab, durvalumab, and the like).

In accordance with the aspects of the present disclosure, it was unexpectedly and surprisingly found that estrogen receptor inhibitors synergize with an amount of an immune checkpoint inhibitor to elicit enhanced inhibition of cell proliferation of cancer cells, such as TNBC cells, melanoma cells, small cell lung cancer cells, as compared to when used individually and separately (i.e., monotherapy treatment).

In accordance with the aspects of the present disclosure, it was unexpectedly and surprisingly found that an estrogen receptor inhibitor (e.g., a compound having the structure of Formula X, Xa, I', I, Ia, Ib, II, IIa, IIb, or pharmaceutically acceptable salt thereof) to elicit enhanced inhibition of cell proliferation of cancer cells, such as TNBC cells, melanoma cells, small cell lung cancer cells. In accordance with the aspects of the present disclosure, it was unexpectedly and surprisingly found that an estrogen receptor inhibitor (e.g., a compound having the structure of Formula X, Xa, I', I, Ia, Ib, II, IIa, IIb, or pharmaceutically acceptable salt thereof) described herein synergize with an amount of an immune checkpoint inhibitor to elicit enhanced inhibition of cell proliferation of cancer cells, such as TNBC cells, melanoma cells, small cell lung cancer cells, as compared to when used individually and separately (i.e., monotherapy treatment).

In accordance with the aspects of the present disclosure, it was unexpectedly and surprisingly found that an estrogen receptor inhibitor (e.g., a compound having the structure of Formula X, Xa, I', I, Ia, Ib, II, IIa, IIb, or pharmaceutically acceptable salt thereof) to increase immune recognition of cancer cells, such as TNBC cells, melanoma cells, small cell lung cancer cells. In accordance with the aspects of the present disclosure, it was unexpectedly and surprisingly found that an estrogen receptor inhibitor (e.g., a compound having the structure of Formula X, Xa, I', I, Ia, Ib, II, IIa, IIb, or pharmaceutically acceptable salt thereof) described herein synergize with an amount of an immune checkpoint inhibitor to increase immune recognition of cancer cells, such as TNBC cells, melanoma cells, small cell lung cancer cells, as compared to when used individually and separately (i.e., monotherapy treatment).

In embodiments, the estrogen receptor inhibitor (e.g., a compound having the structure of Formula X, Xa, I', I, Ia, Ib, II, IIa, IIb, or pharmaceutically acceptable salt thereof) and the immune checkpoint inhibitor are present in the pharmaceutical composition in a synergistic amount. In embodiments, the estrogen receptor inhibitor (e.g., a compound having the structure of Formula X, Xa, I', I, Ia, Ib, II, IIa, IIb, or pharmaceutically acceptable salt thereof) and the immune checkpoint inhibitor such as an anti-PD-1 antibody, an anti-PD-L1 antibody, anti-CTLA4 antibody, nivolumab, pembrolizumab, atezolizumab, avelumab, durvalumab, and the like are present in the pharmaceutical composition in a synergistic amount.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount (e.g., effective amount or therapeutically effective amount) of the estrogen receptor inhibitor (e.g., a compound having the structure of Formula X, Xa, I', I, Ia, Ib, II, IIa, IIb, or pharmaceutically acceptable salt thereof) when administered individually and separately from the immune checkpoint inhibitor (e.g., for achieving the same or similar effect).

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount (e.g., effective amount or therapeutically effective amount) of the immune checkpoint inhibitor when administered individually and separately from the estrogen receptor inhibitor (e.g., a compound having the structure of Formula X, Xa, I', I, Ia, Ib, II, IIa, IIb, or pharmaceutically acceptable salt thereof) (e.g., for achieving the same or similar effect).

The synergistic effect may be an estrogen receptor inhibitor (e.g., a compound having the structure of Formula X, Xa, I', I, Ia, Ib, II, IIa, IIb, or pharmaceutically acceptable salt thereof) activity decreasing effect and/or an immune checkpoint inhibitor decreasing effect. In embodiments, synergy between the estrogen receptor inhibitor (e.g., a compound having the structure of Formula X, Xa, I', I, Ia, Ib, II, IIa, IIb, or pharmaceutically acceptable salt thereof) and the immune checkpoint inhibitor may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease (e.g., decrease of the estrogen receptor inhibitor (e.g., a compound having the structure of Formula X, Xa, I', I, Ia, Ib, II, IIa, IIb, or pharmaceutically acceptable salt thereof) target activity or decrease of the immune checkpoint inhibitor target activity) than the sum of the decrease of the estrogen receptor inhibitor (e.g., a compound having the structure of Formula X, Xa, I', I, Ia, Ib, II, IIa, IIb, or pharmaceutically acceptable salt thereof) target activity and the immune checkpoint inhibitor target activity when used individually and separately. In embodiments, synergy between the compound and the immune checkpoint inhibitor may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater reduction in cancer proliferation or growth than the sum of the reduction in cancer proliferation or growth by the estrogen receptor inhibitor (e.g., a compound having the structure of Formula X, Xa, I', I, Ia, Ib, II, IIa, IIb, or pharmaceutically acceptable salt thereof) and the immune checkpoint inhibitor when used individually and separately.

The synergistic effect may be a hyperproliferative disorder treating effect as described herein.

The synergistic effect may be an estrogen receptor inhibition effect as described herein.

In an embodiment, there is provided a pharmaceutical composition including a pharmaceutically acceptable excipient, an estrogen receptor inhibitor (e.g. compound of Formula X, Xa, I', I, Ia, Ib, II, IIa, IIb, or any embodiment thereof, or in an example, table, figure, or claim). In an embodiment, there is provided a pharmaceutical composition including a pharmaceutically acceptable excipient, an estrogen receptor inhibitor (e.g. compound of formula X, Xa, I', I, Ia, Ib, II, IIa, IIb, or any embodiment thereof, or in an example, table, figure, or claim) and an immune checkpoint inhibitor as defined herein (e.g., an anti-PD-L1 antibody, anti-CTLA4 antibody, nivolumab, pembrolizumab, atezolizumab, avelumab, durvalumab, and the like). In embodiments, the estrogen receptor inhibitor (e.g. compound of formula X, Xa, I', I, Ia, Ib, II, IIa, IIb, or any embodiment thereof, or in an example, table, figure, or claim) is a compound selected from SERD101 to SERD160, as disclosed herein. In embodiments of the pharmaceutical composition, the immune checkpoint inhibitor, and the compound, or pharmaceutically acceptable salt thereof, as described herein, are each included in a therapeutically effective amount.

In embodiments of the pharmaceutical compositions, the pharmaceutical composition includes an additional agent or further agent (e.g. therapeutic agent). In embodiments of the pharmaceutical compositions, the pharmaceutical composition includes a further agent (e.g. therapeutic agent) in a therapeutically effective amount. In embodiments of the pharmaceutical compositions, the further agent is an agent for treating cancer (an anti-cancer agent). In embodiments of the pharmaceutical compositions, the further agent is an agent for treating a hyperproliferative disorder. In embodiments, the further agent is an anti-cancer agent. In embodiments, the further agent is a chemotherapeutic. In embodiments, the further agent is an agent for treating breast cancer. In embodiments, the further agent is an agent for treating triple negative breast cancer (TNBC). In embodiments, the further agent is an agent for treating lung cancer. In embodiments, the further agent is an agent for treating a gynecological cancer. In embodiments, the further agent is an agent for treating ovarian cancer. In embodiments, the further agent is an agent for treating endometrial cancer. In embodiments, the further agent is an agent for treating prostate cancer. In embodiments, the further agent is an agent for treating lymphangioleiomyomatosis. In embodiments, the further agent is a HER-2 inhibitor. In embodiments, the further agent is Herceptin. In embodiments, the further agent is an EGFR inhibitor (e.g. gefitinib (Iressa™), erlotinib (Tarceva™), cetuximab (Erbitux™), lapatinib (TYKERB™), panitumumab (VECTIBIX™), vandetanib (CAPRELSA™), afatinib/BIBW2992, CI-1033/canertinib, neratinib/HKI-272, pelitinib/EKB-569, BMS-599626, TAK-285, CUDC-101, OSI-420/desmethyl erlotinib, CP-724714, dacomitinib/PF299804, AG-490, AG-1478, AST-1306, WZ3146, AZD8931, sapitinib, PD153035, icotinib, ARRY334543/varlitinib, ARRY-380, AEE788, WZ8040, WZ4002, or XL647). In embodiments, the further agent is a mammalian target of rapamycin (mTOR) inhibitor (such as everolimus) for use in treating cancer (e.g. in breast and NSCLC tumors); HER2-targeted therapeutics (such as trastuzumab, lapatinib, trastuzumab-emtansine) for use in treating cancer (e.g. ER-positive breast cancers with over-expression of HER-2 receptors); HER3-targeted agents (e.g. pertuzumab); EGFR-targeted therapeutics (such as erlotinib, gefitinib, afitinib) for treating cancer (e.g. NSCLC expressing mutant EGFR or having EGFR-positivity); tamoxifen or aromatase inhibitors ofr us in treating cancer (e.g. ovarian suppression). In embodiments of the pharmaceutical compositions, the pharmaceutical composition includes a further agent (e.g., a CDK4 inhibitor or CDK6 inhibitor). In embodiments, the pharmaceutical composition includes a CDK4 inhibitor. In embodiments, the pharmaceutical composition includes a CDK6 inhibitor. In embodiments, the pharmaceutical composition includes CDK4 and/or CDK6 inhibitor. In embodiments, the pharmaceutical composition does not include a CDK4 inhibitor. In embodiments, the pharmaceutical composition does not include a CDK6 inhibitor. Exemplary CDK4 and/or CDK6 inhibitor may include, but not limited to, palbociclib, ribociclib or abemaciclib.

In embodiments, the compound is in a first dosage form and an immune checkpoint inhibitor is in a second dosage form. In embodiments, the pharmaceutical composition is a single dosage form.

In embodiments, the compound and the an immune checkpoint inhibitor (e.g., an anti-PD-L1 antibody, anti-CTLA4 antibody, nivolumab, pembrolizumab,atezolizumab, avelumab, durvalumab, and the like) are present in the composition in a synergistic amount.

Kits

In an aspect there is provided a kit including an estrogen receptor inhibitor (e.g. compound of formula X, Xa, I', I, Ia, Ib, II, IIa, IIb, or any embodiment thereof, or in an example, table, figure, or claim). In embodiments, the kit may include a further agent (e.g., a CDK4 inhibitor or CDK6 inhibitor) as described herein. In an aspect there is provided a kit including an estrogen receptor inhibitor (e.g. compound of formula X, Xa, I', I, Ia, Ib, II, IIa, IIb, or any embodiment thereof, or in an example, table, figure, or claim) and an immune checkpoint inhibitor (e.g., an anti-PD-L1 antibody, anti-CTLA4 antibody, nivolumab, pembrolizumab, atezolizumab, avelumab, durvalumab, and the like). In embodiments, the kit may include a further agent (e.g., a CDK4 inhibitor or CDK6 inhibitor) as described herein. In embodiments is included directions for pharmaceutical or therapeutic use, as described herein.

In an aspect there is provided a kit including an estrogen receptor inhibitor (e.g., a compound as described herein, or a pharmaceutically acceptable salt thereof), including a compound having the formula (I)

(I)

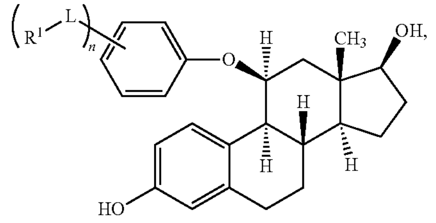

or pharmaceutically acceptable salt thereof. $R^1$ is independently a hydrogen, halogen, $—NR^2R^3$, $—CX^a_3$, —CN, $—SO_{n1}R^{10}$, $—SO_{v1}NR^2R^3$, $—NHNR^2R^3$, $—ONR^2R^3$, $—NHC(O)NHNR^2R^3$, $—NHC(O)NR^2R^3$, $—N(O)_{m1}$, $—C(O)R^9$, $—C(O)OR^9$, $—C(O)NR^2R^3$, $—OR^{10}$, $—NR^2SO_2R^{10}$, $—NR^2C(O)R^9$, $—NR^2C(O)—OR^9$, $—NR^2OR^9$, $—OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. L is independently a bond, $—NR^4—$, $—NR^4C(O)—$, $—C(O)NR^4—$, —O—, —S—, —C(O)—, —S(O)—, $—S(O)_2—$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker. $R^2$ is independently a hydrogen, halogen, $—CX^b_3$, —CN, $—SO_{n2}R^{14}$, $—SO_{v2}NR^{11}R^{12}$, $—NHNH_2$, $—ONR^{11}R^{12}$, $—NHC(O)NHNH_2$, $—NHC(O)NR^{11}R^{12}$, $—N(O)_{m2}$, $—NR^{11}R^{12}$, $—C(O)R^{13}$, $—C(O)—OR^{13}$, $—C(O)NR^{11}R^{12}$, $—OR^{14}$, $—NR^{11}SO_2R^1$, $—NR^{11}C(O)R^{13}$, $—NR^{11}C(O)—OR^{13}$, $—NR^{11}OR^{13}$, $—OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently a hydrogen, halogen, $—CX^c_3$, —CN, $—SO_{n3}R^{18}$, $—SO_{v3}NR^{15}R^{16}$, $—NHNH_2$, $—ONR^{15}R^{16}$, $—NHC(O)NHNH_2$, $—NHC(O)NR^{15}R^{16}$, $—N(O)_{m3}$, $—NR^{15}R^{16}$, $—C(O)R^{17}$, $—C(O)—OR^{17}$, $—C(O)NR^{15}R^{16}$, $—OR^{18}$, $—NR^{15}SO_2R^{18}$, $—NR^{15}C(O)R^{17}$, $—NR^{15}C(O)—OR^{17}$, $—NR^{15}OR^{17}$, $—OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ and $R^3$ substituents may optionally be joined to form a substituted or unsubstituted heterocycloalkyl, or substituted or unsubstituted heteroaryl. $R^4$ is independently a hydrogen, halogen, $—CX^d_3$, —CN, $—SO_{n4}R^{22}$, $—SO_{v4}NR^{19}R^{20}$, $—NHNH_2$, $—ONR^{19}R^{20}$, $—NHC(O)NHNH_2$, $—NHC(O)NR^{19}R^{20}$, $—N(O)_{m4}$, $—NR^{19}R^{20}$, $—C(O)R^{21}$, $—C(O)—OR^{21}$, $—C(O)NR^{14}R^{20}$, $—OR^{22}$, $—NR^{19}SO_2R^{22}$, $—NR^{19}C(O)R^{21}$, $—NR^{19}C(O)—OR^{21}$, $—NR^9OR^{21}$, $—OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl. n is an integer from 0 to 5. m1, m2, m3, m4, v1, v2, v3, and v4 are independently 1 or 2. n1, n2, n3, and n4 are independently an integer from 0 to 4. X, $X^a$, $X^b$, $X^c$ and $X^d$ are independently —Cl, —Br, —I, or —F.

In an aspect there is provided a kit including an immune checkpoint inhibitor; and an estrogen receptor inhibitor (e.g., a compound as described herein, or a pharmaceutically acceptable salt thereof), including a compound having the formula (I):

(I)

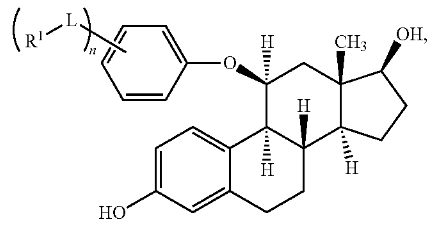

or pharmaceutically acceptable salt thereof.

In embodiments, the estrogen receptor inhibitor (e.g. compound of formula X, Xa, I', I, Ia, Ib, II, IIa, IIb, or any embodiment thereof, or in an example, table, figure, or claim) is in a first dosage form further including a pharmaceutically acceptable excipient.

In embodiments, the estrogen receptor inhibitor (e.g. compound of formula X, Xa, I', I, Ia, Ib, II, IIa, IIb, or any embodiment thereof, or in an example, table, figure, or claim) is in a first dosage form further including a pharmaceutically acceptable excipient, and the immune checkpoint inhibitor is in a second dosage form further including a pharmaceutically acceptable excipient. In embodiments, the estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof, and the immune checkpoint inhibitor are within a dosage form further including a pharmaceutically acceptable excipient.

In embodiments, the kit further includes instructions for pharmaceutical use.

In embodiments, the estrogen receptor inhibitor (e.g. compound of formula X, Xa, I', I, Ia, Ib, II, IIa, IIb, or any embodiment thereof, or in an example, table, figure, or claim) and the immune checkpoint inhibitor are present in the kit in a synergistic amount. In embodiments, the estrogen receptor inhibitor (e.g. compound of formula X, Xa, I', I, Ia, Ib, II, IIa, IIb, or any embodiment thereof, or in an example, table, figure, or claim) and an anti-PD-1 antibody are present in the kit in a synergistic amount. In embodiments, the estrogen receptor inhibitor (e.g. compound of formula X, Xa, I', I, Ia, Ib, II, IIa, IIb, or any embodiment thereof, or in an example, table, figure, or claim) and an anti-PD-L1 antibody are present in the kit in a synergistic amount. In embodiments, the estrogen receptor inhibitor (e.g. compound of formula X, Xa, I', I, Ia, Ib, II, IIa, IIb, or any embodiment thereof, or in an example, table, figure, or claim) and an anti-CTLA4 antibody are present in the kit in a synergistic amount. In embodiments, the estrogen receptor inhibitor (e.g. compound of formula X, Xa, I', I, Ia, Ib, II, IIa, IIb, or any embodiment thereof, or in an example, table, figure, or claim) and nivolumab are present in the kit in a synergistic amount. In embodiments, the estrogen receptor inhibitor (e.g. compound of formula X, Xa, I', I, Ia, Ib, II, IIa, IIb, or any embodiment thereof, or in an example, table, figure, or claim) and pembrolizumab are present in the kit in a synergistic amount. In embodiments, the estrogen receptor inhibitor (e.g. compound of formula X, Xa, I', I, Ia, Ib, II, IIa, IIb, or any embodiment thereof, or in an example, table, figure, or claim) and atezolizumab are present in the kit in a synergistic amount. In embodiments, the estrogen receptor inhibitor (e.g. compound of formula X, Xa, I', I, Ia, Ib, II, IIa, IIb, or any embodiment thereof, or in an example, table, figure, or claim) and avelumab are present in the kit in a synergistic amount. In embodiments, the estrogen receptor inhibitor (e.g. compound of formula X, Xa, I', I, Ia, Ib, II, IIa, IIb, or any embodiment thereof, or in an example, table, figure, or claim) and durvalumab are present in the kit in a synergistic amount. In embodiments, the pharmaceutical compositions provided herein include an estrogen receptor inhibitor as described herein, an immune checkpoint inhibitor, and no other anti-cancer agents. In embodiments, the pharmaceutical compositions provided herein include an estrogen receptor inhibitor as described herein, an immune checkpoint inhibitor, and no other pharmaceutically active agents. In embodiments, the pharmaceutical compositions provided herein include an estrogen receptor inhibitor as described herein, an immune checkpoint inhibitor, a CDK4 or CDK6 inhibitor and no other anti-cancer agents. In embodiments, the pharmaceutical compositions provided herein include an estrogen receptor inhibitor as described herein, an immune checkpoint inhibitor, a CDK4 or CDK6 inhibitor and no other pharmaceutically active agents.

Methods of Treatment

In an aspect is provided a method for treating a hyperproliferative disorder in a subject in need thereof, the method including administering to the subject an effective amount of an estrogen receptor inhibitor (e.g. compound of formula X, Xa, I', I, Ia, Ib, II, IIa, IIb, or any embodiment thereof, or in an example, table, figure, or claim) and the immune checkpoint inhibitor; or the estrogen receptor inhibitor (e.g. compound of formula X, Xa, I', I, Ia, Ib, II, IIa, IIb, or any embodiment thereof, or in an example, table, figure, or claim) and the immune checkpoint inhibitor of the kit as disclosed herein.

In an aspect is provided a method for treating a hyperproliferative disorder in a subject in need thereof, the method including administering to the subject an effective amount of an estrogen receptor inhibitor (e.g. compound of formula X, Xa, I', I, Ia, Ib, II, IIa, IIb, or any embodiment thereof, or in an example, table, figure, or claim), the immune checkpoint inhibitor and a further agent (e.g., a CDK4 inhibitor or CDK6 inhibitor); or the estrogen receptor inhibitor (e.g. compound of formula X, Xa, I', I, Ia, Ib, II, IIa, IIb, or any embodiment thereof, or in an example, table, figure, or claim), the immune checkpoint inhibitor and a further agent (e.g., a CDK4 inhibitor or CDK6 inhibitor) of the kit as disclosed herein. In embodiments, the method includes administering an estrogen receptor inhibitor (e.g. compound of formula X, Xa, I', I, Ia, Ib, II, IIa, IIb, or any embodiment thereof, or in an example, table, figure, or claim) such as a compound of Formula I and embodiments thereof, the immune checkpoint inhibitor, and an additional agent and/or further agent (e.g., a CDK4 inhibitor or CDK6 inhibitor).

In an aspect is provided a method for increasing immune recognition of a hyperproliferative disorder (e.g., cancer) in a subject in need thereof, the method including administering to the subject an effective amount of an estrogen receptor inhibitor (e.g. compound of formula X, Xa, I', I, Ia, Ib, II, IIa, IIb, or any embodiment thereof, or in an example, table, figure, or claim); or the estrogen receptor inhibitor (e.g. compound of formula X, Xa, I', I, Ia, Ib, II, IIa, IIb, or any embodiment thereof, or in an example, table, figure, or claim) of the kit as disclosed herein.

In an aspect is provided a method for increasing immune recognition of a hyperproliferative disorder (e.g., cancer) in a subject in need thereof, the method including administering to the subject an effective amount of an estrogen receptor inhibitor (e.g. compound of formula X, Xa, I', I, Ia, Ib, II, IIa, IIb, or any embodiment thereof, or in an example, table, figure, or claim) and the immune checkpoint inhibitor; or the estrogen receptor inhibitor (e.g. compound of formula X, Xa, I', I, Ia, Ib, II, IIa, IIb, or any embodiment thereof, or in an example, table, figure, or claim) and the immune checkpoint inhibitor of the kit as disclosed herein.

In an aspect is provided a method for increasing immune recognition of a hyperproliferative disorder (e.g., cancer) in a subject in need thereof, the method including administering to the subject an effective amount of an estrogen receptor inhibitor (e.g. compound of formula X, Xa, I', I, Ia, Ib, II, IIa, IIb, or any embodiment thereof, or in an example, table, figure, or claim), the immune checkpoint inhibitor and a further agent (e.g., a CDK4 inhibitor or CDK6 inhibitor); or the estrogen receptor inhibitor (e.g. compound of formula X, Xa, I', I, Ia, Ib, II, IIa, IIb, or any embodiment thereof, or in an example, table, figure, or claim), the immune checkpoint inhibitor and a further agent (e.g., a CDK4 inhibitor or CDK6 inhibitor) of the kit as disclosed herein. In embodiments, the method includes administering an estrogen receptor inhibitor (e.g. compound of formula X, Xa, I', I, Ia, Ib, II, IIa, IIb, or any embodiment thereof, or in an example, table, figure, or claim) such as a compound of Formula I' and embodiments thereof, the immune checkpoint inhibitor, and an additional agent and/or further agent (e.g., a CDK4 inhibitor or CDK6 inhibitor).

In embodiments, the hyperproliferative disorder (e.g., cancer or a breast cancer) is associated with estrogen receptor activity. In embodiments, the hyperproliferative disorder (e.g., cancer) is not associated with estrogen receptor activity. In embodiments, the hyperproliferative disorder is lymphangioleiomyomatosis. In embodiments, the hyperproliferative disorder is a cancer. In embodiments, the hyperproliferative disorder is a cancer resistant to an anti-cancer agent (e.g., tamoxifen, an antiestrogen, an aromatase inhibitor). In embodiments, the cancer is breast cancer. In embodiments, the cancer is breast cancer, lung cancer, a gynecological cancer, ovarian cancer, endometrial cancer, or prostate cancer. In embodiments, the cancer is ER positive breast cancer. In embodiments, the cancer is ER negative breast cancer. In embodiments, the cancer is hormone sensitive breast cancer. In embodiments, the cancer is hormone insensitive breast cancer. In embodiments, the cancer is triple negative breast cancer. In embodiments, the cancer is HER-2 positive breast cancer. In embodiments, the cancer is metastatic breast cancer. In embodiments, the cancer is lung cancer. In embodiments, the cancer is a gynecological cancer. In embodiments, the cancer is ovarian cancer. In embodiments, the cancer is endometrial cancer. In embodiments, the cancer is prostate cancer. In embodiments, the cancer is metastatic cancer. In embodiments, the hyperproliferative disorder (e.g., cancer) is resistant to an antiestrogen. In embodiments, the hyperproliferative disorder (e.g., cancer) is resistant to an endocrine therapy. In embodiments, the hyperproliferative disorder (e.g., cancer) is resistant to an aromatase inhibitor. In embodiments, the hyperproliferative disorder (e.g., cancer) is a cancer of an estrogen target organ or tissue. In embodiments, the cancer is non-small cell lung cancer. In embodiments, the cancer is small cell lung cancer. In embodiments, the lung cancer is adenocarcinoma. In embodiments, the lung cancer is squamous-cell carcinoma. In embodiments, the lung cancer is large-cell carcinoma. In embodiments, the lung cancer is bronchioloalveolar carcinoma. In embodiments, the lung cancer is stage I. In embodiments, the lung cancer is stage II. In embodiments, the lung cancer is stage III. In embodiments, the lung cancer is stage IV.

For instance, when the cancer cell has receptors for estrogen and is responsive, the cancer (e.g., breast cancer) is associated with estrogen receptors (ER-positive). When the cancer cells have no detectable levels of estrogen receptors present on their surface and/or in cytoplasm (cytosol) and nucleus, the cancer (e.g., breast cancer) is ER-negative. When the cancer cells have reduced levels or substantially reduced levels of estrogen receptors present on their surface and/or in cytoplasm (cytosol) and nucleus, the cancer (e.g., breast cancer) is ER-low. With regard to the determination of ER status by immunohistochemistry in the clinic, it is to be noted that current ASCO/CAP guidelines recommend a set of specific criteria (see Hammond et al.; also Harvey et al.). No clinical guidelines at this time consider the role of estrogen receptor expression among cells in the tumor microenvironment in determining 'estrogen status' for the purposes of clinical management. However, the current findings here indicate that these cells in the tumor microenvironment may impact the antitumor effects of antiestrogen treatments going forward. In embodiments, the hyperproliferative disorder (e.g., cancer or breast cancer) is associated with estrogen receptors (ER)-positive and/or ER-low/negative. In embodiments, the hyperproliferative disorder (e.g., cancer or breast cancer) is associated with estrogen receptors (ER)-positive. In embodiments, the hyperproliferative disorder (e.g., cancer or breast cancer) is associated with ER-low/negative. In embodiments, the hyperproliferative disorder (e.g., cancer or breast cancer) is associated with endocrine-resistant tumors.

In embodiments of the method or use, the method or use includes administering a further agent (e.g. therapeutic agent). In embodiments of the method or use, the method or use includes administering a further agent (e.g. therapeutic agent) in a therapeutically effective amount. In embodiments of the method or use, the further agent is an agent for treating cancer. In embodiments of the method or use, the further agent is an agent for treating a hyperproliferative disorder (e.g., cancer). In embodiments, the further agent is an anti-cancer agent. In embodiments, the further agent is a chemotherapeutic. In embodiments, the further agent is an agent for treating breast cancer. In embodiments, the further agent is an agent for treating lung cancer. In embodiments, the further agent is an agent for treating a gynecological cancer. In embodiments, the further agent is an agent for treating ovarian cancer. In embodiments, the further agent is an agent for treating endometrial cancer. In embodiments, the further agent is an agent for treating prostate cancer. In embodiments, the further agent is an agent for treating lymphangioleiomyomatosis (LAM). In embodiments, the further agent is an endocrine therapeutic. In embodiments, the further agent is an anti-cancer agent. In embodiments, the further agent is a chemotherapeutic. In embodiments, the further agent is a HER-2 inhibitor. In embodiments, the method or use does not include an increased risk of endometrial cancer. In embodiments, the method or use does not include an increased risk of a gynecological cancer. In embodiments, the method or use does not include a reduction in bone health.

In embodiments, the method includes administration of a further agent (e.g., a CDK4 inhibitor or CDK6 inhibitor) in combination with the estrogen receptor inhibitor (e.g., compound described herein) such as the compound of Formula I' (or pharmaceutically acceptable salt thereof). In embodiments, the method includes administration of a further agent (e.g., a CDK4 inhibitor or CDK6 inhibitor) in combination with the estrogen receptor inhibitor (e.g., compound described herein) such as the compound of Formula I' (or pharmaceutically acceptable salt thereof) and the immune checkpoint inhibitor. In embodiments, the further agent is a CDK4 inhibitor or CDK6 inhibitor. In embodiments, the further agent is a CDK4 inhibitor. In embodiments, the further agent is a CDK6 inhibitor. In embodiments, the further agent is a CDK4 and/or CDK6 inhibitor. In embodiments, the further agent does not include a CDK4 inhibitor. In embodiments, the further agent does not include a CDK6 inhibitor. Exemplary CDK4 and/or CDK6 inhibitor may include, but not limited to, palbociclib, ribociclib or abemaciclib. In embodiments, the further agent is an anti-cancer compound as disclosed herein. In embodiments, the further agent is Buparlisib (BKM120), Pietilisib (GDC0941), XL-147 (SAT245408), PX-866, BAY80-6946, ZSTK474, $CH_{5132799}$, Taselisib (GDC0032), Alpelisib (BYL719), MLN117 (INK1117), GSK2636771, AZD8186, Idelalisib (CAL-101), Duvelisib (IPI-145), BEZ235, GDC0980, PKI-587, XL-765 (SAR245409), BGT226, DS-7234, PWT33597, or SF1126, as known in the art. In embodiments, the further agent is Buparlisib (BKM120), BAY80-6946, Taselisib (GDC0032), Alpelisib (BYL719), Idelalisib (CAL-101), or Duvelisib (IPI-145). In embodiments, the further agent is an inhibitor of PI3K, AKT, HDAC, Src, IGFR, IGF-2 and FGFR. RAF or MEK. In embodiments, the further agent is dasatinib, entinostat, everolimus, ganitumumab, gefitinib, lapatinib, temsirolimus, MK-2206, XL-147, XL-765, GDC0941, GDC0980, BKM120, MEDI-573, BMS-754807, MM-121, AZD4547, Dovitinib, saracatinib, Palbociclib, LEE011, LY2835219, or enzalutamide, as known in the art.

In embodiments, the further agent is administered contemporaneously with the composition or compound disclosed herein, or pharmaceutically acceptable salt thereof. In embodiments, the further agent is administered sequentially. In embodiments, the further agent is adriamycin, a taxane, cyclophosphamide, fluorouracil, methotrexate, cisplatin, or carboplatin. In embodiments, the further agent is metformin or analog thereof, as known in the art. In embodiments, the further agent is an NFκB inhibitor (e.g., parthenolides or parthenolide derivatives). In embodiments, the further agent inhibits EGFR, HER2 and/or HER3.

In an aspect is provided an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof for use in the treatment of gynecomastia in a subject in need of such treatment. In an aspect is provided an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof in combination with an immune checkpoint inhibitor, for use in the treatment of gynecomastia in a subject in need of such treatment.

The use includes administering to the subject a therapeutically effective amount of a composition described herein, or the estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof. In embodiments, the use may include administering to the subject a therapeutically effective amount of the estrogen receptor inhibitor (e.g. compound of formula X, Xa, I', I, Ia, Ib, II, IIa, IIb, or any embodiment thereof, or in an example, table, figure, or claim) in combination with a therapeutically effective amount of the immune checkpoint inhibitor.

In embodiments, gynecomastia is associated with estrogen receptor activity. In embodiments, gynecomastia is non-physiologic gynecomastia. In embodiments, gynecomastia is physiologic gynecomastia.

In embodiments, the method or use improves (e.g. increases) bone density relative to the absence of the compound. In embodiments, the method or use improves (e.g. increases) bone mass relative to the absence of the compound. In embodiments, the method or use improves (e.g. increases) bone health relative to the absence of the compound. In embodiments, the method or use is a treatment for osteoporosis, osteogenesis imperfecta, or osteopenia. In embodiments, the method or use is a treatment for osteogenesis imperfecta.

In embodiments, the method or use is used to prevent bone deterioration, prevent bone degradation, prevent bone degeneration, prevent loss of bone mass, prevent loss of bone density, stabilize bone deterioration, stabilize bone degradation, stabilize bone degeneration, stabilize the loss of bone mass, stabilize the loss of bone density, decrease bone deterioration, decrease bone degradation, decrease bone degeneration, decrease loss of bone mass, decrease loss of bone density, increase bone mass, increase bone density, or combinations thereof.

In an aspect is provided a method of treating a bone metastasis in a subject in need thereof, including administering to the subject an effective amount of a composition described herein, or an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof. In an aspect is provided a method of treating a bone metastasis in a subject in need thereof, including administering to the subject an effective amount of a composition described herein, or an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof in combination with an immune checkpoint inhibitor.

In an aspect is provided use of a composition as described herein, or an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof or pharmaceutically acceptable salt thereof in the manufacture of a medicament for the treatment of a bone metastasis in a subject in need of such treatment. In an aspect is provided use of a composition as described herein, or an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof or pharmaceutically acceptable salt thereof in combination with an immune checkpoint inhibitor, in the manufacture of a medicament for the treatment of a bone metastasis in a subject in need of such treatment.

In an aspect is provided a composition as described herein, or a estrogen receptor inhibitor (e.g., a compound having the structure of Formula X, Xa, I', I, Ia, Ib, II, IIa, IIb, or pharmaceutically acceptable salt thereof) for use in the treatment of a bone metastasis in a subject in need of such treatment. In an aspect is provided a composition as described herein, or an estrogen receptor inhibitor (e.g., a compound having the structure of Formula X, Xa, I', I, Ia, Ib, II, IIa, IIb, or pharmaceutically acceptable salt thereof) in combination with an immune checkpoint inhibitor, for use in the treatment of a bone metastasis in a subject in need of such treatment. The use includes administering to the subject a composition described herein, or an estrogen receptor inhibitor (e.g., a compound having the structure of Formula X, Xa, I', I, Ia, Ib, II, IIa, IIb, or pharmaceutically acceptable salt thereof). In embodiments, the use includes administering to the subject a composition described herein, or an estrogen receptor inhibitor (e.g., a compound having the structure of Formula X, Xa, I', I, Ia, Ib, II, IIa, IIb, or pharmaceutically acceptable salt thereof) in combination with an immune checkpoint inhibitor. The use may include administering to the subject a therapeutically effective amount of a composition described herein, or an estrogen receptor inhibitor (e.g., a compound having the structure of Formula X, Xa, I', I, Ia, Ib, II, IIa, IIb, or pharmaceutically acceptable salt thereof). The use may include administering to the subject a therapeutically effective amount of a composition described herein, or an estrogen receptor inhibitor (e.g., a compound having the structure of Formula X, Xa, I', I, Ia, Ib, II, IIa, IIb, or pharmaceutically acceptable salt thereof) in combination with an immune checkpoint inhibitor.

In an aspect is provided a method of treating a bone disorder in a subject in need thereof, including administering to the subject an effective amount of a composition described herein, or an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof. In an aspect is provided a method of treating a bone disorder in a subject in need thereof, including administering to the subject an effective amount of a composition described herein, or an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof in combination with an immune checkpoint inhibitor.

In an aspect is provided use of a composition as described herein, or an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof or pharmaceutically acceptable salt thereof in the manufacture of a medicament for the treatment of a bone disorder in a subject in need of such treatment. In an aspect is provided use of a composition as described herein, or an estrogen receptor inhibitor (e.g. compound of formula X, Xa, I', I, Ia, Ib, II, IIa, IIb, or any embodiment thereof, or in an example, table, figure, or claim) or pharmaceutically acceptable salt thereof or pharmaceutically acceptable salt thereof in combination with an immune checkpoint inhibitor, in the manufacture of a medicament for the treatment of a bone disorder in a subject in need of such treatment.

In an aspect is provided a composition as described herein, or a estrogen receptor inhibitor (e.g., a compound having the structure of Formula X, Xa, I', I, Ia, Ib, II, IIa, IIb, or pharmaceutically acceptable salt thereof) for use in the treatment of a bone disorder in a subject in need of such treatment. In an aspect is provided a composition as described herein, or a estrogen receptor inhibitor (e.g., a compound having the structure of Formula X, Xa, I', I, Ia, Ib, II, IIa, IIb, or pharmaceutically acceptable salt thereof) in combination with an immune checkpoint inhibitor, for use in the treatment of a bone disorder in a subject in need of such treatment. The use includes administering to the subject a composition described herein, or an estrogen receptor inhibitor (e.g., a compound having the structure of Formula X, Xa, I', I, Ia, Ib, II, IIa, IIb, or pharmaceutically acceptable salt thereof). In embodiments, the use includes administering to the subject a composition described herein, or an estrogen receptor inhibitor (e.g., a compound having the structure of Formula X, Xa, I', I, Ia, Ib, II, IIa, IIb, or pharmaceutically acceptable salt thereof) in combination with an immune checkpoint inhibitor. The use may include administering to the subject a therapeutically effective amount of a composition described herein, or an estrogen receptor inhibitor (e.g., a compound having the structure of Formula X, Xa, I', I, Ia, Ib, II, IIa, IIb, or pharmaceutically acceptable salt thereof). The use may include administering to the subject a therapeutically effective amount of a composition described herein, or an estrogen receptor inhibitor (e.g., a compound having the structure of Formula X, Xa, I', I, Ia, Ib, II, IIa, IIb, or pharmaceutically acceptable salt thereof) in combination with an immune checkpoint inhibitor.

In embodiments, the bone disorder is osteoporosis, osteogenesis imperfecta, or osteopenia. In embodiments, the bone disorder is osteogenesis imperfecta. In embodiments, the bone disorder is bone deterioration, bone degradation, bone degeneration, loss of bone mass, loss of bone density, or combinations thereof.

In embodiments, the method or use is used to prevent bone deterioration, prevent bone degradation, prevent bone degeneration, prevent loss of bone mass, prevent loss of bone density, stabilize bone deterioration, stabilize bone degradation, stabilize bone degeneration, stabilize the loss of bone mass, stabilize the loss of bone density, decrease bone deterioration, decrease bone degradation, decrease bone degeneration, decrease loss of bone mass, decrease loss of bone density, increase bone mass, increase bone density, or combinations thereof.

In embodiments of the method or use, the method or use includes administering an estrogen receptor inhibitor (e.g., a compound having the structure of Formula X, Xa, I', I, Ia, Ib, II, IIa, IIb, or pharmaceutically acceptable salt thereof) as disclosed herein. In embodiments of the method or use, the method or use includes administering an estrogen receptor inhibitor (e.g., a compound having the structure of Formula X, Xa, I', I, Ia, Ib, II, IIa, IIb, or pharmaceutically acceptable salt thereof) in combination with an immune checkpoint inhibitor as disclosed herein.

In an aspect is provided use of an estrogen receptor inhibitor (e.g., compound described herein) or pharmaceutically accept salt thereof as disclosed herein in the manufacture of a medicament for the treatment of a hyperproliferative disorder (e.g., cancer) in a subject in need of such treatment. In an aspect is provided use of an estrogen receptor inhibitor (e.g., compound described herein) or pharmaceutically accept salt thereof and an immune checkpoint inhibitor as disclosed herein in the manufacture of a medicament for the treatment of a hyperproliferative disorder (e.g., cancer) in a subject in need of such treatment.

In an aspect is provided an estrogen receptor inhibitor (e.g., a compound having the structure of Formula X, Xa, I', I, Ia, Ib, II, IIa, IIb, or pharmaceutically acceptable salt thereof) as disclosed herein for use in the treatment of a hyperproliferative disorder (e.g., cancer) in a subject in need of such treatment. In an aspect is provided an estrogen receptor inhibitor (e.g., a compound having the structure of Formula X, Xa, I', I, Ia, Ib, II, IIa, IIb, or pharmaceutically acceptable salt thereof), and an immune checkpoint inhibitor as disclosed herein for use in the treatment of a hyperproliferative disorder (e.g., cancer) in a subject in need of such treatment. In embodiments, the use includes administering to the subject an estrogen receptor inhibitor (e.g., a compound having the structure of Formula X, Xa, I', I, Ia, Ib, II, IIa, IIb, or pharmaceutically acceptable salt thereof) as disclosed herein. In embodiments, the use may include administering to the subject a therapeutically effective amount of a composition described herein (e.g., an estrogen receptor inhibitor (e.g., a compound having the structure of Formula X, Xa, I', I, Ia, Ib, II, IIa, IIb, or pharmaceutically acceptable salt thereof)). In embodiments, the use includes administering to the subject an estrogen receptor inhibitor (e.g., a compound having the structure of Formula X, Xa, I', I, Ia, Ib, II, IIa, IIb, or pharmaceutically acceptable salt thereof), and an immune checkpoint inhibitor as disclosed herein. In embodiments, the use may include administering to the subject a therapeutically effective amount of a composition described herein (e.g., an estrogen receptor inhibitor (e.g., a compound having the structure of Formula X, Xa, I', I, Ia, Ib, II, IIa, IIb, or pharmaceutically acceptable salt thereof), and an immune checkpoint inhibitor).

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof), and the immune checkpoint inhibitor as disclosed herein are present in the composition in a synergistic amount.

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof) and an anti-PD-1 antibody are present in the composition in a synergistic amount.

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof) and an anti-PD-L1 antibody are present in the composition in a synergistic amount.

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof) and an anti-CTLA4 antibody are present in the composition in a synergistic amount.

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof) and an anti-PD-1 antibody are present in the composition in a synergistic amount.

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof) and nivolumab are present in the composition in a synergistic amount.

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof) and pembrolizumab are present in the composition in a synergistic amount.

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof) and atezolizumab are present in the composition in a synergistic amount.

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof) and avelumab are present in the composition in a synergistic amount.

In embodiments, the method for treating a hyperproliferative disorder (e.g., cancer) includes the administration of a composition where the estrogen receptor inhibitor (e.g., a compound having the structure of Formula X, Xa, I', I, Ia, Ib, II, IIa, IIb, or pharmaceutically acceptable salt thereof) and durvalumab are present in the composition in a synergistic amount.

Methods of Increasing an Immune Response to a Cancer in a Subject

In an aspect is provided a method of increasing an immune response to a cancer in a subject in need thereof. The method includes administering to the subject an effective amount of a composition as disclosed herein (e.g., an estrogen receptor inhibitor (e.g., a compound having the structure of Formula X, Xa, I', I, Ia, Ib, II, IIa, IIb, or pharmaceutically acceptable salt thereof)) or a kit, as disclosed herein. The method includes administering to the subject an effective amount of a composition as disclosed herein (e.g., an estrogen receptor inhibitor (e.g., a compound having the structure of Formula X, Xa, I', I, Ia, Ib, II, IIa, IIb, or pharmaceutically acceptable salt thereof) and an immune checkpoint inhibitor), or a kit, as disclosed herein. Thus, in embodiments, the method includes administering the estrogen receptor inhibitor (e.g., a compound having the structure of Formula X, Xa, I', I, Ia, Ib, II, IIa, IIb, or pharmaceutically acceptable salt thereof and embodiments thereof). In addition, in embodiments, the method includes administering the estrogen receptor inhibitor (e.g., a compound having the structure of Formula X, Xa, I', I, Ia, Ib, II, IIa, IIb, or pharmaceutically acceptable salt thereof and embodiments thereof) and an immune checkpoint inhibitor.

The immune checkpoint inhibitor may include an anti-PD-1 antibody, an anti-PD-L1 antibody, anti-CTLA4 antibody, nivolumab, pembrolizumab, atezolizumab, avelumab, or durvalumab. In embodiments, the immune checkpoint inhibitor is an anti-PD-1 antibody. In embodiments, the immune checkpoint inhibitor is an anti-PD-L1 antibody. In embodiments, the immune checkpoint inhibitor is anti-CTLA4 antibody. In embodiments, the immune checkpoint inhibitor is nivolumab. In embodiments, the immune checkpoint inhibitor is pembrolizumab. In embodiments, the immune checkpoint inhibitor is atezolizumab. In embodiments, the immune checkpoint inhibitor is avelumab. In embodiments, the immune checkpoint inhibitor is durvalumab.

In embodiments, the method includes inhibiting, reducing, or lowering levels of myeloid-derived suppressor cells (MDSC) in the subject. In embodiments, the method includes inhibiting, reducing, or loweri levels of MDSC (e.g., granulocytic (G-MDSC) and monocytic (M-MDSC)) in the subject. In embodiments, the method includes reducing or lowering the levels of MDSC (e.g., granulocytic (G-MDSC) and monocytic (M-MDSC)) in the subject by about 10% compared to control (e.g., non-treated control). In embodiments, the method includes reducing the levels of MDSC (e.g., granulocytic (G-MDSC) and monocytic (M-MDSC)) in the subject by about 20% compared to control (e.g., non-treated control). In embodiments, the method includes reducing the levels of MDSC (e.g., granulocytic (G-MDSC) and monocytic (M-MDSC)) in the subject by about 30% compared to control (e.g., non-treated control). In embodiments, the method includes reducing the levels of MDSC (e.g., granulocytic (G-MDSC) and monocytic (M-MDSC)) in the subject by about 40% compared to control (e.g., non-treated control). In embodiments, the method includes reducing the levels of MDSC (e.g., granulocytic (G-MDSC) and monocytic (M-MDSC)) in the subject by about 50% compared to control (e.g., non-treated control). In embodiments, the method includes reducing the levels of MDSC (e.g., granulocytic (G-MDSC) and monocytic (M-MDSC)) in the subject by about 60% compared to control (e.g., non-treated control). In embodiments, the method includes reducing the levels of MDSC (e.g., granulocytic (G-MDSC) and monocytic (M-MDSC)) in the subject by about 70% compared to control (e.g., non-treated control). In embodiments, the method includes reducing the levels of MDSC (e.g., granulocytic (G-MDSC) and monocytic (M-MDSC)) in the subject by about 80% compared to control (e.g., non-treated control). In embodiments, the method includes reducing the levels of MDSC (e.g., granulocytic (G-MDSC) and monocytic (M-MDSC)) in the subject by about 90% or more compared to control (e.g., non-treated control). In embodiments, the method includes reducing or lowering the levels of MDSC (e.g., granulocytic (G-MDSC) and monocytic (M-MDSC)) in the subject by about 10% relative to the absence of the pharmaceutical composition administration at the effective amount. In embodiments, the method includes reducing the levels of MDSC (e.g., granulocytic (G-MDSC) and monocytic (M-MDSC)) in the subject by about 20% relative to the absence of the pharmaceutical composition administration at the effective amount. In embodiments, the method includes reducing the levels of MDSC (e.g., granulocytic (G-MDSC) and monocytic (M-MDSC)) in the subject by about 30% relative to the absence of the pharmaceutical composition administration at the effective amount. In embodiments, the method includes reducing the levels of MDSC (e.g., granulocytic (G-MDSC) and monocytic (M-MDSC)) in the subject by about 40% relative to the absence of the pharmaceutical composition administration at the effective amount. In embodiments, the method includes reducing the levels of MDSC (e.g., granulocytic (G-MDSC) and monocytic (M-MDSC)) in the subject by about 50% relative to the absence of the pharmaceutical composition administration at the effective amount. In embodiments, the method includes reducing the levels of MDSC (e.g., granulocytic (G-MDSC) and monocytic (M-MDSC)) in the subject by about 60% relative to the absence of the pharmaceutical composition administration at the effective amount. In embodiments, the method includes reducing the levels of MDSC (e.g., granulocytic (G-MDSC) and monocytic (M-MDSC)) in the subject by about 70% relative to the absence of the pharmaceutical composition administration at the effective amount. In embodiments, the method includes reducing the levels of MDSC (e.g., granulocytic (G-MDSC) and monocytic (M-MDSC)) in the subject by about 80% relative to the absence of the pharmaceutical composition administration at the effective amount. In embodiments, the method includes reducing the levels of MDSC (e.g., granulocytic (G-MDSC) and monocytic (M-MDSC)) in the subject by about 90% or more relative to the absence of the pharmaceutical composition administration at the effective amount.

In embodiments, the method includes inhibiting or reducing the level of phosphorylation of STAT3. In embodiments, the method includes reducing the level of phosphorylation of STAT3 in the subject by about 10% compared to control (e.g., non-treated control). In embodiments, the method includes reducing the level of phosphorylation of STAT3 in the subject by about 20% compared to control (e.g., non-treated control). In embodiments, the method includes reducing the level of phosphorylation of STAT3 in the subject by about 30% compared to control (e.g., non-treated control). In embodiments, the method includes reducing the level of phosphorylation of STAT3 in the subject by about 40% compared to control (e.g., non-treated control). In embodiments, the method includes reducing the level of phosphorylation of STAT3 in the subject by about 50% compared to control (e.g., non-treated control). In embodiments, the method includes reducing the level of phosphorylation of STAT3 in the subject by about 60% compared to control (e.g., non-treated control). In embodiments, the method includes reducing the level of phosphorylation of STAT3 in the subject by about 70% compared to control (e.g., non-treated control). In embodiments, the method includes reducing the level of phosphorylation of STAT3 in the subject by about 80% compared to control (e.g., non-treated control). In embodiments, the method includes reducing the level of phosphorylation of STAT3 in the subject by about 90% or more compared to control (e.g., non-treated control). In embodiments, the method includes reducing the level of phosphorylation of STAT3 in the subject by about 10% relative to the absence of the pharmaceutical composition administration at the effective amount. In embodiments, the method includes reducing the level of phosphorylation of STAT3 in the subject by about 20% relative to the absence of the pharmaceutical composition administration at the effective amount. In embodiments, the method includes reducing the level of phosphorylation of STAT3 in the subject by about 30% relative to the absence of the pharmaceutical composition administration at the effective amount. In embodiments, the method includes reducing the level of phosphorylation of STAT3 in the subject by about 40% relative to the absence of the pharmaceutical composition administration at the effective amount. In embodiments, the method includes reducing the level of phosphorylation of STAT3 in the subject by about 50% relative to the absence of the pharmaceutical composition administration at the effective amount. In embodiments, the method includes reducing the level of phosphorylation of STAT3 in the subject by about 60% relative to the absence of the pharmaceutical composition administration at the effective amount. In embodiments, the method includes reducing the level of phosphorylation of STAT3 in the subject by about 70% relative to the absence of the pharmaceutical composition administration at the effective amount. In embodiments, the method includes reducing the level of phosphorylation of STAT3 in the subject by about 80% relative to the absence of the pharmaceutical composition administration at the effective amount. In embodiments, the method includes reducing the level of phosphorylation of STAT3 in the subject by about 90% or more relative to the absence of the pharmaceutical composition administration at the effective amount.

In embodiments, the method includes increasing levels of dendritic cells. In embodiments, the method includes increasing the levels of dendritic cells by about 2-fold or greater compared to control (e.g., non-treated control). In embodiments, the method includes increasing the levels of dendritic cells by about 3-fold or greater compared to control (e.g., non-treated control). In embodiments, the method includes increasing the levels of dendritic cells by about 4-fold or greater compared to control (e.g., non-treated control). In embodiments, the method includes increasing the levels of dendritic cells by about 5-fold or greater compared to control (e.g., non-treated control). In embodiments, the method includes increasing the levels of dendritic cells by about 6-fold or greater compared to control (e.g., non-treated control). In embodiments, the method includes increasing the levels of dendritic cells by about 8-fold or greater compared to control (e.g., non-treated control). In embodiments, the method includes increasing the levels of dendritic cells by about 9-fold or greater compared to control (e.g., non-treated control). In embodiments, the method includes increasing the levels of dendritic cells by about 10-fold or greater or greater compared to control (e.g., non-treated control). In embodiments, the method includes increasing the levels of dendritic cells by about 2-fold or greater relative to the absence of the pharmaceutical composition administration at the effective amount. In embodiments, the method includes increasing the levels of dendritic cells by about 3-fold or greater relative to the absence of the pharmaceutical composition administration at the effective amount. In embodiments, the method includes increasing the levels of dendritic cells by about 4-fold or greater relative to the absence of the pharmaceutical composition administration at the effective amount. In embodiments, the method includes increasing the levels of dendritic cells by about 5-fold or greater relative to the absence of the pharmaceutical composition administration at the effective amount. In embodiments, the method includes increasing the levels of dendritic cells by about 6-fold or greater relative to the absence of the pharmaceutical composition administration at the effective amount. In embodiments, the method includes increasing the levels of dendritic cells by about 7-fold or greater relative to the absence of the pharmaceutical composition administration at the effective amount. In embodiments, the method includes increasing the levels of dendritic cells by about 8-fold or greater relative to the absence of the pharmaceutical composition administration at the effective amount. In embodiments, the method includes increasing the levels of dendritic cells by about 9-fold or greater relative to the absence of the pharmaceutical composition administration at the effective amount. In embodiments, the method includes increasing the levels of dendritic cells by about 10-fold or greater or greater relative to the absence of the pharmaceutical composition administration at the effective amount.

In embodiments, the method includes increasing the levels of $CD8^+$ T cells. In embodiments, the method includes increasing the levels of $CD8^+$ T cells by about 2-fold or greater compared to control (e.g., non-treated control). In embodiments, the method includes increasing the levels of $CD8^+$ T cells by about 3-fold or greater compared to control (e.g., non-treated control). In embodiments, the method includes increasing the levels of $CD8^+$ T cells by about 4-fold or greater compared to control (e.g., non-treated control). In embodiments, the method includes increasing the levels of $CD8^+$ T cells by about 5-fold or greater compared to control (e.g., non-treated control). In embodiments, the method includes increasing the levels of $CD8^+$ T cells by about 6-fold or greater compared to control (e.g., non-treated control). In embodiments, the method includes increasing the levels of $CD8^+$ T cells by about 8-fold or greater compared to control (e.g., non-treated control). In embodiments, the method includes increasing the levels of $CD8^+$ T cells by about 9-fold or greater compared to control (e.g., non-treated control). In embodiments, the method includes increasing the levels of $CD8^+$ T cells by about 10-fold or greater or greater compared to control (e.g., non-treated control). In embodiments, the method includes increasing the levels of $CD8^+$ T cells by about 2-fold or greater relative to the absence of the pharmaceutical composition administration at the effective amount. In embodiments, the method includes increasing the levels of $CD8^+$ T cells by about 3-fold or greater relative to the absence of the pharmaceutical composition administration at the effective amount. In embodiments, the method includes increasing the levels of $CD8^+$ T cells by about 4-fold or greater relative to the absence of the pharmaceutical composition administration at the effective amount. In embodiments, the method includes increasing the levels of $CD8^+$ T cells by about 5-fold or greater relative to the absence of the pharmaceutical composition administration at the effective amount. In embodiments, the method includes increasing the levels of $CD8^+$ T cells by about 6-fold or greater relative to the absence of the pharmaceutical composition administration at the effective amount. In embodiments, the method includes increasing the levels of $CD8^+$ T cells by about 7-fold or greater relative to the absence of the pharmaceutical composition administration at the effective amount. In embodiments, the method includes increasing the levels of $CD8^+$ T cells by about 8-fold or greater relative to the absence of the pharmaceutical composition administration at the effective amount. In embodiments, the method includes increasing the levels of $CD8^+$ T cells by about 9-fold or greater relative to the absence of the pharmaceutical composition administration at the effective amount. In embodiments, the method includes increasing the levels of $CD8^+$ T cells by about 10-fold or greater or greater relative to the absence of the pharmaceutical composition administration at the effective amount.

In embodiments, the method includes increasing the levels of $CD4^+$ T cells. In embodiments, the method includes increasing the levels of $CD4^+$ T cells by about 2-fold or greater compared to control (e.g., non-treated control). In embodiments, the method includes increasing the levels of $CD4^+$ T cells by about 3-fold or greater compared to control (e.g., non-treated control). In embodiments, the method includes increasing the levels of $CD4^+$ T cells by about 4-fold or greater compared to control (e.g., non-treated control). In embodiments, the method includes increasing the levels of $CD4^+$ T cells by about 5-fold or greater compared to control (e.g., non-treated control). In embodiments, the method includes increasing the levels of $CD4^+$ T cells by about 6-fold or greater compared to control (e.g., non-treated control). In embodiments, the method includes increasing the levels of $CD4^+$ T cells by about 8-fold or greater compared to control (e.g., non-treated control). In embodiments, the method includes increasing the levels of $CD4^+$ T cells by about 9-fold or greater compared to control (e.g., non-treated control). In embodiments, the method includes increasing the levels of $CD4^+$ T cells by about 10-fold or greater or greater compared to control (e.g., non-treated control). In embodiments, the method includes increasing the levels of $CD4^+$ T cells by about 2-fold or greater relative to the absence of the pharmaceutical composition administration at the effective amount. In embodiments, the method includes increasing the levels of $CD4^+$ T cells by about 3-fold or greater relative to the absence of the pharmaceutical composition administration at the effective amount. In embodiments, the method includes increasing the levels of $CD4^+$ T cells by about 4-fold or greater relative to the absence of the pharmaceutical composition administration at the effective amount. In embodiments, the method includes increasing the levels of $CD4^+$ T cells by about 5-fold or greater relative to the absence of the pharmaceutical composition administration at the effective amount. In embodiments, the method includes increasing the levels of $CD4^+$ T cells by about 6-fold or greater relative to the absence of the pharmaceutical composition administration at the effective amount. In embodiments, the method includes increasing the levels of $CD4^+$ T cells by about 7-fold or greater relative to the absence of the pharmaceutical composition administration at the effective amount. In embodiments, the method includes increasing the levels of $CD4^+$ T cells by about 8-fold or greater relative to the absence of the pharmaceutical composition administration at the effective amount. In embodiments, the method includes increasing the levels of $CD4^+$ T cells by about 9-fold or greater relative to the absence of the pharmaceutical composition administration at the effective amount. In embodiments, the method includes increasing the levels of $CD4^+$ T cells by about 10-fold or greater or greater relative to the absence of the pharmaceutical composition administration at the effective amount.

In embodiments, the method includes reducing the levels of $CD45^+$ T cells. In embodiments, the method includes reducing the levels of $CD45^+$ T cells by about 10% compared to control (e.g., non-treated control). In embodiments, the method includes reducing the levels of $CD45^+$ T cells by about 20% compared to control (e.g., non-treated control). In embodiments, the method includes reducing the levels of $CD45^+$ T cells by about 30% compared to control (e.g., non-treated control). In embodiments, the method includes reducing the levels of $CD45^+$ T cells by about 40% compared to control (e.g., non-treated control). In embodiments, the method includes reducing the levels of $CD45^+$ T cells by about 50% compared to control (e.g., non-treated control). In embodiments, the method includes reducing the levels of $CD45^+$ T cells by about 60% compared to control (e.g., non-treated control). In embodiments, the method includes reducing the levels of $CD45^+$ T cells by about 70% compared to control (e.g., non-treated control). In embodiments, the method includes reducing the levels of $CD45^+$ T cells by about 80% compared to control (e.g., non-treated control). In embodiments, the method includes reducing the levels of $CD45^+$ T cells by about 90% or more compared to control (e.g., non-treated control). In embodiments, the method includes reducing the levels of $CD45^+$ T cells by about 10% relative to the absence of the pharmaceutical composition administration at the effective amount. In embodiments, the method includes reducing the levels of $CD45^+$ T cells by about 20% relative to the absence of the pharmaceutical composition administration at the effective amount. In embodiments, the method includes reducing the levels of $CD45^+$ T cells by about 30% relative to the absence of the pharmaceutical composition administration at the effective amount. In embodiments, the method includes reducing the levels of $CD45^+$ T cells by about 40% relative to the absence of the pharmaceutical composition administration at the effective amount. In embodiments, the method includes reducing the levels of $CD45^+$ T cells by about 50% relative to the absence of the pharmaceutical composition administration at the effective amount. In embodiments, the method includes reducing the levels of $CD45^+$ T cells by about 60% relative to the absence of the pharmaceutical composition administration at the effective amount. In embodiments, the method includes reducing the levels of $CD45^+$ T cells by about 70% relative to the absence of the pharmaceutical composition administration at the effective amount. In embodiments, the method includes reducing the levels of $CD45^+$ T cells by about 80% relative to the absence of the pharmaceutical composition administration at the effective amount. In embodiments, the method includes reducing the levels of $CD45^+$ T cells by about 90% or more relative to the absence of the pharmaceutical composition administration at the effective amount.

In embodiments, the method or use includes modulation (e.g., inhibition or reduction) of the activity of a cellular pathway (e.g., ras-MAPK containing pathway, PI3K/AKT containing pathway, Shc containing pathway, Src kinase containing pathway, JAK/STAT containing pathway, nitric oxide synthase pathway, VEGF secretion pathway). In embodiments, the method or use includes modulation (e.g., inhibition or reduction) of DNA synthesis. In embodiments, the method or use includes modulation (e.g., inhibition or reduction) of cell growth. In embodiments, the method or use includes modulation (e.g., inhibition or reduction) of cell proliferation. In embodiments, the method or use includes modulation (e.g., inhibition or reduction) of epithelial cell proliferation. In embodiments, the method or use includes modulation (e.g., activation or increasing) of the degradation of ER In embodiments, the method or use includes modulation (e.g., activation or increasing) of the ubiquitination of ER In embodiments, the method or use includes modulation (e.g., activation or increasing) of the degradation of ER by the proteasome. In embodiments, the method or use includes modulation (e.g., inhibition or reduction) of ER interaction with AP-1, NF-κB, MAPK, PI3K, or AKT kinase. In embodiments, the method or use includes modulation (e.g., inhibition or reduction) of ER phosphorylation. In embodiments, the method or use includes modulation (e.g., activation or increasing) of tumor cell apoptosis. In embodiments, the method or use includes modulation (e.g., activation or increasing) of cancer cell apoptosis. In embodiments, the method or use includes modulation (e.g., activation or increasing) of ER expressing cell apoptosis. In embodiments, the method or use includes modulation (e.g., inhibition or reduction) of ER translocation to the nucleus. In embodiments, the method or use includes modulation (e.g., inhibition or reduction) of ER translocation to the cytosol.

In embodiments of the method or use, the method or use includes administering a composition described herein, or an estrogen receptor inhibitor (e.g., a compound having the structure of Formula X, Xa, I', I, Ia, Ib, II, IIa, IIb, or pharmaceutically acceptable salt thereof) as disclosed herein. In embodiments of the method or use, the method or use includes administering a composition described herein, or an estrogen receptor inhibitor (e.g., a compound having the structure of Formula X, Xa, I', I, Ia, Ib, II, IIa, IIb, or pharmaceutically acceptable salt thereof) and an immune checkpoint inhibitor disclosed herein.

In an aspect is provided use of a composition as described herein, or an estrogen receptor inhibitor (e.g., a compound having the structure of Formula X, Xa, I', I, Ia, Ib, II, IIa, IIb, or pharmaceutically acceptable salt thereof) as disclosed herein, in the manufacture of a medicament for inhibiting estrogen receptor activity in a subject in need of such treatment. In an aspect is provided use of a composition as described herein, or an estrogen receptor inhibitor (e.g., a compound having the structure of Formula X, Xa, I', I, Ia, Ib, II, IIa, IIb, or pharmaceutically acceptable salt thereof) and an immune checkpoint inhibitor disclosed herein, in the manufacture of a medicament for inhibiting estrogen receptor activity in a subject in need of such treatment.

In an aspect is provided a composition as described herein, or an estrogen receptor inhibitor (e.g., a compound having the structure of Formula X, Xa, I', I, Ia, Ib, II, IIa, IIb, or pharmaceutically acceptable salt thereof) as disclosed herein, for use in inhibiting estrogen receptor activity in a subject in need of such treatment. In an aspect is provided a composition as described herein, or an estrogen receptor inhibitor (e.g., a compound having the structure of Formula X, Xa, I', I, Ia, Ib, II, IIa, IIb, or pharmaceutically acceptable salt thereof) and an immune checkpoint inhibitor disclosed herein, for use in inhibiting estrogen receptor activity in a subject in need of such treatment.

The use includes administering to the subject a composition, or an estrogen receptor inhibitor (e.g., a compound having the structure of Formula X, Xa, I', I, Ia, Ib, II, IIa, IIb, or pharmaceutically acceptable salt thereof) as disclosed herein disclosed herein. In embodiments, the use includes administering to the subject a composition, or an estrogen receptor inhibitor (e.g., a compound having the structure of Formula X, Xa, I', I, Ia, Ib, II, IIa, IIb, or pharmaceutically acceptable salt thereof) and an immune checkpoint inhibitor disclosed herein disclosed herein. In embodiments, the use may include administering to the subject a therapeutically effective amount of a composition described herein, or an estrogen receptor inhibitor (e.g., a compound having the structure of Formula X, Xa, I', I, Ia, Ib, II, IIa, IIb, or pharmaceutically acceptable salt thereof) as described herein. The use may include administering to the subject a therapeutically effective amount of a composition described herein, or an estrogen receptor inhibitor (e.g., a compound having the structure of Formula X, Xa, I', I, Ia, Ib, II, IIa, IIb, or pharmaceutically acceptable salt thereof) and an immune checkpoint inhibitor disclosed herein described herein.

In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) is present in the composition in a synergistic amount. In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) and the immune checkpoint inhibitor are present in the composition in a synergistic amount.

In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) and an anti-PD-1 antibody are present in the composition in a synergistic amount. In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) and an anti-PD-L1 antibody are present in the composition in a synergistic amount. In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) and an anti-CTLA4 antibody are present in the composition in a synergistic amount. In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) and nivolumab are present in the composition in a synergistic amount. In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) and pembrolizumab are present in the composition in a synergistic amount. In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) and atezolizumab are present in the composition in a synergistic amount. In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) and avelumab are present in the composition in a synergistic amount. In embodiments, the method of inhibiting estrogen receptor activity in a subject includes the administration of a composition where the estrogen receptor inhibitor (e.g., a compound having the structure of Formula X, Xa, I', I, Ia, Ib, II, IIa, IIb, or pharmaceutically acceptable salt thereof) and durvalumab are present in the composition in a synergistic amount.

EMBODIMENTS

Embodiment P1

A pharmaceutical composition comprising a compound having the formula (I)

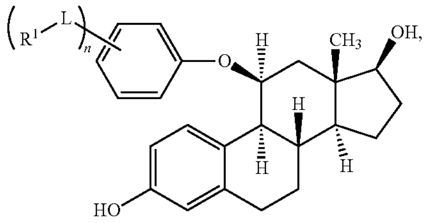

or a pharmaceutically acceptable salt thereof;

an immune checkpoint inhibitor; and a pharmaceutically acceptable excipient, wherein:

$R^1$ is independently a hydrogen, halogen, $-NR^2R^3$, $-CX^a_3$, $-CN$, $-SO_{n1}R^{10}$, $-SO_{v1}NR^2R^3$, $-NHNR^2R^3$, $-ONR^2R^3$, $-NHC(O)NHNR^2R^3$, $-NHC(O)NR^2R^3$, $-N(O)_{m1}$, $-C(O)R^9$, $-C(O)-OR^9$, $-C(O)NR^2R^3$, $-OR^{10}$, $-NR^2SO_2R^{10}$, $-NR^2C(O)R^9$, $-NR^2C(O)-OR^9$, $-NR^2OR^9$, $-OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is independently a bond, $-NR^4-$, $-NR^4C(O)-$, $-C(O)NR^4-$, $-O-$, $-S-$, $-C(O)-$, $-S(O)-$, $-S(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker;

$R^2$ is independently a hydrogen, halogen, $-CX^b_3$, $-CN$, $-SO_{n2}R^{14}$, $-SO_{v2}NR^{11}R^{12}$, $-NHNH_2$, $-ONR^{11}R^{12}$, $-NHC(O)NHNH_2$, $-NHC(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^4$, $-NR^{11}C(O)R^{13}$, $-NR^{11}C(O)-OR^{13}$, $-NR^{11}OR^{13}$, $-OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently a hydrogen, halogen, $-CX^c_3$, $-CN$, $-SO_{n3}R^{18}$, $-SO_{n3}NR^{15}R^{16}$, $-NHNH_2$, $-ONR^{15}R^{16}$, $-NHC(O)NHNH_2$, $-NHC(O)NR^{15}R^{16}$, $-N(O)_{m3}$, $-NR^{15}R^{16}$, $-C(O)R^{17}$, $-C(O)-OR^{17}$, $-C(O)NR^{15}R^{16}$, $-OR^{18}$, $-NR^{15}SO_2R^{18}$, $-NR^{15}C(O)R^{17}$, $-NR^{15}C(O)-OR^{17}$, $-NR^{15}OR^{17}$, $-OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ substituents may optionally be joined to form a substituted or unsubstituted heterocycloalkyl, or substituted or unsubstituted heteroaryl;

$R^4$ is independently a hydrogen, halogen, $-CX^d_3$, $-CN$, $-SO_{n4}R^{22}$, $-SO_4NR^{19}R^{21}$, $-NHNH_2$, $-ONR^{19}R^{20}$, $-NHC(O)NHNH_2$, $-NHC(O)NR^{19}R^{20}$, $-N(O)_{m4}$, $-NR^{19}R^{20}$, $-C(O)R^{21}$, $-C(O)-OR^{21}$, $-C(O)NR^{19}R^{20}$, $-OR^{22}$, $-NR^{19}SO_2R^2$, $-NR^{19}C(O)R^{21}$, $-NR^{19}C(O)-OR^{21}$, $-NR^9OR^{21}$, $-OCX^{d3}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCX_3$, $-OCHX_2$, $-CF_3$, $-OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^1$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl;

n is an integer from 0 to 5;

m1, m2, m3, m4, v1, v2, v3, and v4 are independently 1 or 2;

n1, n2, n3, and n4 are independently an integer from 0 to 4; and

X, $X^a$, $X^b$, $X^c$ and $X^d$ are independently $-Cl$, $-Br$, $-I$, or $-F$.

Embodiment P2

The pharmaceutical composition of Embodiment P1, wherein the immune checkpoint inhibitor is an anti-PD-1 antibody, an anti-PD-L1 antibody, anti-CTLA4 antibody, nivolumab, pembrolizumab, atezolizumab, avelumab, or durvalumab.

Embodiment P3

The pharmaceutical composition of any one of Embodiments P1-P2, wherein the compound has the formula:

(Ia)

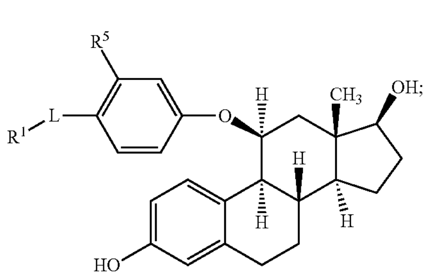

wherein $R^5$ is independently a hydrogen, halogen, $—CX^e_3$, —CN, $—SO_{n5}R^{26}$, $—SO_{v5}NR^{23}R^{24}$, $—NHNH_2$, $—ONR^{23}R^{24}$, $—NHC(O)NHNH_2$, —NHC(O) $NR^{23}R^{24}$, $—N(O)_{m5}$, $—NR^{23}R^{24}$, $—C(O)R^{25}$, $—C(O)—OR^{25}$, $—C(O)NR^{23}R^{24}$, $—OR^{26}$, $—NR^{23}SO_2R^{26}$, $—NR^{23}C(O)R^{25}$, $—NR^{23}C(O)—OR^{25}$, $—NR^{23}OR^{25}$, $—OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{23}$, $R^{24}$, $R^{21}$, and $R^{26}$ are independently hydrogen, halogen, $—CX_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC (O)—OH, —NHOH, $—OCX_3$, $—OCHX_2$, $—CF_3$, $—OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{23}$ and $R^{24}$ substituents bonded to the same nitrogen atom may optionally be joined to form a substituted or unsubstituted heterocycloalkyl or substituted or unsubstituted heteroaryl;

m5 and v5 are independently 1 or 2;

n5 is independently an integer from 0 to 4; and $X^c$ is independently —Cl, —Br, —I, or —F.

Embodiment P4

The pharmaceutical composition of Embodiment P3, wherein $R^5$ is independently a hydrogen, halogen, $—CX^c_3$, or unsubstituted alkyl.

Embodiment P5

The pharmaceutical composition of Embodiment P3, wherein $R^5$ is independently a hydrogen, —F, $—CF_3$, or unsubstituted methyl.

Embodiment P6

The pharmaceutical composition of any one of Embodiments P1-P5, wherein the compound has the formula:

(Ib)

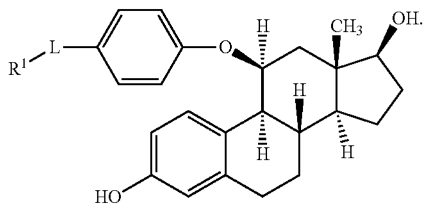

Embodiment P7

The pharmaceutical composition of any one of Embodiments P1-P5, wherein the compound has the formula:

(II)

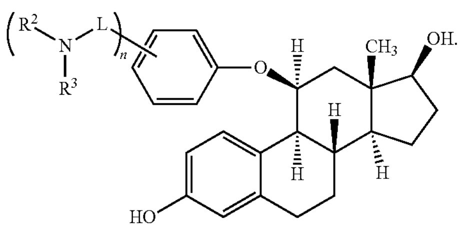

Embodiment P8

The pharmaceutical composition of any one of Embodiments P1-P5, wherein the compound has the formula:

(IIa)

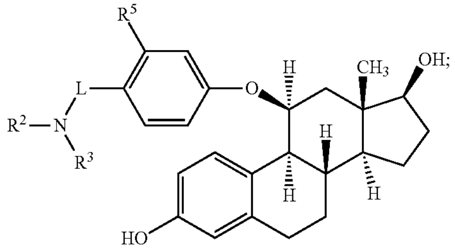

wherein:

$R^5$ is independently a hydrogen, halogen, $—CX^c_3$, —CN, $—SO_{n5}R^{26}$, $—SO_{v5}NR^{23}R^{24}$, $—NHNH_2$, $—ONR^{23}R^{24}$, $—NHC(O)NHNH_2$, —NHC(O) $NR^{23}R^{24}$, $—N(O)_{m5}$, $—NR^{23}R^{24}$, $—C(O)R^{25}$, $—C(O)—OR^{25}$, $—C(O)NR^{23}R^{24}$, $—OR^{26}$, $—NR^{23}SO_2R^{26}$, $—NR^{23}C(O)R^{25}$, $—NR^{23}C(O)—OR^{25}$, $—NR^{23}OR^{25}$, $—OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{23}$, $R^{24}$, $R^{25}$, and $R^{26}$ are independently hydrogen, halogen, $—CX_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC (O)—OH, —NHOH, $—OCX_3$, $—OCHX_2$, $—CF_3$, $—OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{23}$ and $R^{24}$ substituents bonded to the same nitrogen atom may optionally be joined to form a substituted or unsubstituted heterocycloalkyl or substituted or unsubstituted heteroaryl;

m5 and v5 are independently 1 or 2;

n5 is independently an integer from 0 to 4; and $X^c$ is independently —Cl, —Br, —I, or —F.

Embodiment P9

The pharmaceutical composition of Embodiment P8, wherein $R^5$ is independently a hydrogen, halogen, —$CX^c{}_3$, or unsubstituted alkyl.

Embodiment P10

The pharmaceutical composition of Embodiment P8, wherein $R^5$ is independently a hydrogen, —F, —$CF_3$, or unsubstituted methyl.

Embodiment P11

The pharmaceutical composition of any one of Embodiments P1-P5, wherein the compound has the formula:

(IIb)

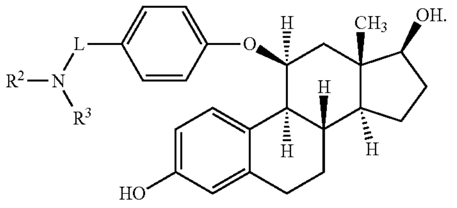

Embodiment P12

The pharmaceutical composition of any one of Embodiments P1-P11, wherein L is a bond.

Embodiment P13

The pharmaceutical composition of any one of Embodiments P1-P11, wherein L is a substituted or unsubstituted heteroalkylene.

Embodiment P14

The pharmaceutical composition of any one of Embodiments P1-P11, wherein L is independently a substituted or unsubstituted 2 to 8 membered heteroalkylene.

Embodiment P15

The pharmaceutical composition of any one of Embodiments P1-P11, wherein L is independently a substituted or unsubstituted 3 to 6 membered heteroalkylene.

Embodiment P16

The pharmaceutical composition of any one of Embodiments P1-P11, wherein L is independently —NH-(substituted or unsubstituted ($C_1$-$C_6$) alkylene).

Embodiment P17

The pharmaceutical composition of any one of Embodiments P1-P11, wherein L is independently —NH-(unsubstituted ($C_1$-$C_4$) alkylene).

Embodiment P18

The pharmaceutical composition of any one of Embodiments P1-P11, wherein L is independently —NHC(O)-(substituted or unsubstituted ($C_1$-$C_4$) alkylene).

Embodiment P19

The pharmaceutical composition of any one of Embodiments P1-P11, wherein L is independently —NHC(O)-(unsubstituted ($C_1$-$C_4$) alkylene).

Embodiment P20

The pharmaceutical composition of any one of Embodiments P1-P19, wherein $R^2$ is independently substituted or unsubstituted alkyl or substituted or unsubstituted heteroalkyl.

Embodiment P21

The pharmaceutical composition of any one of Embodiments P1-P19, wherein $R^2$ is independently substituted or unsubstituted ($C_1$-$C_{10}$) alkyl or substituted or unsubstituted 2 to 10 membered heteroalkyl.

Embodiment P22

The pharmaceutical composition of any one of Embodiments P1-P19, wherein $R^2$ is unsubstituted methyl.

Embodiment P23

The pharmaceutical composition of any one of Embodiments P1-P19, wherein $R^2$ is H.

Embodiment P24

The pharmaceutical composition of any one of Embodiments P1-P23, wherein $R^3$ is independently substituted or unsubstituted alkyl or substituted or unsubstituted heteroalkyl.

Embodiment P25

The pharmaceutical composition of any one of Embodiments P1-P23, wherein $R^3$ is independently substituted or unsubstituted ($C_1$-$C_{10}$) alkyl or substituted or unsubstituted 2 to 10 membered heteroalkyl.

Embodiment P26

The pharmaceutical composition of any one of Embodiments P1-P23, wherein $R^3$ is unsubstituted methyl.

Embodiment P27

The pharmaceutical composition of any one of Embodiments P1-P23, wherein $R^3$ is H.

Embodiment P28

The pharmaceutical composition of any one of Embodiments P1-P19, wherein $R^2$ and $R^3$ are joined to form a substituted or unsubstituted heterocycloalkyl.

Embodiment P29

The pharmaceutical composition of any one of Embodiments P1-P19, wherein $R^2$ and $R^3$ are joined to form a substituted or unsubstituted 3 to 8 membered heterocycloalkyl.

Embodiment P30

The pharmaceutical composition of any one of Embodiments P1-P19, wherein $R^2$ and $R^3$ are joined to form a substituted or unsubstituted 3 to 6 membered heterocycloalkyl.

Embodiment P31

The pharmaceutical composition of any one of Embodiments P1-P19, wherein $R^2$ and $R^3$ are joined to form an unsubstituted 3 to 6 membered heterocycloalkyl.

Embodiment P32

The pharmaceutical composition of any one of Embodiments P1-P19, wherein $R^2$ and $R^3$ and the nitrogen to which they are bonded form

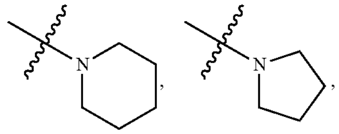

or

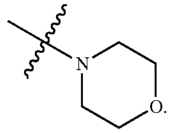

Embodiment P33

The pharmaceutical composition of any one of Embodiments P1-P32, wherein n is 2.

Embodiment P34

The pharmaceutical composition of any one of Embodiments P1-P32, wherein n is 1.

Embodiment P35

The pharmaceutical composition of any one of Embodiments P1-P34, wherein $R^1$ is —$NO_2$ or —$NH_2$.

Embodiment P36

The pharmaceutical composition of Embodiment P1, wherein L is a bond.

Embodiment P37

The pharmaceutical composition of Embodiment P1, wherein the compound has the formula:

(SERD119)

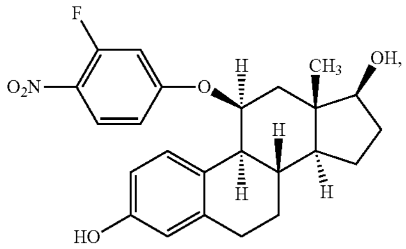

(SERD128)

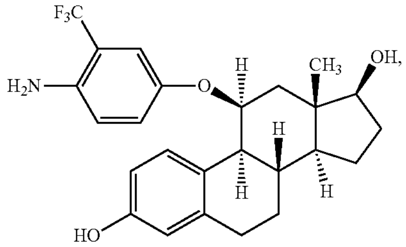

(SERD140)

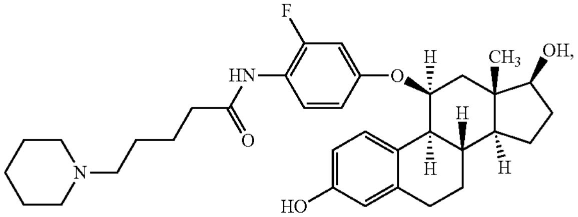

(SERD160)

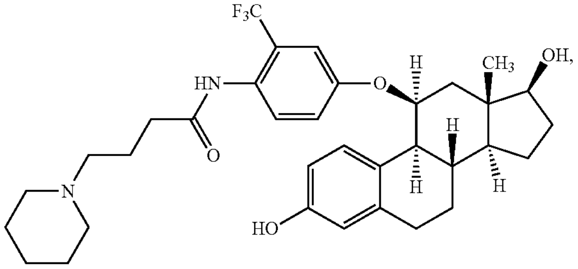

(SERD121)

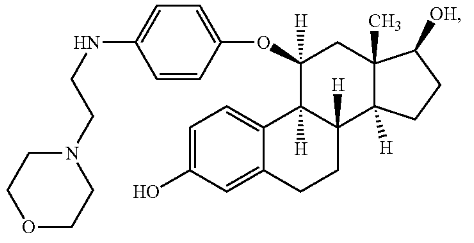

or

-continued (SERD121)

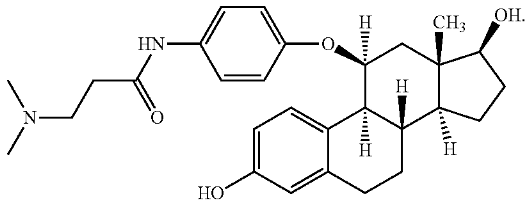

Embodiment P38

The pharmaceutical composition of Embodiment P1, further comprising a CDK4 inhibitor or CDK6 inhibitor.

Embodiment P39

A method of treating a hyperproliferative disorder in a subject in need thereof, comprising administering to said subject an effective amount of a pharmaceutical composition of any one of Embodiments P1-P38.

Embodiment P40

The method of Embodiment P39, wherein said hyperproliferative disorder is associated with estrogen receptors (ER)-positive and ER-low/negative, or endocrine-resistant tumors.

Embodiment P41

The method of Embodiment P39, wherein said hyperproliferative disorder is a cancer.

Embodiment P42

The method of Embodiment P41, wherein said cancer is resistant to an anti-cancer agent.

Embodiment P43

The method of Embodiment P41, wherein said cancer is breast cancer, lung cancer, gynecological cancer, ovarian cancer, endometrial cancer, or prostate cancer.

Embodiment P44

The method of Embodiment P41, wherein said cancer is triple-negative breast cancers (TNBC).

Embodiment P45

A method of increasing an immune response to a cancer in a subject, comprising administering to said subject an effective amount of a pharmaceutical composition of any one of Embodiments P1-P38.

Embodiment P46

The method of Embodiment P45, wherein said cancer is resistant to an anti-cancer agent.

Embodiment P47

The method of Embodiment P45, wherein said cancer is breast cancer, lung cancer, gynecological cancer, ovarian cancer, endometrial cancer, or prostate cancer.

Embodiment P48

The method of Embodiment P45, wherein said cancer is triple-negative breast cancers (TNBC).

Embodiment P49

The method of Embodiment P45, comprising inhibiting level of myeloid-derived suppressor cells (MDSC) in the subject.

Embodiment P50

The method of Embodiment P45, comprising inhibiting phosphorylation of STAT3 in the subject.

Embodiment P51

The method of Embodiment P45, comprising increasing level of $CD8^+$ T cells and/or $CD4^+$ T cells in the subject.

Embodiment P52

A kit comprising a pharmaceutical composition of any one of Embodiments P1-P38.

Embodiment Q1

A pharmaceutical composition comprising a compound having the formula:

(I)

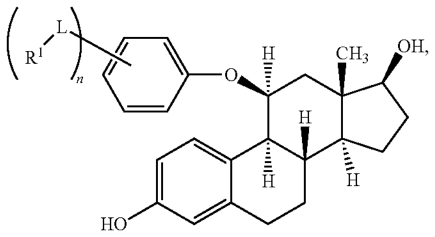

or a pharmaceutically acceptable salt thereof;

an immune checkpoint inhibitor; and a pharmaceutically acceptable excipient, wherein:

$R^1$ is independently a hydrogen, halogen, $-NR^2R^3$, $-CX_3$, $-CN$, $-SO_{n1}R^{10}$, $-SO_{v1}NR^2R^3$, $-NHNR^2R^3$, $-ONR^2R^3$, $-NHC(O)NHNR^2R^3$, $-NHC(O)NR^2R^3$, $-N(O)_{m1}$, $-C(O)R^9$, $-C(O)-OR^9$, $-C(O)NR^2R^3$, $-OR^{10}$, $-NR^2SO_2R^{10}$, $-NR^2C(O)R^9$, $-NR^2C(O)-OR^9$, $-NR^2OR^9$, $-OCX^a_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L is independently a bond, $-NR^4-$, $-NR^4C(O)-$, $-C(O)NR^4-$, $-O-$, $-S-$, $-C(O)-$, $-S(O)-$, $-S(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; or a substituted or unsubstituted spirocyclic linker;

$R^2$ is independently a hydrogen, halogen, $-CX^b_3$, $-CN$, $-SO_{n2}R^{14}$, $-SO_{v2}NR^{11}R^{12}$, $-NHNH_2$, $-ONR^{11}R^{12}$, $-NHC(O)NHNH_2$, $-NHC(O)NR^{11}R^{12}$, $-N(O)_{m2}$, $-NR^{11}R^{12}$, $-C(O)R^{13}$, $-C(O)-OR^{13}$, $-C(O)NR^{11}R^{12}$, $-OR^{14}$, $-NR^{11}SO_2R^{14}$, $-NR^{11}C(O)R^{13}$, $-NR^{11}C(O)-OR^{13}$, $-NR^{11}OR^{13}$, $-OCX^b_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently a hydrogen, halogen, $-CX^c_3$, $-CN$, $-SO_{n3}R^{18}$, $-SO_{v3}NR^{15}R^{16}$, $-NHNH_2$, $-ONR^{15}R^{16}$, $-NHC(O)NHNH_2$, $-NHC(O)NR^{15}R^{16}$, $-N(O)_{m3}$, $-NR^{15}R^{16}$, $-C(O)R^{17}$, $-C(O)-OR^{17}$, $-C(O)NR^{15}R^{16}$, $-OR^{18}$, $-NR^{15}SO_2R'''$, $-NR^{15}C(O)R^{17}$, $-NR^{15}C(O)-OR^{17}$, $-NR^{10}R^{17}$, $-OCX^c_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ and $R^3$ substituents may optionally be joined to form a substituted or unsubstituted heterocycloalkyl, or substituted or unsubstituted heteroaryl;

$R^4$ is independently a hydrogen, halogen, $-CX^d_3$, $-CN$, $-SO_{n4}R^{22}$, $-SO_{v4}NR^{19}R^{21}$, $-NHNH_2$, $-ONR^{19}R^{20}$, $-NHC(O)NHNH_2$, $-NHC(O)NR^{19}R^{20}$, $-N(O)_{m4}$, $-NR^{19}R^{20}$, $-C(O)R^{21}$, $-C(O)-OR^{21}$, $-C(O)NR^{19}R^{20}$, $-OR^{22}$, $-NR^{19}SO_2R^2$, $-NR^{19}C(O)R^{21}$, $-NR^{19}C(O)-OR^{21}$, $-NR^9OR^{21}$, $-OCX^d_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ are independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCX_3$, $-OCHX_2$, $-CF_3$, $-OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $R^{19}$ and $R^{20}$ substituents bonded to the same nitrogen atom may optionally be joined to form a substituted or unsubstituted heterocycloalkyl or substituted or unsubstituted heteroaryl;

n is an integer from 0 to 5;

m1, m2, m3, m4, v1, v2, v3, and v4 are independently 1 or 2;

n1, n2, n3, and n4 are independently an integer from 0 to 4; and

X, $X^a$, $X^b$, $X^c$ and $X^d$ are independently $-Cl$, $-Br$, $-I$, or $-F$.

Embodiment Q2

The pharmaceutical composition of Embodiment Q1, wherein the immune checkpoint inhibitor is an anti-PD-1 antibody, an anti-PD-L1 antibody, anti-CTLA4 antibody, nivolumab, pembrolizumab, atezolizumab, avelumab, or durvalumab.

Embodiment Q3

The pharmaceutical composition of any one of Embodiments Q1-Q2, wherein the compound has the formula:

(Ia)

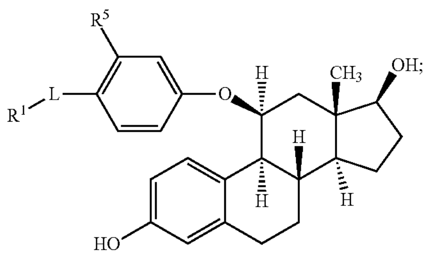

wherein $R^5$ is independently a hydrogen, halogen, $-CX^c_3$, $-CN$, $-SO_{n5}R^{26}$, $-SO_{v5}NR^{23}R^{24}$, $-NHNH_2$, $-ONR^{23}R^{24}$, $-NHC(O)NHNH_2$, $-NHC(O)NR^{23}R^{24}$, $-N(O)_{m5}$, $-NR^{23}R^{24}$, $-C(O)R^{25}$, $-C(O)-OR^{25}$, $-C(O)NR^{23}R^{24}$, $-OR^{26}$, $-NR^{23}SO_2R^{26}$, $-NR^{23}C(O)R^{25}$, $-NR^{23}C(O)-OR^{25}$, $-NR^{23}OR^{25}$, $-OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{23}$, $R^{24}$, $R^{25}$, and $R^{26}$ are independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCX_3$, $-OCHX_2$, $-CF_3$, $-OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{23}$ and $R^{24}$ substituents bonded to the same nitrogen atom may optionally be joined to form a substituted or unsubstituted heterocycloalkyl or substituted or unsubstituted heteroaryl;

m5 and v5 are independently 1 or 2;

n5 is independently an integer from 0 to 4; and $X^c$ is independently $-Cl$, $-Br$, $-I$, or $-F$.

Embodiment Q4

The pharmaceutical composition of Embodiment Q3, wherein $R^5$ is independently a hydrogen, halogen, $-CX^c_3$, or unsubstituted alkyl.

Embodiment Q5

The pharmaceutical composition of Embodiment Q3, wherein $R^5$ is independently a hydrogen, —F, —$CF_3$, or unsubstituted methyl.

Embodiment Q6

The pharmaceutical composition of any one of Embodiments Q1-Q5, wherein the compound has the formula:

(Ib)

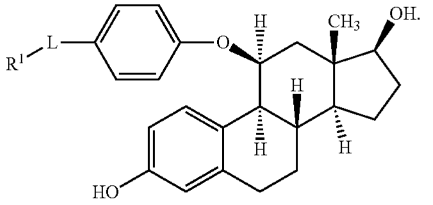

Embodiment Q7

The pharmaceutical composition of any one of Embodiments Q1-Q5, wherein the compound has the formula:

(II)

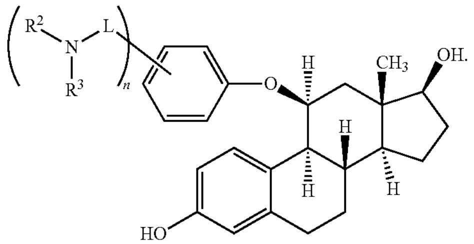

Embodiment Q8

The pharmaceutical composition of any one of Embodiments Q1-Q5, wherein the compound has the formula:

(IIa)

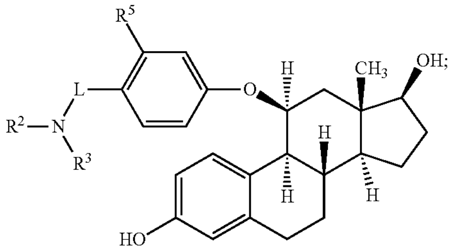

wherein:

$R^5$ is independently a hydrogen, halogen, —$CX^c_3$, —CN, —$SO_{n5}R^{26}$, —$SO_{v5}NR^{23}R^{24}$, —$NHNH_2$, —$ONR^{23}R^{24}$, —$NHC(O)NHNH_2$, —NHC(O)$NR^{23}R^{24}$, —$N(O)_{m5}$, —$NR^{23}R^{24}$, —$C(O)R^{25}$, —C(O)—$OR^{25}$, —$C(O)NR^{23}R^{24}$, —$OR^{26}$, —$NR^{23}SO_2R^{26}$, —$NR^{23}C(O)R^{25}$, —$NR^{23}C(O)$—$OR^{25}$, —$NR^{23}OR^{25}$, —$OCX^e_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{23}$, $R^{24}$, $R^{21}$, and $R^{26}$ are independently hydrogen, halogen, —$CX_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCX_3$, —$OCHX_2$, —$CF_3$, —$OCF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{23}$ and $R^{24}$ substituents bonded to the same nitrogen atom may optionally be joined to form a substituted or unsubstituted heterocycloalkyl or substituted or unsubstituted heteroaryl;

m5 and v5 are independently 1 or 2;

n5 is independently an integer from 0 to 4; and $X^c$ is independently —Cl, —Br, —I, or —F.

Embodiment Q9

The pharmaceutical composition of Embodiment Q8, wherein $R^5$ is independently a hydrogen, halogen, —$CX^c_3$, or unsubstituted alkyl.

Embodiment Q10

The pharmaceutical composition of Embodiment Q8, wherein $R^5$ is independently a hydrogen, —F, —$CF_3$, or unsubstituted methyl.

Embodiment Q11

The pharmaceutical composition of any one of Embodiments Q1-Q5, wherein the compound has the formula:

(IIb)

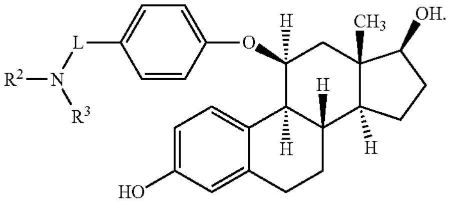

Embodiment Q12

The pharmaceutical composition of any one of Embodiments Q1-Q11, wherein L is a bond.

Embodiment Q13

The pharmaceutical composition of any one of Embodiments Q1-Q11, wherein L is a substituted or unsubstituted heteroalkylene.

Embodiment Q14

The pharmaceutical composition of any one of Embodiments Q1-Q11, wherein L is independently a substituted or unsubstituted 2 to 8 membered heteroalkylene.

Embodiment Q15

The pharmaceutical composition of any one of Embodiments Q1-Q11, wherein L is independently a substituted or unsubstituted 3 to 6 membered heteroalkylene.

Embodiment Q16

The pharmaceutical composition of any one of Embodiments Q1-Q11, wherein L is independently —NH-(substituted or unsubstituted ($C_1$-$C_6$) alkylene).

Embodiment Q17

The pharmaceutical composition of any one of Embodiments Q1-Q11, wherein L is independently —NH-(unsubstituted ($C_1$-$C_4$) alkylene).

Embodiment Q18

The pharmaceutical composition of any one of Embodiments Q1-Q11, wherein L is independently —NHC(O)-(substituted or unsubstituted ($C_1$-$C_4$) alkylene).

Embodiment Q19

The pharmaceutical composition of any one of Embodiments Q1-Q11, wherein L is independently —NHC(O)-(unsubstituted ($C_1$-$C_4$) alkylene).

Embodiment Q20

The pharmaceutical composition of any one of Embodiments Q1-Q19, wherein $R^2$ is independently substituted or unsubstituted alkyl or substituted or unsubstituted heteroalkyl.

Embodiment Q21

The pharmaceutical composition of any one of Embodiments Q1-Q19, wherein $R^2$ is independently substituted or unsubstituted ($C_1$-$C_{10}$) alkyl or substituted or unsubstituted 2 to 10 membered heteroalkyl.

Embodiment Q22

The pharmaceutical composition of any one of Embodiments Q1-Q19, wherein $R^2$ is unsubstituted methyl.

Embodiment Q23

The pharmaceutical composition of any one of Embodiments Q1-Q19, wherein $R^2$ is H.

Embodiment Q24

The pharmaceutical composition of any one of Embodiments Q1-Q23, wherein $R^3$ is independently substituted or unsubstituted alkyl or substituted or unsubstituted heteroalkyl.

Embodiment Q25

The pharmaceutical composition of any one of Embodiments Q1-Q23, wherein $R^3$ is independently substituted or unsubstituted ($C_1$-$C_{10}$) alkyl or substituted or unsubstituted 2 to 10 membered heteroalkyl.

Embodiment Q26

The pharmaceutical composition of any one of Embodiments Q1-Q23, wherein $R^3$ is unsubstituted methyl.

Embodiment Q27

The pharmaceutical composition of any one of Embodiments Q1-Q23, wherein $R^3$ is H.

Embodiment Q28

The pharmaceutical composition of any one of Embodiments Q1-Q19, wherein $R^2$ and $R^3$ are joined to form a substituted or unsubstituted heterocycloalkyl.

Embodiment Q29

The pharmaceutical composition of any one of Embodiments Q1-Q19, wherein $R^2$ and $R^3$ are joined to form a substituted or unsubstituted 3 to 8 membered heterocycloalkyl.

Embodiment Q30

The pharmaceutical composition of any one of Embodiments Q1-Q19, wherein $R^2$ and $R^3$ are joined to form a substituted or unsubstituted 3 to 6 membered heterocycloalkyl.

Embodiment Q31

The pharmaceutical composition of any one of Embodiments Q1-Q19, wherein $R^2$ and $R^3$ are joined to form an unsubstituted 3 to 6 membered heterocycloalkyl.

Embodiment Q32

The pharmaceutical composition of any one of Embodiments Q1-Q19, wherein $R^2$ and $R^3$ and the nitrogen to which they are bonded form,

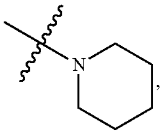
,
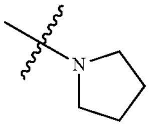
, or
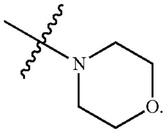

Embodiment Q33

The pharmaceutical composition of any one of Embodiments Q1-Q32, wherein n is 2.

Embodiment Q34

The pharmaceutical composition of any one of Embodiments Q1-Q32, wherein n is 1.

Embodiment Q35

The pharmaceutical composition of any one of Embodiments Q1-Q34, wherein $R^1$ is —$N_{02}$ or —$NH_2$.

Embodiment Q36

The pharmaceutical composition of Embodiment Q1, wherein L is a bond.

Embodiment Q37

The pharmaceutical composition of Embodiment Q1, wherein the compound has the formula:

(SERD119)

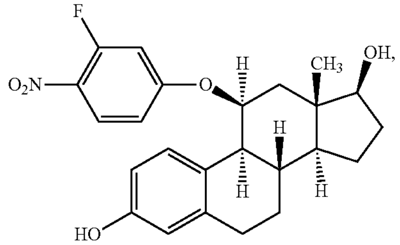

(SERD128)

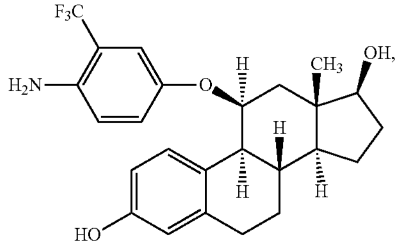

(SERD140)

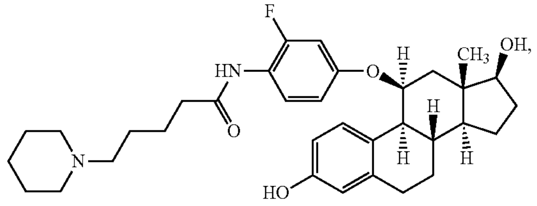

(SERD160)

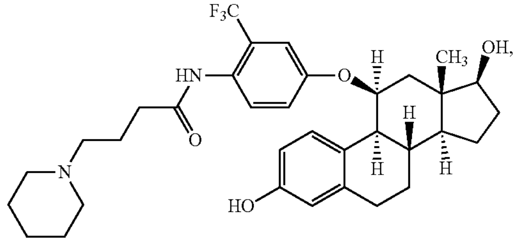

(SERD121)

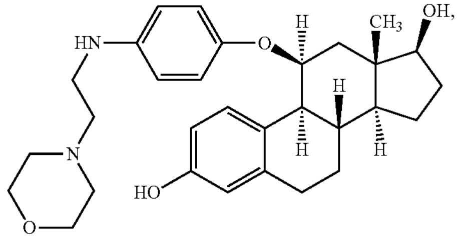

or

-continued (SERD109)

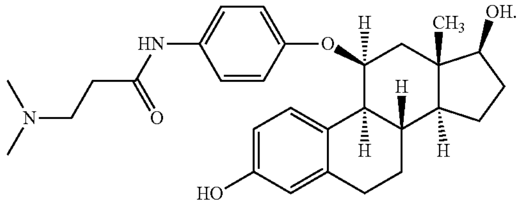

Embodiment Q38

The pharmaceutical composition of Embodiment Q1, further comprising a CDK4 inhibitor or CDK6 inhibitor.

Embodiment Q39

A method of treating a hyperproliferative disorder in a subject in need thereof, comprising administering to said subject an effective amount of a pharmaceutical composition of any one of Embodiments Q1-Q38.

Embodiment Q40

The method of Embodiment Q39, wherein said hyperproliferative disorder is associated with estrogen receptors (ER)-positive and ER-low/negative, or endocrine-resistant tumors.

Embodiment Q41

The method of Embodiment Q39, wherein said hyperproliferative disorder is a cancer.

Embodiment Q42

The method of Embodiment Q41, wherein said cancer is resistant to an anti-cancer agent.

Embodiment Q43

The method of Embodiment Q41, wherein said cancer is breast cancer, lung cancer, gynecological cancer, ovarian cancer, endometrial cancer, or prostate cancer.

Embodiment Q44

The method of Embodiment Q41, wherein said cancer is triple-negative breast cancers (TNBC).

Embodiment Q45

A method of increasing an immune response to a cancer in a subject, comprising administering to said subject an effective amount of a pharmaceutical composition of any one of Embodiments Q1-Q38.

Embodiment Q46

The method of Embodiment Q45, wherein said cancer is resistant to an anti-cancer agent.

Embodiment Q47

The method of Embodiment Q45, wherein said cancer is breast cancer, lung cancer, gynecological cancer, ovarian cancer, endometrial cancer, or prostate cancer.

Embodiment Q48

The method of Embodiment Q45, wherein said cancer is triple-negative breast cancers (TNBC).

Embodiment Q49

The method of Embodiment Q45, comprising inhibiting level of myeloid-derived suppressor cells (MDSC) in the subject.

Embodiment Q50

The method of Embodiment Q45, comprising inhibiting phosphorylation of STAT3 in the subject.

Embodiment Q51

The method of Embodiment Q45, comprising increasing level of $CD8^+$ T cells and/or $CD4^+$ T cells in the subject.

Embodiment Q52

A kit comprising a pharmaceutical composition of any one of Embodiments Q1-Q38.

EXAMPLE

Example 1—Compound Design and Synthesis

Designed herein are new compounds based on the knowledge of how the ER antagonists, e.g., 4-hydroxy-tamoxifen, OHT, bind to the ER and prevent the downstream message to grow rapidly. The phenolic hydroxyl group of OHT binds to the same part of the ligand binding domain (LBD) as does the phenolic hydroxyl group of E2 but, because of the hindered basic amino group in OHT (not present in E2), the way the protein folds around the bound molecule is altered (helix 12 folds in an unusual way) and the signal for DNA synthesis and cancer growth is inhibited. Therefore compounds were designed which are analogues of estradiol but with an additional large substituent at $C_{11}$ of the steroid molecule. In particular a series of 11β-aryloxy estradiols, 1, were prepared having a basic amine positioned on the aryl ring. Molecules have been designed to bind in the LDB but not allow helix 12 to fold in an agonist mode but rather in an antagonist mode in a way similar to that of the ER antagonists.

The synthesis of the molecules began from the known ketone 3, itself prepared in four steps from estradiol 2 (Synthesis 1). Reduction of the ketone 3 with sodium borohydride gave the expected 11β-alcohol 4 due to steric hindrance toward attack of hydride from the β-face. Formation of the anion of 4 with potassium hydride in THF/DMF followed by addition of 4-fluoronitrobenzene afforded the desired nitrophenyl ether 5 via a facile $S_NAr$ reaction. Reduction of the nitro group of 5 with nickel boride gave the aminophenyl ether 6. Removal of the two benzyl ethers from 6 by catalytic hydrogenolysis gave the first analogue, the simple aniline 7, namely 11β-(4-amino-phenyloxy)estradiol. The analogues having a three-atom linker between the aryl ring and the basic amine were all prepared by the same route. Thus the aniline 6 was treated with chloroacetyl chloride in the presence of DMAP to give the intermediate chloromethyl amide which was immediately reacted with any of several secondary amines, e.g., dimethylamine, morpholine, pyrrolidine, and piperidine, to give the amides. Again hydrogenolysis of the benzyl ethers using hydrogen and a palladium catalyst gave the desired analogues, 8a-d (a: $R_2$=$Me_2$; b: $R_2$=$(CH_2CH_2)_2O$; c: $R_2$=$(CH_2)_4$; d: $R_2$=$(CH_2)_5$). After coupling of 6 with the acid chloride to give the amide, hydride reduction afforded the 2-(dialkylamino)ethyl amines, the benzyl ethers of which were hydrogenolyzed to give another set of analogues 9a-d, namely the N-(2-aminoethyl)anilines. In addition the 4-amino group was completely removed to give the simple 11β-phenyl ether 10.

The availability of this bis(benzyl) aniline 6 allowed for the rapid synthesis of several other analogues (Synthesis 2). Thus reacting 3-chloropropionyl chloride with 6 followed by displacement of the chloride with the secondary amines and subsequent hydrogenolysis afforded the analogues with a 5-atom side chain ending in the basic amine, 11a-d. Likewise using 4-chlorobutanoyl chloride, after displacement of the chloride with the secondary amines and subsequent hydrogenolysis, one obtained the analogues with a 6-atom side chain ending in the basic amine, 12a-d. Finally following the same route starting with 5-chloropentanoyl chloride gave the analogues with a 7-atom side chain, 13a-d. Again after coupling of 6 with the 3-carbon acid chloride to give the amide, hydride reduction afforded the 2-(dialkylamino) ethyl amines, the benzyl ethers of which were hydrogenolyzed to give another set of analogues 14a-d, namely the N-(3-aminopropyl)anilines. By substituting the 4-fluoronitrobenzene unit for other aryl fluorides, one could prepare several other sets of analogues. Thus alkylation of the 11β-alcohol 4 with 2,4-difluoronitrobenzene led to the 3-fluoro-4-nitrophenyl ether (which after hydrogenolysis gave the analogue 15). From that compound were prepared the 16 analogues, 17a-d, 18a-d, 19a-d, and 20a-d and the unsubstituted aniline 16 (Synthesis 3). In a similar manner, using 4-fluoro-3-trifluoro-methylnitrobenzene to alkylate the anion of 4 resulted in the 3-trifluoromethyl-4-nitrophenyl ether (which after hydrogenolysis gave the analogue 21) and thus the 16 additional analogues, 23a-d, 24a-d, 25a-d, and 26a-d and the unsubstituted aniline 22.

Synthesis 1: Preparation of the Novel ER Antagonists 7-10 (FIG. 17)
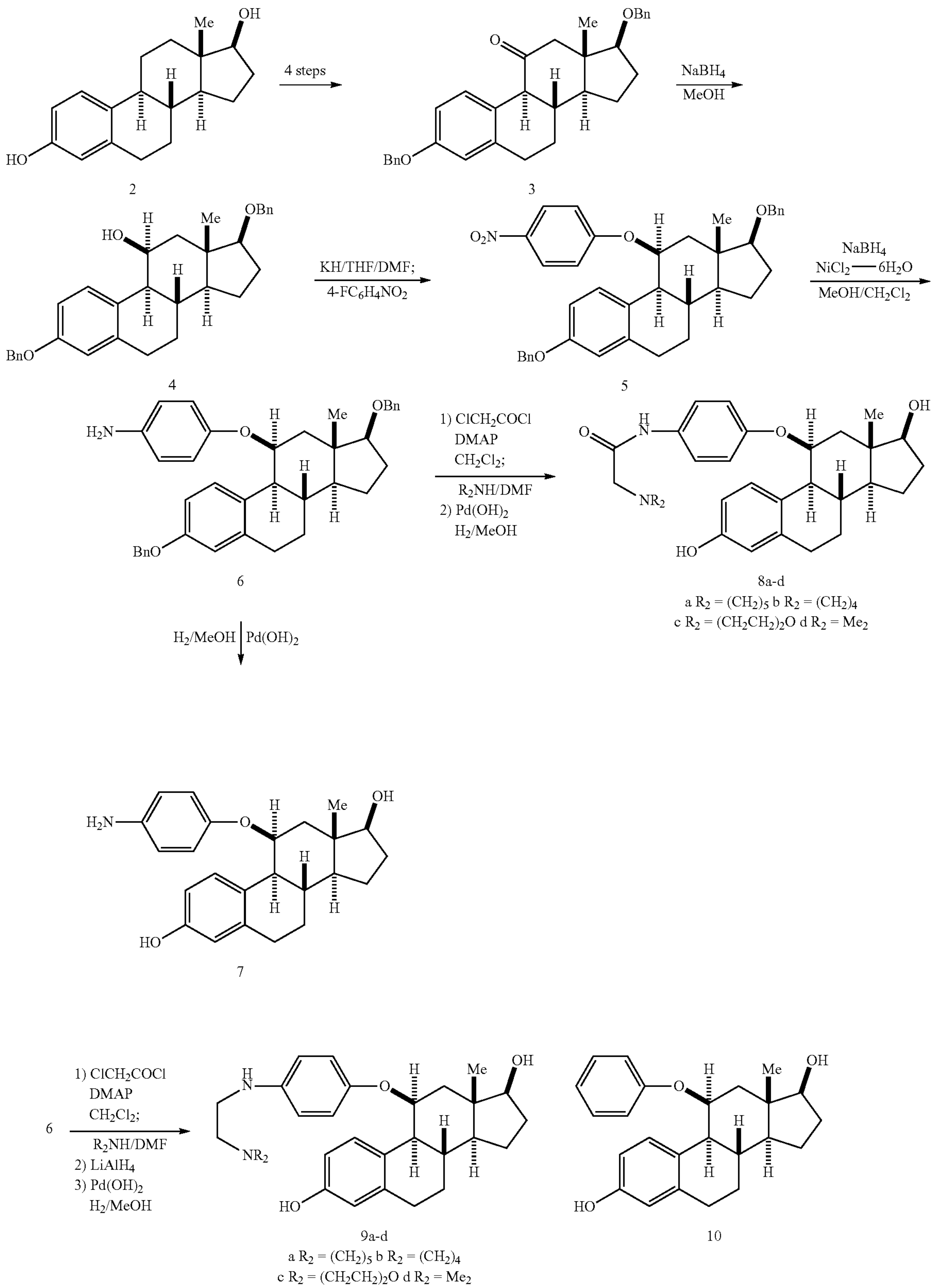

Synthesis 2: Preparation of the Novel ER Antagonist 11-14 (FIG. 18)

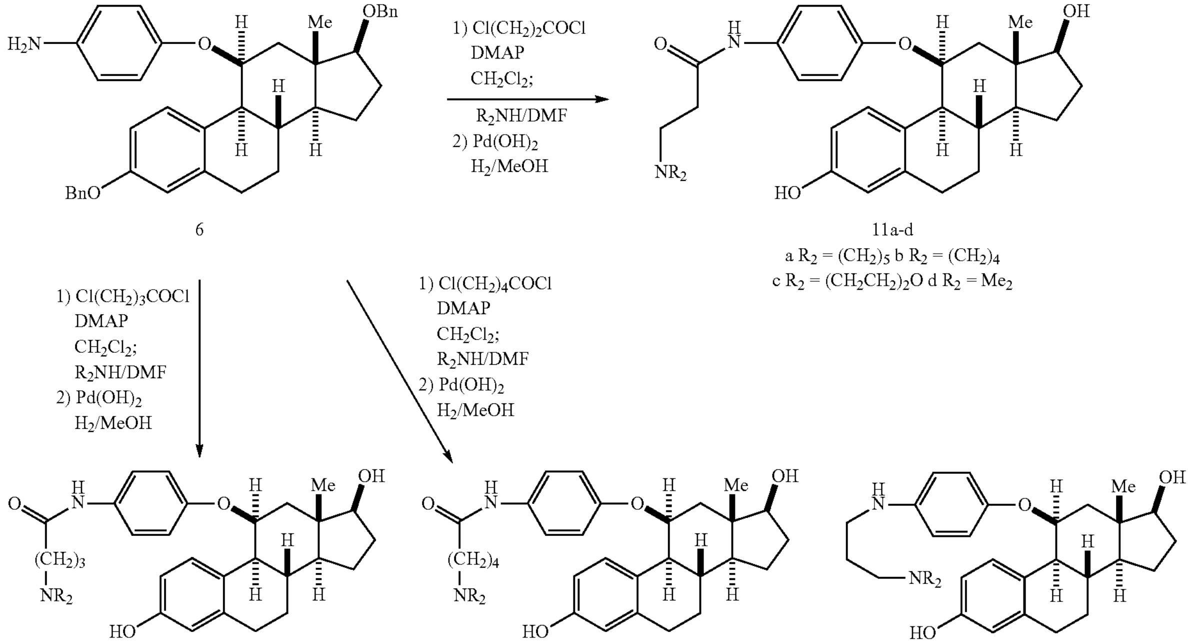

6

11a-d
a $R_2 = (CH_2)_5$ b $R_2 = (CH_2)_4$
c $R_2 = (CH_2CH_2)_2O$ d $R_2 = Me_2$ 12a-d
a $R_2 = (CH_2)_5$ b $R_2 = (CH_2)_4$
c $R_2 = (CH_2CH_2)_2O$ d $R_2 = Me_2$ 13a-d
a $R_2 = (CH_2)_5$ b $R_2 = (CH_2)_4$
c $R_2 = (CH_2CH_2)_2O$ d $R_2 = Me_2$ 14a-d
a $R_2 = (CH_2)_5$ b $R_2 = (CH_2)_4$
c $R_2 = (CH_2CH_2)_2O$ d $R_2 = Me_2$

Synthesis 3: Preparation of the Noel ER Antagonist 15-26 (FIG. 19)

4

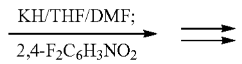

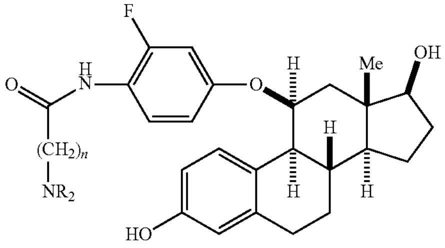

17a-d to 20a-d
17 n = 1
18 n = 2
19 n = 3
20 n = 4
a $R_2 = (CH_2)_5$
b $R_2 = (CH_2)_4$
c $R_2 = (CH_2CH_2)_2O$
d $R_2 = Me_2$

4

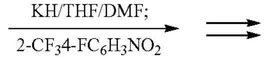

-continued

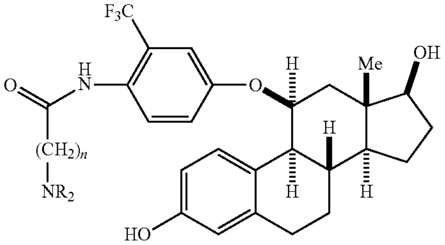

23a-d to 26a-d
23 n = 1
24 n = 2
25 n = 3
26 n = 4
a $R_2 = (CH_2)_5$
b $R_2 = (CH_2)_4$
c $R_2 = (CH_2CH_2)_2O$
d $R_2 = Me_2$

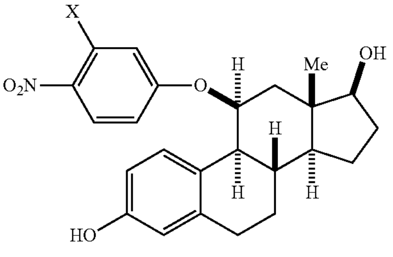

15 X = F
21 X = $CF_3$

-continued

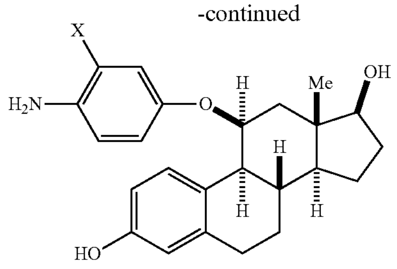

16 X = F
22 X = $CF_3$

General: Tetrahydrofuran (THF) was distilled from benzoquinone ketyl radical under an argon atmosphere. Dichloromethane, toluene, benzene, and pyridine were distilled from calcium hydride under an argon atmosphere. Anhydrous N,N-dimethylformamide (DMF) was purchased from Sigma-Aldrich. All other solvents or reagents were purified according to literature procedures. (8S,9S,13S,14S,17S)-3,17-bis(Benzyloxy)-13-methyl-6,7,8,9,12,13,14,15,16,17-decahydro-11H-cyclopenta[a]phenanthren-11-one (11-ketone) was prepared using literature procedures (Kurti et al.; Lim et al.; and Labaree et al.).

Instrumentation: $^{1}$H NMR, $^{13}$C NMR, and $^{19}$F NMR spectra were obtained at 300 MHz, 400 MHz, or 500 MHz for proton, 75 MHz, 100 MHz, or 125 MHz for carbon, and 282 MHz, or 376 MHz for fluorine are so indicated. The chemical shifts are reported in parts per million (ppm, δ). The coupling constants are reported in Hertz (Hz) and the resonance patterns are reported with notations as the following: br (broad), s (singlet), d (double), t (triplet), q (quartet) and m (multiplet). High-resolution mass spectra were measured on a time-of-flight LC-MS. Thin-layer chromatography (TLC) was carried out using precoated silica gel sheets. Visual detection was performed with ultraviolet light, p-anisaldehyde stain, potassium permanganate stain or iodine. Flash chromatography was performed using silica gel P60 (60 A, 40-63 μm) with compressed air.

(8S,9S,11S,13S,14S,17S)-3,17-bis(Benzyloxy)-13-methyl-7,8,9,11,12,13,14,15,16,17-deca-hydro-6H-cyclopenta[a]phenanthren-11-ol: A solution of sodium borohydride (12 wt. % in 14 M NaOH, 43.2 μL, 0.188 mmol) was added gradually to a solution of the bis(benzyl-oxy)ketone (0.1459 g, 0.313 mmol) in MeOH (3.0 mL) at 0° C. The mixture was stirred at 22° C. until TLC indicated complete consumption of the starting material. An aqueous saturated $NH_4Cl$ solution was added to quench the reaction. Ethyl acetate (3×40 mL) was added to the mixture. The combined organic phases were washed with water and brine, and dried over anhydrous $MgSO_4$. Flash column chromatography on silica gel eluting with 6/1 hexanes/ethyl acetate gave the target compound, the 11β-alcohol. $^{1}$H NMR (400 MHz, $CDCl_3$): δ 7.23-7.50 (m, 10H), 7.21 (d, J=8.5 Hz, 1H), 6.83 (dd, J=8.6, 2.7 Hz, 1H), 6.76 (d, J=2.4 Hz, 1H), 5.04 (s, 2H), 4.71 (m, 1H), 4.61 (d, J=12.1 Hz, 1H), 4.57 (d, J=12.1 Hz, 1H), 3.49 (dd, J=8.6, 7.6 Hz, 1H), 2.75-2.89 (m, 2H), 2.33-2.45 (m, 2H), 1.13 (s, 3H), 0.81-2.10 (m, 10H). $^{13}$C NMR (100 MHz, $CDCl_3$): δ 157.0, 140.1, 139.2, 137.2, 128.6 (2C), 128.3 (2C), 128.2, 127.9, 127.4 (2C), 127.32 (2C), 127.30, 126.1, 115.7, 113.1, 88.8, 71.6, 69.9, 67.7, 50.9, 50.1, 43.9, 43.1, 33.1, 30.0, 27.9, 26.7, 23.0, 14.2.

General procedure: (8S,9S,11S,13S,14S,17S)-3,17-bis (Benzyloxy)-13-methyl-11-(4-nitro-phenoxy)-7,8,9,11,12,13,14,15,16,17-decahydro-6H-cyclopenta[a]phenanthrene:

A solution of the 11β-alcohol (0.117 g, 0.25 mmol) in anhydrous THF (2.0 mL) was added gradually to the solution of potassium hydride (25 mg, 0.625 mmol) in DMF (1.0 mL) at 0° C. The mixture was stirred for 10 min at 0° C. The solution of 1-fluoro-4-nitrobenzene (80 μL, 0.75 mmol) in THF (0.5 mL) was added slowly to the reaction system. The reaction was stirred until TLC indicated complete consumption of the starting material. A saturated $NH_4Cl$ aqueous solution was added to quench the reaction. Ethyl acetate (3×40 mL) was added to the mixture. The combined organic phases were washed with water and brine, and dried over anhydrous $MgSO_4$. Flash column chromatography on silica gel eluting with 6/1 hexanes/ethyl acetate gave the target compound, the 4-nitrophenyl ether. $^{1}$H NMR (400 MHz, $CDCl_3$) δ 8.18 (d, J=9.3 Hz, 2H), 8.13 (d, J=9.4 Hz, 1H), 7.10-7.39 (m, 8H), 6.91 (d, J=9.3 Hz, 2H), 6.84 (d, J=8.7 Hz, 1H), 6.73 (d, J=2.6 Hz, 1H), 6.61 (m, 2H), 5.35 (m, 1H), 4.98 (s, 2H), 4.54 (d, J=12.2 Hz, 1H), 4.44 (d, J=12.2 Hz, 1H), 3.50 (dd, J=8.1, 8.1 Hz, 1H), 2.79-2.96 (m, 2H), 2.60 (d, J=10.9 Hz, 1H), 2.51 (dd, J=14.2, 2.4 Hz, 1H), 1.95-2.08 (m, 2H), 0.95 (s, 3H), 0.75-1.8 (m, 7H). $^{13}$C NMR (100 MHz, $CDCl_3$): δ 163.0, 156.8, 141.2, 139.0, 138.6, 137.2, 129.1, 128.5 (2C), 128.3 (2C), 128.0, 127.9, 127.4 (2C), 127.3, 126.3 (2C), 126.0 (2C), 115.2 (2C), 112.6, 110.2, 88.4, 73.1, 71.6, 69.9, 50.6, 48.7, 43.0, 40.3, 39.4, 33.7, 27.6, 27.3, 23.1, 13.8.

General procedure: (8S,9S,11S,13S,14S,17S)-11-(4-aminophenoxy)-13-methyl-7,8,9,11,12,13,14,15,16,17-decahydro-6H-cyclopenta[a]phenanthrene-3,17-diol, SERD105: Sodium borohydride (30 mg, 0.79 mmol) was added gradually to a solution of $NiCl_2$-$6H_2O$ (59 mg, 0.25 mmol) and the 11β-(4-nitrophenyl)ether (0.121 g, 0.205 mmol) in MeOH (1.5 mL) and dichloromethane (3.0 mL) at 0° C. The mixture was stirred at 22° C. until TLC indicated the complete consumption of the starting material. Diethyl ether (15 mL) and citric acid aqueous solution (5%, 10 mL) was added and stirred vigorously to quench the reaction. Diethyl ether (3×40 mL) was added to the mixture. The combined organic phases were washed with water and brine, and dried over anhydrous $MgSO_4$. The mixture was concentrated. The resulting residue was dissolved in MeOH (15 mL) and added with $Pd(OH)_2$ (20 mg). A stream of argon was passed over the mixture and then the argon was replaced with hydrogen and the mixture was stirred vigorously for 1 h. The mixture was filtered through a thick pad of CELITE® and the organic phase was evaporated. The residue was purified via flash column chromatography on silica gel eluting with 6/1 hexanes/ethyl acetate gave the target compound, the 4-aminophenyl ether diol. $^{1}$H NMR (500 MHz, $CDCl_3$) δ 6.99 (d, J=8.6 Hz, 1H), 6.76 (d, J=8.4 Hz, 2H), 6.65 (d, J=8.4 Hz, 2H), 6.58 (s, 1H), 6.53 (d, J=7.9 Hz, 1H), 5.16 (m, 1H), 3.74 (m, 1H), 1.00 (s, 3H), 0.69-3.0 (m, 17H). $^{13}$C NMR (125 MHz, $CDCl_3$): δ 153.3, 150.9, 139.4, 138.7, 128.5, 126.8, 116.8 (2C), 116.6 (2C), 115.5, 113.0, 82.4, 72.2, 50.8, 49.0, 43.0, 38.3, 34.0, 30.5, 29.6, 27.4, 23.1, 12.9.

General procedure: N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-2-(dimethyl-amino)acetamide: Sodium borohydride (30 mg, 0.79 mmol) was added gradually to a solution of $NiCl_2$-$6H_2O$ (59 mg, 0.25 mmol) and 11β-(4-nitrophenyl) ether (0.121 g, 0.205 mmol) in MeOH (1.5 mL) and dichloromethane (3.0 mL) at 0° C. The mixture was stirred at 22° C. until TLC indicated the complete consumption of the starting material. Diethyl ether (15 mL) and citric acid aqueous solution (5%, 10 mL) was added and stirred vigorously to quench the reaction. Diethyl ether (3×40 mL) was added to the mixture. The combined organic phases were washed with water and brine, dried over anhydrous $MgSO_4$. The mixture was concentrated. The resulting residue was dissolved in dichloromethane (2.0 mL) and DMAP (cat.) and $Et_3N$ (0.82 mmol) were added. Chloroacetyl chloride (0.65 mmol) was added gradually to the mixture at 0° C. and the reaction mixture was stirred at 22° C. for 2 h. Ethyl acetate (3×40 mL) was added to the mixture. The combined organic phases were washed with water and brine, and dried over anhydrous $MgSO_4$. The organic phase was concentrated. The resulting residue was dissolved in dimethylformamide (2.0 mL) and dimethylamine (1.0 mmol) was added to the reaction system at 22° C. The reaction was stirred until TLC indicated the complete consumption of the starting material. Ethyl acetate (3×40 mL) was added to the mixture. The combined organic phases were washed with water and brine, dried over anhydrous $MgSO_4$ and the organic phase was evaporated. The residue was purified via flash column chromatography on silica gel eluting with 2/1 hexanes/ethyl acetate gave the targeted compounds. $^1H$ NMR (300 MHz, $CDCl_3$): δ 9.00 (s, 1H), 7.12-7.53 (m, 12H), 6.95 (d, J=8.4 Hz, 1H), 6.85 (d, J=8.9 Hz, 2H), 6.68 (d, J=2.6 Hz, 1H), 6.65 (dd, J=8.4, 2.4 Hz, 1H), 5.20 (m, 1H), 4.98 (s, 2H), 4.51 (d, J=12.3 Hz, 1H), 4.47 (d, J=12.3 Hz, 1H), 3.47 (m, 2H), 2.38 (s, 6H), 1.01 (s, 3H), 0.80-3.11 (m, 14H). $^{13}C$ NMR (75 MHz, $CDCl_3$): δ 168.4, 156.6, 154.5, 139.1, 138.5, 137.4, 130.5, 128.8, 128.5 (2C), 128.3 (2C), 127.8, 127.5 (2C), 127.4 (2C), 127.35, 126.6, 121.3 (2C), 115.8 (2C), 115.0, 112.6, 88.6, 71.9, 71.6, 69.9, 63.6, 51.0, 48.9, 46.0 (2C), 43.2, 39.4, 33.7, 29.7, 27.8, 27.5, 23.1, 13.7. HR-MS (ESI) calcd for $[C_{42}H_{48}N_2O_4H]^+$ 645.3693, found 645.3707.

General procedure: N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-2-(dimethyl-amino)acetamide, SERD104: To a solution of the dibenzyl amide (0.065 g, 0.1 mmol) in MeOH (5.0 mL) was added $Pd(OH)_2$ (10 mg). Argon was passed over the mixture and then the argon was replaced with hydrogen and the mixture was stirred vigorously for 1 h. The mixture was filtered through a thick pad of Celite and the organic phase was evaporated. The residue was purified via flash column chromatography on silica gel eluting with 15/1 dichloromethane/MeOH to give the target compound, the amide diol. $^1H$ NMR (400 MHz, MeOD): δ 7.41 (d, J=9.7 Hz, 2H), 6.88 (d, J=8.7 Hz, 1H), 6.86 (d, J=9.7 Hz, 2H), 6.48 (d, J=2.7 Hz, 1H), 6.40 (dd, J=8.7, 2.7 Hz, 1H), 5.31 (m, 1H), 3.60-3.69 (m, 1H), 3.33 (s, 2H), 2.40 (br s, 6H), 0.88 (s, 3H), 0.80-3.38 (m, 13H). $^{13}C$ NMR (100 MHz, MeOD): δ 169.4, 156.3, 154.8, 138.6, 130.6, 127.7, 126.8, 122.4 (2C), 115.4 (2C), 115.1, 112.9, 81.9, 72.3, 62.8, 50.8, 49.2, 44.8, 43.2 (2C), 38.4, 34.6, 29.8, 29.5, 27.6, 23.0, 12.7. HR-MS (ESI) calcd for $[C_{28}H_{37}N_2O_4H]^+$ 465.2753, found 465.2759.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-2-morpholino-acetamide: $^1H$ NMR (400 MHz, $CDCl_3$): δ 8.91 (s, 1H), 7.18-7.49 (m, 12H), 6.96 (d, J=8.9 Hz, 1H), 6.86 (d, J=8.9 Hz, 2H), 6.71 (d, J=2.6 Hz, 1H), 6.65 (dd, J=8.6, 2.6 Hz, 1H), 5.22 (m, 1H), 4.98 (s, 2H), 4.51 (d, J=12.0 Hz, 1H), 4.47 (d, J=12.0 Hz, 1H), 4.09 (m, 1H), 3.70-3.82 (m, 2H), 3.40-3.52 (m, 1H), 1.01 (s, 3H), 0.80-3.20 (m, 20H). $^{13}C$ NMR (100 MHz, $CDCl_3$): δ 167.6, 156.6, 154.6, 139.1, 138.5, 137.3, 130.2, 128.8, 128.5 (2C), 128.3 (2C), 127.8, 127.5 (2C), 127.4, 127.3 (2C), 126.5, 121.4 (2C), 115.8 (2C), 114.9, 112.6, 88.5, 71.9, 71.5, 69.9, 67.1 (2C), 62.4, 53.8 (2C), 50.9, 48.9, 43.1, 39.3, 33.7, 29.8, 27.7, 23.1, 19.1, 13.7.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-2-morpholinoacetamide, SERD103: $^1H$ NMR (400 MHz, MeOD): δ 7.41 (d, J=9.0 Hz, 2H), 6.88 (d, J=8.0 Hz, 1H), 6.85 (d, J=9.0 Hz, 2H), 6.48 (d, J=2.3 Hz, 1H), 6.40 (dd, J=8.5, 2.7 Hz, 1H), 5.30 (m, 1H), 3.75 (t, J=4.0 Hz, 4H), 3.13 (s, 2H), 2.57 (t, J=4.0 Hz, 4H), 0.88 (s, 3H), 0.8-3.3 (m, 14H). $^{13}C$ NMR (100 MHz, MeOD): δ 169.1, 154.9, 154.4, 138.2, 130.1, 127.3, 126.3, 122.0 (2C), 115.1 (2C), 114.8, 112.5, 81.5, 71.9, 66.4 (2C), 61.8, 53.4 (2C), 50.4, 48.7, 42.8, 38.0, 34.2, 29.4, 29.1, 27.2, 22.6, 12.3. HR-MS (ESI) calcd for $[C_{30}H_{38}N_2O_5H]^+$ 507.2859, found 507.2843.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-2-(pyrrolidin-1-yl)acetamide: $^1H$ NMR (300 MHz, $CDCl_3$): δ 8.99 (s, 1H), 7.20-7.51 (m, 12H), 6.95 (d, J=8.7 Hz, 1H), 6.84 (d, J=8.7 Hz, 2H), 6.71 (d, J=2.8 Hz, 1H), 6.65 (dd, J=8.9, 3.0 Hz, 1H), 5.20 (m, 1H), 4.98 (s, 2H), 4.51 (d, J=11.7 Hz, 1H), 4.47 (d, J=11.7 Hz, 1H), 3.47 (s, 2H), 2.70 (m, 4H), 1.86 (m, 4H), 1.05 (s, 3H), 0.80-3.56 (m, 14H). $^{13}C$ NMR (75 MHz, $CDCl_3$): δ 168.8, 156.6, 154.5, 139.1, 138.5, 137.4, 130.5, 128.8, 128.5 (2C), 128.3 (2C), 127.8, 127.5 (2C), 127.4 (2C), 127.3, 126.6, 121.4 (2C), 115.8 (2C), 115.0, 112.5, 88.5, 71.9, 71.6, 69.9, 59.7, 54.6 (2C), 51.0, 48.9, 43.1, 39.4, 33.7, 29.8, 27.8, 27.5, 24.1 (2C), 23.1, 13.7.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-2-(pyrrolidin-1-yl) acetamide, SERD102: $^1H$ NMR (400 MHz, MeOD): δ 7.40 (d, J=8.9 Hz, 2H), 6.88 (d, J=8.0 Hz, 1H), 6.85 (d, J=8.9 Hz, 2H), 6.48 (d, J=2.7 Hz, 1H), 6.40 (dd, J=8.0, 2.4 Hz, 1H), 5.32 (m, 1H), 3.65 (m, 1H), 3.40 (s, 2H), 2.78 (m, 4H), 1.88 (m, 4H), 0.88 (s, 3H), 0.80-2.60 (m, 13H). $^{13}C$ NMR (100 MHz, MeOD): δ 170.1, 156.3, 155.8, 139.6, 131.6, 128.7, 123.4 (2C), 123.3, 116.5 (2C), 116.2, 113.9, 79.3, 73.3, 55.4 (2C), 51.8, 50.2, 49.5, 44.2, 39.4, 35.6, 30.8, 30.5, 28.6, 24.6 (2C), 24.0, 13.8. MS (ESI) m/z (%) 491 ([M+1]+, 100), 447 (15), 155 (28). HR-MS (ESI) calcd for $[C_{20}H_2O_5H]^+$ 491.2910, found 491.2926.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-2-(piperidin-1-yl)acetamide: $^1H$ NMR (300 MHz, $CDCl_3$): δ 9.05 (s, 1H), 7.10-7.55 (m, 12H), 6.95 (d, J=8.4 Hz, 1H), 6.85 (d, J=9.0 Hz, 2H), 6.71 (d, J=2.4 Hz, 1H), 6.66 (d, J=8.4 Hz, 1H), 5.22 (m, 1H), 4.98 (s, 2H), 4.51 (d, J=12.3 Hz, 1H), 4.47 (d, J=12.3 Hz, 1H), 2.72 (m, 4H), 1.86 (m, 4H), 1.01 (s, 3H), 0.70-3.60 (m, 18H). $^{13}C$ NMR (75 MHz, $CDCl_3$): δ 168.5, 156.7, 154.4, 139.0, 138.4, 137.3, 130.5, 128.7, 128.5 (2C), 128.2 (2C), 127.8, 127.4 (2C), 127.3 (2C), 127.27, 126.5, 121.4 (2C), 115.7 (2C), 114.9, 112.5, 88.5, 71.8, 71.5, 69.8, 59.6, 54.5 (2C), 51.0, 48.8, 43.1, 39.3, 38.5, 33.7, 29.7, 29.6, 27.7, 24.0 (2C), 23.0, 14.1.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-2-(piperidin-1-yl) acetamide, SERD101: $^1H$ NMR (400 MHz, MeOD): δ 7.40 (d, J=8.9 Hz, 2H), 6.88 (d, J=8.4 Hz, 1H), 6.85 (d, J=8.9 Hz, 2H), 6.47 (d, J=2.6 Hz, 1H), 6.39 (dd, J=8.4, 2.6 Hz, 1H), 5.31 (m, 1H), 3.43 (s, 2H), 2.81 (m, 4H), 1.89 (m, 4H), 0.88 (s, 3H), 0.75-3.7 (m, 16H). $^{13}C$ NMR (100 MHz, MeOD): δ 169.9, 156.3, 155.8, 139.6, 131.6, 128.7, 127.7, 123.4 (2C), 116.4 (2C), 116.1, 113.9, 82.9, 73.3, 61.5, 59.9, 55.4, 51.8, 50.2, 44.2 (2C), 39.4, 35.6, 30.8, 30.5, 28.6, 24.6 (2C), 24.0, 13.7. HR-MS (ESI) calcd for $[C_{31}H_{40}N_2O_4H]^+$ 491.2910, found 491.2892.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-3-morpholinopropanamide: $^1$H NMR (300 MHz, $CDCl_3$): δ 10.5 (s, 1H), 7.20-7.50 (m, 12H), 6.96 (d, J=8.4 Hz, 1H), 6.85 (d, J=8.7 Hz, 2H), 6.71 (d, J=2.4 Hz, 1H), 6.65 (dd, J=7.7, 2.4 Hz, 1H), 5.20 (m, 1H), 4.98 (s, 2H), 4.51 (d, J=12.0 Hz, 1H), 4.47 (d, J=12.0 Hz, 1H), 3.82 (t, J=4.2 Hz, 4H), 2.61 (t, J=4.2 Hz, 4H), 1.01 (s, 3H), 0.72-3.78 (m, 18H). $^{13}$C NMR (75 MHz, $CDCl_3$): δ 169.9, 156.6, 154.1, 139.1, 138.5, 137.3, 131.3, 128.8, 128.5 (2C), 128.2 (2C), 127.8, 127.4 (2C), 127.32, 127.30 (2C), 126.5, 121.2 (2C), 115.8 (2C), 114.9, 112.5, 88.5, 71.9, 71.4, 69.9, 67.0 (2C), 54.3, 52.8 (2C), 50.9, 48.9, 43.1, 39.3, 33.7, 32.1, 29.7, 27.7, 27.4, 23.0, 13.7.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-3-morpholinopropanamide, SERD106: $^1$H NMR (300 MHz, MeOD): δ 7.38 (d, J=9.0 Hz, 2H), 6.89 (d, J=8.4 Hz, 1H), 6.85 (d, J=9.0 Hz, 2H), 6.48 (d, J=2.7 Hz, 1H), 6.40 (dd, J=8.4, 2.4 Hz, 1H), 5.32 (m, 1H), 3.71 (t, J=4.5 Hz, 4H), 2.54 (t, J=4.5 Hz, 4H), 0.89 (s, 3H), 0.80-3.69 (m, 18H). $^{13}$C NMR (75 MHz, MeOD): δ 172.5, 156.1, 155.8, 139.6, 132.2, 128.7, 127.7, 123.2 (2C), 116.5 (2C), 116.2, 113.9, 82.9, 73.3, 67.7 (2C), 55.6, 54.4 (2C), 51.8, 50.2, 44.2, 39.4, 35.6, 34.4, 30.8, 30.5, 28.6, 24.0, 13.7. HR-MS (ESI) calcd for $[C_{31}H_{40}N_2O_5H]^+$ 521.3016, found 521.3010.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-3-(piperidin-1-yl)propan-amide: $^1$H NMR (300 MHz, $CDCl_3$): δ 10.75 (s, 1H), 7.20-7.55 (m, 12H), 6.96 (d, J=8.4 Hz, 1H), 6.84 (d, J=8.7 Hz, 2H), 6.71 (d, J=2.4 Hz, 1H), 6.66 (dd, J=8.3, 2.4 Hz, 1H), 5.21 (m, 1H), 4.98 (s, 2H), 4.50 (d, J=11.6 Hz, 1H), 4.48 (d, J=11.6 Hz, 1H), 2.60 (m, 4H), 1.72 (m, 4H), 1.01 (s, 3H), 0.70-3.75 (m, 20H). $^{13}$C NMR (75 MHz, $CDCl_3$): δ 169.9, 156.6, 154.0, 139.1, 138.4, 137.3, 131.6, 128.8, 128.5 (2C), 128.2 (2C), 127.8, 127.4 (2C), 127.31 (2C), 127.27, 126.5, 121.1 (2C), 115.8 (2C), 114.9, 112.5, 88.5, 71.8, 71.5, 69.9, 54.3, 53.6 (2C), 51.0, 48.9, 43.1, 39.3, 33.7, 32.4, 29.7, 27.7, 27.5, 25.5 (2C), 23.8, 23.0, 13.7. HR-MS (ESI) calcd for $[C_{46}H_{54}N_2O_4H]^+$ 699.4162, found 699.4180.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-3-(piperidin-1-yl)propanamide, SERD107: $^1$H NMR (400 MHz, MeOD): δ 7.41 (d, J=8.8 Hz, 2H), 6.88 (d, J=8.2 Hz, 1H), 6.85 (d, J=8.8 Hz, 2H), 6.48 (d, J=2.6 Hz, 1H), 6.40 (dd, J=8.2, 2.6 Hz, 1H), 5.31 (m, 1H), 2.87 (m, 4H), 1.84 (m, 4H), 0.87 (s, 3H), 0.79-3.75 (m, 20H). $^{13}$C NMR (100 MHz, MeOD): δ 169.7, 156.2, 155.8, 139.6, 132.0, 128.7, 127.8, 123.2 (2C), 116.5 (2C), 116.2, 113.9, 82.8, 73.3, 54.6, 54.3, 51.8, 50.1, 44.2 (2C), 39.4, 35.6, 31.4, 30.9, 30.5, 28.6, 24.4 (2C), 24.0, 22.8, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-3-(pyrrolidin-1-yl)propan-amide: $^1$H NMR (300 MHz, $CDCl_3$): δ 10.50 (s, 1H), 7.20-7.49 (m, 12H), 6.96 (d, J=8.7 Hz, 1H), 6.84 (d, J=9.0 Hz, 2H), 6.71 (d, J=2.4 Hz, 1H), 6.66 (dd, J=8.6, 2.6 Hz, 1H), 5.20 (m, 1H), 4.98 (s, 2H), 4.50 (d, J=12.6 Hz, 1H), 4.48 (d, J=12.6 Hz, 1H), 2.85 (m, 4H), 1.92 (m, 4H), 1.00 (s, 3H), 0.82-3.55 (m, 18H). $^{13}$C NMR (75 MHz, $CDCl_3$): δ 169.4, 156.5, 154.1, 139.1, 138.4, 137.3, 131.3, 128.8, 128.4 (2C), 128.2 (2C), 127.7, 127.4 (2C), 127.3 (2C), 127.2, 126.5, 121.4 (2C), 115.7 (2C), 112.5, 112.5, 88.5, 71.8, 71.5, 69.8, 53.4 (2C), 51.5, 50.9, 48.8, 43.0, 39.2, 34.1, 33.6, 29.7, 27.7, 27.4, 23.5 (2C), 23.0, 13.6. HR-MS (ESI) calcd for $[C_{45}H_{52}N_2O_4H]^+$ 685.4005, found 685.4021.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-3-(pyrrolidin-1-yl)propanamide, SERD108: $^1$H NMR (400 MHz, MeOD): δ 7.40 (d, J=8.7 Hz, 2H), 6.87 (d, J=8.1 Hz, 1H), 6.84 (d, J=8.7 Hz, 2H), 6.50 (d, J=2.6 Hz, 1H), 6.42 (dd, J=8.1, 2.6 Hz, 1H), 5.27 (m, 1H), 2.87 (m, 4H), 1.27 (m, 4H), 0.88 (s, 3H), 0.80-3.74 (m, 18H). $^{13}$C NMR (75 MHz, MeOD): δ 169.0, 155.8, 155.3, 139.4, 131.5, 128.4, 127.4, 122.8 (2C), 116.3 (2C), 116.0, 113.7, 82.5, 73.0, 55.1 (2C), 52.1, 51.5, 43.9, 39.1, 35.2, 32.4, 30.5, 30.4, 30.3, 28.3, 23.8 (2C), 23.7, 13.6. HR-MS (ESI) calcd for $[C_{31}H_4ON_2O_4H]^+$ 505.3066, found 505.3045.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-3-(dimethylamino)propan-amide: $^1$H NMR (300 MHz, $CDCl_3$): δ 8.01 (s, 1H), 7.19-7.55 (m, 12H), 6.95 (d, J=8.4 Hz, 1H), 6.84 (d, J=8.9 Hz, 2H), 6.65 (d, J=2.6 Hz, 1H), 6.62 (dd, J=8.4, 2.4 Hz, 1H), 5.18 (m, 1H), 4.98 (s, 2H), 4.51 (d, J=11.3 Hz, 1H), 4.48 (d, J=11.3 Hz, 1H), 2.52 (s, 6H), 1.02 (s, 3H), 0.80-3.80 (m, 18H). $^{13}$C NMR (75 MHz, $CDCl_3$): δ 166.2, 156.5, 154.5, 139.0, 138.4, 137.2, 130.7, 128.7, 128.4 (2C), 128.2 (2C), 127.7, 127.3 (2C), 127.2 (2C), 126.8, 126.4, 121.7 (2C), 115.6 (2C), 114.9, 112.4, 88.4, 72.0, 71.4, 69.7, 50.8, 48.8, 45.8, 43.0 (2C), 39.2, 33.6, 29.7, 29.6, 27.6, 27.3, 23.0, 20.5, 13.6.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-3-(dimethylamino)propanamide, SERD109: $^1$H NMR (300 MHz, MeOD): δ 7.38 (d, J=9.0 Hz, 2H), 6.89 (d, J=8.4 Hz, 1H), 6.84 (d, J=9.0 Hz, 2H), 6.48 (d, J=2.7 Hz, 1H), 6.41 (dd, J=8.4, 2.7 Hz, 1H), 5.28 (m, 1H), 2.14 (s, 6H), 0.88 (s, 3H), 0.80-3.70 (m, 18H). $^{13}$C NMR (75 MHz, MeOD): δ 175.1, 156.0, 155.8, 139.5, 132.4, 128.7, 127.7, 123.3 (2C), 116.4 (2C), 116.2, 113.9, 82.9, 73.3, 51.8, 50.1, 44.2 (2C), 39.4, 35.6, 30.8, 30.7, 30.5, 28.6, 24.0, 13.7, 10.4.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-4-morpholinobutanamide: $^1$H NMR (300 MHz, $CDCl_3$): δ 8.15 (s, 1H), 7.20-7.50 (m, 12H), 6.97 (d, J=8.7 Hz, 1H), 6.85 (d, J=8.7 Hz, 2H), 6.71 (d, J=2.5 Hz, 1H), 6.67 (dd, J=8.4, 2.6 Hz, 1H), 5.19 (m, 1H), 4.99 (s, 2H), 4.52 (d, J=12.9 Hz, 1H), 4.49 (d, J=12.9 Hz, 1H), 3.75 (t, J=4.3 Hz, 4H), 2.53 (t, J=4.3 Hz, 4H), 1.03 (s, 3H), 0.9-3.8 (m, 20H). $^{13}$C NMR (75 MHz, $CDCl_3$): δ 170.8, 156.5, 154.3, 139.0, 138.4, 137.2, 130.8, 128.7, 128.4 (2C), 128.2 (2C), 127.7, 127.3 (2C), 127.26, 127.22 (2C), 126.4, 121.6 (2C), 115.7 (2C), 114.8, 112.4, 88.4, 71.8, 71.4, 69.7, 66.7 (2C), 57.4, 53.3 (2C), 50.8, 48.8, 43.0, 39.2, 35.1, 33.6, 29.7, 27.6, 27.3, 23.0, 21.7, 13.6. HR-MS (ESI) calcd for $[C_{46}H_{54}N_2O_5H]^+$ 715.4111, found 715.4106.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-4-morpholinobutanamide, SERD110: $^1$H NMR (300 MHz, MeOD): δ 7.40 (d, J=9.0 Hz, 2H), 6.88 (d, J=8.7 Hz, 1H), 6.85 (d, J=9.0 Hz, 2H), 6.49 (d, J=2.4 Hz, 1H), 6.41 (dd, J=8.1, 2.4 Hz, 1H), 5.28 (m, 1H), 3.82 (m, 4H), 2.49 (m, 4H), 0.88 (s, 3H), 0.80-3.70 (m, 20H). $^{13}$C NMR (75 MHz, MeOD): δ 173.0, 156.1, 155.8, 139.6, 132.1, 128.7, 127.8, 123.4 (2C), 116.5 (2C), 116.2, 113.9, 82.8, 73.3, 66.0 (2C), 58.6, 53.7 (2C), 51.8, 50.0, 44.2, 39.3, 35.6, 34.8, 30.8, 30.5, 28.6, 24.0, 21.6, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-4-(pyrrolidin-1-yl)butan-amide: $^1$H NMR (300 MHz, MeOD): δ 7.19-7.42 (m, 12H), 6.95 (d, J=8.8 Hz, 1H), 6.82 (d, J=9.0 Hz, 2H), 6.66 (d, J=2.7 Hz, 1H), 6.56 (dd, J=8.7, 2.8 Hz, 1H), 5.26 (m, 1H), 4.93 (s, 2H), 4.46 (d, J=11.4 Hz, 1H), 4.42 (d, J=11.4 Hz, 1H), 2.50 (m, 4H), 2.05 (m, 4H), 0.94 (s, 3H), 0.82-3.60 (m, 20H). $^{13}$C NMR (75 MHz, MeOD): δ 172.4, 157.9, 156.0, 140.4, 139.7, 139.0, 132.2, 130.2, 129.4, 129.3 (2C), 128.7 (2C), 128.6, 128.5 (2C), 128.46 (2C), 127.8, 123.4 (2C), 116.5 (2C), 115.8, 113.6, 90.2, 73.3, 72.8, 70.8, 55.9, 55.1 (2C), 54.8, 51.8, 50.0, 44.3, 40.2, 35.2, 34.2, 30.9, 28.7, 28.5, 24.0 (2C), 23.0, 14.4.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-4-(pyrrolidin-1-yl) butanamide, SERD111: $^1$H NMR (300 MHz, MeOD): δ 7.38 (d, J=9.0 Hz, 2H), 6.88 (d, J=8.1 Hz, 1H), 6.85 (d, J=9.0 Hz, 2H), 6.48 (d, J=2.4 Hz, 1H), 6.40 (dd, J=8.7, 2.7 Hz, 1H), 5.33 (m, 1H), 3.00 (m, 4H), 1.95 (m, 4H), 0.89 (s, 3H), 0.79-3.80 (m, 20H). $^{13}$C NMR (75 MHz, MeOD): δ 172.7, 156.5, 156.3, 139.4, 132.5, 128.7, 128.0, 123.3 (2C), 116.5 (2C), 116.3, 114.0, 82.9, 73.3, 56.6, 54.9 (2C), 51.6, 50.1, 44.1, 39.3, 35.7, 34.9, 30.8, 30.6, 28.4, 24.3, 24.2 (2C), 24.1, 13.4.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-4-(piperidin-1-yl)butanamide: $^1$H NMR (300 MHz, $CDCl_3$): δ 9.52 (s, 1H), 7.56 (d, J=8.7 Hz, 2H), 7.18-7.48 (m, 10H), 6.95 (d, J=8.7 Hz, 1H), 6.81 (d, J=9.0 Hz, 2H), 6.70 (d, J=2.4 Hz, 1H), 6.65 (dd, J=8.4, 2.4 Hz, 1H), 5.18 (m, 1H), 4.97 (s, 2H), 4.49 (d, J=12.3 Hz, 1H), 4.46 (d, J=12.3 Hz, 1H), 2.90 (m, 4H), 1.60 (m, 4H), 0.99 (s, 3H), 0.80-3.78 (m, 22H). $^{13}$C NMR (75 MHz, $CDCl_3$): δ 169.8, 156.5, 154.2, 139.1, 138.4, 137.3, 131.2, 128.8, 128.4 (2C), 128.2 (2C), 127.7, 127.4 (2C), 127.3 (2C), 127.2, 126.5, 121.6 (2C), 115.6 (2C), 114.9, 112.5, 88.4, 71.7, 71.4, 69.8, 60.6, 56.5, 53.5 (2C), 50.9, 48.8, 43.0, 39.2, 33.6, 31.4, 29.6 (2C), 27.7, 27.4, 23.0, 22.7, 20.3, 13.6. HR-MS (ESI) calcd for $[C_{47}H_{56}N_2O_4H]^+$ 713.4318, found 713.4321.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-4-(piperidin-1-yl) butanamide, SERD112: $^1$H NMR (300 MHz, MeOD): δ 7.38 (d, J=9.0 Hz, 2H), 6.89 (d, J=9.0 Hz, 1H), 6.84 (d, J=9.0 Hz, 2H), 6.48 (d, J=2.4 Hz, 1H), 6.40 (dd, J=8.4, 2.7 Hz, 1H), 5.29 (m, 1H), 2.50 (m, 4H), 1.65 (m, 4H), 0.88 (s, 3H), 0.80-3.71 (m, 22H). $^{13}$C NMR (75 MHz, MeOD): δ 173.5, 156.0, 155.8, 139.5, 132.2, 128.7, 127.7, 123.3 (2C), 116.4 (2C), 116.2, 113.9, 82.8, 73.3, 59.4, 55.2 (2C), 51.8, 50.1, 44.2, 39.3, 35.6, 35.5, 30.8, 30.5, 28.6, 26.1 (2C), 24.8, 24.0, 23.1, 13.7. HR-MS (ESI) calcd for $[C_{33}H_{44}N_2O_4H]^+$ 533.3380, found 533.3358.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-4-(dimethylamino)butan-amide: $^1$H NMR (300 MHz, $CDCl_3$): δ 9.50 (s, 1H), 7.15-7.70 (m, 12H), 6.97 (d, J=8.1 Hz, 1H), 6.84 (d, J=8.4 Hz, 2H), 6.71 (d, J=2.6 Hz, 1H), 6.68 (dd, J=8.4, 2.4 Hz, 1H), 5.21 (m, 1H), 4.98 (s, 2H), 4.51 (d, J=11.4 Hz, 1H), 4.49 (d, J=11.4 Hz, 1H), 2.41 (s, 6H), 1.02 (s, 3H), 0.79-3.80 (m, 20H). $^{13}$C NMR (75 MHz, $CDCl_3$): δ 171.1, 156.5, 154.0, 139.0, 138.4, 137.2, 131.5, 128.7, 128.4 (2C), 128.2 (2C), 127.7, 127.4 (2C), 127.3 (2C), 127.2, 126.5, 121.2 (2C), 115.7 (2C), 114.9, 112.4, 88.4, 71.8, 71.4, 69.8, 58.9, 50.8, 48.8, 45.0 (2C), 43.0, 39.2, 36.5, 33.6, 29.7, 27.6, 27.4, 23.0, 22.8, 13.6. HR-MS (ESI) calcd for $[C_{44}H_{52}N_2O_4H]^+$ 673.4005, found 673.4008.

N-(4-(((8S,9S,11S,13S,14S,17S)-3,17-dihydroxy-13-methyl-7,8,9,11,12,13,14,15,16,17-deca-hydro-6H-cyclopenta[a]phenanthren-11-yl)oxy)phenyl)-4-(dimethylamino) butanamide, SERD116: $^1$H NMR (300 MHz, MeOD): δ 7.42 (d, J=9.0 Hz, 2H), 6.88 (d, J=8.7 Hz, 1H), 6.84 (d, J=9.0 Hz, 2H), 6.49 (d, J=2.1 Hz, 1H), 6.42 (dd, J=8.6, 2.6 Hz, 1H), 5.29 (m, 1H), 2.90 (s, 6H), 0.87 (s, 3H), 0.80-3.70 (m, 20H). $^{13}$C NMR (75 MHz, MeOD): δ 172.4, 156.0, 155.7, 139.5, 132.0, 128.7, 127.7, 123.4 (2C), 116.4 (2C), 116.2, 113.9, 82.8, 73.3, 58.7, 51.7, 50.0, 44.1, 43.7 (2C), 39.3, 35.5, 34.2 30.8, 30.4, 28.5, 23.9, 21.6, 13.8. HR-MS (ESI) calcd for $[C_{30}H_{40}N_2O_4H]^+$ 493.3066, found 493.3063.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-5-morpholino-pentanamide: $^1$H NMR (300 MHz, $CDCl_3$): δ 7.50 (s, 1H), 7.20-7.48 (m, 12H), 6.96 (d, J=8.4 Hz, 1H), 6.84 (d, J=9.0 Hz, 2H), 6.71 (d, J=2.4 Hz, 1H), 6.65 (dd, J=8.4, 2.4 Hz, 1H), 5.21 (m, 1H), 4.98 (s, 2H), 4.51 (d, J=12.8 Hz, 1H), 4.48 (d, J=12.8 Hz, 1H), 3.72 (t, J=4.2 Hz, 4H), 2.48 (t J=4.2 Hz, 4H), 1.01 (s, 3H), 0.80-3.70 (m, 22H). $^{13}$C NMR (75 MHz, $CDCl_3$): δ 170.9, 156.5, 154.4, 139.0, 138.4, 137.2, 130.6, 128.7, 128.4 (2C), 128.2 (2C), 127.7, 127.4 (2C), 127.3 (2C), 127.2, 126.4, 121.8 (2C), 115.7 (2C), 114.9, 112.5, 88.4, 71.8, 71.4, 69.8, 66.7 (2C), 58.4, 53.5 (2C), 50.8, 48.8, 43.0, 39.2, 37.1, 33.6, 29.7, 27.6, 27.4, 25.8, 23.4, 23.0, 13.6. HR-MS (ESI) calcd for $[C_{47}H_{56}N_2O_5H]^+$ 729.4268, found 729.4296.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-5-morpholinopentanamide, SERD113: $^1$H NMR (300 MHz, MeOD): δ 7.39 (d, J=9.0 Hz, 2H), 6.89 (d, J=8.7 Hz, 1H), 6.84 (d, J=9.0 Hz, 2H), 6.48 (d, J=2.7 Hz, 1H), 6.41 (dd, J=8.4, 2.4 Hz, 1H), 5.29 (m, 1H), 3.76 (d, J=4.2 Hz, 4H), 2.78 (t, J=4.2 Hz, 4H), 0.88 (s, 3H), 0.80-3.70 (m, 22H). $^{13}$C NMR (75 MHz, MeOD): δ 173.7, 156.0, 155.8, 139.6, 132.3, 128.7, 127.8, 123.3 (2C), 116.4 (2C), 116.2, 113.9, 82.8, 73.3, 66.5 (2C), 59.1, 54.1 (2C), 51.8, 50.1, 44.2, 39.3, 37.1, 35.6, 30.8, 30.5, 28.6, 25.7, 24.3, 24.0, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-5-(pyrrolidin-1-yl)pentan-amide: $^1$H NMR (300 MHz, $CDCl_3$): δ 9.27 (s, 1H), 7.19-7.72 (m, 12H), 6.96 (d, J=8.4 Hz, 1H), 6.81 (m, 2H), 6.69 (s, 1H), 6.64 (d, J=8.4 Hz, 1H), 5.20 (m, 1H), 4.95 (s, 2H), 4.49 (d, J=11.6 Hz, 1H), 4.46 (d, J=11.6 Hz, 1H), 2.80 (m, 4H), 1.78 (m, 4H), 0.99 (s, 3H), 0.80-3.60 (m, 22H). $^{13}$C NMR (75 MHz, $CDCl_3$): δ 171.3, 156.5, 153.9, 139.0, 138.4, 137.2, 131.6, 128.8, 128.4 (2C), 128.2 (2C), 127.7, 127.4 (2C), 127.3 (2C), 127.2, 126.5, 121.7 (2C), 115.5 (2C), 114.8, 112.4, 88.4, 71.6, 71.4, 69.7, 54.8, 53.3 (2C), 50.8, 48.7, 45.5, 43.0, 39.1, 36.5, 33.6, 29.71, 29.68, 27.6, 27.3, 26.0, 23.0 (2C), 13.7.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-5-(pyrrolidin-1-yl) pentanamide, SERD114: $^1$H NMR (300 MHz, MeOD): δ 7.42 (d, J=8.1 Hz, 2H), 6.90 (m, 1H), 6.89 (d, J=8.1 Hz, 2H), 6.48 (s, 1H), 6.42 (d, J=6.5 Hz, 1H), 5.30 (m, 1H), 2.49 (m, 4H), 1.71 (m, 4H), 0.88 (s, 3H), 0.80-3.70 (m, 22H). $^{13}C$ NMR (75 MHz, MeOD): δ 173.5, 156.0, 155.8, 139.6, 132.3, 128.7, 127.7, 123.3 (2C), 116.5 (2C), 116.2, 113.9, 82.8, 73.3, 55.9 (2C), 55.0, 51.8, 50.1, 44.2, 39.4, 36.7, 35.6, 30.8, 30.7, 30.5, 28.6, 26.5, 24.0 (2C), 23.7, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-5-(piperidin-1-yl)pentan-amide: $^{1}H$ NMR (300 MHz, $CDCl_3$): δ 8.55 (s, 1H), 7.51 (d, J=8.7 Hz, 2H), 7.20-7.46 (m, 10H), 6.96 (d, J=8.4 Hz, 1H), 6.82 (d, J=8.7 Hz, 2H), 6.69 (d, J=2.3 Hz, 1H), 6.65 (dd, J=8.3, 2.5 Hz, 1H), 5.20 (m, 1H), 4.97 (s, 2H), 4.49 (d, J=11.4 Hz, 1H), 4.46 (d, J=11.4 Hz, 1H), 2.58 (m, 4H), 1.71 (m, 4H), 1.00 (s, 3H), 0.80-3.55 (m, 24H). $^{13}C$ NMR (75 MHz, $CDCl_3$): δ 171.1, 156.5, 154.2, 139.0, 138.4, 137.2, 131.2, 128.7, 128.4 (2C), 128.2 (2C), 127.7, 127.4 (2C), 127.3 (2C), 127.2, 126.5, 121.8 (2C), 115.6 (2C), 114.8, 112.4, 88.4, 71.8, 71.4, 69.8, 57.6, 53.8 (2C), 50.8, 48.8, 43.0, 39.2, 36.5, 33.6, 29.7, 27.6, 27.3, 24.6, 24.1 (2C), 23.2, 23.1, 23.0, 14.1.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-5-(piperidin-1-yl) pentanamide, SERD115: $^{1}H$ NMR (300 MHz, MeOD): δ 7.42 (d, J=8.7 Hz, 2H), 6.89 (d, J=8.7 Hz, 1H), 6.85 (d, J=8.7 Hz, 2H), 6.49 (d, J=2.1 Hz, 1H), 6.42 (dd, J=8.4, 2.7 Hz, 1H), 5.30 (m, 1H), 2.42 (m, 4H), 1.75 (m, 4H), 0.88 (s, 3H), 0.80-3.70 (m, 24H). $^{13}C$ NMR (75 MHz, MeOD): δ 173.4, 156.0, 155.8, 139.6, 132.2, 128.7, 127.8, 123.3 (2C), 116.5 (2C), 116.2, 113.9, 82.8, 73.3, 57.9, 54.3 (2C), 51.8, 50.1, 44.2, 39.3, 36.7, 35.6, 30.8, 30.5, 28.6, 24.5, 24.2 (2C), 24.0, 23.7, 22.7, 13.8.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)phenyl)-5-(dimethyl-amino)pentan-amide: $^{1}H$ NMR (300 MHz, $CDCl_3$): δ 8.04 (s, 1H), 7.18-7.46 (m, 12H), 6.96 (d, J=8.4 Hz, 1H), 6.83 (d, J=8.7 Hz, 2H), 6.70 (d, J=2.3 Hz, 1H), 6.66 (dd, J=8.3, 2.8 Hz, 1H), 5.20 (m, 1H), 4.97 (s, 2H), 4.50 (d, J=11.6 Hz, 1H), 4.47 (d, J=11.6 Hz, 1H), 2.30 (s, 6H), 1.00 (s, 3H), 0.80-3.60 (m, 22H). $^{13}C$ NMR (75 MHz, $CDCl_3$): δ 171.1, 156.5, 154.2, 139.0, 138.4, 137.2, 130.9, 128.7, 128.4 (2C), 128.1 (2C), 127.7, 127.3 (2C), 127.2 (2C), 127.15, 126.4, 121.7 (2C), 115.6 (2C), 114.8, 112.4, 88.4, 71.8, 71.4, 69.7, 58.8, 50.8, 48.8, 45.3 (2C), 43.0, 39.2, 36.9, 33.6, 31.8, 29.7, 27.6, 26.5, 23.4, 21.5, 13.8.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)phenyl)-5-(dimethylamino) pentanamide, SERD117: $^{1}H$ NMR (300 MHz, MeOD): δ 7.39 (d, J=9.0 Hz, 2H), 6.89 (d, J=8.4 Hz, 1H), 6.85 (d, J=8.7 Hz, 2H), 6.48 (d, J=2.1 Hz, 1H), 6.41 (dd, J=8.3, 2.7 Hz, 1H), 5.29 (m, 1H), 2.50 (s, 6H), 0.88 (s, 3H), 0.80-3.70 (m, 22H). $^{13}C$ NMR (75 MHz, MeOD): δ 173.7, 156.0, 155.8, 139.6, 132.3, 128.7, 127.7, 123.3 (2C), 116.4 (2C), 116.2, 113.9, 82.8, 73.3, 59.4, 51.8, 50.1, 44.4 (2C), 44.2, 39.3, 37.1, 35.6 30.8, 30.5, 28.6, 26.5, 24.2, 24.0, 13.8.

(8S,9S,11S,13S,14S,17S)-3,17-bis(Benzyloxy)-11-(3-fluoro-4-nitrophenoxy)-13-methyl-7,8,9,11,12,13,14,15,16,17-decahydro-6H-cyclopenta[a]phenanthrene: $^{1}H$ NMR (300 MHz, $CDCl_3$): δ 7.88 (dd, J=9.0, 6.0 Hz, 1H), 7.15-7.5 (m, 10H), 6.87 (dd, J=10.6, 2.4 Hz, 1H), 6.78 (d, J=8.7 Hz, 1H), 6.72 (d, J=2.4 Hz, 1H), 6.66 (tt, J=7.3, 2.3 Hz, 1H), 6.57 (dd, J=8.5, 2.6 Hz, 1H), 5.29 (m, 1H), 4.99 (s, 2H), 4.60 (d, J=12.3 Hz, 1H), 4.50 (d, J=12.3 Hz, 1H), 3.54 (dd, J=8.1, 8.1 Hz, 1H), 1.04 (s, 3H), 0.80-3.12 (m, 13H). $^{13}C$ NMR (75 MHz, $CDCl_3$): δ 165.8 (d, J=256.5 Hz), 156.6, 154.2 (d, J=11.8 Hz), 139.0, 138.9, 137.2, 135.9 (d, J=3.5 Hz), 128.5 (d, J=2.4 Hz), 128.4 (2C), 128.2 (2C), 127.7, 127.6, 127.41 (2C), 127.37, 127.31 (2C), 125.4, 115.0, 112.6, 106.7 (d, J=23.9 Hz), 102.0 (d, J=26.8 Hz), 88.5, 76.0, 71.5, 69.8, 50.6, 49.2, 43.0, 39.8, 33.6, 29.8, 27.6, 26.9, 23.0, 13.5. $^{19}F$ NMR (282 MHz, $CDCl_3$): δ −100.89.

(8S,9S,11S,13S,14S,17S)-11-(3-Fluoro-4-nitrophenoxy)-13-methyl-7,8,9,11,12,13,14,15,16,17-decahydro-6H-cyclopenta[a]phenanthrene-3,17-diol, SERD119: $^{1}H$ NMR (300 MHz, MeOD): δ 7.85 (dd, J=9.0, 6.1 Hz, 1H), 6.86 (dd, J=10.4, 2.4 Hz, 1H), 6.70 (d, J=8.6 Hz, 1H), 6.65 (d, J=1.8 Hz, 1H), 6.53 (d, J=2.1 Hz, 1H), 6.39 (m, 1H), 5.29 (m, 1H), 0.93 (s, 3H), 0.75-3.85 (m, 14H). $^{13}C$ NMR (75 MHz, MeOD): δ 165.9 (d, J=256.1 Hz), 154.1 (d, J=11.3 Hz), 153.4, 139.1, 135.9, 128.4 (d, J=11.3 Hz), 127.1, 125.6, 115.8, 112.9, 106.8 (d, J=23.5 Hz), 102.1 (d, J=26.6 Hz), 82.3, 76.0, 50.4, 49.1, 42.9, 38.9, 33.9, 30.6, 29.6, 26.8, 23.0, 12.6. $^{19}F$ NMR (282 MHz, $CDCl_3$): δ −100.74. HR-MS (ESI) calcd for $[C_{24}H_{26}FNO_5H]^+$ 428.1873, found 428.1879.

(8S,9S,11S,13S,14S,17S)-11-(4-Amino-3-fluorophenoxy)-13-methyl-7,8,9,11,12,13,14,15,16,17-decahydro-6H-cyclopenta[a]phenanthrene-3,17-diol, SERD120: $^{1}H$ NMR (300 MHz, $CDCl_3$): δ 7.26 (s, 2H), 6.71 (m, 2H), 6.49 (m, 2H), 6.38 (m, 1H), 5.29 (m, 1H), 0.99 (s, 3H), 0.70-3.80 (m, 18H). $^{13}C$ NMR (75 MHz, $CDCl_3$): δ 156.5 (d, J=227.6 Hz), 153.5, 146.6 (d, J=9.7 Hz), 138.6, 132.1, 127.7, 126.4, 115.434 (d, J=9.4 Hz), 115.427, 113.1, 106.2 (d, J=22.2 Hz), 100.2 (d, J=27.1 Hz), 82.2, 74.0, 50.4, 49.1, 42.8, 39.0, 34.4, 30.4, 29.6, 27.1, 23.0, 12.8. $^{19}F$ NMR (282 MHz, $CDCl_3$): δ −123.5.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-2-(piperidin-1-yl)acet-amide: $^{1}H$ NMR (300 MHz, $CDCl_3$): δ 8.99 (s, 1H), 8.34 (dd, J=8.9, 6.4 Hz, 1H), 7.15-7.50 (m, 10H), 6.68 (m, 5H), 5.28 (m, 1H), 4.94 (s, 2H), 4.50 (d, J=12.3 Hz, 1H), 4.47 (d, J=12.3 Hz, 1H), 2.55 (m, 4H), 1.61 (m, 4H), 1.01 (s, 3H), 0.80-3.60 (m, 18H). $^{13}C$ NMR (75 MHz, $CDCl_3$): δ 168.5, 158.9 (d, J=241.2 Hz), 156.7, 147.6 (d, J=9.6 Hz), 138.9, 138.0, 137.1, 128.4 (2C), 128.2 (2C), 127.9, 127.8, 127.5, 127.34 (2C), 127.29 (2C), 126.2, 124.1 (d, J=3.2 Hz), 120.7 (d, J=8.8 Hz), 115.0, 112.2, 106.3 (d, J=22.5 Hz), 99.6 (d, J=26.7 Hz), 88.4, 73.6, 71.6, 69.7, 63.2, 54.7 (2C), 50.5, 48.5, 46.8, 42.7, 40.6, 33.8, 29.1, 27.6, 27.4, 24.6 (2C), 23.7, 13.8. HR-MS (ESI) calcd for $[C_{45}H_{51}FN_2O_4H]^+$ 703.3911, found 703.3939.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-2-(piperidin-1-yl)acet-amide, SERD122: $^{1}H$ NMR (300 MHz, MeOD): δ 8.10 (dd, J=9.0, 6.3 Hz, 1H), 7.04 (dd, J=10.9, 2.7 Hz, 1H), 6.72 (d, J=8.5 Hz, 1H), 6.63 (dt, J=8.5, 2.6 Hz, 1H), 6.50 (d, J=2.4 Hz, 1H), 6.35 (dd, J=8.6, 2.5 Hz, 1H), 5.37 (m, 1H), 2.45 (m, 4H), 1.48 (m, 4H). 0.89 (s, 3H), 0.80-3.80 (m, 18H). $^{13}C$ NMR (75 MHz, MeOD): δ 169.9, 161.2 (d, J=240.8 Hz), 156.1, 150.2 (d, J=10.1 Hz), 139.4, 128.2, 127.6, 124.6, 122.6 (d, J=9.3 Hz), 116.3, 113.9, 107.0 (d, J=21.8 Hz), 101.6 (d, J=27.6 Hz), 82.7, 75.8, 63.2, 55.8 (2C), 51.5, 49.7, 43.9, 40.0, 35.7, 30.4, 30.3, 28.6, 26.5 (2C), 24.5, 24.1, 13.9. $^{19}F$ NMR (282 MHz, $CDCl_3$): δ −117.41. HR-MS (ESI) calcd for $[C_{31}H_{39}FN_2O_4H]^+$ 523.2972, found 523.2956.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-2-(pyrrolidin-1-yl)ac-etamide: $^{1}H$ NMR (300 MHz, $CDCl_3$): δ

9.00 (s, 1H), 8.37 (dd, J=8.9, 6.4 Hz, 1H), 7.25-7.50 (m, 10H), 6.76 (d, J=2.5 Hz, 1H), 6.72 (d, J=4.2 Hz, 1H), 6.69 (d, J=2.5 Hz, 1H), 6.64 (m, 1H), 6.56 (dd, J=8.6, 2.6 Hz, 1H), 5.19 (m, 1H), 4.97 (s, 2H), 4.56 (d, J=12.3 Hz, 1H), 4.50 (d, J=12.3 Hz, 1H), 2.59 (m, 4H), 1.75 (m, 4H), 0.99 (s, 3H), 0.80-3.60 (m, 16H). $^{13}$C NMR (75 MHz, $CDCl_3$): δ 168.7, 159.0 (d, J=241.0 Hz), 156.6, 147.5 (d, J=9.8 Hz), 138.9, 138.0, 137.1, 128.5 (2C), 128.3 (2C), 127.9, 127.8, 127.41, 127.39 (2C), 127.32 (2C), 126.1, 124.1 (d, J=3.0 Hz), 120.3 (d, J=9.2 Hz), 115.0, 112.3, 106.2 (d, J=22.1 Hz), 99.4 (d, J=26.8 Hz), 88.4, 73.7, 71.6, 69.7, 60.5, 54.6 (2C), 50.5, 48.6, 42.8, 39.7, 33.9, 29.3, 27.6, 27.3, 24.2 (2C), 23.2, 13.7. $^{19}$F NMR (282 MHz, $CDCl_3$): δ −116.81. HR-MS (ESI) calcd for $[C_{44}H_{49}FN_2O_4H]^+$ 689.3755, found 689.3782.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-2-(pyrrolidin-1-yl)acet-amide, SERD125: $^1$H NMR (300 MHz, MeOD): δ 8.16 (dd, J=8.9, 6.4 Hz, 1H), 6.99 (dd, J=10.7, 2.4 Hz, 1H), 6.70 (d, J=8.5 Hz, 1H), 6.61 (td, J=8.7, 2.5 Hz, 1H), 6.51 (s, 1H), 6.35 (d, J=8.5 Hz, 1H), 5.32 (m, 1H), 2.55 (m, 4H), 1.79 (m, 4H), 0.86 (s, 3H), 0.80-3.75 (m, 16H). $^{13}$C NMR (75 MHz, MeOD): δ 170.8, 160.9 (d, J=245.4 Hz), 156.1, 149.9 (d, J=10.1 Hz), 139.4, 128.1, 127.5, 124.7 (d, J=3.3 Hz), 121.8 (d, J=9.6 Hz), 116.2, 113.9, 106.8 (d, J=22.0 Hz), 101.2 (d, J=27.4 Hz), 82.7, 75.7, 61.1, 55.6 (2C), 51.4, 49.8, 43.9, 39.9, 35.7, 30.7, 30.5, 28.5, 25.2 (2C), 24.1, 13.9. $^{19}$F NMR (282 MHz, MeOD): δ −117.59.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-2-morpholinoacet-amide: $^1$H NMR (300 MHz, $CDCl_3$): δ 8.76 (s, 1H), 8.30 (dd, J=9.1, 6.5 Hz, 1H), 7.20-7.40 (m, 10H), 6.45-6.80 (m, 5H), 5.15 (m, 1H), 4.91 (s, 2H), 4.50 (d, J=12.1 Hz, 1H), 4.43 (d, J=12.1 Hz, 1H), 3.48 (m, 4H), 2.55 (m, 4H), 0.94 (s, 3H), 0.80-3.75 (m, 16H). $^{13}$C NMR (75 MHz, $CDCl_3$): δ 168.7, 159.0 (d, J=242.1 Hz), 156.5, 147.4 (d, J=9.6 Hz), 138.7, 137.7, 136.9, 128.2 (2C), 128.0 (2C), 127.7, 127.6, 127.2, 127.14 (2C), 127.12 (2C), 126.1, 123.7 (d, J=3.3 Hz), 120.4 (d, J=9.6 Hz), 114.6, 112.3, 106.2 (d, J=21.4 Hz), 99.6 (d, J=26.2 Hz), 88.1, 73.7, 71.4, 69.5, 66.4 (2C), 62.7, 53.5 (2C), 50.2, 48.2, 42.5, 33.9, 29.4, 27.4, 27.1, 24.2, 23.0, 13.6. $^{19}$F NMR (282 MHz, $CDCl_3$): δ −116.34. HR-MS (ESI) calcd for $[C_{44}H_{49}FN_2O_5H]^+$ 705.3704, found 705.3690.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-2-morpholinoacetamide, SERD126: $^1$H NMR (300 MHz, MeOD): δ 8.17 (dd, J=9.0, 6.3 Hz, 1H), 7.04 (dd, J=10.9, 2.7 Hz, 1H), 6.71 (d, J=8.6 Hz, 1H), 6.63 (dt, J=8.3, 2.7 Hz, 1H), 6.51 (d, J=2.5 Hz, 1H), 6.35 (dd, J=8.5, 2.6 Hz, 1H), 5.37 (m, 1H), 3.30 (m, 4H), 2.39 (m, 4H), 0.89 (s, 3H), 0.80-3.80 (m, 16H). $^{13}$C NMR (75 MHz, MeOD): δ 170.0, 161.2 (d, J=240.6 Hz), 156.2, 149.9 (d, J=9.8 Hz), 139.3, 128.2, 127.6, 124.7 (d, J=3.1 Hz), 122.2 (d, J=9.5 Hz), 116.3, 114.0, 106.9 (d, J=22.2 Hz), 101.5 (d, J=27.7 Hz), 82.7, 75.6, 67.8 (2C), 63.5, 54.8 (2C), 51.5, 49.6, 43.9, 39.9, 35.9, 30.4, 30.3, 28.6, 24.1, 13.9. $^{19}$F NMR (282 MHz, MeOD): δ −117.53. HR-MS (ESI) calcd for $[C_{30}H_{37}FN_2O_5H]^+$ 525.2765, found 525.2782.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-2-(dimethylamino)ac-etamide: $^1$H NMR (300 MHz, $CDCl_3$): δ 9.25 (s, 1H), 8.35 (dd, J=8.7, 6.5 Hz, 1H), 7.15-7.55 (m, 10H), 6.50-6.85 (m, 5H), 5.19 (m, 1H), 4.97 (s, 2H), 4.57 (d, J=12.0 Hz, 1H), 4.49 (d, J=12.0 Hz, 1H), 2.11 (s, 6H), 0.97 (s, 3H), 0.80-3.60 (m, 16H). $^{13}$C NMR (75 MHz, $CDCl_3$): δ 168.2, 159.8 (d, J=287.4 Hz), 156.6, 147.3 (d, J=9.6 Hz), 138.9, 138.0, 137.1, 128.4 (2C), 128.2 (2C), 128.0, 127.8, 127.4 (2C), 127.31, 127.3 (2C), 126.1, 124.0 (d, J=2.7 Hz), 119.9 (d, J=9.5 Hz), 115.0, 112.4, 106.1 (d, J=21.6 Hz), 99.1 (d, J=26.8 Hz), 88.4, 73.1, 71.6, 69.7, 63.6, 50.4, 48.7, 45.7 (2C), 42.7, 39.3, 34.1, 29.7, 27.6, 27.4, 23.1, 13.5. $^{19}$F NMR (282 MHz, $CDCl_3$): δ −116.79. HR-MS (ESI) calcd for $[C_{42}H_{47}FN_2O_4H]^+$ 663.3598, found 663.3624.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-2-(dimethylamino)acet-amide, SERD129: $^1$H NMR (300 MHz, MeOD): δ 8.14 (dd, J=8.9, 6.3 Hz, 1H), 6.98 (dd, J=10.8, 2.6 Hz, 1H), 6.74 (d, J=8.5 Hz, 1H), 6.61 (dt, J=8.6, 2.7 Hz, 1H), 6.50 (d, J=2.5 Hz, 1H), 6.37 (dd, J=8.5, 2.6 Hz, 1H), 5.33 (m, 1H), 3.70 (dd, J=8.3, 8.3 Hz, 1H), 2.16 (s, 6H), 0.84 (s, 3H), 0.80-3.75 (m, 15H). $^{13}$C NMR (75 MHz, MeOD): δ 170.4, 161.0 (d, J=241.6 Hz), 156.1, 149.6 (d, J=10.2 Hz), 139.4, 128.2, 127.5, 124.7 (d, J=3.1 Hz), 121.4 (d, J=8.7 Hz), 116.3, 114.0, 106.6 (d, J=22.4 Hz), 101.0 (d, J=27.8 Hz), 82.7, 75.1, 64.2, 51.4, 49.9, 46.1 (2C), 43.9, 39.5, 35.9, 30.8, 30.4, 28.6, 24.1, 13.6. $^{19}$F NMR (282 MHz, MeOD): δ −117.74. HR-MS (ESI) calcd for $[C_{28}H_{35}FN_2O_4H]^+$ 483.2659, found 483.2660.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-3-(piperidin-1-yl)pro-panamide: $^1$H NMR (300 MHz, $CDCl_3$): δ 8.01 (s, 1H), 7.20-7.60 (m, 11H), 6.75 (m, 3H), 6.61 (m, 2H), 5.06 (m, 1H), 4.98 (s, 2H), 4.58 (d, J=12.0 Hz, 1H), 4.50 (d, J=12.0 Hz, 1H), 2.58 (m, 4H), 1.66 (m, 4H), 1.00 (s, 3H), 0.80-3.60 (m, 20H). $^{13}$C NMR (75 MHz, $CDCl_3$): δ 168.4, 159.3 (d, J=243.2 Hz), 156.6, 149.1 (d, J=9.6 Hz), 138.9, 138.7, 137.0, 128.4 (2C), 128.2 (2C), 128.0, 127.8, 127.4, 127.30 (2C), 127.28 (2C), 126.3, 123.8 (d, J=3.2 Hz), 121.7 (d, J=9.0 Hz), 115.5, 112.2, 106.8 (d, J=22.2 Hz), 100.8 (d, J=27.1 Hz), 88.4, 76.9, 71.6, 69.7, 53.5 (2C), 53.3, 50.2, 49.1, 42.9, 40.8, 34.2, 33.0, 29.7, 27.6, 26.9, 24.3 (2C), 23.2, 22.9, 13.7. $^{19}$F NMR (282 MHz, $CDCl_3$): δ −115.87. HR-MS (ESI) calcd for $[C_{46}H_{53}FN_2O_4H]^+$ 717.4067, found 717.4052.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-3-(piperidin-1-yl)propan-amide, SERD130: $^1$H NMR (500 MHz, MeOD): δ 7.71 (dd, J=8.8, 6.3 Hz, 1H), 7.02 (dd, J=10.6, 2.4 Hz, 1H), 6.75 (d, J=8.6 Hz, 1H), 6.63 (td, J=8.5, 2.5 Hz, 1H), 6.55 (d, J=2.1 Hz, 1H), 6.38 (dd, J=8.5, 2.3 Hz, 1H), 5.24 (m, 1H), 3.70 (dd, J=8.3, 8.3 Hz, 1H), 2.80 (m, 4H), 1.70 (m, 4H), 0.87 (s, 3H), 0.78-3.40 (m, 19H). $^{13}$C NMR (125 MHz, MeOD): δ 170.6, 161.7 (d, J=242.0 Hz), 156.2, 152.1 (d, J=10.2 Hz), 139.8, 128.3, 127.9, 125.0 (d, J=9.7 Hz), 124.4 (d, J=3.1 Hz), 116.5, 114.3, 107.3 (d, J=22.9 Hz), 102.4 (d, J=26.9 Hz), 82.7, 77.7, 54.73 (2C), 54.65, 51.3, 50.3, 44.1, 40.7, 35.9, 32.6, 30.9, 30.4, 28.3, 25.3 (2C), 24.0, 23.8, 13.7. $^{19}$F NMR (282 MHz, MeOD): δ −116.52. HR-MS (ESI) calcd for $[C_{32}H_{41}FN_2O_4H]^+$ 537.3129, found 537.3132.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-3-(pyrrolidin-1-yl)propanamide: $^1$H NMR (500 MHz, $CDCl_3$): δ 9.47 (br s, 1H), 7.98 (dd, J=8.9, 6.3 Hz, 1H), 7.20-7.45 (m, 9H), 7.13 (s, 1H), 6.84 (d, J=2.1 Hz, 1H), 6.78 (dd, J=10.1, 2.5 Hz, 1H), 6.72 (d, J=8.7 Hz, 1H), 6.64 (dt, J=8.7, 2.6 Hz, 1H), 6.55 (dd, J=8.6, 2.4 Hz, 1H), 5.03 (m, 1H), 5.01 (d, J=11.7 Hz, 1H), 4.96 (d, J=11.7 Hz, 1H), 4.60 (d, J=12.2 Hz, 1H), 4.50 (d, J=12.2 Hz, 1H), 3.52 (dd, J=8.1, 8.1 Hz, 1H), 2.90 (m, 4H), 1.88 (m, 4H), 1.00 (s, 3H), 0.80-3.20 (m, 17H). $^{13}$C NMR (125 MHz, $CDCl_3$): δ 167.3, 159.3 (d, J=243.2 Hz), 156.5, 149.2 (d, J=9.7 Hz), 139.1, 138.9, 136.9, 128.5 (2C), 128.3 (2C), 128.2, 127.8, 127.4, 127.33 (2C), 127.30 (2C), 126.3, 123.7 (d, J=3.3 Hz), 121.5 (d, J=9.6 Hz), 115.7, 112.1, 107.0 (d, J=21.5 Hz), 101.1 (d, J=26.7 Hz), 88.3, 77.7, 71.6, 69.7, 53.2 (2C), 50.5, 50.1, 49.2, 43.0, 41.1, 34.1, 33.4, 29.7, 27.6, 26.8, 23.2 (2C), 22.9, 13.8. $^{19}$F NMR (282 MHz, $CDCl_3$): δ −115.73. HR-MS (ESI) calcd for $[C_{45}H_{51}FN_2O_4H]^+$ 703.3911, found 703.3906.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-3-(pyrrolidin-1-yl)propan-amide, SERD132: $^1$H NMR (500 MHz, MeOD): δ 7.75 (dd, J=8.8, 6.3 Hz, 1H), 7.03 (dd, J=10.6, 2.6 Hz, 1H), 6.75 (d, J=8.6 Hz, 1H), 6.64 (td, J=8.6, 2.6 Hz, 1H), 6.57 (d, J=2.3 Hz, 1H), 6.38 (dd, J=8.5, 2.5 Hz, 1H), 5.23 (m, 1H), 3.71 (dd, J=8.3, 8.3 Hz, 1H), 3.30 (dt, J=3.2, 1.6 Hz, 3H), 3.17 (m, 4H), 2.02 (m, 4H), 0.88 (s, 3H), 0.80-3.10 (m, 13H). $^{13}$C NMR (125 MHz, MeOD): δ 169.8, 161.7 (d, J=243.9 Hz), 156.2, 152.1 (d, J=10.2 Hz), 139.9, 128.4, 127.9, 124.8 (d, J=9.8 Hz), 124.4 (d, J=3.2 Hz), 116.5, 114.3, 107.3 (d, J=22.5 Hz), 102.5 (d, J=26.5 Hz), 82.7, 78.1, 55.2 (2C), 52.1, 51.3, 50.3, 44.1, 40.8, 35.8, 33.2, 30.9, 30.4, 28.3, 24.1 (2C), 24.0, 13.7. $^{19}$F NMR (282 MHz, MeOD): δ −116.52.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-3-(dimethylamino)-propanamide: $^1$H NMR (500 MHz, $CDCl_3$): δ 8.96 (br s, 1H), 8.01 (dd, J=8.9, 6.3 Hz, 1H), 7.43 (s, 1H), 7.20-7.40 (m, 9H), 6.79 (d, J=2.5 Hz, 1H), 6.77 (dd, J=7.9, 2.6 Hz, 1H), 6.73 (d, J=8.7 Hz, 1H), 6.64 (td, J=8.6, 2.6 Hz, 1H), 6.56 (dd, J=8.6, 2.6 Hz, 1H), 5.06 (m, 1H), 4.98 (d, J=11.5 Hz, 1H), 4.96 (d, J=11.5 Hz, 1H), 4.60 (d, J=12.2 Hz, 1H), 4.50 (d, J=12.2 Hz, 1H), 3.52 (dd, J=8.2, 8.2 Hz, 1H), 2.35 (s, 6H), 1.00 (s, 3H), 0.80-3.00 (m, 17H). $^{13}$C NMR (125 MHz, $CDCl_3$): δ 168.1, 159.3 (d, J=282.8 Hz), 156.6, 149.0 (d, J=9.8 Hz), 138.9, 138.7, 136.9, 128.5 (2C), 128.3 (2C), 128.1, 127.9, 127.4, 127.37 (2C), 127.34 (2C), 126.4, 123.8 (d, J=3.1 Hz), 121.7 (d, J=9.4 Hz), 115.6, 112.2, 106.9 (d, J=21.1 Hz), 100.9 (d, J=27.5 Hz), 88.3, 76.9, 71.6, 69.7, 53.5, 50.2, 49.1, 43.5 (2C), 42.9, 40.8, 34.1, 33.0, 29.6, 27.6, 26.9, 23.0, 13.7. $^{19}$F NMR (282 MHz, $CDCl_3$): δ −115.94. HR-MS (ESI) calcd for $[C_{43}H_{49}FN_2O_4H]^+$ 677.3755, found 677.3738.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-3-(dimethylamino)propan-amide, SERD133: $^1$H NMR (500 MHz, MeOD): δ 7.74 (dd, J=8.8, 6.3 Hz, 1H), 6.98 (dd, J=10.7, 2.5 Hz, 1H), 6.73 (d, J=8.6 Hz, 1H), 6.64 (td, J=8.6, 2.5 Hz, 1H), 6.54 (d, J=2.2 Hz, 1H), 6.38 (dd, J=8.5, 2.4 Hz, 1H), 5.20 (m, 1H), 3.56 (dd, J=8.2, 8.2 Hz, 1H), 2.46 (s, 6H), 0.94 (s, 3H), 0.80-3.40 (m, 15H). $^{13}$C NMR (125 MHz, MeOD): δ 169.4, 161.6 (d, J=242.9 Hz), 156.2, 152.0 (d, J=10.4 Hz), 139.9, 128.4, 127.9, 124.9 (d, J=9.7 Hz), 124.3 (d, J=3.3 Hz), 116.5, 114.3, 107.3 (d, J=22.5 Hz), 102.4 (d, J=26.5 Hz), 82.7, 77.8, 55.2, 51.3, 50.3, 44.2 (2C), 44.1, 40.7, 35.8, 32.4, 30.8, 30.4, 28.3, 24.9, 14.3. $^{19}$F NMR (282 MHz, MeOD): δ −116.56.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-3-morpholinopropan-amide: $^1$H NMR (500 MHz, $CDCl_3$): δ 9.12 (s, 1H), 8.04 (dd, J=8.8, 6.4 Hz, 1H), 7.20-7.50 (m, 10H), 6.79 (m, 1H), 6.76 (m, 1H), 6.74 (m, 1H), 6.66 (m, 1H), 6.57 (m, 1H), 5.27 (m, 1H), 4.98 (s, 2H), 4.59 (d, J=12.5 Hz, 1H), 4.52 (d, J=12.5 Hz, 1H), 3.65 (t, J=4.1 Hz, 4H), 2.93 (t, J=4.1 Hz, 4H), 0.99 (s, 3H), 0.75-3.40 (m, 18H). $^{13}$C NMR (125 MHz, $CDCl_3$): δ 169.0, 159.2 (d, J=245.3 Hz), 156.7, 148.8 (d, J=9.8 Hz), 138.8, 138.2, 136.8, 128.43 (2C), 128.41, 128.2 (2C), 127.8, 127.4, 127.30 (2C), 127.27 (2C), 126.3, 123.8 (d, J=2.9 Hz), 121.7 (d, J=9.4 Hz), 115.4, 112.3, 106.8 (d, J=21.9 Hz), 100.8 (d, J=12.7 Hz), 88.2, 76.5, 71.6, 69.7, 66.6 (2C), 54.0, 53.1 (2C), 50.0, 49.0, 42.8, 40.6, 34.4, 34.2, 29.8, 27.5, 26.9, 22.9, 13.7. $^{19}$F NMR (282 MHz, $CDCl_3$): δ −116.07. HR-MS (ESI) calcd for $[C_{45}H_{51}FN_2O_5H]^+$ 719.3860, found 719.3887.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-3-morpholinopropan-amide, SERD134: $^1$H NMR (500 MHz, MeOD): δ 7.69 (dd, J=8.5, 6.5 Hz, 1H), 7.02 (dd, J=10.7, 2.7 Hz, 1H), 6.76 (d, J=8.6 Hz, 1H), 6.63 (td, J=8.4, 2.1 Hz, 1H), 6.54 (s, 1H), 6.39 (dd, J=8.3, 1.9 Hz, 1H), 5.25 (m, 1H), 3.65 (m, 4H), 2.55 (m, 4H), 0.85 (s, 3H), 0.70-3.80 (m, 18H). $^{13}$C NMR (125 MHz, MeOD): δ 171.8, 161.7 (d, J=242.1 Hz), 156.3, 152.0 (d, J=10.3 Hz), 139.7, 128.2, 127.8, 125.2 (d, J=9.7 Hz), 124.3 (d, J=3.2 Hz), 116.6, 114.3, 107.3 (d, J=22.3 Hz), 102.3 (d, J=27.3 Hz), 82.7, 77.3, 67.4 (2C), 55.2, 54.2 (2C), 51.3, 50.2, 44.0, 40.4, 36.0, 34.1, 30.9, 30.4, 28.3, 24.0, 13.7. $^{19}$F NMR (282 MHz, MeOD): δ −116.52. HR-MS (ESI) calcd for $[C_{45}H_{54}N_2O_4H]^+$ 687.4162, found 687.4188.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-4-morpholinobutan-amide: $^1$H NMR (500 MHz, $CDCl_3$): δ 9.89 (s, 1H), 8.12 (dd, J=8.8, 6.4 Hz, 1H), 7.20-7.50 (m, 9H), 6.84 (s, 1H), 6.76 (dd, J=5.9, 2.4 Hz, 1H), 6.74 (m, 2H), 6.64 (td, J=8.6, 2.4 Hz, 1H), 6.57 (dd, J=8.6, 2.4 Hz, 1H), 5.06 (m, 1H), 4.96 (s, 2H), 4.60 (d, J=12.2 Hz, 1H), 4.51 (d, J=12.2 Hz, 1H), 3.65 (t, J=3.2 Hz, 4H), 2.42 (t, J=3.2 Hz, 4H), 0.98 (s, 3H), 0.70-3.70 (m, 20H). $^{13}$C NMR (125 MHz, $CDCl_3$): δ 169.9, 158.9 (d, J=242.4 Hz), 156.8, 148.3 (d, J=9.8 Hz), 138.9, 138.5, 136.8, 128.5 (2C), 128.3 (2C), 127.9, 127.85, 127.5, 127.4 (2C), 127.3 (2C), 126.3, 124.3 (d, J=2.9 Hz), 120.6 (d, J=9.3 Hz), 115.4, 112.4, 107.0 (d, J=21.5 Hz), 100.7 (d, J=26.1 Hz), 88.3, 77.0, 71.7, 69.7, 66.5 (2C), 57.8, 53.2 (2C), 50.1, 49.3, 43.0, 40.9, 34.9, 34.5, 29.9, 27.6, 26.8, 23.0, 21.6, 13.8. $^{19}$F NMR (282 MHz, $CDCl_3$): δ −116.60. HR-MS (ESI) calcd for $[C_{46}H_{53}FN_2O_5H]^+$ 733.4017, found 733.4049.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-4-morpholinobutanamide, SERD135: $^1$H NMR (500 MHz, MeOD): δ 7.77 (dd, J=8.9, 6.3 Hz, 1H), 7.01 (dd, J=10.6, 2.6 Hz, 1H), 6.77 (d, J=8.6 Hz, 1H), 6.63 (td, J=8.6, 2.6 Hz, 1H), 6.55 (d, J=2.4 Hz, 1H), 6.39 (dd, J=8.5, 2.5 Hz, 1H), 5.25 (m, 1H), 3.69 (t, J=4.8 Hz, 4H), 2.56 (d, J=4.8 Hz, 4H), 0.86 (s, 3H), 0.75-3.30 (m, 20H). $^{13}$C NMR (125 MHz, MeOD): δ 173.0, 161.4 (d, J=243.5 Hz), 156.3, 151.5 (d, J=10.2 Hz), 139.8, 128.2, 127.8, 124.7 (d, J=3.0 Hz), 124.1 (d, J=9.7 Hz), 116.6, 114.4, 107.3 (d, J=22.6 Hz), 102.3 (d, J=26.7 Hz), 82.7, 77.8, 67.3 (2C), 59.0, 54.4 (2C), 51.2, 50.3, 44.1, 40.6, 36.1, 35.5, 31.0, 30.4, 28.2, 23.9, 22.7, 13.8. $^{19}$F NMR (282 MHz, MeOD): δ −116.93.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-4-(piperidin-1-yl)butanamide: $^1$H NMR (300 MHz, $CDCl_3$): δ 9.03 (br. s, 1H), 8.02 (dd, J=8.9, 6.3 Hz, 1H), 7.15-7.40 (m, 10H), 6.78 (d, J=2.5 Hz, 1H), 6.76 (s, 1H), 6.72 (d, J=8.6 Hz, 1H), 6.63 (td, J=8.6, 2.6 Hz, 1H), 6.55 (dd, J=8.5, 2.4 Hz, 1H), 5.03 (m, 1H), 5.00 (d, J=11.8 Hz, 1H), 4.96 (d, J=11.8 Hz, 1H), 4.59 (d, J=12.2 Hz, 1H), 4.50 (d, J=12.2 Hz, 1H), 3.52 (dd, J=8.0, 8.0 Hz, 1H), 2.76 (m, 4H), 1.78 (m, 4H), 0.98 (s, 3H), 0.78-3.00 (m, 21H). $^{13}$C NMR (75 MHz, $CDCl_3$): δ 168.8, 159.1 (d, J=243.1 Hz), 156.7, 148.7 (d, J=9.8 Hz), 138.9, 138.8, 136.8, 128.5 (2C), 128.3 (2C), 128.0, 127.9, 127.5, 127.4 (2C), 127.3 (2C), 126.4, 124.0 (d, J=2.9 Hz), 120.6 (d, J=9.3 Hz), 115.4, 112.6, 107.1 (d, J=21.9 Hz), 101.1 (d, J=26.9 Hz), 88.3, 77.8, 71.6, 69.8, 56.6, 53.0 (2C), 50.1, 49.3, 43.0, 41.2, 34.4, 33.3, 30.0, 27.6, 27.0, 26.7, 23.0 (2C), 22.7, 22.4, 13.9. $^{19}$F NMR (282 MHz, $CDCl_3$): δ −116.13. HR-MS (ESI) calcd for $[C_{47}H_{55}FN_2O_4H]^+$ 731.4224, found 731.4240.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-4-(piperidin-1-yl)butan-amide, SERD137: $^1$H NMR (500 MHz, MeOD): δ 7.74 (dd, J=8.9, 6.3 Hz, 1H), 7.03 (dd, J=10.6, 2.6 Hz, 1H), 6.76 (d, J=8.5 Hz, 1H), 6.64 (td, J=8.6, 2.6 Hz, 1H), 6.56 (d, J=2.5 Hz, 1H), 6.38 (dd, J=8.5, 2.6 Hz, 1H), 5.24 (m, 1H), 3.71 (dd, J=8.3, 8.3 Hz, 1H), 2.59 (m, 4H), 1.85 (m, 4H), 0.88 (s, 3H), 0.80-3.40 (m, 21H). $^{13}$C NMR (125 MHz, MeOD): δ 172.1, 161.6 (d, J=242.5 Hz), 156.2, 152.1 (d, J=10.2 Hz), 140.0, 128.34, 127.9, 124.62 (d, J=9.3 Hz), 124.56 (d, J=3.0 Hz), 116.5, 114.3, 107.4 (d, J=22.4 Hz), 102.5 (d, J=27.6 Hz), 82.7, 78.2, 58.0, 54.4 (2C), 51.3, 50.4, 44.2, 40.9, 36.0, 34.1, 31.0, 30.4, 28.3, 24.5 (2C), 24.0, 22.8, 20.6, 13.7. $^{19}$F NMR (376 MHz, MeOD): δ −118.84. HR-MS (ESI) calcd for $[C_{33}H_{43}FN_2O_4H]^+$ 551.3285, found 551.3287.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-4-(pyrrolidin-1-yl)bu-tanamide: $^1$H NMR (500 MHz, $CDCl_3$): δ 11.31 (s, 1H), 8.00 (dd, J=8.9, 6.3 Hz, 1H), 7.20-7.45 (m, 10H), 6.78 (d, J=1.8 Hz, 1H), 6.73 (m, 2H), 6.63 (td, J=8.6, 2.5 Hz, 1H), 6.54 (dd, J=8.6, 2.4 Hz, 1H), 5.03 (m, 1H), 4.99 (d, J=11.6 Hz, 1H), 4.95 (d, J=11.7 Hz, 1H), 4.60 (d, J=12.2 Hz, 1H), 4.49 (d, J=12.2 Hz, 1H), 3.52 (dd, J=8.1, 8.1 Hz, 1H), 2.92 (m, 4H), 1.92 (m, 4H), 0.98 (s, 3H), 0.80-3.20 (m, 19H). $^{13}$C NMR (125 MHz, $CDCl_3$): δ 168.6, 159.1 (d, J=243.0 Hz), 156.7, 148.8 (d, J=9.9 Hz), 138.9, 138.8, 136.8, 128.5 (2C), 128.3 (2C), 128.1, 127.9, 127.5, 127.4 (2C), 127.3 (2C), 126.4, 123.9 (d, J=3.1 Hz), 120.5 (d, J=9.4 Hz), 115.4, 112.7, 107.1 (d, J=21.7 Hz), 101.2 (d, J=26.4 Hz), 88.3, 78.0, 71.6, 69.9, 54.5, 53.2 (2C), 50.0, 49.3, 43.0, 41.2, 34.5, 32.8, 30.0, 27.6, 26.7, 23.2 (2C), 22.9, 20.8, 13.9. $^{19}$F NMR (282 MHz, $CDCl_3$): δ −115.96. HR-MS (ESI) calcd for $[C_{46}H_{53}FN_2O_4H]^+$ 717.4067, found 717.4094.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-4-(pyrrolidin-1-yl)butan-amide, SERD138: $^1$H NMR (500 MHz, MeOD): δ 7.75 (dd, J=8.9, 6.3 Hz, 1H), 7.03 (dd, J=10.6, 2.5 Hz, 1H), 6.76 (d, J=8.6 Hz, 1H), 6.63 (td, J=8.6, 2.5 Hz, 1H), 6.57 (d, J=2.2 Hz, 1H), 6.38 (dd, J=8.5, 2.4 Hz, 1H), 5.24 (m, 1H), 3.71 (dd, J=8.2, 8.2 Hz, 1H), 2.57 (m, 4H), 1.89 (m, 4H), 0.88 (s, 3H), 0.80-3.40 (m, 19H). $^{13}$C NMR (125 MHz, MeOD): δ 171.8, 161.6 (d, J=242.7 Hz), 156.2, 152.0 (d, J=10.1 Hz), 140.0, 128.3, 127.9, 124.6 (d, J=3.3 Hz), 124.5 (d, J=9.8 Hz), 116.5, 114.3, 107.3 (d, J=22.1 Hz), 102.5 (d, J=27.0 Hz), 82.7, 78.2, 55.8, 55.2 (2C), 51.3, 50.4, 44.2, 40.9, 36.0, 33.8, 31.0, 30.4, 28.3, 24.02 (2C), 23.96, 22.4, 13.7. $^{19}$F NMR (282 MHz, MeOD): δ −116.87. HR-MS (ESI) calcd for $[C_{32}H_{41}FN_2O_4H]^+$ 537.3129, found 537.3135.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-4-(dimethylamino)bu-tanamide: $^1$H NMR (500 MHz, $CDCl_3$): δ 8.06 (dd, J=8.8, 6.4 Hz, 1H), 7.20-7.50 (m, 10H), 6.82 (s, 1H), 6.77 (m, 2H), 6.73 (d, J=8.8 Hz, 1H), 6.63 (td, J=8.6, 2.4 Hz, 1H), 6.56 (dd, J=8.5, 2.2 Hz, 1H), 5.05 (m, 1H), 4.97 (s, 2H), 4.60 (d, J=12.2 Hz, 1H), 4.50 (d, J=12.2 Hz, 1H), 3.52 (dd, J=8.1, 8.1 Hz, 1H), 2.41 (s, 6H), 0.98 (s, 3H), 0.80-3.00 (m, 19H). $^{13}$C NMR (125 MHz, $CDCl_3$): δ 169.3, 159.1 (d, J=242.8 Hz), 156.8, 148.6 (d, J=9.8 Hz), 138.9, 138.7, 136.9, 128.6 (2C), 128.3 (2C), 128.02, 127.95, 127.5, 127.41 (2C), 127.38 (2C), 126.4, 124.1 (d, J=3.2 Hz), 120.6 (d, J=9.5 Hz), 115.4, 112.6, 107.0 (d, J=21.7 Hz), 100.9 (d, J=27.1 Hz), 88.3, 77.5, 71.7, 69.9, 57.7, 50.1, 49.3, 43.8, 43.0 (2C), 41.1, 34.5, 33.8, 29.9, 27.6, 26.8, 23.0, 21.1, 13.9. $^{19}$F NMR (282 MHz, $CDCl_3$): δ −116.34. HR-MS (ESI) calcd for $[C_{44}H_{51}FN_2O_4H]^+$ 691.3911, found 691.3903.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-4-(dimethylamino)butan-amide, SERD139: $^1$H NMR (500 MHz, MeOD): δ 7.77 (dd, J=8.8, 6.3 Hz, 1H), 7.02 (dd, J=10.6, 2.4 Hz, 1H), 6.78 (d, J=8.5 Hz, 1H), 6.63 (td, J=8.7, 2.6 Hz, 1H), 6.54 (d, J=2.0 Hz, 1H), 6.38 (dd, J=8.5, 2.2 Hz, 1H), 5.26 (m, 1H), 3.70 (dd, J=8.3, 8.3 Hz, 1H), 2.30 (s, 6H), 0.87 (s, 3H), 0.80-3.40 (m, 19H). $^{13}$C NMR (125 MHz, MeOD): δ 172.8, 161.4 (d, J=251.5 Hz), 156.4, 151.7 (d, J=10.2 Hz), 139.8, 128.1, 127.8, 124.8 (d, J=3.0 Hz), 124.2 (d, J=9.7 Hz), 116.6, 114.4, 107.3 (d, J=22.3 Hz), 102.3 (d, J=27.0 Hz), 82.7, 77.9, 59.7, 51.3, 50.4, 45.2 (2C), 44.2, 40.8, 36.1, 35.3, 31.0, 30.4, 28.3, 24.0, 23.8, 13.3. $^{19}$F NMR (282 MHz, MeOD): δ −117.24. HR-MS (ESI) calcd for $[C_{30}H_{39}FN_2O_4H]^+$ 511.2972, found 511.2961.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-5-(piperidin-1-yl)pen-tanamide: $^1$H NMR (500 MHz, $CDCl_3$): δ 8.63 (br s, 1H), 8.06 (dd, J=8.9, 6.3 Hz, 1H), 7.32 (m, 9H), 6.78 (d, J=2.1 Hz, 1H), 6.76 (s, 1H), 6.75 (dd, J=10.4, 2.5 Hz, 1H), 6.71 (d, J=8.7 Hz, 1H), 6.60 (td, J=8.7, 2.4 Hz, 1H), 6.53 (dd, J=8.6, 2.3 Hz, 1H), 5.01 (m, 1H), 4.97 (d, J=11.5 Hz, 1H), 4.94 (d, J=11.5 Hz, 1H), 4.57 (d, J=12.2 Hz, 1H), 4.46 (d, J=12.2 Hz, 1H), 2.69 (m, 4H), 1.72 (m, 4H), 0.96 (s, 3H), 0.80-3.60 (m, 24H). $^{13}$C NMR (125 MHz, $CDCl_3$): δ 169.4, 158.8 (d, J=243.3 Hz), 156.6, 148.1 (d, J=9.8 Hz), 138.78, 138.77, 136.8, 128.4 (2C), 128.2 (2C), 128.0, 127.8, 127.4 (2C), 127.3, 127.2 (2C), 126.2, 124.0 (d, J=3.0 Hz), 120.4 (d, J=9.1 Hz), 115.5, 112.0, 106.8 (d, J=22.5 Hz), 100.7 (d, J=26.6 Hz), 88.2, 77.2, 71.5, 69.7, 56.8, 52.8 (2C), 49.9, 49.1, 42.8, 40.8, 35.9, 34.3, 29.8, 27.4, 26.6, 23.0, 22.8, 22.4 (2C), 22.2, 22.0, 13.8. $^{19}$F NMR (282 MHz, $CDCl_3$): δ −116.30. HR-MS (ESI) calcd for $[C_{48}H_{57}FN_2O_4H]^+$ 745.4380, found 745.4357.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-5-(piperidin-1-yl)pentan-amide, SERD140: $^1$H NMR (500 MHz, MeOD): δ 7.81 (dd, J=8.9, 6.3 Hz, 1H), 7.01 (dd, J=10.5, 2.5 Hz, 1H), 6.75 (d, J=8.6 Hz, 1H), 6.63 (td, J=8.6, 2.6 Hz, 1H), 6.59 (d, J=2.3 Hz, 1H), 6.39 (dd, J=8.5, 2.4 Hz, 1H), 5.22

(m, 1H), 3.71 (dd, J=8.3, 8.3 Hz, 1H), 2.57 (m, 4H), 1.86 (m, 4H), 0.86 (s, 3H), 0.80-3.40 (m, 23H). $^{13}C$ NMR (125 MHz, MeOD): δ 172.6, 161.3 (d, J=241.8 Hz), 156.3, 151.5 (d, J=10.1 Hz), 139.9, 128.2, 127.8, 124.8 (d, J=3.2 Hz), 123.8 (d, J=10.0 Hz), 116.6, 114.3, 107.3 (d, J=21.8 Hz), 102.3 (d, J=29.8 Hz), 82.6, 78.1, 57.8, 54.2 (2C), 51.2, 50.3, 44.1, 40.8, 36.6, 36.0, 31.0, 30.4, 28.2, 24.5, 24.3 (2C), 23.9, 23.3, 22.7, 13.7. $^{19}F$ NMR (376 MHz, MeOD): δ −117.03. HR-MS (ESI) calcd for $[C_{34}H_{45}FN_2O_4H]^+$ 565.3442, found 565.3444.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-5-morpholinopentan-amide: $^1H$ NMR (500 MHz, $CDCl_3$): δ 8.13 (dd, J=8.8, 6.4 Hz, 1H), 7.20-7.40 (m, 10H), 6.81 (s, 1H), 6.76 (m, 3H), 6.64 (td, J=8.7, 2.4 Hz, 1H), 6.57 (dd, J=8.6, 2.4 Hz, 1H), 5.05 (m, 1H), 4.96 (s, 2H), 4.61 (d, J=12.2 Hz, 1H), 4.50 (d, J=12.2 Hz, 1H), 3.71 (t, J=4.4 Hz, 4H), 3.53 (dd, J=8.1, 8.1 Hz, 1H), 2.45 (t, J=4.4 Hz, 4H), 0.98 (s, 3H), 0.80-3.00 (m, 21H). $^{13}C$ NMR (125 MHz, $CDCl_3$): δ 170.1, 158.9 (d, J=242.5 Hz), 156.8, 148.3 (d, J=9.7 Hz), 138.9, 138.4, 136.8, 128.5 (2C), 128.3 (2C), 127.87, 127.86, 127.5, 127.4 (2C), 127.3 (2C), 126.3, 124.2 (d, J=3.0 Hz), 120.5 (d, J=9.3 Hz), 115.5, 112.3, 106.9 (d, J=21.6 Hz), 100.6 (d, J=27.4 Hz), 88.3, 76.9, 71.6, 69.7, 66.4 (2C), 58.2, 53.2 (2C), 50.0, 49.2, 42.9, 40.8, 37.1, 34.5, 30.0, 27.6, 26.8, 25.5, 23.1, 23.0, 13.8. $^{19}F$ NMR (282 MHz, $CDCl_3$): δ −116.61. HR-MS (ESI) calcd for $[C_{47}H_{55}FN_2O_5H]^+$ 747.4173, found 747.4177.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-5-morpholinopentan-amide, SERD141: $^1H$ NMR (500 MHz, MeOD): δ 7.81 (dd, J=8.9, 6.3 Hz, 1H), 7.00 (dd, J=10.6, 2.6 Hz, 1H), 6.76 (d, J=8.6 Hz, 1H), 6.62 (td, J=8.6, 2.6 Hz, 1H), 6.56 (d, J=2.4 Hz, 1H), 6.39 (dd, J=8.5, 2.5 Hz, 1H), 5.22 (m, 1H), 3.76 (t, J=4.6 Hz, 4H), 3.70 (dd, J=8.3, 8.3 Hz, 1H), 2.59 (t, J=4.6 Hz, 4H), 0.86 (s, 3H), 0.80-3.35 (m, 21H). $^{13}C$ NMR (125 MHz, MeOD): δ 173.0, 161.3 (d, J=242.1 Hz), 156.4, 151.4 (d, J=10.2 Hz), 139.8, 128.1, 127.8, 124.9 (d, J=3.2 Hz), 123.7 (d, J=9.6 Hz), 116.6, 114.4, 107.3 (d, J=21.5 Hz), 102.3 (d, J=26.8 Hz), 82.7, 78.0, 66.7 (2C), 59.1, 54.1 (2C), 51.2, 50.4, 44.1, 40.8, 37.3, 36.1, 31.0, 30.4, 28.3, 25.8, 24.1, 24.0, 13.7. $^{19}F$ NMR (282 MHz, MeOD): δ −117.17. HR-MS (ESI) calcd for $[C_{33}H_{43}FN_2O_5H]^+$ 567.3234, found 567.3226.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl-5-(dimethylamino)-pentanamide: $^1H$ NMR (500 MHz, $CDCl_3$): δ 8.08 (dd, J=8.9, 6.3 Hz, 1H), 7.10-7.50 (m, 10H), 6.78 (m, 2H), 6.74 (d, J=9.2 Hz, 2H), 6.63 (td, J=8.6, 2.4 Hz, 1H), 6.57 (dd, J=8.6, 2.3 Hz, 1H), 5.04 (m, 1H), 4.97 (d, J=11.5 Hz, 1H), 4.95 (d, J=11.5 Hz, 1H), 4.60 (d, J=12.2 Hz, 1H), 4.49 (d, J=12.2 Hz, 1H), 3.52 (dd, J=8.1, 8.1 Hz, 1H), 2.52 (s, 6H), 0.98 (s, 3H), 0.80-3.00 (m, 21H). $^{13}C$ NMR (125 MHz, $CDCl_3$): δ 169.5, 159.0 (d, J=241.2 Hz), 156.7, 148.5 (d, J=9.9 Hz), 138.91, 138.85, 136.9, 128.6 (2C), 128.3 (2C), 128.1, 128.0, 127.50 (2C), 127.48, 127.4 (2C), 126.4, 124.2 (d, J=3.0 Hz), 120.5 (d, J=9.3 Hz), 115.7, 112.2, 107.0 (d, J=22.0 Hz), 100.9 (d, J=27.1 Hz), 88.3, 77.3, 71.7, 69.8, 57.7, 50.1, 49.3, 43.1 (2C), 43.0, 41.0, 36.1, 34.5, 29.9, 27.6, 26.8, 24.4, 23.0, 22.2, 13.9. $^{19}F$ NMR (282 MHz, $CDCl_3$): δ −116.36. HR-MS (ESI) calcd for $[C_{45}H_{53}FN_2O_4H]^+$ 705.4067, found 705.4076.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-5-(dimethylamino)pentan-amide, SERD142: $^1H$ NMR (500 MHz, MeOD): δ 7.80 (dd, J=8.9, 6.3 Hz, 1H), 7.02 (dd, J=10.6, 2.6 Hz, 1H), 6.77 (d, J=8.6 Hz, 1H), 6.63 (td, J=8.6, 2.6 Hz, 1H), 6.59 (d, J=2.4 Hz, 1H), 6.39 (dd, J=8.5, 2.5 Hz, 1H), 5.25 (m, 1H), 3.71 (dd, J=8.3, 8.3 Hz, 1H), 2.84 (s, 6H), 0.87 (s, 3H), 0.80-3.40 (m, 21H). $^{13}C$ NMR (125 MHz, MeOD): δ 172.6, 161.4 (d, J=240.7 Hz), 156.3, 151.5 (d, J=10.1 Hz), 139.9, 128.3, 127.8, 124.8 (d, J=3.1 Hz), 123.9 (d, J=9.8 Hz), 116.6, 114.3, 107.3 (d, J=21.4 Hz), 102.3 (d, J=27.3 Hz), 82.7, 78.1, 58.6, 51.3, 50.4, 44.1, 43.5 (2C), 40.8, 36.6, 36.1, 31.0, 30.4, 28.3, 25.2, 24.0, 23.1, 13.7. $^{19}F$ NMR (282 MHz, MeOD): δ −117.17. HR-MS (ESI) calcd for $[C_{31}H_{41}FN_2O_4H]^+$ 525.3129, found 525.3121.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-fluorophenyl)-5-(pyrrolidin-1-yl)-pentanamide: $^1H$ NMR (500 MHz, $CDCl_3$): δ 8.06 (dd, J=9.0, 6.3 Hz, 1H), 7.20-7.45 (m, 10H), 6.78 (d, J=2.5 Hz, 1H), 6.76 (s, 1H), 6.75 (d, J=2.6 Hz, 1H), 6.73 (d, J=8.7 Hz, 1H), 6.61 (td, J=8.6, 2.6 Hz, 1H), 6.55 (dd, J=8.6, 2.6 Hz, 1H), 5.02 (m, 1H), 4.98 (d, J=11.5 Hz, 1H), 4.95 (d, J=11.5 Hz, 1H), 4.58 (d, J=12.2 Hz, 1H), 4.47 (d, J=12.2 Hz, 1H), 3.50 (dd, J=8.1, 8.1 Hz, 1H), 2.81 (m, 4H), 1.76 (m, 4H), 0.97 (s, 3H), 0.80-3.30 (m, 21H). $^{13}C$ NMR (125 MHz, $CDCl_3$): δ 169.4, 158.9 (d, J=245.0 Hz), 156.6, 148.4 (d, J=10.1 Hz), 138.83, 138.81, 136.8, 128.4 (2C), 128.2 (2C), 128.1, 127.9, 127.4 (2C), 127.34, 127.27 (2C), 126.3, 124.0 (d, J=3.2 Hz), 120.4 (d, J=9.3 Hz), 115.6, 112.0, 106.8 (d, J=22.1 Hz), 100.8 (d, J=26.9 Hz), 88.2, 77.3, 71.5, 69.7, 54.9, 53.2 (2C), 50.0, 49.2, 42.9, 40.9, 35.9, 34.3, 29.8, 27.5, 26.6, 25.0, 23.1 (2C), 22.8, 22.1, 13.8. $^{19}F$ NMR (282 MHz, $CDCl_3$): δ −116.29. HR-MS (ESI) calcd for $[C_{47}H_{55}FN_2O_4H]^+$ 731.4224, found 731.4247.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-fluorophenyl)-5-(pyrrolidin-1-yl)pentan-amide, SERD143: $^1H$ NMR (500 MHz, MeOD): δ 7.81 (dd, J=8.9, 6.3 Hz, 1H), 7.01 (dd, J=10.6, 2.5 Hz, 1H), 6.75 (d, J=8.6 Hz, 1H), 6.63 (dt, J=8.4, 2.8 Hz, 1H), 6.60 (d, J=2.3 Hz, 1H), 6.40 (dd, J=8.5, 2.4 Hz, 1H), 5.22 (m, 1H), 3.71 (dd, J=8.2, 8.2 Hz, 1H), 2.57 (m, 4H), 1.65 (m, 4H), 0.86 (s, 3H), 0.75-3.50 (m, 21H). $^{13}C$ NMR (125 MHz, MeOD): δ 172.6, 161.3 (d, J=242.5 Hz), 156.3, 151.5 (d, J=10.1 Hz), 139.9, 128.2, 127.8, 124.8 (d, J=3.3 Hz), 123.8 (d, J=9.9 Hz), 116.6, 114.3, 107.3 (d, J=22.1 Hz), 102.3 (d, J=27.4 Hz), 82.6, 78.0, 55.7, 55.0 (2C), 51.2, 50.3, 44.1, 40.8, 36.7, 36.0, 31.0, 30.4, 28.2, 26.5, 23.97 (2C), 23.95, 23.3, 13.7. $^{19}F$ NMR (282 MHz, MeOD): δ −117.06. HR-MS (ESI) calcd for $[C_{33}H_{43}FN_2O_4H]^+$ 551.3285, found 551.3286.

(8S,9S,11S,13S,14S,17S)-3,17-bis(Benzyloxy)-13-methyl-11-(4-nitro-3-(trifluoromethyl)-phenoxy)-7,8,9,11,12,13,14,15,16,17-decahydro-6H-cyclopenta[a]phenanthrene: $^1H$ NMR (300 MHz, $CDCl_3$): δ 8.02 (d, J=9.0 Hz, 1H), 7.25-7.50 (m, 11H), 7.22 (d, J=2.4 Hz, 1H), 7.11 (dd, J=9.0, 2.5 Hz, 1H), 6.83 (d, J=8.6 Hz, 1H), 6.76 (d, J=2.2 Hz, 1H), 6.66 (dd, J=8.6, 2.4 Hz, 1H), 5.38 (m, 1H), 5.00 (s, 2H), 4.56 (d, J=12.2 Hz, 1H), 4.47 (d, J=12.2 Hz, 1H), 3.55 (d, J=7.5, 7.5 Hz, 1H), 0.96 (s, 3H), 0.80-3.20 (m, 13H). $^{13}C$ NMR (75 MHz, $CDCl_3$): δ 161.1, 156.8, 140.4 (q, J=1.6 Hz), 138.9, 138.6, 137.1, 128.5 (2C), 128.33, 128.25 (2C), 127.8, 127.7, 127.42, 127.37 (2C), 127.3 (2C), 125.7, 124.9 (q, J=182.9 Hz), 120.0 (q, J=5.1 Hz), 116.9, 115.6 (q, J=5.7 Hz), 115.3, 112.6, 88.2, 73.8, 71.6, 69.8, 50.5, 48.6, 43.0, 39.1, 33.7, 29.7, 27.5, 27.2, 23.0, 13.9. $^{19}F$ NMR (282 MHz, $CDCl_3$): δ −59.97.

4-(((8S,9S,11S,13S,14S,17S)-3,17-bis(Benzyloxy)-13-methyl-7,8,9,11,12,13,14,15,16,17-deca-hydro-6H-cyclopenta[a]phenanthren-11-yl)oxy)-2-(trifluoromethyl)aniline: $^{1}$H NMR (300 MHz, $CDCl_3$): δ 7.20-7.50 (m, 10H), 7.00 (s, 1H), 6.98 (d, J=3.8 Hz, 1H), 6.89 (dd, J=8.7, 2.7 Hz, 1H), 6.74 (m, 2H), 6.67 (d, J=8.9 Hz, 1H), 5.13 (m, 1H), 5.01 (s, 2H), 4.55 (d, J=12.2 Hz, 1H), 4.50 (d, J=12.2 Hz, 1H), 3.86 (br s, 2H), 3.50 (dd, J=7.9, 7.9 Hz, 1H), 1.05 (s, 3H), 0.90-3.10 (m, 13H). $^{13}$C NMR (75 MHz, $CDCl_3$): δ 156.6, 149.9, 140.4, 139.1, 138.5, 137.9 (q, J=1.8 Hz), 137.3, 128.7, 128.5 (2C), 128.2 (2C), 127.8, 127.4 (2C), 127.3 (2C), 126.5, 122.7 (q, J=195.4 Hz), 121.2, 120.6 (q, J=12.5 Hz), 118.8, 115.0, 113.1 (q, J=5.3 Hz), 112.5, 88.5, 72.8, 71.5, 69.8, 50.9, 48.9, 43.1, 39.2, 33.7, 29.8, 27.7, 27.3, 23.0, 13.8. $^{19}$F NMR (282 MHz, $CDCl_3$): δ −62.57. HR-MS (ESI) calcd for $[C_{39}H_{40}F_3NO_3H]^+$ 628.3038, found 628.3016.

(8S,9S,11S,13S,14S,17S)-11-(4-Amino-3-(trifluoromethyl)phenoxy)-13-methyl-7,8,9,11,12,13,14,15,16,17-decahydro-6H-cyclopenta[a]phenanthrene-3,17-diol, SERD128: $^{1}$H NMR (300 MHz, MeOD): δ 6.90 (m, 3H), 6.79 (m, 1H), 6.49 (m, 2H), 5.17 (m, 1H), 3.64 (dd, J=7.2, 7.2 Hz, 1H), 0.90 (s, 3H), 0.80-3.40 (m, 13H). $^{13}$C NMR (75 MHz, MeOD): δ 155.8, 150.9, 140.3 (q, J=2.0 Hz), 139.6, 128.7, 127.8, 123.1 (q, J=223.5 Hz), 122.5, 120.3, 118.1 (q, J=14.9 Hz), 116.2, 113.9, 113.7 (q, J=5.7 Hz), 82.9, 74.4, 51.8, 50.2, 44.2, 39.3, 35.6, 30.9, 30.5, 28.5, 23.9, 13.8. $^{19}$F NMR (282 MHz, MeOD): δ −64.06. HR-MS (ESI) calcd for $[C_{25}H_{28}F_3NO_3H]^+$ 448.2100, found 448.2087.

(8S,9S,11S,13S,14S,17S)-13-Methyl-11-(4-nitro-3-(trifluoromethyl)phenoxy)-7,8,9,11,12,13,14,15,16,17-decahydro-6H-cyclopenta[a]phenanthrene-3,17-diol, SERD146: $^{1}$H NMR (500 MHz, MeOD): δ 8.05 (d, J=9.0 Hz, 1H), 7.32 (dd, J=9.1, 2.6 Hz, 1H), 7.25 (d, J=2.6 Hz, 1H), 6.84 (d, J=8.5 Hz, 1H), 6.50 (d, J=2.5 Hz, 1H), 6.41 (dd, J=8.5, 2.6 Hz, 1H), 5.54 (m, 1H), 3.68 (dd, J=8.3, 8.3 Hz, 1H), 2.60 (d, J=11.1 Hz, 1H), 2.44 (dd, J=14.5, 2.4 Hz, 1H), 0.84 (s, 3H), 0.80-3.50 (m, 11H). $^{13}$C NMR (125 MHz, MeOD): δ 162.7, 156.0, 141.6, 139.7, 129.5, 127.9, 127.2, 126.7 (q, J=35.4 Hz), 123.4 (q, J=272.8 Hz), 118.8, 116.41, 116.37 (q, J=6.0 Hz), 114.0, 82.6, 75.5, 54.7, 51.4, 44.1, 39.2, 35.5, 30.7, 30.4, 28.3, 23.9, 13.8. $^{19}$F NMR (282 MHz, MeOD): δ −61.45. HR-MS (ESI) calcd for $[C_{25}H_{26}F_3NO_5H]^+$ 478.1841, found 478.1840.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-2-morpbo-linoacetamide: $^{1}$H NMR (300 MHz, $CDCl_3$): δ 9.65 (s, 1H), 8.19 (d, J=9.2 Hz, 1H), 7.20-7.41 (m, 11H), 7.07 (s, 1H), 6.89 (d, J=8.7 Hz, 1H), 6.72 (d, J=2.5 Hz, 1H), 6.65 (dd, J=8.6, 2.6 Hz, 1H), 5.24 (m, 1H), 4.98 (s, 2H), 4.52 (d, J=12.3 Hz, 1H), 4.46 (d, J=12.3 Hz, 1H), 3.77 (t, J=4.2 Hz, 4H), 2.62 (t, J=4.2 Hz, 4H), 0.98 (s, 3H), 0.80-3.70 (m, 16H). $^{13}$C NMR (75 MHz, $CDCl_3$): δ 168.4, 156.6, 154.0, 139.0, 138.5, 137.2, 128.4 (2C), 128.3, 128.2 (2C), 127.8, 127.5, 127.4 (2C), 127.31, 127.3 (2C), 126.2, 125.1, 121.3 (q, J=274.6 Hz), 120.7 (q, J=40.7 Hz), 118.5, 115.0, 113.5 (q, J=4.0 Hz), 112.5, 88.3, 72.3, 71.5, 69.8, 66.9 (2C), 62.1, 53.7 (2C), 50.7, 48.7, 43.0, 39.0, 33.7, 29.6, 27.6, 27.3, 23.0, 13.7. $^{19}$F NMR (282 MHz, $CDCl_3$): δ −60.70. HR-MS (ESI) calcd for $[C_{45}H_{49}F_3N_2O_5H]^+$ 755.3672, found 755.3695.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-2-morpholino-acetamide, SERD144: $^{1}$H NMR (300 MHz, MeOD): δ 7.85 (d, J=8.8 Hz, 1H), 7.18 (dd, J=9.0, 2.6 Hz, 1H), 7.13 (d, J=2.7 Hz, 1H), 6.86 (d, J=8.5 Hz, 1H), 6.49 (d, J=2.4 Hz, 1H), 6.40 (dd, J=8.5, 2.5 Hz, 1H), 5.39 (m, 1H), 3.74 (t, J=4.2 Hz, 4H), 3.67 (dd, J=8.3, 8.3 Hz, 1H), 2.61 (m, 4H), 0.87 (s, 3H), 0.80-3.32 (m, 15H). $^{13}$C NMR (75 MHz, MeOD): δ 171.6, 156.8, 156.0, 139.6, 128.9, 128.4, 128.04 (q, J=1.0 Hz), 127.5, 124.6 (q, J=29.9 Hz), 121.9 (q, J=226.6 Hz), 120.1, 116.3, 114.2 (q, J=5.7 Hz), 114.0, 82.8, 74.2, 68.0 (2C), 62.8, 54.8 (2C), 51.7, 50.0, 44.2, 39.2, 35.6, 30.8, 30.5, 28.5, 23.9, 13.8. $^{19}$F NMR (282 MHz, MeOD): δ −62.32. HR-MS (ESI) calcd for $[C_{31}H_{37}F_3N_2O_5H]^+$ 575.2733, found 575.2729.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-2-(piper-idin-1-yl)acetamide: $^{1}$H NMR (300 MHz, $CDCl_3$): δ 9.76 (s, 1H), 8.11 (d, J=8.6 Hz, 1H), 7.64 (dd, J=5.7, 3.3 Hz, 1H), 7.46 (dd, J=5.7, 3.3 Hz, 1H), 7.10-7.40 (m, 9H), 6.99 (s, 1H), 6.83 (d, J=8.6 Hz, 1H), 6.64 (d, J=2.4 Hz, 1H), 6.58 (d, J=8.5 Hz, 1H), 5.18 (m, 1H), 4.91 (s, 2H), 4.45 (d, J=12.2 Hz, 1H), 4.39 (d, J=12.2 Hz, 1H), 2.50 (m, 4H), 1.58 (m, 4H), 0.90 (s, 3H), 0.75-3.50 (m, 18H). $^{13}$C NMR (75 MHz, $CDCl_3$): δ 167.5, 156.4, 153.7, 138.8, 138.3, 137.0, 132.2, 130.7, 128.6, 128.3 (2C), 128.2, 128.0 (2C), 127.6, 127.2 (2C), 127.1 (2C), 126.05, 121.5 (q, J=273.0 Hz), 121.3 (q, J=65.7 Hz), 118.2, 114.8, 112.9 (q, J=61.1 Hz), 112.3, 88.2, 72.1, 71.3, 69.6, 67.9, 54.7 (2C), 48.5, 42.8, 40.5, 38.8, 38.5, 33.5, 29.4, 28.7, 25.8 (2C), 23.5, 22.7, 13.5. $^{19}$F NMR (282 MHz, MeOD): δ −61.14. HR-MS (ESI) calcd for $[C_{46}H_{51}F_3N_2O_4H]^+$ 753.3879, found 753.3917.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-2-(piperidin-1-yl)acetamide, SERD145: $^{1}$H NMR (300 MHz, MeOD): δ 7.83 (d, J=8.7 Hz, 1H), 7.18 (d, J=9.0 Hz, 1H), 7.13 (d, J=3.1 Hz, 1H), 6.87 (d, J=8.5 Hz, 1H), 6.49 (d, J=2.4 Hz, 1H), 6.42 (d, J=8.2 Hz, 1H), 5.40 (m, 1H), 3.67 (dd, J=7.2, 7.2 Hz, 1H), 2.67 (m, 4H), 1.69 (m, 4H), 0.87 (s, 3H), 0.75-3.40 (m, 17H). $^{13}$C NMR (75 MHz, MeOD): δ 171.3, 156.8, 156.0, 139.6, 129.0, 128.4, 127.9 127.5, 125.1 (q, J=272.4 Hz), 124.8 (q, J=29.9 Hz), 120.1, 116.3, 114.1 (q, J=5.5 Hz), 114.0, 82.8, 74.2, 62.6, 55.8 (2C), 51.7, 50.0, 44.2, 39.2, 35.6, 30.8, 30.5, 28.5, 26.7 (2C), 24.4, 24.0, 13.8. $^{19}$F NMR (282 MHz, MeOD): δ −62.47. HR-MS (ESI) calcd for $[C_{32}H_{39}F_3N_2O_4H]^+$ 573.2940, found 573.2942.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-2-(pyrro-lidin-1-yl)acetamide: $^{1}$H NMR (300 MHz, $CDCl_3$): δ 9.76 (s, 1H), 8.22 (t, J=10.3 Hz, 1H), 7.71 (m, 1H), 7.53 (m, 1H), 7.10-7.40 (m, 8H), 7.06 (s, 1H), 6.91 (d, J=8.8 Hz, 1H), 6.72 (m, 2H), 6.66 (d, J=8.7 Hz, 1H), 5.24 (m, 1H), 4.99 (s, 2H), 4.52 (d, J=12.1 Hz, 1H), 4.47 (d, J=12.1 Hz, 1H), 2.72 (m, 4H), 1.60 (m, 4H), 0.98 (s, 3H), 0.804.30 (m, 16H). $^{13}$C NMR (75 MHz, $CDCl_3$): δ 167.7, 156.7, 153.9, 139.0, 138.5, 137.2, 132.4, 130.8, 128.8, 128.5 (2C), 128.2 (2C), 127.8, 127.4 (2C), 127.3 (2C), 126.2, 125.1, 124.6 (q, J=274.9 Hz), 118.4, 117.9 (q, J=7.9 Hz), 115.1, 113.6 (q, J=4.3 Hz), 112.5, 88.4, 72.3, 71.5, 69.8, 68.1, 54.3 (2C), 50.7, 48.7, 43.0, 39.1, 38.7, 30.3, 29.7, 28.9, 24.0 (2C), 22.9, 14.0. $^{19}$F NMR (282 MHz, $CDCl_3$): δ −61.20. HR-MS (ESI) calcd for $[C_{45}H_{49}F_3N_2O_4H]^+$ 739.3723, found 739.3746.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-2-(pyrrolidin-1-yl)acetamide, SERD147: $^{1}$H NMR (500 MHz, MeOD): δ 7.70 (d, J=8.9 Hz, 1H), 7.19 (dd, J=8.9, 2.7 Hz, 1H), 7.14 (d, J=2.7 Hz, 1H), 6.87 (d, J=8.6

Hz, 1H), 6.49 (d, J=2.4 Hz, 1H), 6.41 (dd, J=8.5, 2.6 Hz, 1H), 5.42 (m, 1H), 3.67 (dd, J=8.3, 8.3 Hz, 1H), 2.89 (m, 4H), 1.92 (m, 4H), 0.86 (s, 3H), 0.80-3.60 (m, 15H). $^{13}C$ NMR (125 MHz, MeOD): δ 171.1, 157.2, 155.9, 139.6, 130.1, 128.4, 127.7, 127.5, 126.0 (q, J=30.3 Hz), 125.0 (q, J=272.3 Hz), 120.1, 116.3, 114.2 (q, J=5.4 Hz), 114.0, 82.8, 74.1, 59.1, 55.4 (2C), 51.6, 50.0, 44.2, 39.2, 35.6, 30.8, 30.4, 28.5, 24.7 (2C), 23.9, 13.8. $^{19}F$ NMR (282 MHz, MeOD): δ −62.61. HR-MS (ESI) calcd for $[C_{31}H_{37}F_3N_2O_4H]^+$ 559.2784, found 559.2797.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-2-(dimeth-ylamino)acetamide: $^{1}H$ NMR (300 MHz, $CDCl_3$): δ 9.62 (s, 1H), 8.14 (d, J=9.6 Hz, 1H), 7.10-7.50 (m, 9H), 7.07 (s, 1H), 6.90 (d, J=8.5 Hz, 1H), 6.72 (m, 2H), 6.67 (d, J=8.5 Hz, 2H), 5.24 (m, 1H), 4.99 (s, 2H), 4.53 (d, J=12.2 Hz, 1H), 4.48 (d, J=12.2 Hz, 1H), 3.48 (dd, J=8.3, 8.3 Hz, 1H), 2.40 (s, 6H), 0.99 (s, 3H), 0.75-3.40 (m, 15H). $^{13}C$ NMR (75 MHz, $CDCl_3$): δ 169.3, 156.7, 154.1, 139.0, 138.5, 137.2, 128.5 (2C), 128.4, 128.2 (2C), 128.1, 127.8, 127.7, 127.4 (2C), 127.3 (2C), 126.2, 125.5, 123.1 (q, J=250.0 Hz), 121.6 (q, J=28.3 Hz), 118.4, 115.1, 113.6 (q, J=5.6 Hz), 112.5, 88.4, 72.3, 71.5, 69.8, 63.3, 50.8, 48.7, 45.8 (2C), 43.0, 39.1, 33.7, 29.7, 27.6, 27.3, 23.0, 13.7. $^{19}F$ NMR (282 MHz, $CDCl_3$): δ −61.15. HR-MS (ESI) calcd for $[C_{43}H_{47}F_3N_2O_4H]^+$ 713.3566, found 713.3575.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-2-(dimethylam-ino)acetamide, SERD148: $^{1}H$ NMR (500 MHz, MeOD): δ 7.67 (d, J=8.9 Hz, 1H), 7.19 (dd, J=8.9, 2.7 Hz, 1H), 7.14 (d, J=2.8 Hz, 1H), 6.87 (d, J=8.5 Hz, 1H), 6.49 (d, J=2.4 Hz, 1H), 6.41 (dd, J=8.5, 2.5 Hz, 1H), 5.41 (m, 1H), 3.67 (dd, J=8.2, 8.2 Hz, 1H), 2.48 (s, 6H), 0.86 (s, 3H), 0.78-3.50 (m, 15H). $^{13}C$ NMR (125 MHz, MeOD): δ 171.3, 157.3, 155.9, 139.6, 130.4, 128.4, 127.7, 127.5, 126.2 (q, J=30.4 Hz), 124.9 (q, J=271.4 Hz), 120.0, 116.3, 114.2 (q, J=5.5 Hz), 114.0, 82.8, 74.1, 63.1, 51.6, 50.0, 45.8 (2C), 44.2, 39.1, 35.6, 30.8, 30.4, 28.5, 23.9, 13.8. $^{19}F$ NMR (282 MHz, MeOD): δ −62.60. HR-MS (ESI) calcd for $[C_{29}H_{35}F_3N_2O_4H]^+$ 533.2627, found 533.2650.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-3-(piper-idin-1-yl)propanamide: $^{1}H$ NMR (500 MHz, $CDCl_3$): δ 10.60 (s, 1H), 7.71 (d, J=9.7 Hz, 1H), 7.10-7.48 (m, 10H), 7.06 (s, 1H), 7.05 (dd, J=6.9, 3.1 Hz, 1H), 6.90 (d, J=8.6 Hz, 1H), 6.71 (d, J=2.5 Hz, 1H), 6.67 (dd, J=8.6, 2.6 Hz, 1H), 5.24 (m, 1H), 4.98 (s, 2H), 4.53 (d, J=12.3 Hz, 1H), 4.46 (d, J=12.3 Hz, 1H), 3.47 (d, J=6.5, 6.5 Hz, 1H), 2.48 (m, 4H), 1.60 (m, 4H), 0.97 (s, 3H), 0.80-3.30 (m, 19H). $^{13}C$ NMR (125 MHz, $CDCl_3$): δ 171.7, 156.5, 154.5, 138.9, 138.4, 137.1, 129.0, 128.4 (2C), 128.3, 128.2 (2C), 127.7, 127.4 (2C), 127.28 (2C), 127.27, 126.2, 124.1 (q, J=29.6 Hz), 123.4 (q, J=273.6 Hz), 119.2 (q, J=20.8 Hz), 117.9, 115.0, 113.2 (q, J=5.4 Hz), 112.5, 88.2, 71.9, 71.4, 69.7, 54.3, 53.8 (2C), 50.6, 48.6, 46.7, 42.9, 40.5, 38.9, 33.6, 32.1, 29.6, 26.5, 25.1 (2C), 24.6, 13.6. $^{19}F$ NMR (282 MHz, $CDCl_3$): δ −60.92. HR-MS (ESI) calcd for $[C_{47}H_{53}F_3N_2O_4H]^+$ 767.4036, found 767.4003.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-3-(piperidin-1-yl)propanamide, SERD149: $^{1}H$ NMR (500 MHz, MeOD): δ 7.53 (d, J=8.8 Hz, 1H), 7.33 (d, J=8.9 Hz, 1H), 7.28 (d, J=2.1 Hz, 1H), 7.02 (d, J=8.6 Hz, 1H), 6.65 (d, J=1.7 Hz, 1H), 6.57 (dd, J=8.4, 2.0 Hz, 1H), 5.56 (m, 1H), 3.83 (dd, J=8.2, 8.2 Hz, 1H), 2.98 (m, 4H), 1.92 (m, 4H), 1.01 (s, 3H), 0.90-3.60 (m, 19H). $^{13}C$ NMR (125 MHz, MeOD): δ 172.8, 157.9, 155.9, 139.6, 133.0, 128.4, 128.5 (q, J=30.0 Hz), 127.5, 127.4, 124.8 (q, J=272.7 Hz), 119.9, 116.3, 114.1 (q, J=4.6 Hz), 114.0, 82.7, 74.0, 54.6 (2C), 54.5, 51.6, 49.9, 44.2, 39.1, 35.6, 31.8, 30.8, 30.4, 28.5, 25.1 (2C), 23.9, 23.6, 13.8. $^{19}F$ NMR (282 MHz, MeOD): δ −62.44. HR-MS (ESI) calcd for $[C_{33}H_{41}F_3N_2O_4H]^+$ 587.3097, found 587.3116.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-3-morpho-linopropanamide: $^{1}H$ NMR (500 MHz, $CDCl_3$): δ 10.27 (s, 1H), 7.80 (d, J=9.7 Hz, 1H), 7.20-7.49 (m, 10H), 7.08 (m, 2H), 6.91 (d, J=8.7 Hz, 1H), 6.73 (d, J=2.6 Hz, 1H), 6.67 (dd, J=8.6, 2.6 Hz, 1H), 5.26 (m, 1H), 4.99 (s, 2H), 4.54 (d, J=12.3 Hz, 1H), 4.46 (d, J=12.2 Hz, 1H), 3.76 (m, 4H), 3.58 (dd, J=5.5, 5.5 Hz, 1H), 2.60 (m, 4H), 0.98 (s, 3H), 0.80-3.90 (m, 17H). $^{13}C$ NMR (125 MHz, $CDCl_3$): δ 171.1, 156.6, 154.4, 138.9, 138.4, 137.1, 128.5, 128.4 (2C), 128.3, 128.2 (2C), 128.1, 127.7, 127.4 (2C), 127.3 (2C), 126.2, 123.6 (q, J=273.9 Hz), 123.5 (q, J=29.8 Hz), 119.3 (q, J=22.2 Hz), 118.0, 115.0, 113.2 (q, J=4.8 Hz), 112.5, 88.2, 72.0, 71.4, 69.7, 66.2 (2C), 54.3, 53.0 (2C), 50.6, 48.6, 42.9, 38.9, 33.6, 31.8, 29.6, 27.5, 27.3, 23.0, 13.7. $^{19}F$ NMR (282 MHz, $CDCl_3$): δ −60.71. HR-MS (ESI) calcd for $[C_{46}H_{51}F_3N_2O_5H]^+$ 769.3828, found 769.3804.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-3-morpholino-propanamide, SERD152: $^{1}H$ NMR (500 MHz, MeOD): δ 7.44 (d, J=8.8 Hz, 1H), 7.19 (dd, J=8.5, 2.1 Hz, 1H), 7.14 (d, J=2.4 Hz, 1H), 6.88 (d, J=8.6 Hz, 1H), 6.50 (d, J=1.9 Hz, 1H), 6.42 (dd, J=8.5, 2.2 Hz, 1H), 5.41 (m, 1H), 3.72 (t, J=4.2 Hz, 4H), 3.68 (dd, J=8.4, 8.4 Hz, 1H), 2.62 (m, 4H), 0.87 (s, 3H), 0.80-3.50 (m, 17H). $^{13}C$ NMR (125 MHz, MeOD): δ 174.4, 157.6, 155.9, 139.6, 132.5, 128.4, 127.8 (q, J=29.5 Hz), 127.7, 127.5, 124.9 (q, J=272.6 Hz), 119.9, 116.3, 114.04 (q, J=2.5 Hz), 114.0, 82.7, 74.0, 67.5 (2C), 55.3, 54.2 (2C), 51.6, 49.9, 44.2, 39.1, 35.6, 33.2, 30.8, 30.4, 28.5, 23.9, 13.8. $^{19}F$ NMR (282 MHz, MeOD): δ −62.30. HR-MS (ESI) calcd for $[C_{32}H_{39}F_3N_2O_5H]^+$ 589.2889, found 589.2883.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-3-(pyrro-lidin-1-yl)propanamide: $^{1}H$ NMR (500 MHz, $CDCl_3$): δ 10.96 (s, 1H), 7.90 (d, J=8.6 Hz, 1H), 7.20-7.45 (m, 10H), 7.08 (d, J=2.7 Hz, 1H), 7.06 (s, 1H), 6.91 (d, J=8.7 Hz, 1H), 6.72 (d, J=2.4 Hz, 1H), 6.67 (dd, J=8.6, 2.5 Hz, 1H), 5.25 (m, 1H), 4.99 (s, 2H), 4.54 (d, J=12.3 Hz, 1H), 4.47 (d, J=12.3 Hz, 1H), 3.48 (dd, J=6.0, 6.0 Hz, 1H), 2.66 (m, 4H), 1.84 (m, 4H), 0.98 (s, 3H), 0.80-3.50 (m, 17H). $^{13}C$ NMR (125 MHz, $CDCl_3$): δ 171.4, 156.6, 154.1, 139.0, 138.4, 137.2, 128.4 (2C), 128.3, 128.2 (2C), 127.8, 127.7, 127.4 (2C), 127.28 (2C), 127.27, 126.2, 123.5 (q, J=273.7 Hz), 123.1 (q, J=29.9 Hz), 119.2 (q, J=21.6 Hz), 118.0, 115.0, 113.2 (q, J=5.4 Hz), 112.5, 88.3, 72.0, 71.4, 69.7, 53.2 (2C), 51.4, 50.7, 48.6, 42.9, 38.9, 34.3, 33.6, 29.7, 27.6, 27.3, 23.2 (2C), 23.0, 13.6. $^{19}F$ NMR (282 MHz, $CDCl_3$): δ −61.58. HR-MS (ESI) calcd for $[C_{46}H_{51}F_3N_2O_4H]^+$ 753.3879, found 753.3881.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-3-(pyrrolidin-1-yl)propanamide, SERD150: $^{1}H$ NMR (500 MHz, MeOD): δ 7.43 (d, J=8.8 Hz, 1H), 7.18 (dd, J=8.8, 2.1 Hz, 1H), 7.13 (d, J=2.4 Hz, 1H), 6.87 (d, J=8.6 Hz, 1H), 6.50 (d, J=1.9 Hz, 1H), 6.42 (dd, J=8.4, 2.2 Hz, 1H), 5.40 (m, 1H), 3.67 (dd, J=8.2, 8.2 Hz, 1H), 2.82 (t, J=6.7 Hz, 4H), 1.98 (m, 4H), 0.85 (s, 3H), 0.80-3.40 (m, 17H). $^{13}$C NMR (125 MHz, MeOD): δ 172.6, 157.8, 155.9, 139.6, 132.7, 128.4, 127.5, 128.12, 128.10 (q, J=15.8 Hz), 124.7 (q, J=276.1 Hz), 119.9, 116.3, 114.1 (q, J=5.3 Hz), 114.0, 82.7, 74.0, 55.0 (2C), 52.1, 51.5, 49.8, 44.1, 39.1, 35.6, 33.5, 30.8, 30.4, 28.5, 24.1 (2C), 23.9, 13.8. $^{19}$F NMR (282 MHz, MeOD): δ −62.51. HR-MS (ESI) calcd for $[C_{32}H_{39}F_3N_2O_4H]^+$ 573.2940, found 573.2943.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-3-(dimeth-ylamino)propanamide: $^1$H NMR (500 MHz, $CDCl_3$): δ 11.22 (s, 1H), 7.97 (d, J=9.7 Hz, 1H), 7.20-7.45 (m, 10H), 7.06 (m, 2H), 6.91 (d, J=8.7 Hz, 1H), 6.72 (d, J=2.6 Hz, 1H), 6.67 (dd, J=8.6, 2.7 Hz, 1H), 5.24 (m, 1H), 4.99 (s, 2H), 4.54 (d, J=12.3 Hz, 1H), 4.47 (d, J=12.3 Hz, 1H), 3.48 (dd, J=8.1, 8.1 Hz, 1H), 2.32 (s, 6H), 0.98 (s, 3H), 0.80-3.00 (m, 17H). $^{13}$C NMR (125 MHz, $CDCl_3$): δ 171.2, 156.6, 153.9, 139.0, 138.4, 137.2, 128.5 (2C), 128.4, 128.2 (2C), 127.8, 127.4 (2C), 127.3 (2C), 127.28, 127.26, 126.2, 123.7 (q, J=230.8 Hz), 122.5 (q, J=12.0 Hz), 119.2 (q, J=22.1 Hz), 118.0, 115.0, 113.4 (q, J=5.1 Hz), 112.5, 88.3, 72.0, 71.5, 69.8, 54.5, 50.7, 48.6, 44.1 (2C), 43.0, 39.0, 33.6, 33.0, 29.7, 27.6, 27.3, 23.0, 13.7. $^{19}$F NMR (282 MHz, $CDCl_3$): δ −61.80. HR-MS (ESI) calcd for $[C_{44}H_{49}F_3N_2O_4H]^+$ 727.3723, found 727.3730.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-3-(dimethylam-ino)propanamide, SERD151: $^1$H NMR (500 MHz, MeOD): δ 7.47 (d, J=8.8 Hz, 1H), 7.19 (dd, J=8.8, 2.5 Hz, 1H), 7.14 (d, J=2.6 Hz, 1H), 6.88 (d, J=8.6 Hz, 1H), 6.51 (d, J=2.3 Hz, 1H), 6.42 (dd, J=8.5, 2.4 Hz, 1H), 5.42 (m, 1H), 3.68 (dd, J=8.2, 8.2 Hz, 1H), 2.57 (s, 6H), 0.87 (s, 3H), 0.80-3.50 (m, 17H). $^{13}$C NMR (125 MHz, MeOD): δ 173.2, 157.7, 155.9, 139.6, 132.4, 128.4, 128.1 (q, J=29.7 Hz), 127.7, 127.5, 124.8 (q, J=273.4 Hz), 120.2, 116.3, 114.1 (q, J=5.2 Hz), 114.0, 82.7, 74.0, 55.4, 51.6, 49.9, 44.4 (2C), 44.2, 39.1, 35.6, 32.7, 30.8, 30.4, 28.5, 23.9, 13.8. $^{19}$F NMR (282 MHz, MeOD): δ −62.65. HR-MS (ESI) calcd for $[C_{30}H_{37}F_3N_2O_4H]^+$ 547.2784, found 547.2759.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-4-(piperi-din-1-yl)butanamide: $^1$H NMR (500 MHz, $CDCl_3$): δ 8.44 (s, 1H), 7.52 (d, J=8.7 Hz, 1H), 7.20-7.40 (m, 10H), 7.05 (s, 1H), 7.02 (d, J=9.1 Hz, 1H), 6.85 (d, J=8.6 Hz, 1H), 6.69 (s, 1H), 6.64 (d, J=8.6 Hz, 1H), 5.22 (m, 1H), 4.96 (s, 2H), 4.50 (d, J=12.2 Hz, 1H), 4.43 (d, J=12.3 Hz, 1H), 3.45 (dd, J=6.8, 6.8 Hz, 1H), 2.65 (m, 4H), 1.58 (m, 4H), 0.94 (s, 3H), 0.80-3.30 (m, 21H). $^{13}$C NMR (125 MHz, $CDCl_3$): δ 171.1, 156.5, 155.5, 138.9, 138.4, 137.1, 129.9, 128.39 (2C), 128.2 (2C), 127.7, 127.35 (2C), 127.26 (2C), 127.23, 126.6, 126.1, 125.6 (q, J=29.0 Hz), 123.3 (q, J=272.5 Hz), 118.1, 115.0, 113.4 (q, J=5.4 Hz), 112.4, 88.2, 72.1, 71.4, 69.7, 56.4, 53.3 (2C), 50.6, 48.5, 42.9, 38.9, 33.6, 33.1, 32.3, 29.6, 27.5, 22.9, 22.7 (2C), 22.2, 19.8, 13.6. $^{19}$F NMR (282 MHz, $CDCl_3$): δ −60.65. HR-MS (ESI) calcd for $[C_{48}H_{55}F_3N_2O_4H]^+$ 781.4192, found 781.4221.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-4-(piperidin-1-yl)butanamide, SERD160: $^1$H NMR (500 MHz, MeOD): δ 7.31 (d, J=8.8 Hz, 1H), 7.18 (dd, J=8.8, 2.7 Hz, 1H), 7.14 (d, J=2.7 Hz, 1H), 6.87 (d, J=8.5 Hz, 1H), 6.49 (d, J=2.5 Hz, 1H), 6.41 (dd, J=8.5, 2.6 Hz, 1H), 5.42 (m, 1H), 3.67 (dd, J=8.3, 8.3 Hz, 1H), 2.40 (m, 4H), 1.48 (m, 4H), 0.86 (s, 3H), 0.80-3.50 (m, 21H). $^{13}$C NMR (125 MHz, MeOD): δ 175.6, 158.1, 155.9, 139.6, 133.3, 129.1 (q, J=31.4 Hz), 128.4, 127.8, 127.5, 124.8 (q, J=270.6 Hz), 119.9, 116.3, 114.2 (q, J=5.5 Hz), 114.0, 82.7, 74.1, 59.3, 55.3 (2C), 51.6, 50.0, 44.2, 43.7, 39.1, 35.6, 34.8, 30.8, 28.5, 26.1 (2C), 24.8, 23.9, 23.0, 13.8. $^{19}$F NMR (282 MHz, MeOD): δ −62.51. HR-MS (ESI) calcd for $[C_{34}H_{43}F_3N_2O_4H]^+$ 601.3253, found 601.3267.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-4-morpho-linobutanamide: $^1$H NMR (500 MHz, $CDCl_3$): δ 7.84 (d, J=9.6 Hz, 1H), 7.70 (s, 1H), 7.20-7.50 (m, 10H), 7.06 (m, 2H), 6.89 (d, J=8.7 Hz, 1H), 6.72 (d, J=2.5 Hz, 1H), 6.67 (dd, J=8.6, 2.7 Hz, 1H), 5.25 (m, 1H), 4.99 (s, 2H), 4.54 (d, J=12.3 Hz, 1H), 4.46 (d, J=12.3 Hz, 1H), 3.70 (m, 4H), 3.48 (dd, J=8.2, 8.2 Hz, 1H), 2.45 (m, 4H), 0.97 (s, 3H), 0.80-3.80 (m, 19H). $^{13}$C NMR (125 MHz, $CDCl_3$): δ 171.5, 156.6, 154.7, 138.9, 138.5, 137.1, 128.5 (2C), 128.2 (2C), 128.1, 127.8, 127.5, 127.4 (2C), 127.34, 127.32 (2C), 127.1, 126.2, 123.6 (q, J=273.7 Hz), 123.3 (q, J=30.8 Hz), 118.3, 115.0, 113.5 (q, J=5.5 Hz), 112.5, 88.2, 72.2, 71.5, 69.8, 66.8 (2C), 57.5, 53.5 (2C), 50.7, 48.7, 43.0, 38.9, 35.0, 33.6, 29.7, 27.6, 27.3, 23.0, 21.9, 13.7. $^{19}$F NMR (282 MHz, $CDCl_3$): δ −60.74. HR-MS (ESI) calcd for $[C_{47}H_{53}F_3N_2O_5H]^+$ 783.3985, found 783.3984.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-4-morpholino-butanamide, SERD153: $^1$H NMR (500 MHz, MeOD): δ 7.32 (d, J=8.7 Hz, 1H), 7.18 (dd, J=8.7, 1.7 Hz, 1H), 7.14 (s, 1H), 6.87 (d, J=8.6 Hz, 1H), 6.49 (d, J=1.7 Hz, 1H), 6.41 (dd, J=8.5, 2.1 Hz, 1H), 5.42 (m, 1H), 3.73 (t, J=4.3 Hz, 4H), 3.67 (dd, J=8.2, 8.2 Hz, 1H), 2.64 (m, 4H), 0.86 (s, 3H), 0.80-3.40 (m, 19H). $^{13}$C NMR (125 MHz, MeOD): δ 175.5, 158.0, 155.9, 139.6, 133.2, 129.0 (q, J=30.8 Hz), 128.4, 127.8, 127.5, 124.8 (q, J=273.1 Hz), 119.9, 116.3, 114.2 (q, J=5.3 Hz), 114.0, 82.7, 74.1, 67.2 (2C), 59.0, 54.5 (2C), 51.6, 49.9, 44.2, 39.1, 35.6, 34.5, 30.8, 30.4, 28.5, 23.9, 22.7, 13.8. $^{19}$F NMR (282 MHz, MeOD): δ −62.47. HR-MS (ESI) calcd for $[C_{33}H_{41}F_3N_2O_5H]^+$ 603.3046, found 603.3047.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-4-(pyrroli-din-1-yl)butanamide: $^1$H NMR (500 MHz, $CDCl_3$): δ 8.35 (s, 1H), 7.53 (d, J=8.7 Hz, 1H), 7.20-7.40 (m, 10H), 7.06 (s, 1H), 7.04 (d, J=9.0 Hz, 1H), 6.85 (d, J=8.6 Hz, 1H), 6.70 (s, 1H), 6.65 (d, J=8.6 Hz, 1H), 5.23 (m, 1H), 4.97 (s, 2H), 4.52 (d, J=12.2 Hz, 1H), 4.44 (d, J=12.2 Hz, 1H), 0.95 (s, 3H), 0.80-3.50 (m, 28H). $^{13}$C NMR (125 MHz, $CDCl_3$): δ 171.0, 156.6, 155.6, 138.9, 138.4, 137.1, 130.0, 128.5, 128.4 (2C), 128.2 (2C), 127.8, 127.4 (2C), 127.31 (2C), 127.29, 126.5, 126.1, 125.6 (q, J=27.6 Hz), 123.4 (q, J=274.1 Hz), 118.2, 115.0, 113.5 (q, J=5.3 Hz), 112.5, 88.2, 72.2, 71.5, 69.8, 54.4, 53.7 (2C), 50.6, 48.6, 42.9, 38.9, 33.6, 32.8, 29.6, 27.6, 27.3, 23.3 (2C), 23.0, 21.8, 13.7. $^{19}$F NMR (282 MHz, $CDCl_3$): δ −60.61. HR-MS (ESI) calcd for $[C_{47}H_{53}F_3N_2O_4H]^+$ 767.4036, found 767.4067.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-4-(pyrrolidin-1-yl)butanamide, SERD154: $^1$H NMR (500 MHz, MeOD): δ 7.31 (d, J=8.7 Hz, 1H), 7.18 (dd, J=8.8, 2.3 Hz, 1H), 7.14 (d, J=2.5 Hz, 1H), 6.86 (d, J=8.6 Hz, 1H), 6.48 (d, J=2.0 Hz, 1H), 6.40 (dd, J=8.5, 2.2 Hz, 1H), 5.42 (m, 1H), 3.67 (dd, J=8.2, 8.2 Hz, 1H), 2.57 (m, 4H), 1.81 (m, 4H), 0.86 (s, 3H), 0.80-3.50 (m, 19H). $^{13}C$ NMR (125 MHz, MeOD): δ 175.7, 158.0, 156.4, 139.6, 133.2, 129.0 (q, J=29.3 Hz), 128.1, 127.9, 127.5, 124.8 (q, J=272.2 Hz), 119.9, 116.4, 114.2 (q, J=5.0 Hz), 114.16, 82.8, 74.1, 56.8, 55.0 (2C), 51.7, 50.0, 44.2, 39.2, 35.7, 35.0, 30.8, 30.5, 28.6, 25.7, 24.2 (2C), 24.0, 13.8. $^{19}F$ NMR (282 MHz, MeOD): δ −62.53. HR-MS (ESI) calcd for $[C_{33}H_{41}F_3N_2O_4H]^+$ 587.3097, found 587.3122.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-4-(dimeth-ylamino)butanamide: $^1H$ NMR (500 MHz, $CDCl_3$): δ 8.36 (s, 1H), 7.61 (d, J=8.7 Hz, 1H), 7.20-7.40 (m, 10H), 7.07 (s, 1H), 7.05 (d, J=12.3 Hz, 1H), 6.87 (d, J=8.7 Hz, 1H), 6.71 (s, 1H), 6.67 (dd, J=8.6, 2.2 Hz, 1H), 5.24 (m, 1H), 4.98 (s, 2H), 4.53 (d, J=12.3 Hz, 1H), 4.45 (d, J=12.3 Hz, 1H), 3.47 (dd, J=7.7, 7.7 Hz, 1H), 2.61 (s, 6H), 0.96 (s, 3H), 0.80-3.00 (m, 19H). $^{13}C$ NMR (125 MHz, $CDCl_3$): δ 171.1, 156.6, 155.3, 138.9, 138.4, 137.1, 129.4, 128.5, 128.4 (2C), 128.2 (2C), 127.8, 127.4 (2C), 127.34, 127.3 (2C), 126.7, 126.1, 125.0 (q, J=32.4 Hz), 123.4 (q, J=275.1 Hz), 118.2, 115.0, 113.4 (q, J=5.0 Hz), 112.5, 88.2, 72.2, 71.4, 69.8, 57.4, 50.6, 48.6, 43.5 (2C), 42.9, 38.9, 33.6, 33.5, 29.6, 27.5, 27.3, 23.0, 21.1, 13.7. $^{19}F$ NMR (282 MHz, $CDCl_3$): δ −60.68. HR-MS (ESI) calcd for $[C_{45}H_{51}F_3N_2O_4H]^+$ 741.3879, found 741.3911.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-4-(dimethylam-ino)butanamide, SERD155: $^1H$ NMR (500 MHz, MeOD): δ 7.31 (d, J=8.7 Hz, 1H), 7.17 (dd, J=8.8, 2.6 Hz, 1H), 7.14 (d, J=2.7 Hz, 1H), 6.86 (d, J=8.5 Hz, 1H), 6.48 (d, J=2.4 Hz, 1H), 6.40 (dd, J=8.5, 2.6 Hz, 1H), 5.41 (m, 1H), 3.67 (dd, J=8.3, 8.3 Hz, 1H), 2.25 (s, 6H), 0.86 (s, 3H), 0.80-3.40 (m, 19H). $^{13}C$ NMR (125 MHz, MeOD): δ 175.6, 158.0, 156.4, 139.6, 133.2, 129.0 (q, J=29.9 Hz), 128.1, 127.9, 127.5, 124.8 (q, J=273.0 Hz), 119.9, 116.5, 114.2 (q, J=5.2 Hz), 114.17, 82.8, 74.1, 59.9, 51.7, 50.0, 45.4 (2C), 44.2, 39.1, 35.7, 34.8, 30.8, 30.5, 28.6, 24.3, 24.0, 13.8. $^{19}F$ NMR (282 MHz, MeOD): δ −62.52. HR-MS (ESI) calcd for $[C_{31}H_{39}F_3N_2O_4H]^+$ 561.2940, found 561.2912.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-5-(piperid-in-1-yl)pentanamide: $^1H$ NMR (500 MHz, $CDCl_3$): δ 7.75 (d, J=9.5 Hz, 1H), 7.62 (s, 1H), 7.20-7.40 (m, 10H), 7.05 (s, 1H), 7.04 (dd, J=7.4, 2.9 Hz, 1H), 6.87 (d, J=8.7 Hz, 1H), 6.70 (d, J=2.1 Hz, 1H), 6.65 (dd, J=8.6, 2.3 Hz, 1H), 5.85 (br.s, 1H), 5.23 (m, 1H), 4.97 (s, 2H), 4.52 (d, J=12.3 Hz, 1H), 4.44 (d, J=12.2 Hz, 1H), 3.47 (dd, J=8.1, 8.1 Hz, 1H), 2.61 (m, 4H), 1.48 (m, 4H), 0.96 (s, 3H), 0.80-3.00 (m, 23H). $^{13}C$ NMR (125 MHz, $CDCl_3$): δ 171.5, 156.6, 154.8, 138.9, 138.4, 137.1, 128.43, 128.39 (2C), 128.2, 128.15 (2C), 127.7, 127.34 (2C), 127.29, 127.26 (2C), 127.0, 126.1, 123.8 (q, J=29.3 Hz), 123.5 (q, J=273.3 Hz), 118.2, 115.0, 113.4 (q, J=5.1 Hz), 112.4, 88.2, 72.2, 71.4, 69.7, 57.9, 53.9 (2C), 50.6, 48.6, 42.9, 38.9, 36.5, 33.8, 33.6, 29.6, 27.5, 27.2, 24.8, 24.4 (2C), 23.4, 23.1, 13.6. $^{19}F$ NMR (282 MHz, $CDCl_3$): δ −60.75. HR-MS (ESI) calcd for $[C_{49}H_{57}F_3N_2O_4H]^+$ 795.4349, found 795.4334.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-5-(piperidin-1-yl)pentanamide, SERD156: $^1H$ NMR (500 MHz, MeOD): δ 7.33 (d, J=8.7 Hz, 1H), 7.18 (d, J=8.8 Hz, 1H), 7.13 (d, J=1.9 Hz, 1H), 6.87 (d, J=8.6 Hz, 1H), 6.50 (s, 1H), 6.42 (dd, J=8.4, 2.0 Hz, 1H), 5.40 (m, 1H), 3.67 (dd, J=8.2, 8.2 Hz, 1H), 2.48 (t, J=7.6 Hz, 4H), 1.74 (t, J=7.6 Hz, 4H), 0.85 (s, 3H), 0.80-3.40 (m, 23H). $^{13}C$ NMR (125 MHz, MeOD): δ 175.3, 158.0, 155.9, 139.6, 133.4, 129.0 (q, J=30.7 Hz), 128.4, 127.8, 127.5, 124.8 (q, J=271.6 Hz), 119.9, 116.3, 114.2 (q, J=5.4 Hz), 114.0, 82.7, 74.0, 57.8, 54.2 (2C), 51.6, 49.9, 44.2, 39.1, 35.9, 35.6, 30.8, 30.4, 28.5, 24.5, 24.2 (2C), 23.9, 23.7, 22.8, 13.8. $^{19}F$ NMR (376 MHz, MeOD): δ −62.96. HR-MS (ESI) calcd for $[C_{35}H_{45}F_3N_2O_4H]^+$ 615.3409, found 615.3400.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-5-morpho-linopentanamide: $^1H$ NMR (500 MHz, $CDCl_3$): δ 7.87 (d, J=9.6 Hz, 1H), 7.35 (m, 11H), 7.07 (d, J=2.7 Hz, 2H), 6.90 (d, J=8.7 Hz, 1H), 6.73 (d, J=2.4 Hz, 1H), 6.67 (dd, J=8.6, 2.6 Hz, 1H), 5.25 (m, 1H), 4.99 (s, 2H), 4.55 (d, J=12.3 Hz, 1H), 4.46 (d, J=12.3 Hz, 1H), 3.73 (t, J=4.4 Hz, 4H), 3.49 (dd, J=8.1, 8.1 Hz, 1H), 2.45 (m, 4H), 0.99 (s, 3H), 0.80-3.80 (m, 21H). $^{13}C$ NMR (125 MHz, $CDCl_3$): δ 171.3, 156.6, 154.6, 138.9, 138.4, 137.1, 128.5, 128.4 (2C), 128.21, 128.17 (2C), 127.7, 127.6, 127.35 (2C), 127.27 (2C), 127.1, 126.1, 123.6 (q, J=273.4 Hz), 123.0 (q, J=29.7 Hz), 118.2, 115.0, 113.4 (q, J=5.2 Hz), 112.5, 88.2, 72.2, 71.4, 69.7, 66.8 (2C), 58.4, 53.6 (2C), 50.6, 48.6, 42.9, 38.9, 37.1, 33.6, 29.7, 27.5, 27.3, 25.8, 23.3, 22.9, 13.7. $^{19}F$ NMR (282 MHz, $CDCl_3$): δ −60.73. HR-MS (ESI) calcd for $[C_{48}H_{55}F_3N_2O_5H]^+$ 797.4141, found 797.4163.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-5-morpholino-pentanamide, SERD157: $^1H$ NMR (500 MHz, MeOD): δ 7.31 (d, J=8.7 Hz, 1H), 7.17 (dd, J=8.8, 2.6 Hz, 1H), 7.13 (d, J=2.7 Hz, 1H), 6.86 (d, J=8.6 Hz, 1H), 6.49 (d, J=2.4 Hz, 1H), 6.41 (dd, J=8.5, 2.6 Hz, 1H), 5.40 (m, 1H), 3.72 (t, J=4.6 Hz, 4H), 3.67 (dd, J=8.3, 8.3 Hz, 1H), 2.59 (m, 4H), 0.86 (s, 3H), 0.80-3.50 (m, 21H). $^{13}C$ NMR (125 MHz, MeOD): δ 175.9, 158.0, 155.9, 139.6, 133.3, 129.0 (q, J=29.7 Hz), 128.4, 127.9, 127.5, 124.8 (q, J=272.4 Hz), 119.9, 116.3, 114.2 (q, J=6.7 Hz), 114.0, 82.7, 74.0, 67.2 (2C), 59.4, 54.5 (2C), 51.6, 49.9, 44.2, 39.1, 36.6, 35.6, 30.8, 30.4, 28.5, 26.2, 24.5, 23.9, 13.8. $^{19}F$ NMR (376 MHz, MeOD): δ −63.01. HR-MS (ESI) calcd for $[C_{34}H_{43}F_3N_2O_5H]^+$ 617.3203, found 617.3230.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-5-(pyrro-lidin-1-yl)pentanamide: $^1H$ NMR (500 MHz, $CDCl_3$): δ 7.74 (s, 1H), 7.65 (d, J=8.6 Hz, 1H), 7.20-7.40 (m, 10H), 7.05 (s, 1H), 7.043 (d, J=9.2 Hz, 1H), 6.87 (d, J=8.7 Hz, 1H), 6.71 (d, J=2.2 Hz, 1H), 6.65 (dd, J=8.6, 2.3 Hz, 1H), 5.23 (m, 1H), 4.97 (s, 2H), 4.52 (d, J=12.3 Hz, 1H), 4.44 (d, J=12.2 Hz, 1H), 3.47 (dd, J=8.4, 8.4 Hz, 1H), 2.48 (m, 4H), 1.25 (m, 4H), 0.95 (s, 3H), 0.80-3.40 (m, 21H). $^{13}C$ NMR (125 MHz, $CDCl_3$): δ 171.3, 156.6, 155.2, 138.9, 138.4, 137.2, 129.1, 128.49, 128.45 (2C), 128.23, 128.21 (2C), 127.8, 127.41 (2C), 127.36, 127.32 (2C), 126.7, 126.2, 123.5 (q, J=274.5 Hz), 118.2, 115.0, 113.4 (q, J=5.5 Hz), 112.5, 88.3, 72.2, 71.5, 69.8, 54.7, 53.4 (2C), 50.6, 48.6, 43.0, 38.9, 35.7, 33.6, 29.7, 27.6, 27.3, 25.0, 23.2 (2C), 23.0, 22.3, 13.7. $^{19}F$ NMR (282 MHz, $CDCl_3$): δ −60.75. HR-MS (ESI) calcd for $[C_{48}H_{55}F_3N_2O_4H]^+$ 781.4192, found 781.4170.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-5-(pyrrolidin-1-yl)pentanamide, SERD158: $^{1}$H NMR (500 MHz, MeOD): δ 7.33 (d, J=8.8 Hz, 1H), 7.19 (dd, J=8.8, 2.7 Hz, 1H), 7.14 (d, J=2.7 Hz, 1H), 6.87 (d, J=8.6 Hz, 1H), 6.50 (d, J=2.4 Hz, 1H), 6.41 (dd, J=8.5, 2.6 Hz, 1H), 5.41 (m, 1H), 3.67 (dd, J=8.1, 8.1 Hz, 1H), 2.48 (t, J=6.9 Hz, 4H), 2.07 (m, 4H), 0.86 (s, 3H), 0.80-3.50 (m, 21H). $^{13}$C NMR (125 MHz, MeOD): δ 175.4, 158.1, 155.9, 139.6, 133.4, 129.1 (q, J=30.3 Hz), 128.4, 127.8, 127.5, 124.8 (q, J=272.5 Hz), 119.9, 116.3, 114.2 (q, J=5.1 Hz), 114.0, 82.7, 74.1, 55.8, 55.0 (2C), 51.6, 49.9, 44.2, 39.1, 35.9, 35.6, 30.8, 30.4, 28.5, 26.4, 24.0 (2C), 23.9, 23.5, 13.8. $^{19}$F NMR (376 MHz, MeOD): δ −63.01. HR-MS (ESI) calcd for $[C_{34}H_{43}F_3N_2O_4H]^+$ 601.3253, found 601.3257.

N-(4-(((8S,9S,11S,13S,14S,17S)-3,17-bis(Benzyloxy)-13-methyl-7,8,9,11,12,13,14,15,16,17-decahydro-6H-cyclopenta[a]phenanthren-11-yl)oxy)-2-(trifluoromethyl)phenyl)-5-(dimeth-ylamino)pentanamide: $^{1}$H NMR (500 MHz, $CDCl_3$): δ 7.74 (d, J=9.6 Hz, 1H), 7.57 (s, 1H), 7.20-7.40 (m, 10H), 7.06 (s, 1H), 7.05 (dd, J=6.6, 3.1 Hz, 1H), 6.87 (d, J=8.7 Hz, 1H), 6.71 (d, J=2.3 Hz, 1H), 6.66 (dd, J=8.6, 2.5 Hz, 1H), 5.24 (m, 1H), 4.98 (s, 2H), 4.53 (d, J=12.3 Hz, 1H), 4.45 (d, J=12.3 Hz, 1H), 3.47 (dd, J=8.1, 8.1 Hz, 1H), 2.55 (s, 6H), 0.96 (s, 3H), 0.80-3.00 (m, 21H). $^{13}$C NMR (125 MHz, $CDCl_3$): δ 171.3, 156.6, 155.0, 139.0, 138.5, 137.2, 128.52, 128.48 (2C), 128.3, 128.2 (2C), 128.1, 127.8, 127.4 (2C), 127.35 (2C), 126.9, 126.2, 124.0 (q, J=30.4 Hz), 123.6 (q, J=273.4 Hz), 118.3, 115.0, 113.5 (q, J=5.3 Hz), 112.5, 88.3, 72.3, 71.5, 69.8, 57.9, 50.7, 48.7, 43.7 (2C), 43.0, 39.0, 36.2, 33.7, 29.7, 27.6, 27.3, 24.8, 23.0, 22.6, 13.7. $^{19}$F NMR (376 MHz, $CDCl_3$): δ −61.39. HR-MS (ESI) calcd for $[C_{46}H_{53}F_3N_2O_4H]^+$ 755.4036, found 755.4004.

N-(4-(((8S,9S,11S,13S,14S,17S)-3,17-Dihydroxy-13-methyl-7,8,9,11,12,13,14,15,16,17-deca-hydro-6H-cyclopenta[a]phenanthren-11-yl)oxy)-2-(trifluoromethyl)phenyl)-5-(dimethylam-ino)pentanamide, SERD159: $^{1}$H NMR (500 MHz, MeOD): δ 7.31 (d, J=8.7 Hz, 1H), 7.17 (dd, J=8.8, 2.6 Hz, 1H), 7.14 (d, J=2.7 Hz, 1H), 6.87 (d, J=8.6 Hz, 1H), 6.49 (d, J=2.3 Hz, 1H), 6.41 (dd, J=8.5, 2.5 Hz, 1H), 5.41 (m, 1H), 3.67 (dd, J=8.3, 8.3 Hz, 1H), 2.35 (s, 6H), 0.86 (s, 3H), 0.80-3.50 (m, 21H). $^{13}$C NMR (125 MHz, MeOD): δ 175.8, 158.0, 156.0, 139.6, 133.3, 129.0 (q, J=30.2 Hz), 128.3, 127.9, 127.5, 124.8 (q, J=274.7 Hz), 119.9, 116.3, 114.2 (q, J=5.2 Hz), 114.0, 82.7, 74.1, 60.0, 51.6, 49.9, 45.0 (2C), 44.2, 39.1, 36.6, 35.6, 30.8, 30.4, 28.5, 27.2, 24.4, 23.9, 13.8. $^{19}$F NMR (376 MHz, MeOD): δ −63.08. HR-MS (ESI) calcd for $[C_{32}H_{41}F_3N_2O_4H]^+$ 575.3097, found 575.3123.

Example 2: Compound Functional Characterization

For the biological testing alternative code names for the compounds were used, namely SERD101-SERD160. The correspondence of the compound numbers in the design and synthesis and the code names for functional characterization are given in Table 1.

TABLE 1

Correspondence of the Novel ER Antagonists Chemical names and their alternative Code Names for Functional Characterization.

| Cmpd | Code |
|---|---|
| 8a | SERD101 |
| 8b | SERD102 |
| 8c | SERD103 |
| 8d | SERD104 |
| 7 | SERD105 |
| 11c | SERD106 |
| 11a | SERD107 |
| 11b | SERD108 |
| 11d | SERD109 |
| 12c | SERD110 |
| 12b | SERD111 |
| 12a | SERD112 |
| 13c | SERD113 |
| 13b | SERD114 |
| 13a | SERD115 |
| 12d | SERD116 |
| 13d | SERD117 |
| 10 | SERD118 |
| 15 | SERD119 |
| 20, 16 | SERD120 |
| 9c | SERD121 |
| 17a | SERD122 |
| 9b | SERD123 |
| 9a | SERD124 |
| 17b | SERD125 |
| 17c | SERD126 |
| 9d | SERD127 |
| 22 | SERD128 |
| 17d | SERD129 |
| 18a | SERD130 |
| 14c | SERD131 |
| 18b | SERD132 |
| 18d | SERD133 |
| 18c | SERD134 |
| 19c | SERD135 |
| 14a | SERD136 |
| 19a | SERD137 |
| 19b | SERD138 |
| 19d | SERD139 |
| 20a | SERD140 |
| 20c | SERD141 |
| 20d | SERD142 |
| 20b | SERD143 |
| 23c | SERD144 |
| 23a | SERD145 |
| 21 | SERD146 |
| 23b | SERD147 |
| 23d | SERD148 |
| 24a | SERD149 |
| 24b | SERD150 |
| 24d | SERD151 |
| 24c | SERD152 |
| 25c | SERD153 |
| 25b | SERD154 |
| 25d | SERD155 |
| 26a | SERD156 |
| 26c | SERD157 |
| 26b | SERD158 |
| 26d | SERD159 |
| 25a | SERD160 |

Example 3: Estrogens Act to Boost Antitumor Immunity and Breast Cancer Progression In addition to breast cancer (BC) cells, the tumor microenvironment may also play a role in malignant progression and the response to therapy. Notably, several types of CD45-expressing leukocytes infiltrate the BC microenvironment, including $CD4^+$ and $CD8^+$ T-cells, CD20+ B-cells and multiple myeloid-derived cells identified by specific IHC markers (1, 2). The presence of these tumor-infiltrating immune cells is reported to predict patient survival. Recent reports also show that BCs from patients with residual disease after chemotherapy contain relatively higher levels of infiltrating myeloid-derived cells (2). Importantly, estrogen receptors (ERs) particularly ERα are expressed in immune cells that occur in the BC microenvironment including T-cells and myeloid-derived suppressor cells (MDSC), yet the potential mechanistic role of estrogen signaling in modulating antitumor immunity remains to be clarified (1-3) (see FIG. 1).

Figure 1:
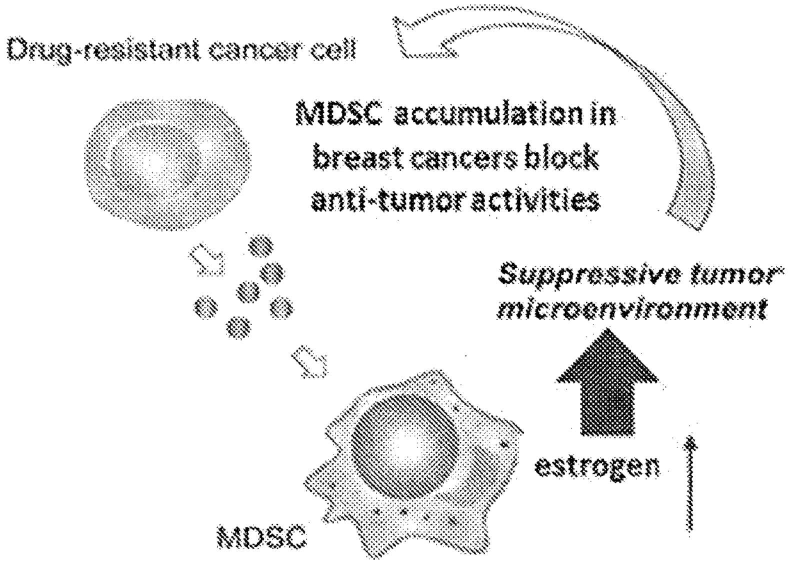
FIG. 1 schematically shows that myeloid-derived suppressor cells (MDSC) promote human breast cancer progression by blocking antitumor activities of natural immune cells particularly $CD8^+$ T-cells in vivo, and estrogen signaling is reported to be crucial for pathologic activation of MDSCs that allow BCs to escape immune attack (1-4).

MDSCs are not present in the steady state of healthy individuals but do appear in pathologic conditions associated with chronic inflammation and cancer (3). Emerging data show that estrogen signaling accelerates BC progression by driving expansion and mobilization of myelomonocytic and granulocytic MDSC and enhancing the intrinsic immunosuppressive activity of granulocytic MDSCs (G-MDSCs) which can in turn markedly boost BC progression (1) (FIG. 1). ERα is reported to activate the STAT3 pathway in human bone marrow myeloid precursor cells, and estrogen signaling is hypothesized to be a crucial mechanism underlying myelopoiesis in cancer. Indeed, gender-dependent differences in myelopoiesis of bone marrow precursor cells are reported, with estrogen targeting proliferation in bone marrow cells from female animals. Tumor immune tolerance can result from expansion and recruitment of MDSC populations in the BC microenvironment (2). Thus, emerging data from our laboratory indicate that new selective estrogen receptor downregulators (SERDs) may have benefits in BCs independent of ER expression in tumor cells and may synergize with immunotherapies such as immune checkpoint inhibitors to extend patient survival (see below). These findings offer a rationale to block ER signaling in MDSC cells with new SERD agents, an action that may thereby benefit patients with both ER-positive and ER-low/negative, or endocrine-resistant tumors such as triple-negative breast cancers (TNBC).

Figure 2A:
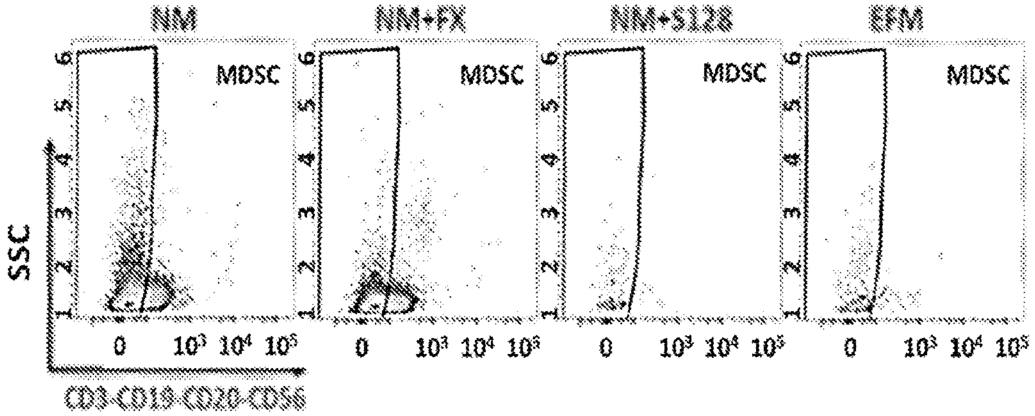
FIG. 2 shows that SERDs suppress the expansion of myeloid-derived suppressor cells (MDSC). Bone Marrow cells from three breast cancer patients were purified by established methods including red blood cell lysis and Ficoll gradients (1-3,5, 5-7) and then cultured in the presence of IL-6 and GM-CSF in either estrogen-free medium (EFM), normal medium with control vehicle (NM) (which contains estrogens), normal medium with 1-μM fulvestrant (NM+FULV) or normal medium with 1-μM S128 (NM+S128). After 5 days, myeloid-derived cell populations were then identified by following the gating strategy of Ruffell et al. (2) as modified by Svoronos et al. (1). A) Percentage of total MDSC within $CD45^+$ population. B) Total cell numbers of MDSCs were substantially decreased in the absence of estrogen (EFM) or in the presence of either fulvestrant (NM+FX) or S128 (SERD128) (NM+S128) when these agents were administered at the same dose level. These data were confirmed in further experiments of similar design in FIG. 3A-3B.
Figure 2B:
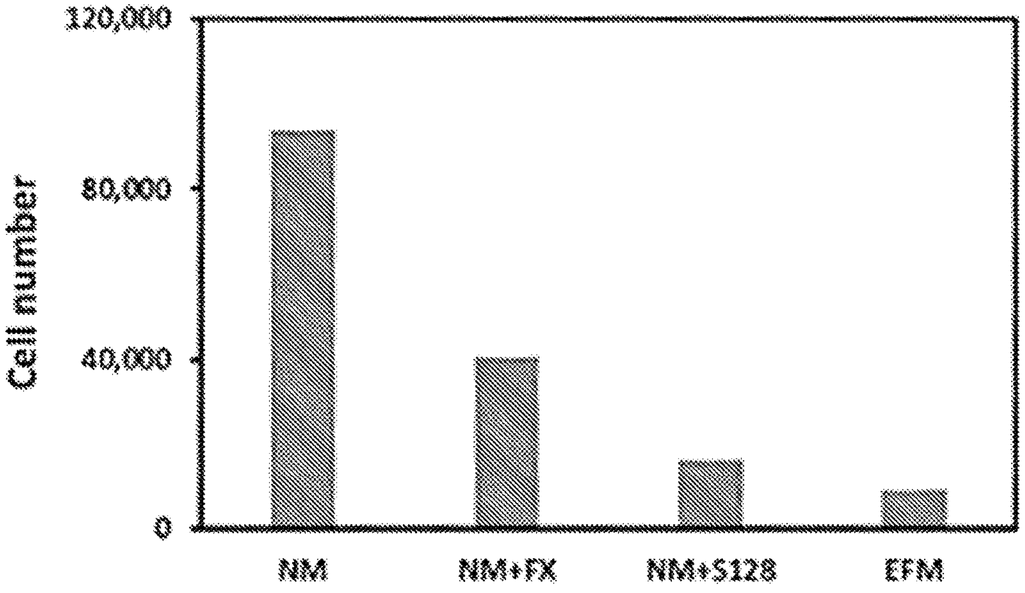
Figure 3A:
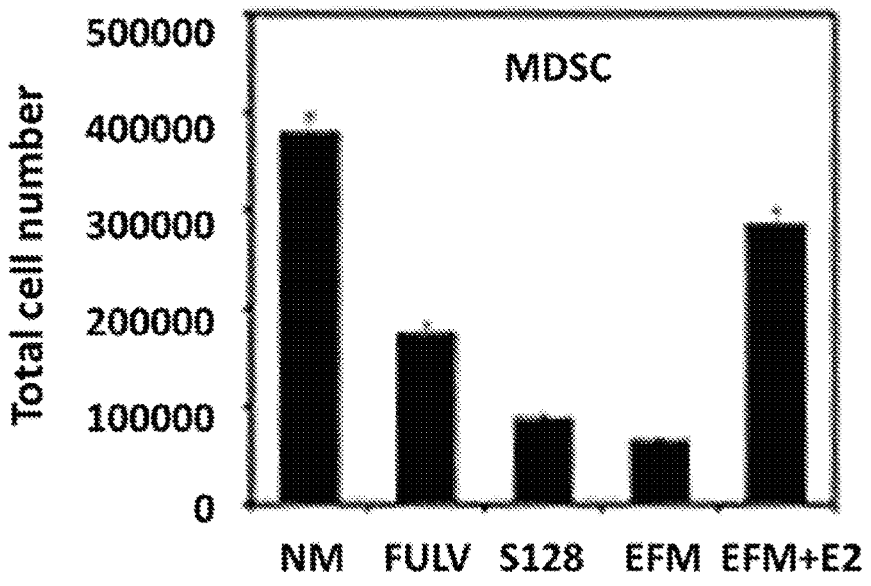
FIG. 3A shows that Expansion of MDSC is dependent on estrogen signaling. E2 increases the percentage and total number of MDSC. Total number of human MDSC derived from bone marrow (BM) of three of three BC patients (P<0.05). Cells were incubated in the presence of GM-CSF and IL-6 for 6 days in either regular RPMI medium+15% FBS (NM) (contains estrogens) or in phenol red-free medium with 15% charcoal coated-dextran treated FBS (EFM)(estrogen-depleted) with or without the addition of 100 nM estradiol-17β (EFM+E2). Normal cell culture medium (NM) drives E2-dependent signaling due to the presence of various estrogens in FBS as well as the estrogenic properties of phenol red. These effects were inhibited by the SERDs fulvestrant (FULV) and S128 at 1 μM

Example 4: Novel Selective Estrogen Receptor Downregulators in Breast Cancer Immunotherapy S128 inhibits expansion of myeloid-derived suppressor cells (MDSC). Tumors generate a suppressive microenvironment to evade the immune response by various mechanisms including recruitment of MDSCs (3). These cells are key contributors to tumor immune suppression, angiogenesis, drug resistance and promotion of metastases (3). In malignancy, myeloid cell differentiation into mature macrophage, $CD8^+$ T cells and granulocytes is often diverted into pathways that favor differentiation of pathological MDSC. We note that two main subsets of MDSCs have been characterized: myelomonocytic MDSC (M-MDSC) and granulocytic MDSC (G-MDSC) (1,3). Emerging data indicate that estrogen (E2) may accelerate progression of E2-sensitive and -insensitive BCs by stimulating deregulated myelopoiesis via E2-induced expansion and mobilization of MDSCs and enhancement of their intrinsic immunosuppressive activity in vivo—notably among tumor—infiltrating $CD8^+$ T-cells (1-3). As high levels of BC MDSCs correlate with poor prognosis (2), these findings offer a rationale to study the activity of SERDs in immune system components that regulate tumor progression. Studies in FIGS. 2 and 3A show that S128 inhibits E2-induced expansion of MDSC in bone marrow specimens of BC patients.

Figure 3B:
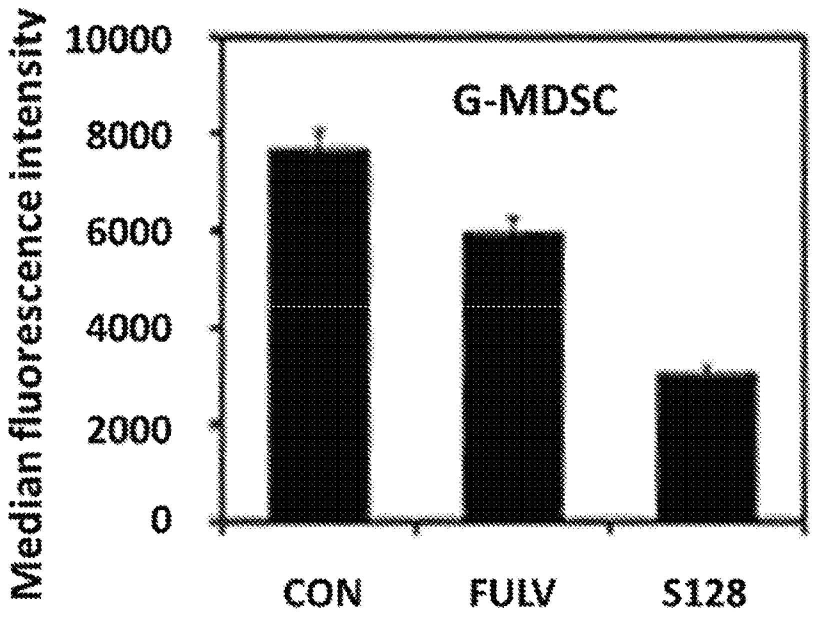
FIG. 3B shows that antiestrogen S128 blocks phosphorylation/activation of STAT3 in G-MDSC subpopulations. Bone marrow cells from three breast cancer patients were incubated with GM-CSF and IL6 in the following groups: normal medium (contains estradiol) in the presence of vehicle (CON), 1 μM fulvestrant (FULV) or 1 μM S128. After 6 days, cells were subjected to flow cytometry using an antibody directed to phosphorylated STAT3 (p-STAT; 1). The results show median fluorescence intensity for p-STAT3 in G-MDSC subpopulations ($CD45^+HLA^-DR^-CD11b^+CD33^+CD15^+$) after expansion of human total MDSC as before (1,2).

In addition, data in FIG. 3B indicate that estrogen activates and S128 inhibits the STAT signaling pathway that is reported to be crucial for pathologic myelopoiesis and for the enhanced immunosuppressive potential of MDSCs in malignancy (1).

SERD S128 combined with immune checkpoint inhibitor stops 4T1 breast tumor progression in a syngeneic mouse model. Although direct proliferative effects of estradiol on ER-positive tumors are well known, estrogens may also participate in cancer pathogenesis and metastasis in ways not yet fully understood. In this preliminary study, we assessed antitumor efficacy of S128 alone and combined with an anti-PD-L1 antibody (e.g. an immune checkpoint inhibitor) in mice with highly aggressive murine 4T1 tumor implants that metastasize widely to cause early mortality in syngeneic mice with intact immune systems. Notably, S128 treatment elicits inhibition of 4T1 TNBC progression in vivo, potentially by blocking the expansion and activation of MDSCs, notably the subset termed G-MDSC (FIG. 4).

Figure 4A:
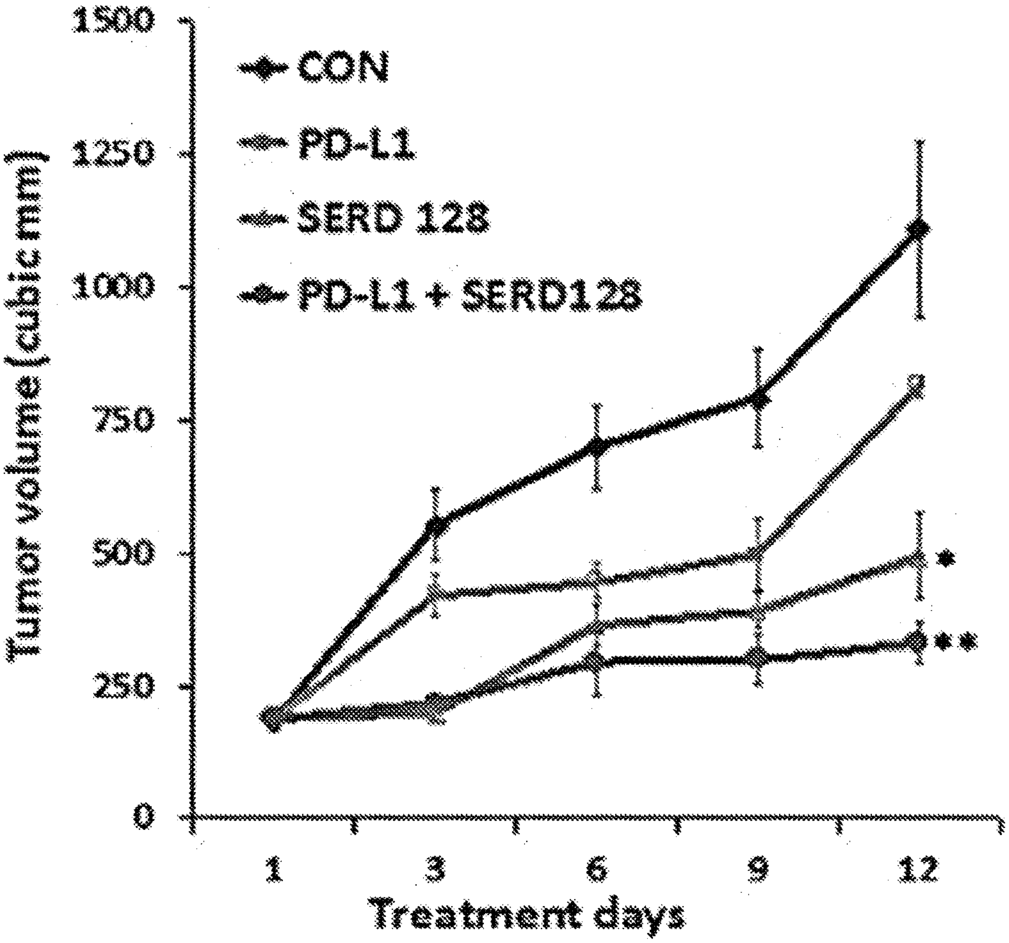
FIG. 4A shows that therapy with SERD128 combined with anti-PD-L1 antibody inhibits 4T1 tumor progression. Ovariec-tomized 6-wk-old female BALC/c mice supplemented with E2 pellets (0.36 mg/60 day release pellet) were implanted SC with 2.5×105 4T1 cells. After tumors reached approx. 200 mm3, mice were randomized and treated with control vehicle (CON), 100 μg of anti-PD-L1 (antibody clone 10F.9G2, BioXCell) Q3 days (PD-L1), 50 mg/kg SERD128 by oral gavage (SERD128) or combined antibody+SERD (PD-L1+SERD128). Tumors were measured Q3 days, with tumor volume calculated as V=(W(2)×L)/2), with mean+SE (*P<0.05, **P<0.01 vs CON).
Figure 4B:
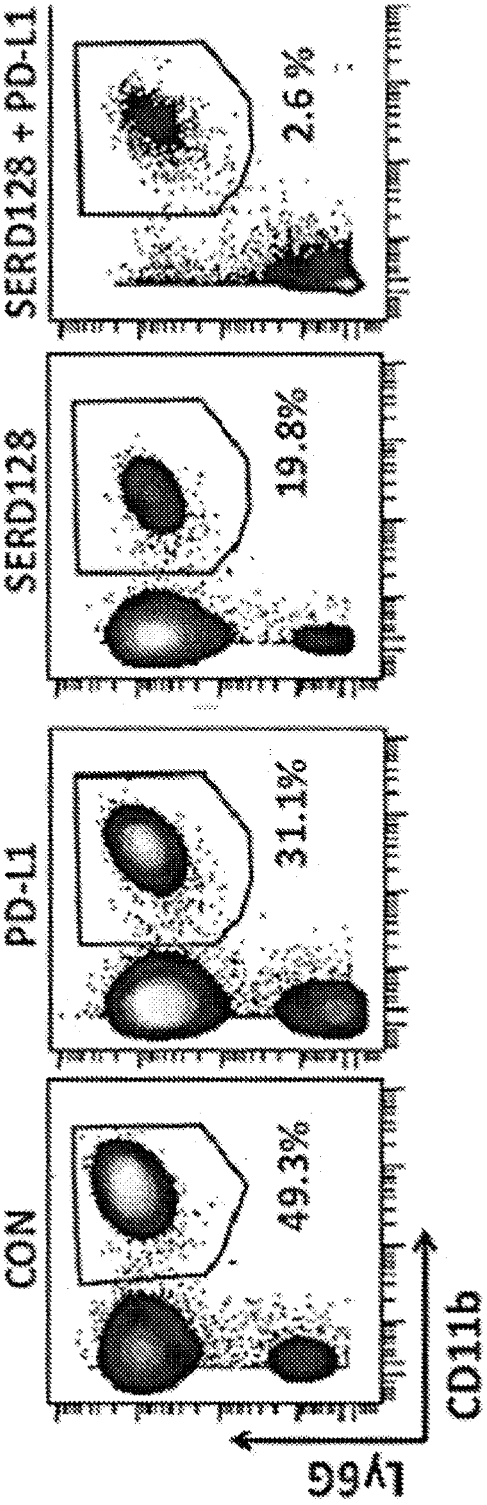
FIG. 4B shows that SERD128 therapy in combination with anti-PD-L1 antibody results in significantly reduced recruitment of tumor G-MDSC subsets to tumor sites (P<0.001). Single cell suspensions were prepared from 4T1 tumors grown in BALC/c mice treated for 12 days with control (CON), 100 μg of anti-PD-L1 antibody Q3 days (PD-L1), 50 mg/kg SERD128 via oral gavage (SERD128) or combined (PD-L1+SERD128). Cells were labeled with specific antibodies and analyzed by mass cytometry (cyTOF). Graph shows representative example of G-MDSC (CD11b+Ly6G+) subsets present in the tumor bed as % $CD45^+$ cells.
Figure 5A:
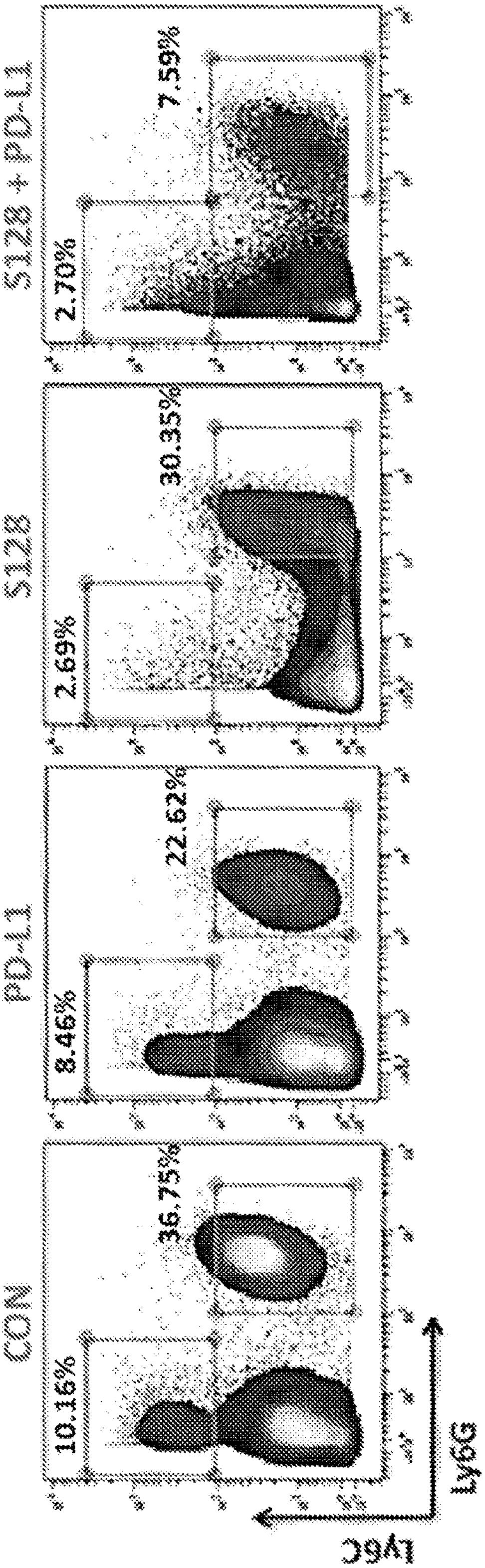
FIGS. 5A-5B show SERD128 therapy combined with anti-PD-L1 antibody treatment results in significantly reduced recruit-ment of tumor G-MDSC subsets to tumor sites.
Figure 5B:
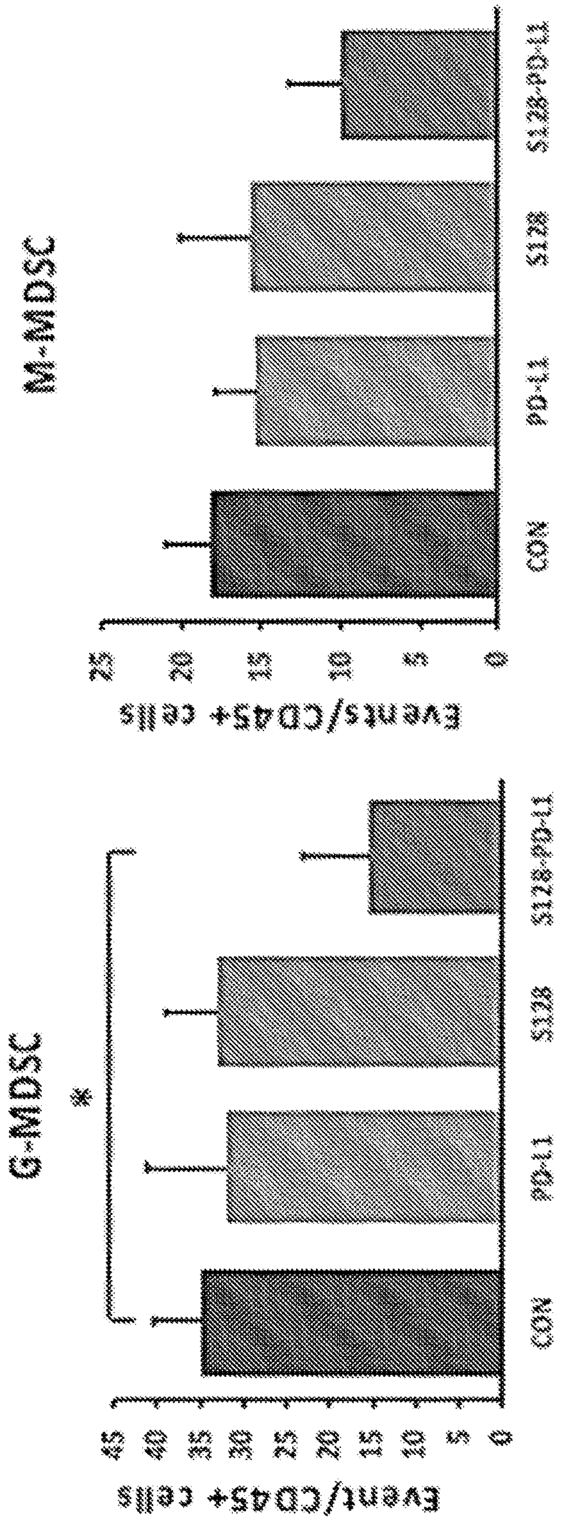

Further, S128 combined with anti-PD-L1 checkpoint inhibitor elicits additional antitumor activity as compared to controls (FIG. 4). Although 4T1 tumors are EPα-negative, ERα is expressed in MDSCs (confirmed by mass cytometry) and may thereby promote formation and metastases (predominantly to lung) of tumors in response to estrogens (FIG. 4; 1). As described before, MDSC have recently emerged as major regulators of the immune response in cancer, with potent immunosuppressive activity attributed to MDSCs. Two major subsets of MDSCs have been described in humans and mice based on their phenotypic, morphological and functional characteristics: granulocytic (G-MDSC) and monocytic (M-MDSC). G-MDSC subsets appear to be more significantly reduced overall with the combination therapy of SERD128 and anti-PD-L1 antibody (FIGS. 5A and 5B).

Figure 6A:
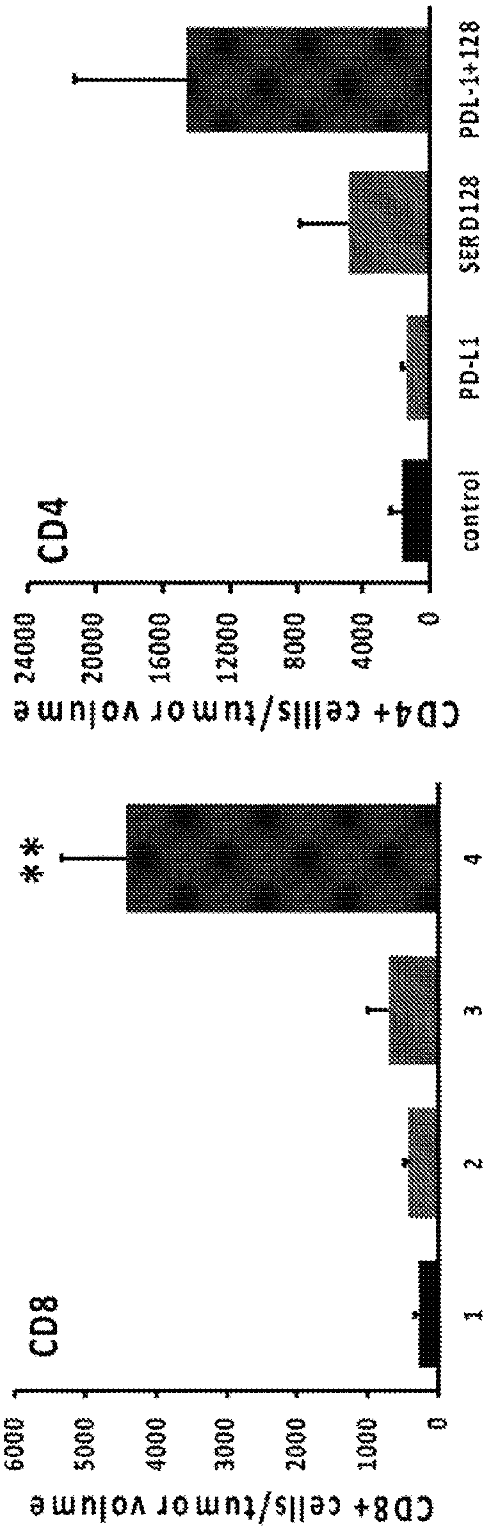
FIGS. 6A-FIG. 6B show tumor infiltrating lymphocytes (TILs) in 4T1 tumors harvested from Balb/c mice as detailed in FIG. 4A and FIG. 4B, respectively, with $CD8^+$ and $CD4^+$ TILs shown. Groups include mice who were treated with control vehicle (CON), anti-PD-L 1 antibody (PD-L1), S128 or the combination of S128 and anti-PD-L1 antibody (S128+PD-L1). Numbers of $CD8^+$ and $CD4^+$ TILs are shown relative to tumor volumes.
Figure 6B:
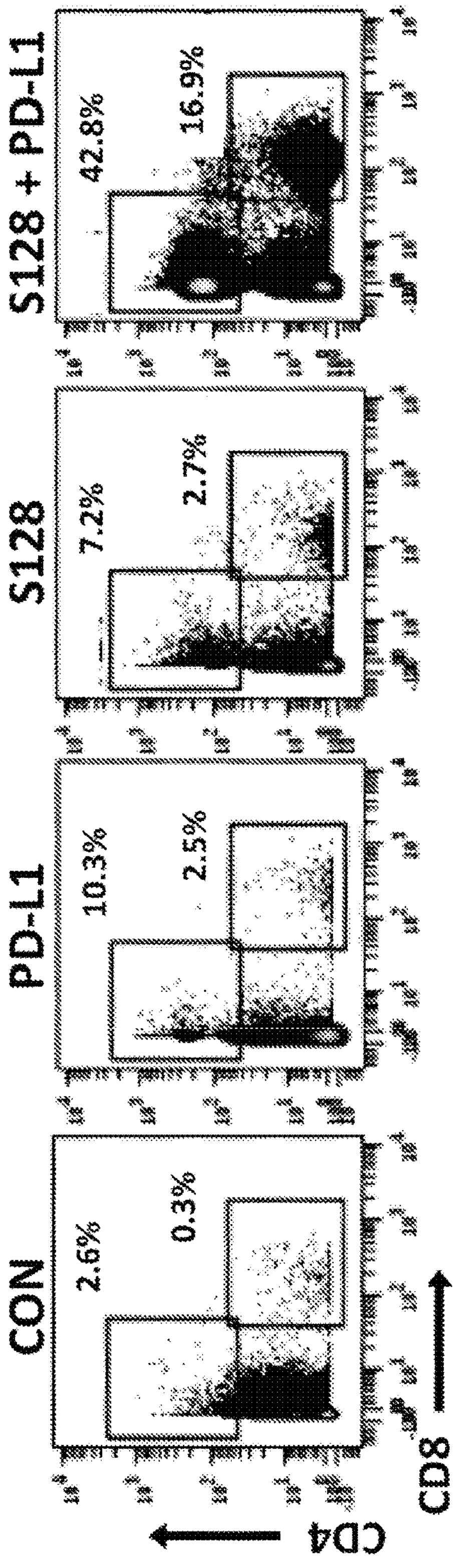

CyTOF analyses further indicate that $CD8^+$ T-cell levels in tumors are several-fold higher in mice treated with S128 combined with PD-L1 antibody as compared to control ($P<0.01$) (FIG. 6). These data suggest a novel way in which estrogen promotes tumor progression, with implications for application of SERD therapies to treat BC in women with ER-positive and potentially ER-negative and/or endocrine-resistant tumors. We note that $CD8^+$ TILs are associated with better overall patient survival in TNBC (8,9).

Figure 7:
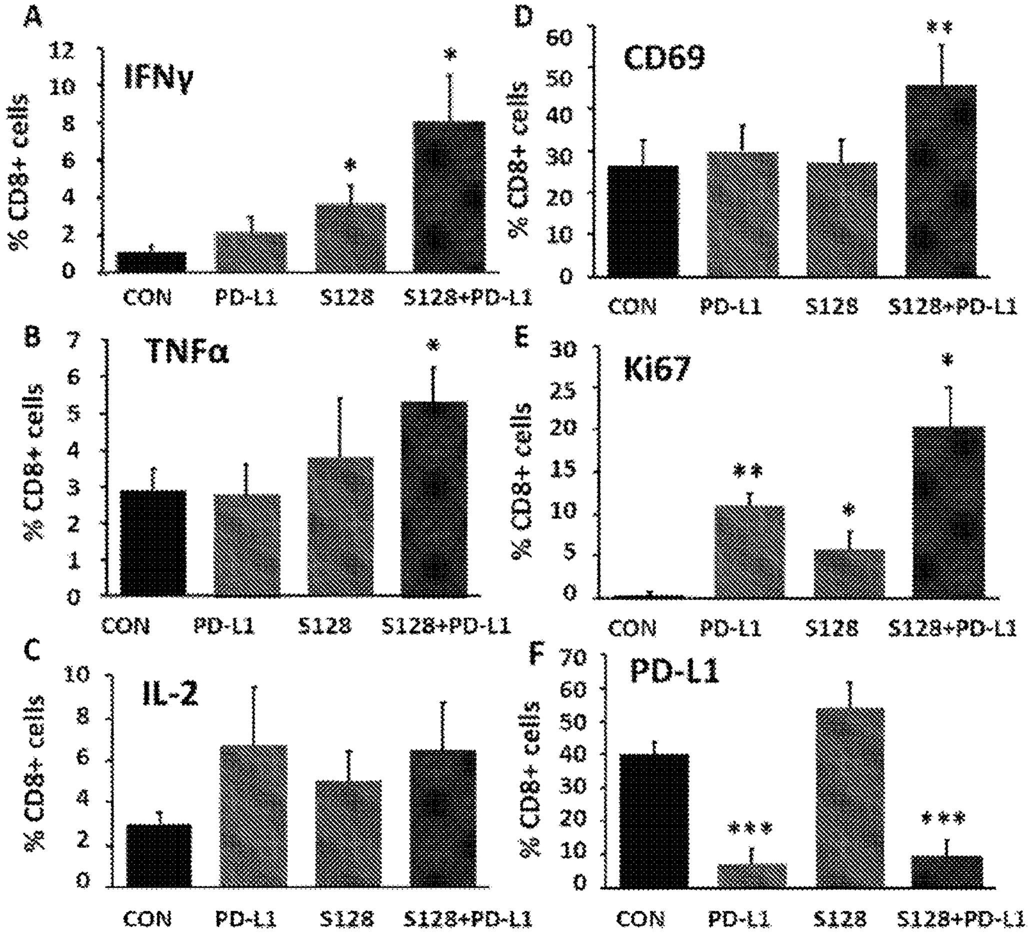

Infiltration of immune cells, in particular anti-tumor type 1 lymphocytes, predicts improved prognosis in many different tumor types including breast cancer (8-11). An adaptive T-cell response, which requires antigen recognition, is composed of both cytotoxic $CD8^+$ T cells and $CD4^+$ T cells. Animal models have demonstrated that in vivo eradication of tumors is, for the most part, mediated by cytotoxic T-cells. The presence of intratumoral T-cells is an independent predictor of improved survival (11) and has also been associated with a Th1 cytokine signature in malignant $CD8^+$ T-cells stimulated by cancer cell antigens, with increased secretion of IFNγ, IL-2 and TNFα (FIG. 7 A,B,C) (12). Other selected markers of $CD8^+$ TIL activation and/or proliferation were also increased by S128 and/or S128 combined with anti-PD-L1 antibody (FIG. 7 D, E).

Importantly, the breast tumor microenvironment (TME) has recently emerged as an important factor in tumor progression. The TME comprises immune system elements (such as macrophages and lymphocytes), blood vessels, fibroblasts, myofibroblasts and mesenchymal stem cells, adipocytes and extracellular matrix (13). Among all these cells, tumor-associated macrophages (TAM) are prominent components of the TME in breast cancers. Macrophages are key modulators and effector cells in the immune response that exhibit high plasticity in response to various external signals (14). Depending on the microenvironment signals present, macrophages have been classified into two distinct phenotypes. M1 macrophages have been associated with tumoricidal activity, and exhibit high production of reactive nitrogen and oxygen intermediates and pro-inflammatory cytokines. In contrast, M2 macrophages are considered to be involved in tumor progression and to have immuno-regulatory functions (15). The M2 phenotype is reported to predominate among TAMs, and a high density of TAMs correlates with poor prognosis in breast cancer (15). Therapy with SERD128 alone or combined with anti-PD-L1 antibody elicits an increase in the M1 tumoricidal population of macrophages in the tumor bed and a notable decrease in the M2 phenotype that associates with tumor progression and poor patient survival (FIG. 8).

While most of the work has been focused on the role of T cells in anti-tumor response, it is well known that B cells have been found in many solid tumors, including breast cancer (20). In murine models of cancer as well as in human cancers, the function of B cells is controversial reporting pro- and anti-tumor roles. B cells are an essential part of the humoral response and function mainly by secreting antibodies in response to T cells and antigen presenting cells as well as secretion of cytokines that modulate other immune cells. Diverse subsets of B-lymphocytes have been identified that occur through their developmental stages that can be identified with different markers. Among these populations are B1 and B2 cells. In murine cancer models such as the 4T1, a subset of poorly proliferative but active mature B2 cells ($CD19^+$ $CD25^+$ $CD69^+$) have been found to induce conversion of $CD4^+$ T cells to $FoxP3^+$ Tregs (21). Treatment with SERD128 decrease expression of this subpopulation as well as combination treatment in our 4T1 breast cancer model, confirming previous reports (FIG. 10). This population phenotypically resembles tumor-evoked B regulatory cells or Bregs required for 4T1 tumors to efficiently produce lung metastasis.

Recent findings suggest cells of the innate immune system are important players in the decision between an effective immune response and induction of tolerance. Among cells of the innate immune system are $CD8^+$ T cells (DC), these cells have a special function linking innate immune response with the induction of adaptive immunity. In the murine immune system, two major subgroups of DCs have been described namely myeloid DCs (mDCs) and plasmacytoid DCs. These cells play a major role in the immune response by processing and presenting antigens to T and B cells to generate an immune response. Stimulatory DCs promote effective immune responses by stimulating T cell proliferation and shaping T cell response phenotypes such as TH1, TH2 or TH17 (22). Treatment with SERD128 alone or in combination with anti-PD-L1 antibody increased population of mDCs in 4T1 tumors as well as the total population of DCs.

Key data in preliminary work on SERD128 prototype prepared in chemistry and tested in oncology:

- SERD128 inhibits expansion and activation of ER+myeloid-derived suppressor cells (MDSCs) that promote TNBC immune escape.
- SERD128 promotes enhanced proliferation and activation of $CD8^+$ T-cells in the tumor microenvironment.
- SERD128 alone or combined with anti-PD-L1 antibody increases the ER+M1-tumoricidal subset of macrophages in the tumor bed and reduces the M2-phenotype associated with tumor progression and poor patient survival.
- SERD 128 combined with anti-PD-L1 antibody exerts enrichment of inactivated Treg cells that act to maintain tumor immune tolerance, a process that may be related to simultaneous reduction of active mature B2 cells ($CD19^+$ $CD25^+$ $CD69^+$) that induce conversion of $CD4^+$ T cells to $FoxP3^+$ Tregs.
- SERD128 combined with anti-PD-L1 antibody enhances myeloid $CD8^+$ T cells (mDCs) that play a major role in the immune response by processing and presenting antigens to T- and B-cells to generate immune responses.
- SERD128 has potential for use as a dual therapy with immune checkpoint inhibitors such as anti-PD-L1 or anti-PD-1 antibodies to promote the survival of patients with breast cancer.

REFERENCES CITED IN EXAMPLES 3-4 AND FIGS. 1-14

1. Svoronos N, Perales-Puchalt A, Allegrezza M J, Rutkowski M R, Payne K K, Tesone A, Nguyen J M, Curiel T J, Cadungog M G, Singhal S, Eruslanov E B, Zhang P, Tchou J, Zhang R, Conejo-Garcia J R (2017). Tumor Cell-Independent Estrogen Signaling Drives Disease Progression through Mobilization of Myeloid-Derived Suppressor Cells. Cancer Discov. 7(1):72-85. PMCID: PMC5222699
2. Ruffell B1, Au A, Rugo H S, Esserman L J, Hwang E S, Coussens L M (2012). Leukocyte composition of human breast cancer. Proc Natl Acad Sci USA. 109(8):2796-801. PMCID: PMC3287000.
3. Gabrilovich D I (2017). Myeloid-Derived Suppressor Cells. Cancer Immunol Res. 5(1):3-8. PMCID: PMC5426480.
4. Ouyang L, Chang W, Fang B, Qin J, Qu X, Cheng F (2016). Estrogen-induced SDF-1α production promotes the progression of E R-negative breast cancer via the accumulation of MDSCs in the tumor microenvironment. Sci Rep. 6:39541. PMCID: PMC5172230.
5. Hu-Lieskovan S, Mok S, Homet Moreno B, *Tsoi* J, Robert L, Goedert L, Pinheiro E M, Koya R C, Graeber T G, Comin-Anduix B, Ribas A (2015). Improved antitumor activity of immunotherapy with BRAF and MEK inhibitors in BRAF(V600E) melanoma. Sci Transl Med. 7(279):279. PMCID: PMC4765379.
6. Wong D J, Rao A, Avramis E, Matsunaga D R, Komatsubara K M, Atefi M S, Escuin-Ordinas H, Chodon T, Koya R C, Ribas A, Comin-Anduix B (2014). Exposure to a histone deacetylase inhibitor has detrimental effects on human lymphocyte viability and function. Cancer Immunol Res. 2(5):459-68. PMCID: PMC4010948.
7. Comin-Anduix B, Sazegar H, Chodon T, Matsunaga D, Jalil J, von Euw E, Escuin-Ordinas H, Balderas R, Chmielowski B, Gomez-Navarro J, Koya R C, Ribas A (2010). Modulation of cell signaling networks after CTLA4 blockade in patients with metastatic melanoma. PLoS One. 5(9):e12711. PMCID: PMC2939876.
8. Mahmoud S M, Paish E C, Powe D G, Macmillan R D, Grainge M J, Lee A H, Ellis I O, Green A R (2011). Tumor-infiltrating $CD^{8+}$ lymphocytes predict clinical outcome in breast cancer. J Clin Oncol. 20; 29(15):1949-55.
9. Stanton S E, Disis M L (2016). Clinical significance of tumor-infiltrating lympocytes in breast cancer. J Immunother Cancer, 4:59.
10. Eikawa S, Nishida M, Mizukami S, Yamazaki C, Nakayama E, Udono H (2015). Immune-mediated antitumor effect by type 2 diabetes drug, metformin. Proc Natl Acad Sci U S. 112(6):1809-14.
11. Luen S J, Savas P, Fox S B, Salgado R, Loi S (2017). Tumour-infiltrating lymphocytes and the emerging role of immunotherapy in breast cancer. Pathology 2017 February; 49(2):141-155.

12. Disis M L (2010). Immune Regulation of Cancer J Clin Oncol. 28(29): 4531-4538.
13. Choi J, Gyamfi J, Jang H, Koo J S (2018). The role of tumor-associated macrophage in breast cancer biology. Histol Histopathol 33(2):133-145.
14. Sica A, Mantovani A (2012). Macrophage plasticity and polarization: in vivo veritas. J Clin Invest 122(3):787-795.
15. Martinez F O, Gordon S (2014). The M1 and M2 paradigm of macrophage activation: time for reassessment. F1000Primer Rep 6:13.
16. Sakaguchi, S., T. Yamaguchi, T. Nomura, and M. Ono. 2008. Regulatory T cells and immune tolerance. Cell 133: 775-787.
17. Facciabene A, Motz G T, Coukos G. T Regulatory Cells: Key Players in Tumor Immune Escape and Angiogenesis. Cancer Res. 2012, 72(9):2162-2171.
18. Chang L Y, Lin Y C, Kang C W, Hsu C Y, Chu Y Y, Huang C T, Day Y J, Chen T C, Yeh C T, Lin C Y. The Indispensable Role of CCR5 for In Vivo Suppressor Function of Tumor-Derived CD103+Effector/Memory Regulatory T Cells. J Immunol 2012; 189:567-574.
19. Anz D, Mueller W, Golic M, Kunz W G, Rapp M, Koelzer V H, Ellermeier J, Ellwart J W, Schnurr M, Bourquin C, Endres S (2011). CD103 is a hallmark of tumor-infiltrating regulatory T cells. Int J. Cancer; 129 (10):2417-26.
20. Flynn N J, Somasundaram R, Arnold K M, Sims-Mourtada J (2017). The Multifaceted Roles of B cells in Solid Tumors: Emerging Treatment Opportunities. Targ Oncol 12:139-152.
21. Olkhanud P B, Damdinsuren B, Bodogai M, Gress R E, Sen R, Wejksza K, Malchinkhuu E, Wersto R P, Biragyn A (2011). Tumor-evoked regulatory B cells promote breast cancer metastasis by converting resting $CD4^+$ T cells to T-regulatory cells. Cancer Res 15; 71(10):3505-15.
22. Schmidt S V, Nino-Castro A C, Schultze J L (2012). Regulatory $CD8^+$ T cells: there is more than just immune activation. Front Immunol 3:1.

Example 5: New Selective Estrogen Receptor Antagonists to Treat Breast Cancer Breast cancers (BC) with expression of estrogen receptor-alpha (ERα) occur in more than 70% of newly-diagnosed patients in the U.S. Endocrine therapy with antiestrogens or aromatase inhibitors is an important intervention for BCs that express ERα, and it remains one of the most effective targeted treatment strategies. However, a substantial proportion of patients with localized disease, and essentially all patients with metastatic BC, become resistant to current endocrine therapies. ERα is present in most resistant BCs, and in many of these its activity continues to regulate BC growth. Fulvestrant represents one class of ERα antagonists termed selective ER downregulators (SERDs). Treatment with fulvestrant causes ERα down-regulation, an event that helps overcome several resistance mechanisms. Unfortunately, full antitumor efficacy of fulvestrant is limited by its poor bioavailability in clinic. We have designed and tested a new generation of SERDs. Using ERα-positive BC cells in vitro, we find that these steroid-like compounds suppress ERα protein levels with efficacy similar to fulvestrant. Moreover, these new SERDs markedly inhibit ERα-positive BC cell proliferation in vitro even in the presence of estradiol-17β. In vivo, SERD128 significantly inhibited tumor growth in MCF-7 xenograft models in a dose-dependent manner ($P<0.001$). Further, our findings indicate that these SERDs also interact with immune cells expressing ER such as myeloid-derived suppressor cells (MDSC). Of note, MDSCs act to protect tumors from immune recognition in vivo. SERD-induced blockade of MDSCs may allow interaction of immune checkpoint inhibitors with BC cells thereby leading to enhanced tumor killing. Since monotherapy with checkpoint inhibitors has not been effective for most BCs with resistance to endocrine therapy, combination therapies with SERDs that enhance immune recognition may increase immunotherapy responses in BC and improve patient survival. Hence, these new ERα antagonists that also promote ER degradation may potentially benefit patients who are unresponsive to current endocrine therapies.

Example 6: Antiestrogens in Combination with Immune Checkpoint Inhibitors in Breast Cancer Immunotherapy Breast cancers (BC) with expression of estrogen receptor-alpha (ERα) occur in more than 70% of newly-diagnosed patients in the U.S. Endocrine therapy with antiestrogens or aromatase inhibitors is an important intervention for BCs that express ERα, and it remains one of the most effective targeted treatment strategies. However, a substantial proportion of patients with localized disease, and essentially all patients with metastatic BC, become resistant to current endocrine therapies. ERα is present in most resistant BCs, and in many of these its activity continues to regulate BC growth. Fulvestrant represents one class of ERα antagonists termed selective ER downregulators (SERDs). Treatment with fulvestrant causes ERα down-regulation, an event that helps overcome several resistance mechanisms. Unfortunately, full antitumor efficacy of fulvestrant is limited by its poor bioavailability in clinic. We have designed and tested a new generation of steroid-like SERDs. Using ERα-positive BC cells in vitro, we find that these compounds suppress ERα protein levels with efficacy similar to fulvestrant. Moreover, these new SERDs markedly inhibit ERα-positive BC cell transcription and proliferation in vitro even in the presence of estradiol-17β. In vivo, the SERD termed SERD128 significantly inhibited tumor growth in MCF-7 xenograft models in a dose-dependent manner ($P<0.001$). Further, our findings indicate that these SERDs also interact with ER-positive immune cells in the tumor microenvironment such as myeloid-derived suppressor cells (MDSC), tumor infiltrating lymphocytes and other selected immune cell subpopulations. SERD-induced inhibition of MDSCs and concurrent actions on $CD8^+$ and $CD4^+$ T-cells promotes interaction of immune checkpoint inhibitors with BC cells in preclinical models, thereby leading to enhanced tumor killing even among highly aggressive BCs such as triple-negative BC that lack ERα expression. Since monotherapy with immune checkpoint inhibitors has not been effective for most BCs, combination therapies with SERDs that enhance immune recognition may increase immunotherapy responses in BC and improve patient survival. Hence, ERα antagonists that also promote ER downregulation may potentially benefit patients who are unresponsive to current endocrine therapies.

Endocrine therapies that target the estrogen receptor (ER) in breast cancer (BC) have significant clinical benefit when used to treat ER-positive tumors and are often an effective targeted treatment for metastatic disease. However, a substantial number of patients with localized disease, and almost all patients with metastatic breast cancer, become resistant to endocrine therapies [1-3]. In the absence of options to current treatments such as antiestrogens (tamoxifen) or aromatase inhibitors (AI), cytotoxic chemotherapy is often the only alternative. Similarly, chemotherapies are often used for patients with triple-negative breast cancer (TNBC). The TNBC subtype occurs in 15-20% of BC patients and cannot be managed with endocrine or HER2-targeted therapies because TNBCs lack ERα and progesterone receptor (PR) expression and have no HER2 overexpression. However, recent clinical trials reveal that 20-30% of TNBC patients respond to immunotherapy such as immune checkpoint inhibitors (ICI) [4, 5]. Despite this advance, the great majority of patients with TNBC and other BC subtypes do not benefit from ICIs.

In the context of estrogen signaling in BC in vivo, it is important to note that estrogens do not only act directly on BC cells. Rather, it is known that estrogens also regulate the development and function of immune cells that occupy the tumor microenvironment (TME) [6-8]. Despite well-known sex-related differences in immune responses in various autoimmune diseases [9], little is known to date about the effect of estrogens or antiestrogens on tumor immune tolerance and immune checkpoint blockade in breast cancer. ERα, the major ER form, is known to exhibit high expression in early hematopoietic progenitors in bone marrow such as hematopoietic stem cells and common lymphoid and myeloid progenitors [6-8, 10, 11]. The programmed death-1 (PD-1) pathway is an immune checkpoint used by many tumor cells to evade detection and attack by tumor-directed T-cells [12-14] that are known to express ER [11]. PD-1 is expressed at the surface of activated T-cells where it interacts with its ligands, such as programmed death ligand-1 (PD-L1), to attenuate T-cell signaling, resulting in down-regulation of T-cell proliferation, activation and the antitumor immune response. Although PD-L1 is rarely expressed in normal breast tissue, it is expressed in some BC cells and surrounding immune cells where it can mediate inhibition of tumor-infiltrating lymphocytes (TILs) which are a known prognostic indicator for benefit from ICIs [15, 16].

Among the subpopulations of immature myeloid cells that frequently arise during tumor progression and metastasis, myeloid-derived suppressor cells (MDSC) are known to express ER, and estrogen signaling is reported to promote MDSC expansion and activation in preclinical studies [7]. MDSCs are also identified in the TME of BC biopsies from the clinic [16, 17] and consist of two large groups of immune cells termed granulocytic or polymorphonuclear cells (G-MDSCs), which are phenotypically and morphologically similar to neutrophils, and monocytic cells (M-MDSCs) similar to monocytes. Immune suppression is a major property of MDSCs, with T-cells the main targets of MDSC action [16, 17]. Accordingly, estrogen antagonists may disrupt BC progression by diminishing MDSC numbers and associated pro-tumorigenic functions potentially regardless of the ER status of the tumor. Among the challenges to make immuno-therapy a more effective intervention in BC management going forward, it is important to find ways to manipulate additional mechanisms of tumor immune tolerance and to enhance T-effector cell infiltration and access to the tumor. It is therefore reasonable to investigate the concept that BC escape from immune attack may be blocked by potent antiestrogens that exert antitumor activity in certain ER-positive immune cells, actions that should boost the action of ICIs.

It is well established that estrogens modulate BC gene transcription by binding ER with high affinity, thereby activating downstream signaling by use of genomic pathways that involve direct DNA binding of ligand-bound ER to estrogen-responsive elements in the promoter regions of responsive genes. In addition, nongenomic pathways often involve indirect modulation of transcription by ER interactions with components of other transcription or growth factor receptor kinase signaling complexes (such as MAPK, PI3K/AKT) via specific protein-protein interactions [18]. Current reports indicate that estrogen signaling in MDSCs occurs in part by the induced phosphorylation and activation of STAT3 which stimulates downstream signaling for the expansion of MDSCs [7]. STAT3 is required for MDSC survival and proliferation and also modulates expression of S100A8 and S100A9 proteins that are important for regulating MDSC expansion and migration to tumor sites [7, 8].

Antiestrogen therapy with tamoxifen has been widely used for more than 40 years, with evidence from clinical trials for significant reductions in BC mortality in ER-positive early BC [1, 19]. Although effective, tamoxifen has important drawbacks, including a limited period of activity before drug resistance; and an increased risk of endometrial cancer and thromboemboli due to its partial agonist activity as a selective ER modulator [2, 3, 20]. Use of AIs for postmenopausal patients has yielded better outcomes than the standard of 5 years tamoxifen [2, 19, 21]; but in patients with advanced breast cancer, only about ⅓ of ER-positive BCs respond to AIs, and resistance can evolve due to ER activation by different mechanisms such as ligand-independent activation [2, 3, 20-22] or emergence of ESR1 mutations [23, 24]. Consequently, a search is underway to discover new antiestrogens that lack agonist activity and override endocrine-resistance [20, 25]. As long as ER is present in breast tumors, growth may be stimulated by estrogen, partial agonists or estrogen-independent action. The first selective ER downregulator (SERD), fulvestrant, has no major agonist activity and good antitumor efficacy [20, 26, 27]. However, fulvestrant has very low bioavailability that is a significant liability in clinic [28]. Although fulvestrant has activity in ER-positive BCs that progress after AIs or tamoxifen including some patients with ESR1 mutations, discovery of improved SERDs with improved bioavailability and antitumor activity is a key goal. In 14-20% of metastatic ER-positive BCs from patients with multiple prior endocrine therapies, there is evidence for acquisition of functionally-aberrant ESR1 with point mutations often occurring in the ER ligand-binding domain, most commonly at D538G and Y537S [23, 24]. Some mutant ESR1 variants may continue to respond to fulvestrant, but higher doses of fulvestrant are required to achieve wild-type levels of tumor inhibition. Current data show that achievement of higher optimal doses of fulvestrant by intramuscular drug delivery is not feasible and underscore the need to develop more potent SERDs with enhanced bioavailability in advanced BC. A number of non-steroidal SERD candidates have been assessed, with many failing to advance beyond Phase I-II trials due to agonist activity in normal tissues, other off-target adverse side-effects or for unknown reasons [29, 30]. With this history, we elected to design estradiol-like SERDs targeting ER that differ from proposed nonsteroidal drugs. These new SERDs and fulvestrant were then assessed for antitumor activity in BCs as well as in ER-positive immune cells that occupy the TME and interactions with immune checkpoint inhibitors that may be beneficial to management of both ER-positive and potentially ER-negative BCs in the clinic.

Materials and Methods

Chemistry Procedures for Synthesis of 11β-Aryloxy-Estradiol Derivatives

Reagents: Tetrahydrofuran (THF) was distilled from benzoquinone ketyl radical under an argon atmosphere. Dichloromethane, toluene, benzene, and pyridine were distilled from calcium hydride under an argon atmosphere. Anhydrous N, N-dimethylformamide (DMF) was purchased from Sigma-Aldrich. All ther solvents or reagents were purified according to standard procedures. (8S, 9S, 13S, 14S, 17S)-3,17-bis(Benzyloxy)-13-methyl-6, 7, 8, 9, 12, 13, 14, 15, 16, 17-decahydro-11H-cyclopenta[a]phenanthren-11-one (11-ketone) was prepared using established procedures [31-34].

Instrumentation: $^{1}H$ NMR, $^{13}C$ NMR, and $^{19}F$ NMR spectra were obtained at 300 MHz, 400 MHz, or 500 MHz for proton, 75 MHz, 100 MHz, or 125 MHz for carbon, and 282 MHz, or 376 MHz for fluorine are so indicated. The chemical shifts are reported in parts per million (ppm, δ). The coupling constants are reported in Hertz (Hz) and the resonance patterns are reported with notations as the following: br (broad), s (singlet), d (double), t (triplet), q (quartet) and m (multiplet). High-resolution mass spectra were measured on a time-of-flight LC-MS. Thin-layer chromatography (TLC) was carried out using precoated silica gel sheets. Visual detection was performed with ultraviolet light, p-anisaldehyde stain, potassium permanganate stain or iodine. Flash chromatography was done using silica gel P60 (60 A, 40-63 μm) with compressed air.

General chemistry procedures to prepare the several antiestrogen compounds described in this report are presented in detail in Example 1.

Cell Culture

Cell lines were obtained from the American Type Culture Collection (ATCC) and cultured according to ATCC recommendations. Briefly, ERG-positive human BC cells MCF-7, T47D and ZR-75 were cultured in DMEM or RPMI-1640 media as before [35, 36], and MCF-7 cells with HER-2 overexpression [37] and MCF-7 cells with acquired tamoxifen resistance were established and cultivated as reported previously [38, 39]. Mouse triple-negative (ERα−/PR−/HER2−) 4T1 breast tumor cells were cultured in RPMI-1640 medium. Media were supplemented with 10% fetal bovine serum (FBS; Gemini Bio-Products), 100 units/ml penicillin, 100 μg/ml streptomycin sulfate and 2.5 μg/ml amphotericin B (Gemini Bio-Products). Cultures were maintained at 37° C. in a 5% CO2 incubator. For steroid-free conditions, medium was changed 48 hrs before studies to phenol red-free DMEM or phenol red-free RPMI-1640 with 5% dextran-coated, charcoal-treated (DCC-FBS) as before [35].

Cell Proliferation Assays

MCF-7 and other selected BC cells were seeded in 96-well plates at 3-5×$10^5$ cells/well in complete medium. After 24 hours, medium was switched to estrogen-free conditions as described above. After 48 hrs, cells were treated with indicated concentrations of antiestrogens for 72 hrs with or without estradiol-17β (E2). Cell number and viability were determined by either cell counts or by colorimetric assays using the CELLTITER 96 AQUEOUS (Promega) assay or the cell proliferation ELISA BrdU assay (Roche) as per manufacturer's instructions. Treatments were done in quadruplicate, and experiments were repeated at least three times. In selected experiments using the INCUCYTE™ Live Cell System (Essen Bioscience) as per the manufacturer's instructions, the proliferation of 4T1 cells maintained in a tissue culture incubator was monitored by using the NucLight Rapid Red Reagent for cell labeling in 6-well plates. Images for cell confluence were obtained every 4-6 hrs; as cells proliferate, the confluence increases, and confluence is therefore a surrogate for proliferation. Images were analyzed using the Live-Cell Analysis System (Essen Bioscience).

Polyacrylamide Gel Electrophoresis and Western Immunoblotting

MCF7 cells were plated in regular medium. After 24 hrs, cells were incubated in the presence of antiestrogens or fulvestrant for 4 hrs in phenol-red free medium without FBS. Cell lysates were prepared using RIPA buffer, and protein concentration was determined using the BCA Protein Assay Kit (PIERCE/ThermoFisher Scientific). Forty micrograms of total cell protein was resolved by 4-15% SDS-PAGE, transferred to a PVDF membrane and probed with antibody directed against ERα (1D5, 1:100, ThermoFisher cat #MA5-13191). RPL13A (dilution 1:1000, Invitrogen/ThermoFisher cat #PA5-58528) was used as loading control.

Competition Binding Assays in ER-Positive Human Breast Tumor Cells

Specific estradiol-17β (E2) binding and competition for binding by antiestrogen SERD128 or fulvestrant was assessed in human MCF-7 breast cancer cells using methods as described before [36, 40]. In brief, MCF-7 cells were suspended in phenol red-free RPMI medium to a concentration of 1×$10^7$ cells/ml, and incubations for 60 min were begun with the addition of [2,4,6,7-$^3H$ (N)]-estradiol-17β (99 Ci/mmol; New England Nulcear/Perkin Elmer, Waltham, MA) at 37° C. with shaking. A 100-fold molar excess of unlabeled estradiol-170 was present in paired samples to determine displaceable binding [40]. Competitive ligand binding to ER-positive MCF-7 cells is detected by the ability of a test compound to displace labeled estradiol-17β from the cells in vitro.

Estrogen Receptor-Dependent Transcriptional Activity

A stable ER-positive T47D ERE luciferase reporter cell line, in which the ERE and the reporter luciferase gene are consistently expressed in the cell line were used in this study (Signosis). The cell line was established by transfection of luciferase reporter vector along with neomycin expression vector followed by neomycin selection, with neomycin-resistant clones subsequently screened for E2 induced luciferase activity or for measurement of potential antiestrogenic activity. Early passages of cells were cultured in complete medium containing RPMI supplemented with penicillin (100 units/mL), streptomycin (100 μg/ml), 10% FBS and G418 (75 μg/ml). At 24 hrs prior to assays, cells were trypsinized, washed and plated in each well of a 96-well plate with 5×$10^4$ cells in 100 μl with phenol-red-free medium containing 0.1% dextran-coated charcoal-treated FBS[41, 42]. Cells were then treated with 17β-estradiol alone or combined with fulvestrant or SERD128 for 24 hrs. Thereafter, media was removed by aspiration and 100 μl of PBS was added to each well, followed by aspiration of medium and addition of 50 μl of lysis buffer to each well. Cells were incubated in lysis buffer for 30 min at room temperature. Lysate was mixed 1:1 with luciferase substrate (Promega), and luminescence was measured using a MLX microtiter plate luminometer (Dynex) and quantified as relative light units (RLU) according to established procedures [41, 42]. Total protein was quantified using BioRad Protein Assay (BioRad).

In Vivo Breast Tumor Models

Animals were housed in a pathogen-free environment with controlled light and humidity and received food and water ad libitum. All studies were approved by the UCLA Animal Research Protection Committee.

For experiments using human BC cells as subcutaneous xenografts, ovariectomized female nude mice at 6 weeks of age were obtained from Charles River. MCF-7 human BC cells ($2\times10^7$) were implanted in the flanks of mice who had been primed three days before cell injections with estradiol-17β (0.36 mg, 60 days slow-release pellets, Innovative Research of America) as before [35, 36, 43]. When tumors grew to 50-100 $mm^3$, animals were randomized to different treatment groups including a) vehicle control, b) SERD128 at 15 mg/kg (by oral gavage daily for 28 days) and c) SERD128 at 75 mg/kg (by oral gavage daily for 28 days). Tumor volumes for mice in experimental and control groups were measured every 3-4 days, with tumor volume calculated by (l×w×w)/2, with tumor length l, and tumor width w in mm. Data were presented as the mean±SEM for tumor volumes measured in cubic mm. Data were analyzed by use of ANOVA and student's t-test statistical approaches as before [35, 36, 43].

To determine the potential effect of estrogen depletion on the progression of tumors in vivo, 4T1 murine TNBC cells (ATCC) were injected in the $4^{th}$ mammary fat pad ($2\times10^5$ cells) of either ovariectomized or sham-operated 6-week-old syngeneic female BALB/c mice (Jackson Laboratory). Tumors were measured every 3-4 days, and tumor volume was calculated as (l×w×w)/2 as above.

In further studies to determine the effects of antiestrogen treatment alone or in combination with anti-PD-L1 antibody on murine tumor progression in vivo, ovariectomized 6-week-old female syngeneic BALB/c mice were used (Jackson Laboratory). Three days prior to tumor cell inoculation, mice were injected with estradiol-17β (0.36 mg, 60 days slow-release pellets, Innovative Research of America). 4T1 cells were inoculated in the $4^{th}$ mammary fat pad ($2\times10^1$ cells), and mice were randomized after tumors reached an average size of 200-250 $mm^3$. For treatment, mice were divided into 6 groups: a) vehicle control or isotype IgG (IgG2b, κ, RTK4530, Biolegend), b) anti-PD-L1 antibody (Biolegend anti-CD274/B7-H1/PD-L1 clone 10F.9G2, 100 μg/mouse by intraperitoneal injection, every third day), c) fulvestrant (5 mg/mouse subcutaneous, once a week), d) SERD128 (50 mg/kg by oral gavage, daily) and e) combination treatment of fulvestrant and anti-PD-L1 antibody or f) SERD128 and anti-PD-L1 antibody at doses as described for treatment as single agents. Tumors were measured every 3-4 days, and tumor volume was calculated as above. After 10-12 days, mice were anesthetized by established methods, with blood collected by cardiac puncture in BD vacutainer vials with EDTA (terminal procedure). An approved secondary method of euthanasia was then used to ensure animals were deceased. Tumors were harvested, with final tumor weights and sizes compared among groups. Mass cytometry studies to assess selected immune cell populations and biomarkers were performed as detailed below.

Mass Cytometry for Analyses of Immune Cell Subpopulations. Cytokines and Selected Biomarkers Tumors from each mouse were harvested after 10-12 days of treatment as described above. Single cell suspensions were generated from tumors using the MACS mouse tumor dissociation kit (Miltenyi Biotech Cat. 130-096-730) following manufacturer's instructions. One million cells per tumor were resuspended in PBS and labeled with Cell-ID Cisplatin (Fluidigm, Cat. 201064) to assess for live/dead cells. For antibody labeling, we used the recommended cell surface staining procedure (Fluidigm) followed by the FoxP3/Transcription Staining Buffer Set protocol (eBiosciences™). Cells were labeled with a panel of 28 metal-conjugated antibodies to determine different immune lineages in addition to memory, trafficking, activation, and exhaustion markers (see Tables 2-3 for list of antibodies). After washing and centrifugation, cells were fixed using MaxPar Fix and Perm buffer (Fluidigm, Cat. 201067) and labelled for single cell discrimination with Cell-ID Intercalator-Ir (Fluidigm, Cat. 201192A). Samples were resuspended with 10% EQ four-element calibration beads (Fluidigm, Cat. 201078), and filtered through a 40 μm mesh filter prior to acquisition on a HELIOS' mass cytometer (Fluidigm), at a rate of 300-500 events/s.

TABLE 2

List of antibodies used in mass cytometry experiments

| | Mass/Element | Target protein | Clone | Vendor |
|---|---|---|---|---|
| 1 | 89Y | CD45 | 30-F11 | Fluidigm |
| 2 | 115In | Ki67 | SolA15 | eBiosciences |
| 3 | 139La | ERα | C-542 | Abcam |
| 4 | 141Pr | TNFα | MP6-XT22 | Fluidigm |
| 5 | 142Nd | CD11c | N418 | Fluidigm |
| 6 | 143Nd | CD69 | H1.2F3 | Fluidigm |
| 7 | 144Nd | IL-2 | JES6-5H4 | Fluidigm |
| 8 | 146Nd | F4/80 | BM8 | Fluidigm |
| 9 | 147Sm | EOMES | Dan11mag | Thermofisher Scientific |
| 10 | 148Nd | CD11b (Mac-1) | M1/70 | Fluidigm |
| 11 | 149Sm | CD19 | 6D5 | Fluidigm |
| 12 | 150Nd | Ly-6C | HK1.4 | Fluidigm |
| 13 | 151Eu | Ly-6G | 1A8 | Fluidigm |
| 14 | 152Sm | CD3e | 145-2C11 | Fluidigm |
| 15 | 153Eu | CD274 (PD-L1) | 10F.9G2 | Fluidigm |
| 16 | 155Gd | CD25 (IL-2R) | 3C7 | Biolegend |
| 17 | 158Gd | FoxP3 | FJK-16S | Fluidigm |
| 18 | 159Tb | CD279 (PD1) | 29F.1A12 | Fluidigm |
| 19 | 160Gd | CD62L (L-selectin) | MEL-14 | Fluidigm |
| 20 | 162Dy | CD366 (TIM3) | RMT3-23 | Fluidigm |
| 21 | 165Ho | IFNg | XMG1.2 | Fluidigm |
| 22 | 167Er | CD335(Nkp46) | 29A1.4 | Fluidigm |
| 23 | 168Er | CD8a | 53-6.7 | Fluidigm |
| 24 | 169Tm | Tbet | 4B10 | Biolegend |
| 25 | 171Yb | CD44 | IM7 | Fluidigm |
| 26 | 172Yb | CD4 | Rm4-5 | Fluidigm |
| 27 | 174Yb | I-A/I-E (MHC class II) | M5/114.15.2 | Fluidigm |
| 28 | 175Lu | CD103 | 2E7 | Biolegend |

Antibodies that were purchased unlabeled were processed for metal conjugation by the UCLA Flow Cytometry Core. All conjugations were performed at 100 g scale using $X_8$ polymer as per manufacturer's protocol (Fluidigm). Appropriate antibody dilution of custom conjugated antibodies was determined by serial dilution staining experiments with replicates of relevant biological samples.

TABLE 3

List of antibodies used for Flow Cytometry.

| Target | clone | Fluorochrome | Isotype | company | Ref |
|---|---|---|---|---|---|
| CD45 | H130 | APC-Cy7 | Mouse IgG1, K | Biolegend | 304042 |
| CD15 | W6D3 | Ax647 | Mouse IgG1, K | Biolegend | 323012 |
| CD14 | M5E2 | BV785 | Mouse IgG2a, K | Biolegend | 301839 |
| CD11b | ICRF44 | PeCy7 | Mouse IgG1K | Biolegend | 301322 |
| CD3 | UCHT1 | PerCpCy5/PC5 | Mouse IgG1K | Biolegend | 300410 |
| CD19 | 3G8 | PerCpCy5/PC5 | Mouse IgG1, K | Biolegend | 302010 |
| CD20 | L27 | PerCpCy5/PC5 | IgG1, K | BD Biosciences | 340955 |
| CD56 | B159 | PerCpCy5/PC5 | Ms IgG1, K | BD Bioscience | 555517 |
| HLA DR | FITC | FITC | Immu-357 | Beckman Coulter | IM1638U |
| CD11c | 3.9 | BV711 | Mouse IgG1, K | Biolegend | 301629 |
| CD49d | 9F10 | BV605 | Mouse IgG1, K | Biolegend | 3044324 |
| Live/Dead | Aqua | (BV510) | — | Biolegend | |
| pSTAT3(pY705) | 4/P-Stat3 | PE | Ms IgG2a, K | BD Bioscience | 612569 |
| STAT3 | 15H2B45 | PE | Mouse IgG1, K | Biolegend | 371804 |

Dimensionality Reduction, Cluster Analysis and Visualization

Collected mass cytometry data was analyzed as previously described [44]. Briefly, samples were normalized utilizing a bead standard. First, each cytometry file was processed in FLOWJO (v10.3), then manually gated for stability of signal over time, followed by exclusion of normalization beads, ratio of DNA intercalators (191Ir+vs 193Ir+), with finally single cell events (Ir193 vs event length) (FIG. 24A). After that, viable (195Pt−)CD45+ events were exported and uploaded into the X-shift (VorteX) clustering environment to obtain the k-nearest-neighbor density estimation as described before [44, 45]. Dimensionality reduction of unclustered data was performed using the t-stochastic neighborhood embedding (t-SNE) and PhenoGraph algorithms implemented in the Cytofkit library [46], supplied by BIOCONDUCTOR v.3.4 and run in RSTUDIO v.1.1.463. A fixed number of 10,000 cells were sampled without replacement from each file and combined for analysis. Resulting t-SNE plots were subsequently filtered by marker expression to visualize differences between different treatment groups. Heatmaps were generated using Z-scores based on median marker expression (excel and Prism v7). Then, we used Wei et al. [47] criteria to exclude clusters from analyses that had an expression level lower than 0.5%.

Flow Cytometry and Bone Marrow Cell Analysis

Human myeloid-derived suppressor cells were expanded from bone marrow (BM) specimens of BC patients after standard Ficoll gradient purification and red blood cell lysis. Briefly, $2\times10^6$ BM cells were cultured in the presence of 1000 IU/ml of GM-CSF and 40 ng/ml IL-6 in different media conditions including regular RPMI-1640 with 15% FBS or phenol red-free medium with 15% DCC-FBS with or without 100 nM E2 (7). After 6 days of culture, cells were harvested, stained with a 14 antibody panel including anti-phospho-STAT3 (pSTAT3) and analyzed by flow cytometry with an LSRII with a 5 lasers (UV, violet, blue, green-yellow and red). Data was processed using FlowJo (v10.3). De-identified BM specimens were retrospectively-collected and deposited in the UCLA Pathology Tumor Bank according to Human Subject Protection Committee guidelines at our institution.

Statistics

For in vitro studies, triplicates of experiments were done to verify results. ANOVA or t-tests were used as appropriate to compare interventions. Analyses of cells were evaluated using bar and scatter graphs with mean, standard deviation (SD) and standard error (SE). Repeated measures ANOVA was used as appropriate to assess time, condition, and time by condition interaction effects. For in vivo studies, mice with similar tumor size were randomized to different treatment groups with controls for up to 28 days. Data analyses by appropriate parametric or nonparametric methods were applied [22, 35-37]. Briefly, these analyses use mixed-effects models with tumor size as outcome measure (transformed as needed). Analyses of mass and flow cytometry data were performed using GraphPad Prism version 7.0 (GraphPad, San Diego, CA) using one-way ANOVA followed Bonferroni's multiple comparisons test or two-tailed unpaired Student's t-test approaches as described before [44, 45, 48, 49]. Differences were considered significant for P values less than 0.05.

Results

SERD Synthesis and Properties

We designed, synthesized and screened more than 65 new SERD candidates, all of which have the general structure shown in 1', namely 11β-aryloxy estradiols, with a basic amine positioned at the 4-position of the aryl ring (FIG. 16). The basic amine is connected to the aryl unit either directly or via a spacer that varies from 3-6 atoms. In some of the more active compounds, we also attached an electron-withdrawing group, e.g. a trifluoromethyl unit or a fluoride atom, in the 3-positon (ortho to the amino chain). Of these compounds, several had activity comparable to fulvestrant 2' but SERD128, 22, in particular was more potent than fulvestrant in a number of antitumor assays as shown below. We note that this new class of steroid-like SERDs lack the prototypical side chain (as in fulvestrant) widely used to design other drugs with ERα antagonism, but these SERD candidates generate a full antagonist profile and induce significant ERα down-regulation, likely similar to significant 'indirect' receptor antagonism as reported in previous independent studies of 11β-substitutions in ERα [51, 52] and other structural changes as in an independent report [53].

This new series of estradiol analogues, namely 11β-(4-aminoalkyl) aryloxy-estradiols, are expected to bind the ER ligand-binding domain since they are close structural analogues of estradiol (cf. Hansen et al. [52]). The 11β-aryloxy group, bearing a variable length chain ending in a basic dialkylamino group, would be expected to block the folding of helix-12 by potentially both steric hindrance and a salt bridge formation between the protonated amine and an acidic side chain on helix 12. Thus, these ER antagonists should bind to ER in such a way as to prevent the folding of helix-12 and thereby potentially inhibit BC proliferation.

The synthesis of the new analogues (FIG. 17) started with estradiol 2 which was converted into the bis (benzyloxy) ketone 3 by a known route [31-34] (protection, benzylic oxidation to the 9, 11-alkene, hydroboration-oxidation, and final oxidation to the ketone). Reduction of this protected ketone 3 with sodium borohydride afforded the expected 11β-alcohol 4 by attack of the hydride on the less hindered α-face, away from the hindering 13β-methyl group. Formation of the 11β-alkoxide anion of 4 using potassium hydride in THF/DMF followed by addition of 4-fluoronitrobenzene effected a clean SNAr reaction to afford the 4-nitrophenyl ether 5. Nickel boride reduction [54, 55] of the nitro group (sodium borohydride with $NiCl_2 \cdot 6H_2O$ in methanol) gave the aminophenyl ether 6 in good yield. Removal of the two benzyl ethers from 6 by catalytic hydrogenolysis using $Pd(OH)_2$ in methanol gave the first analogue, the simple aniline 7 (SERD105), namely 11β-(4-aminophenyloxy) estradiol. For nearly all of the other analogues, the crude aniline 6 was not isolated but rather treated directly with an acid chloride. The analogues having a three-atom linker between the aryl ring and the basic amine were all prepared by the same route. Thus, treatment of 6 with chloroacetyl chloride and catalytic DMAP in triethylamine afforded the intermediate chloroacetamide, which was immediately reacted with one of four secondary amines, e.g., piperidine, pyrrolidine, morpholine, and dimethylamine, to give the amides.

Again hydrogenolysis of the benzyl ethers using hydrogen and a palladium catalyst gave the desired analogues, 8a-d (SERD101-SERD104). After coupling of 6 with the acid chloride to give the amide, hydride reduction afforded the 2-(dialkylamino)ethyl amines, the benzyl ethers of which were hydrogenolyzed to give another set of analogues 9a-d, namely the N-(2-aminoethyl)anilines. In addition the 4-amino group was completely removed to give the simple 11β-phenyl ether 10.

The next set of analogues each had a 3-carbon chain between the aniline and the secondary amine (see FIG. 18). Thus treatment of the crude aniline 6 with 3-chloropropionyl chloride furnished the 3-chloropropanamide and displacement of the chloride with the secondary amines and subsequent hydrogenolysis afforded the analogues with a 5-atom side chain ending in the basic amine, 11a-d (SERD106-109).

Likewise using 4-chlorobutanoyl chloride, after displacement of the chloride with the secondary amines and subsequent hydrogenolysis, one obtained the analogues with a 6-atom side chain ending in the basic amine, 12a-d (SERD110-112, SERD116). Finally, following the same route starting with 5-chloropentanoyl chloride gave the analogues with a 7-atom side chain, 13a-d. Again after coupling of 6 with the 3-carbon acid chloride to give the amide, hydride reduction afforded the 2-(dialkylamino)ethyl amines, the benzyl ethers of which were hydrogenolyzed to give another set of analogues 14a-d, namely the N-(3-aminopropyl) anilines. By substituting the 4-fluoronitrobenzene unit for other aryl fluorides, one could prepare several other sets of analogues (see FIG. 19). Thus, alkylation of the 11β-alcohol 4 with 2, 4-difluoronitro-benzene led to the 3-fluoro-4-nitrophenyl ether (which after hydrogenolysis gave the analogue 15). From that compound were prepared the 16 analogues, 17a-d, 18a-d, 19a-d, and 20a-d and the unsubstituted aniline 16. In a similar manner, using 4-fluoro-2-(trifluoromethyl) nitrobenzene to alkylate the anion of 6 resulted in the 3-trifluoromethyl-4-nitrophenyl ether (which after hydrogenolysis gave the analogue 21) and thus the 16 additional analogues, 23a-d, 24a-d, 25a-d, and 26a-d and the unsubstituted aniline 22.

Selected Steroid-Like SERD Candidates Promote ER Downregulation. Bind ER-Positive Breast Tumor Cells and Block ER-Dependent Transcription In Vitro.

We used different assays to screen antiestrogen/SERD candidates (see FIGS. 16-19), including determination of the effect of antiestrogens on downregulation of ERα protein using PAGE and Western immunoblots (FIG. 20A). As shown in the figure, SERD candidates 128 and 140 were most effective in reducing ER protein levels in ER-positive MCF-7 BC cells in vitro, with the effect of 128 comparable to that of fulvestrant. Additional studies were also done to assess competitive binding of SERD128 in MCF-7 cells (FIG. 20B) and inhibition of ER-dependent transcription in ER-positive T47D BC cells stably transfected with an ER-dependent luciferase reporter gene (FIG. 20C).

The combined results of these studies indicate that SERD128 is a promising SERD with ER antagonist activity in ER downregulation, target cell binding and ER-dependent transcription comparable to that of the pure antiestrogen fulvestrant.

Steroid-Like SERD128 Inhibits Human BC Progression In Vitro and in Xenograft Models In Vivo.

Investigations of the properties of SERD128 in blocking the progression of human breast tumors in vitro and in vivo. As shown in FIG. 21A, the E2-induced proliferation of several ER-positive BC cells including MCF-7, T47D and ZR75 cells was significantly inhibited by treatment with 10 nM SERD128 (all at $P<0.001$).

This antiproliferative action of SERD128 was also found with different MCF-7 cell populations that included cells with no HER2-overexpression (MCF-7/PAR), cells with HER2-overexpression (MCF-7/HER2) and MCF-7 cells with tamoxifen resistance (MCF-7/TMR).

In FIG. 21B, orally administered SERD128 is shown to inhibit the growth of human MCF-7 breast tumor xenografts in vivo in a dose-dependent manner. MCF-7 cells were subcutaneously inoculated in nude mice previously primed with estradiol pellets. When animals developed tumors of comparable size, they were randomized to treatment with vehicle control (vehicle) or SERD128 at 15 and 75 mg/kg once a day by oral gavage. It is important to note that SERD128, in contrast to fulvestrant [28], has potent biologic action in blocking the progression of breast tumors in vivo via an oral route of administration.

Effects of Estrogen and Antiestrogens on Expansion and Activation of Human Immune MDSCs Emerging findings indicate that E2 can modulate expansion/activity of MDSCs [7, 8, 17]. Since MDSCs that often occur in the TME reportedly play a critical role in tumor immune tolerance and cancer progression, we assessed effects of E2 and potential antagonist effects of fulvestrant and SERD128 (FIGS. 22A-22B).

In these studies, we used archival retrospectively-collected bone marrow (BM) cells from de-identified BC patients. The BM cells were purified by established methods and then stimulated with cytokines under conditions specified in FIGS. 22A-22B. Thereafter, MDSC cells were detected using established gating strategies by flow cytometry. When compared to MDSCs derived from BM cultivated in normal medium containing E2 and cytokines, several findings are apparent: a) MDSC levels are markedly reduced in E2-free medium; b) addition of E2 to E2-depleted medium stimulates significant expansion of MDSC numbers; c) SERD128 and fulvestrant each block E2-induced expansion of MDSCs, and the effect of SERD128 exceeds that of fulvestrant at equivalent doses (all at $P<0.05$; FIG. 22B, top panel). Furthermore, the accumulation of MDSCs is known to involve the expansion of immature myeloid cells and activation/conversion of immature cells to MDSCs, a process that appears to be driven at least in part by STAT3 signaling [17]. Importantly, estrogen is reported to activate such signaling pathways in MDSCs via the phosphorylation of STAT3 [7]. Accordingly, antiestrogen SERD128 is especially effective in blocking the phosphorylation and activation of STAT3 in G-MDSC subsets, an action that may be crucial for blocking the enhanced immunosuppressive activity of MDSCs in BC (FIG. 22B, lower panel).

Effects of Estrogens and Antiestrogens on ERα-Negative Tumor Growth In Vitro and In Vivo.

TNBC cells that lack expression of ERα, PR and HER2 amplification were selected for use in experiments to investigate the potential actions of antiestrogens primarily on immune cells in the TME. In mice with implants of E2-insensitive orthotopic tumors, Svoronos et al. [7] reported a significant survival benefit associated with ovariectomy (OVX; estrogen depletion) when compared to non-OVX controls (normal estrogen levels), while treatment of OVX mice with E2 reversed the protective effect of OVX. Further, the survival benefit of OVX was not observed in immune-deficient as compared to wild-type mice, suggesting that immune activity is critical in the antitumor effect of E2 depletion [7]. We confirm in our experiments that OVX reduces the progression of 4T1 TNBCs as compared to that of intact animals in a murine model, thus suggesting that ovarian E2 may play a role in stimulating TNBC growth in vivo (FIG. 23A) $P<0.0001$. To determine if estrogens have a direct effect on 4T1 TNBC (ERα-negative) cell proliferation, we used the Incucyte™ system as described in methods to investigate 4T1 cell progression in vitro. No growth stimulation of cells as monitored by cell confluence was observed when tumor cells were grown in the presence of E2 as compared to control-treated 4T1 cells over a time course of 5 days (FIG. 23B). Furthermore, treatment with SERD128 at doses ranging from 10-1000 nM did not elicit any significant effect on cell growth in vitro as shown in FIG. 23B. Together, these data indicate that effects of sex steroids on progression of 4T1 tumors in vivo are likely due to interactions with cells in the TME.

Furthermore, in this in vivo study, we assessed antitumor efficacy of SERD128 alone and combined with an anti-PD-L1 checkpoint antibody. The 4T1 tumor cells implanted in mammary glands exhibit highly aggressive behavior and are generally found to metastasize widely to cause early mortality. In contrast to a lack of effects of either estrogens or antiestrogens on 4T1 tumor progression in vitro, we find that the antiestrogens fulvestrant (not shown) and SERD128 are each effective in inhibition of 4T1 tumor growth in vivo in syngeneic BALB/c mouse models (FIG. 23C). Since these mice are immune-intact, we next assessed the effect of treatment with an anti-PD-L1 checkpoint inhibitor alone and in combination with SERD128. As shown in FIG. 23C, anti-PD-L1 antibody alone elicited no significant effect on 4T1 tumor progression, while SERD128 were each able to induce significant suppression of 4T1 tumor progression in vivo. These results appear to be consistent with the notion that antiestrogens interact with immune cells in the TME and may play an important role in stopping tumor progression in vivo. To investigate effects of antiestrogens and immune checkpoint inhibitors when administered in combination, we next used mass cytometry to study the immune cell subpopulations present in the TME in vivo.

Mass Cytometry Analyses Show that Antiestrogens Reduce MDSCs in Murine 4T1 Tumors in Syngeneic Mice.

To explore mechanistic pathways that underlie the antitumor effects of antiestrogens alone and combined with an ICI (FIG. 23C), we used mass cytometry by time of flight analyses (cyTOF) with a panel of selected labeled antibodies to track the levels and activities of immune cell subsets in the TME.

Figure 24F:
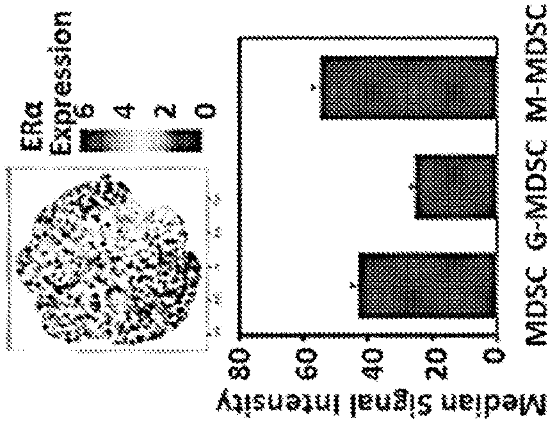

Single cell suspensions were prepared from 4T1 tumors grown in BALB/c mice that were treated for 12 days as detailed in FIG. 23C. Cells were then labeled and analyzed by cyTOF. Results of these analyses are summarized in FIGS. 24A-F. Of the two major MDSC subsets that have been described in humans and mice based on their phenotypic, morphological and functional characteristics (e.g. G-MDSC and M-MDSC), both G-MDSC and M-MDSC subsets are significantly reduced on treatments with either antiestrogens alone or when given in combination with anti-PD-L1 antibody as compared to appropriate controls (FIGS. 24D, 24E), with a somewhat enhanced effect on the G-MDSC population. The results indicate that this biologic effect of antiestrogens may be due to expression of ERα in both G-MDSC and M-MDSC subsets (FIG. 24F).

Effects of Antiestrogens on Tumor-Infiltrating Lymphocytes and Cytokines in 4T1 Tumors In Vivo.

In order to gain a better understanding of all tumor infiltrating leukocytes, we analyzed single cell suspensions from tumors (FIGS. 23C and 24A-24E) by looking at $CD8^+$ and $CD4^+$ TILs. An adaptive T-cell response, which requires antigen recognition, is composed of both cytotoxic $CD8^+$ T cells and $CD4^+$ T cells [56]. Animal models have shown that in vivo eradication of tumors is for the most part mediated by cytotoxic T-cells. The presence of intratumoral T-cells is an independent predictor of improved survival and has also been associated with increased secretion of interferon-gamma (IFNγ), interleukin-2 (IL-2) and TNFα [16, 57, 58]. As in FIG. 23C, treatment groups included mice treated with control vehicle, anti-PD-L1 antibody, fulvestrant, SERD128 or the combination of fulvestrant with anti-PD-L1 antibody or SERD128 and anti-PD-L1 antibody (FIGS. 25A-25F).

A sequential gating strategy to analyze tumor $CD3^+$ cell subsets is shown in FIG. 25A, while the normalized median intensity of distinct protein markers are show in a heatmap for all clusters analyzed by Cytofkit in FIG. 25B [44, 45]. tSNE scatter plots for visualization of $CD3^+$ cells that show clusters of $CD8^+$, $CD4^+$ and Tregs cells are presented in FIG. 25C. Importantly, the results show that both effector and effector memory $CD8^+$ and $CD4^+$ T-cells in tumors are several-fold higher in mice treated with either fulvestrant or SERD128 antiestrogens when combined with PD-L1 antibody as compared to controls ($P<0.05$) (FIG. 25D). In addition, we find increased expression of known activation cytokines IFNγ, IL-2 and TNFα in $CD8^+$ and $CD4^+$ TIL subpopulations (FIG. 25E). These data appear to complement reports on estrogen-specific alterations of these cytokines in independent murine models [59]. Finally, antiestrogen treatments evoke a significant reduction of T-regulatory T-cells (Tregs) (FIG. 25F) which are known to play an important role in the maintenance of tumor immune tolerance [60]. In the process of tumor progression, Treg cells tend to accumulate in tumors and suppress T-cell responses at the tumor site. The number of tumor-infiltrating $CD25^+$ $FoxP3^+$ Tregs is associated with poor prognosis and is identified as a significant predictor of poor outcome [61].

Effects of Antiestrogens Combined with ICIs on Macrophage and Dendritic Cell Subsets in 4T1 Tumors In Vivo.

Since recent findings suggest that cells of the innate immune system play an important role in the decision between an effective immune response versus induction of immune tolerance, we also investigated levels of dendritic cells (DC) that have a special function linking the innate immune response with the induction of adaptive immunity. These cells play a major role by processing and presenting antigens to T and B cells to generate an immune response. Stimulatory DCs promote effective immune responses by stimulating T-cell proliferation and shaping specific T-cell response phenotypes [62]. Importantly, treatment with both antiestrogens fulvestrant and SERD128 alone as well as combined with anti-PD-L1 antibody (as in FIG. 23C) increased the population of DCs in 4T1 tumors (FIG. 26A).

Further, it is well documented that the highly inflammatory microenvironment of tumors tends to recruit macrophages and peripheral blood monocytes [16]. These myeloid cells receive tumor-derived signals that alter gene expression and phenotype. A prominent myeloid cell subset that develops in the breast TME is the tumor-associated macrophage (TAM). Macrophages are key modulators and effector cells in the immune response that exhibit high plasticity in response to various external signals (61). Depending on TME signals, macrophages occur as M1 macrophages associated with 'tumoricidal' activity with high production of reactive nitrogen and oxygen intermediates and pro-inflammatory cytokines or M2 macrophages involved in tumor progression and immunoregulatory functions [63]. The M2 phenotype predominates among TAMs, and a high density of TAMs correlates with poor prognosis in BC [64]. CyTOF analyses based on experiments noted in FIG. 23C reveal that therapy with SERD128 combined with anti-PD-L1 antibody elicits a significant increase in the M1 tumoricidal subset of macrophages in the TME ($P<0.05$) while simultaneously trending toward a reduction in the M2 macrophage subset ($P=0.05$) (FIG. 26B), thus contributing to overall antitumor actions of dual antiestrogen-ICI therapy.

Discussion

The role of estrogen signaling in the progression of BCs with ERα expression is well-established by the successful use of ER antagonists in the clinic [2, 3, 19]. In addition, the present findings indicate that antiestrogens also have a significant effect on antitumor immunity independent of their direct activity on BC cells. Independent work has demonstrated that ICIs can improve overall survival for subsets of patients with advanced melanoma, lung and TNBC [4, 13], but the bulk of patients with BC, particularly ER-positive disease, do not have significant benefit from this promising therapeutic approach [4, 14]. Despite known sex-related differences in immune responses [9, 65, 66], little is known about the effect of sex hormones on immunotherapy in malignancy. An important question regarding the use of targeted therapies is whether these agents may positively or negatively affect immune cells. There is increasing awareness of the role of nonmalignant cells in the TME in regulating the tumor response to therapies. As indicated in the present report, the TME plays a critical role in modulating cancer progression and therapeutic responses. The presence of tumor-infiltrating lymphocytes in the TME is a prognostic indicator for benefit from ICI in TNBC, and T-cell inhibitory pathways in the TME such as MDSCs are identified [7, 8, 17]. Most immune cells including MDSC and $CD8^+$ T-cells express estrogen receptors, ERα and ERP, with ERα the predominant receptor type [7, 8, 10, 11, 17]. The accumulation of MDSCs is a complex process involving expansion of immature myeloid cells and pathologic activation and conversion of immature cells to MDSCs. Mechanistically, E2 signaling via JAK/STAT pathways may accelerate progression of E2-responsive and -unresponsive tumors by driving the expansion of MDSCs and enhancing their immunosuppressive activity in vivo as reported here and in previous work [7]. In contrast, blockade of E2 action appears to delay tumor progression due to a decrease in MDSC numbers and immunosuppressive activity that promotes T-cell-dependent antitumor immunity. Our findings suggest that antiestrogens particularly when administered in combination with anti-PD-L1 antibodies act to inhibit BC progression in part by blocking the expansion and mobilization of MDSCs that would otherwise promote tumor immune tolerance. In addition, emerging findings show that serine/threonine protein kinase casein kinase 2 that is known to be overexpressed in BC plays a critical role in the differentiation of myeloid cells. Importantly, inhibition of casein kinase 2 disrupts the differentiation of myeloid cells in BCs and enhances the efficacy of immunotherapy in mice [67]. This report is relevant to the present investigation because ERα signaling is known to activate transcription of casein kinase 2 [68], and ER antagonists block this action. We also note that Hamilton et al. [69] report that targeting the ER with fulvestrant enhances the immune-mediated cytotoxicity of human lung cancer cells.

In general, MDSCs are not present in healthy individuals but occur in pathologic states associated with chronic inflammation and cancer [17]. For example, BC biopsies from patients with residual disease after chemotherapy contain relatively high levels of infiltrating myeloid-derived cells [16]. However, recent reports suggest that these mechanisms may also be important during pregnancy, where E2 may drive the expansion and activation of MDSCs to promote maternal-fetal immune tolerance [70, 71]. Importantly, the current findings provide evidence in preclinical human and murine models that blockade of estrogen signaling acts to inhibit the expansion of MDSCs that are major contributors to pathologic myelopoiesis and immune tolerance in BC [7, 17]. In addition, ovariectomized mice with estrogen depletion have significantly reduced progression of murine E2-insensitive TNBCs when grown as implants in syngeneic immune-intact mice. These results are consistent with earlier reports on the crucial role of MDSCs and TILs on modulating antitumor immunity [7]. We note an independent report that treatment with the antiestrogen tamoxifen is also reported to block development of myeloproliferative neoplasms in mice without detrimental effects on normal hematopoiesis in preclinical models [72].

Antitumor immunity includes several functional steps required for an immune response to eliminate tumors, such as blockade of immunosuppression, promotion of immune infiltration, activation of antigen-presenting cells and enhancement of effector cell activity [73]. The presence of TILs in the TME is predictive of patient survival. Several types of $CD45^+$ leukocytes infiltrate the TME including $CD4^+$ and $CD8^+$ T-cells identified by specific phenotypic markers. It is recognized that effective antitumor immune responses require the involvement of both $CD4^+$ and $CD8^+$ T cells, with $CD4^+$ T cells critical for priming of tumor-specific $CD8^+$ T cells and for the secondary expansion and memory of $CD8^+$ T cells [74]. However, $CD4^+$ $FoxP3^+$ Treg cell-induced immune suppression represents a major obstacle for successful antitumor immunity. Accordingly, our data show that antiestrogens stimulate increments in the levels of effector and effector memory $CD8^+$ and $CD4^+$ T cells, while simultaneously suppressing the levels of immunosuppressive $CD4^+$ $FoxP3^+$ Treg cells. Furthermore, MDSCs are reported in turn to suppress antitumor activities of effector and memory effector $CD8^+$ T-cells in vivo [17] and other natural immune cells such as macrophages and dendritic cells [70, 75], actions that appear to be reversed on treatment with antiestrogens combined with ICIs in murine models in vivo. As suggested from our findings, cytokine secretion modulated by antiestrogen therapy may also play a role as functional chemo-attractants for selected immune cells. Hence, the current data provide evidence that beneficial antitumor effects occur on treatment of murine TNBCs with antiestrogens combined with ICIs in syngeneic, immune-intact mice, including promotion of effector and memory effector T-cells in the TME and modulation of macrophage and dendritic cell subsets. Thus, SERDs that enhance and/or maintain the activation status of effector T-cells may be used in dual therapies to enhance the effects of ICIs. A schematic representation of postulated effects of E2 signaling on immune cells in the TME is shown in FIG. 15.

Evidence suggests E2 may promote tumor immune tolerance through inhibition of $CD8^+$ and $CD4^+$ T cell effector responses, as well as NK and antigen-presenting cells such as M1 macrophages and dendritic cells (DC). In addition E2 signaling also stimulates immunosuppressive actions of MDSC that can increase Tregs and M2 macrophages for tumor-promoting activity. Antiestrogen therapy with SERDs helps to reverse the several actions of E2 and may represent a novel option in combination with immune checkpoint inhibitors to overcome an immunosuppressive BC microenviroment and stimulate more effective anti-tumor responses (FIG. 15).

Tumor mutational burden (TMB) and the expression of immune checkpoints such as PD-L1 also play an important role in determining tumor sensitivity to ICIs [4, 13, 76]. Reduced TMB and low expression of PD-L1 may be important factors that explain the relative resistance of most BCs to ICI therapies [4, 14]. In this regard, recent reports indicate that immunotherapeutic target expression on BCs such as α-lactalbumin, a lactation protein negatively regulated by E2, can be amplified several-fold by antiestrogen therapy and thereby potentially enhance the efficacy of ICIs if administered together with antiestrogens [77]. In addition, estrogens are also found to modulate the expression of PD-L1 in endometrial tissues [78, 79], in immune cells from reproductive tract and in ER-positive breast tumor cells in vitro [80, 81]. The latter work provides evidence that E2 may upregulate PD-L1 expression in ERα-positive BC cells to potentially suppress immune functions of T-cells in the TME and drive cancer progression. Of note, only 19.4% of patients with ER-positive/HER2-negative BCs were found to be PD-L1 positive in recent clinical trials, while 58.6% of TNBC patients screened in trials were PD-L1 positive [14, 82]. This difference in PD-L1 expression appears to account in part for a corresponding difference in clinical responses to ICI treatment. These reports raise the possibility of using antiestrogens as a priming approach to reverse immune-resistant 'cold' BCs to immune-sensitive 'hot' tumors more likely to respond to ICIs.

The current results also have implications for understanding potential gender- and/or age-dependent differences in tumor initiation and malignant progression. Humans show strong sex differences in immunity to infection and autoimmunity, suggesting sex hormones play a role in regulating immune responses. Indeed, receptors for E2 regulate cells and pathways in the innate and adaptive immune system, as well as immune cell development [83] and T cell functions [11, 80]. In malignancy, a recent meta-analysis of clinical trial data using ICIs (anti-PD-L1 and anti-CDLT4) found an overall survival hazard ratio of 0.72 for men receiving ICIs and 0.86 for women receiving ICIs, prompting a conclusion that the magnitude of benefit was sex-dependent and that different immuno-therapeutic approaches may be needed for men versus women [84]. However, another recent meta-analysis that included data on additional immunotherapy agents showed no statistically significant difference in the overall survival advantage between men and women [85]. Clearly, access to further updated data will be required to address limitations to such meta-analysis studies.

We note that ATP-competitive inhibitors of cyclin-dependent kinases 4/6 (CDK 4/6) such as abemaciclib were also reported recently to enhance the action of ICIs. The mechanism for this effect appears to involve modulation of T-cell activation and down-regulation of immunosuppressive myeloid populations [86]. This action may be dependent in part on the activity of E2, since E2 is well-known to stimulate expression/activity of cyclin D which is a requisite partner of CDK 4/6 to induce hyper-phosphorylation of Rb, thereby promoting cell proliferation and regulation of the cell cycle [87, 88].

Results of this translational research indicate that SERDs with strong antiestrogen activity such as SERD128 and fulvestrant and potentially other antiestrogens [89-92] can augment the action of immune checkpoint inhibitors to inhibit BC progression. This work provides a preclinical rationale for considering treatment combinations and schedules that include antiestrogens. Thus, use of antiestrogens together with ICIs could lead to timely introduction of this dual treatment strategy in both ER-positive and potentially ER-negative or treatment-resistant breast cancers, thus significantly expanding the application and life-extending benefits of these drugs in the clinic to promote patient survival.

REFERENCES CITED IN EXAMPLE 6

[1] Early Breast Cancer Trialists' Collaborative Group. Tamoxifen for early breast cancer: an overview of the randomised trials. Lancet 351(9114) (1998) 1451-1467.

[2] S. A. Hurvitz, R. J. Pietras, Rational management of endocrine resistance in breast cancer: a comprehensive review of estrogen receptor biology, treatment options, and future directions, Cancer 113(9) (2008) 2385-2397.

[3] C. K. Osborne, R. Schiff, Mechanisms of endocrine resistance in breast cancer, Annu Rev Med 62 (2011) 233-247.

[4] L. A. Emens, C. Cruz, J. P. Eder, F. Braiteh, C. Chung, S. M. Tolaney, I. Kuter, R. Nanda, P. A. Cassier, J. P. Delord, M. S. Gordon, E. ElGabry, C. W. Chang, I. Sarkar, W. Grossman, C. O'Hear, M. Fasso, L. Molinero, P. Schmid, Long-term Clinical Outcomes and Biomarker Analyses of Atezolizumab Therapy for Patients With Metastatic Triple-Negative Breast Cancer: A Phase 1 Study, JAMA Oncol (2018).

[5] P. Schmid, S. Adams, H. S. Rugo, A. Schneeweiss, C. H. Barrios, H. Iwata, V. Dieras, R. Hegg, S. A. Im, G. Shaw Wright, V. Henschel, L. Molinero, S. Y. *Chui*, R. Funke, A. Husain, E. P. Winer, S. Loi, L. A. Emens, I. M. T. Investigators, Atezolizumab and Nab-Paclitaxel in Advanced Triple-Negative Breast Cancer, N Engl J Med 379(22) (2018) 2108-2121.

[6] X. Jiang, D. J. Shapiro, The immune system and inflammation in breast cancer, Mol Cell Endocrinol 382(1) (2014) 673-682.

[7] N. Svoronos, A. Perales-Puchalt, M. J. Allegrezza, M. R. Rutkowski, K. K. Payne, A. J. Tesone, J. M. Nguyen, T. J. Curiel, M. G. Cadungog, S. Singhal, E. B. Eruslanov, P. Zhang, J. Tchou, R. Zhang, J. R. Conejo-Garcia, Tumor Cell-Independent Estrogen Signaling Drives Disease Progression through Mobilization of Myeloid-Derived Suppressor Cells, Cancer Discov 7(1) (2017) 72-85.

[8] T. Welte, X. H. Zhang, J. M. Rosen, Repurposing Antiestrogens for Tumor Immunotherapy, Cancer Discov 7(1) (2017) 17-19.

[9] V. R. Moulton, Sex Hormones in Acquired Immunity and Autoimmune Disease, Front Immunol 9 (2018) 2279.

[10] K. C. Lambert, E. M. Curran, B. M. Judy, G. N. Milligan, D. B. Lubahn, D. M. Estes, Estrogen receptor alpha (ERα lpha) deficiency in macrophages results in increased stimulation of $CD4^+$ T cells while 17beta-estradiol acts through ERα lpha to increase IL-4 and GATA-3 expression in $CD4^+$ T cells independent of antigen presentation, J Immunol 175(9) (2005) 5716-5723.

[11] I. Mohammad, I. Starskaia, T. Nagy, J. Guo, E. Yatkin, K. Vaananen, W. T. Watford, Z. Chen, Estrogen receptor alpha contributes to T cell-mediated autoimmune inflammation by promoting T cell activation and proliferation, Sci Signal 11(526) (2018).

[12] M. Black, I. B. Barsoum, P. Truesdell, T. Cotechini, S. K. Macdonald-Goodfellow, M. Petroff, D. R. Siemens, M. Koti, A. W. Craig, C. H. Graham, Activation of the PD-1/P D-L1 immune checkpoint confers tumor cell chemoresistance associated with increased metastasis, Oncotarget 7(9) (2016) 10557-10567.

[13] A. Ribas, J. D. Wolchok, Cancer immunotherapy using checkpoint blockade, Science 359(6382) (2018) 1350-1355.

[14] H. S. Rugo, J. P. Delord, S. A. Im, P. A. Ott, S. A. Piha-Paul, P. L. Bedard, J. Sachdev, C. L. Tourneau, E. M. J. van Brummelen, A. Varga, R. Salgado, S. Loi, S. Saraf, D. Pietrangelo, V. Karantza, A. R. Tan, Safety and Antitumor Activity of Pembrolizumab in Patients with Estrogen Receptor-Positive/Human Epidermal Growth Factor Receptor 2-Negative Advanced Breast Cancer, Clin Cancer Res 24(12) (2018) 2804-2811.

[15] H. R. Ali, S. E. Glont, F. M. Blows, E. Provenzano, S. J. Dawson, B. Liu, L. Hiller, J. Dunn, C. J. Poole, S. Bowden, H. M. Earl, P. D. Pharoah, C. Caldas, P D-L1 protein expression in breast cancer is rare, enriched in basal-like tumours and associated with infiltrating lymphocytes, Ann Oncol 26(7) (2015) 1488-1493.

[16] B. Ruffell, A. Au, H. S. Rugo, L. J. Esserman, E. S. Hwang, L. M. Coussens, Leukocyte composition of human breast cancer, Proc Natl Acad Sci USA 109(8) (2012) 2796-2801.

[17] D. I. Gabrilovich, Myeloid-Derived Suppressor Cells, Cancer Immunol Res 5(1) (2017) 3-8.

[18] V. Boonyaratanakomkit, N. Hamilton, D. C. Marquez-Garban, P. Pateetin, E. M. McGowan, R. J. Pietras, Extranuclear signaling by sex steroid receptors and clinical implications in breast cancer, Mol Cell Endocrinol 466 (2018) 51-72.

[19] Early Breast Cancer Trialists' Collaborative Group, Effects of chemotherapy and hormonal therapy for early breast cancer on recurrence and 15-year survival: an overview of the randomised trials, Lancet 365(9472) (2005) 1687-1717.

[20] J. F. Robertson, J. Lindemann, S. Gamett, E. Anderson, R. I. Nicholson, I. Kuter, J. M. Gee, A good drug made better: the fulvestrant dose-response story, Clin Breast Cancer 14(6) (2014) 381-389.

[21] A. Howell, J. Cuzick, M. Baum, A. Buzdar, M. Dowsett, J. F. Forbes, G. Hoctin-Boes, J. Houghton, G. Y. Locker, J. S. Tobias, A. T. Group, Results of the ATAC (Arimidex, Tamoxifen, Alone or in Combination) trial after completion of 5 years' adjuvant treatment for breast cancer, Lancet 365(9453) (2005) 60-62.

[22] R. J. Pietras, D. C. Marquez-Garban, Membrane-associated estrogen receptor signaling pathways in human cancers, Clin Cancer Res 13(16) (2007) 4672-4676.

[23] W. Toy, Y. Shen, H. Won, B. Green, R. A. Sakr, M. Will, Z. Li, K. Gala, S. Fanning, T. A. King, C. Hudis, D. Chen, T. Taran, G. Hortobagyi, G. Greene, M. Berger, J. Baselga, S. Chandarlapaty, ESR1 ligand-binding domain mutations in hormone-resistant breast cancer, Nat Genet 45(12) (2013) 1439-1445.

[24] Q. X. Zhang, A. Borg, D. M. Wolf, S. Oesterreich, S. A. Fuqua, An estrogen receptor mutant with strong hormone-independent activity from a metastatic breast cancer, Cancer Res 57(7) (1997) 1244-1249.

[25] K. J. Kieser, D. W. Kim, K. E. Carlson, B. S. Katzenellenbogen, J. A. Katzenellenbogen, Characterization of the pharmacophore properties of novel selective estrogen receptor downregulators (SERDs), J Med Chem 53(8) (2010) 3320-3329.

[26] A. E. Wakeling, K M. O'Connor, E. Newboult, Comparison of the biological effects of tamoxifen and a new antioestrogen (LY 117018) on the immature rat uterus, J Endocrinol 99(3) (1983) 447-453.

[27] A. L. Wijayaratne, D. P. McDonnell, The human estrogen receptor-alpha is a ubiquitinated protein whose stability is affected differentially by agonists, antagonists, and selective estrogen receptor modulators, J Biol Chem 276(38) (2001) 35684-35692.

[28] M. van Kruchten, E. G. de Vries, A W. Glaudemans, M. C. van Lanschot, M. van Faassen, I. P. Kema, M. Brown, C. P. Schroder, E. F. de Vries, G. A. Hospers, Measuring residual estrogen receptor availability during fulvestrant therapy in patients with metastatic breast cancer, Cancer Discov 5(1) (2015) 72-81.

[29] Evaluating an E R Degrader for Breast Cancer, Cancer Discov 5(7) (2015) OF15.

[30] A. Lai, M. Kahraman, S. Govek, J. Nagasawa, C. Bonnefous, J. Julien, K. Douglas, J. Sensintaffar, N. Lu, K J. Lee, A. Aparicio, J. Kaufman, J. Qian, G. Shao, R. Prudente, M. J. Moon, J. D. Joseph, B. Darimont, D. Brigham, K. Grillot, R. Heyman, P. J. Rix, J. H. Hager, N. D. Smith, Identification of GDC-0810 (ARN-810), an Orally Bioavailable Selective Estrogen Receptor Degrader (SERD) that Demonstrates Robust Activity in Tamoxifen-Resistant Breast Cancer Xenografts, J Med Chem 58(12) (2015) 4888-4904.

[31] L. Kurti, B. Czako, E. J. Corey, A short, scalable synthesis of the carbocyclic core of the anti-angiogenic cortistatins from (+)-estrone by B-ring expansion, Org Lett 10(22) (2008) 5247-5250.

[32] D. C. Labaree, J. X. Zhang, H. A. Harris, C. O'Connor, T. Y. Reynolds, R. B. Hochberg, Synthesis and evaluation of B-, C-, and D-ring-substituted estradiol carboxylic acid esters as locally active estrogens, J Med Chem 46(10) (2003) 1886-1904.

[33] E. G. Lim C, Perrault W R, Pearlman B A, An environmentally friendly and cost effective synthesis of estradiol featuring two novel reagents: Si(0)/K F and PMHS/hexamethyldisiloxane/pTSA, Tetrahedron Letters 47(36) (2006) 6417-6420.

[34] F. R. Tedesco R, Napolitano E, Novel Stereoselective Synthesis of 11.beta.-Carbon-Substituted Estradiol Derivatives, J. Org. Chem 60(16) (1995) 5316-5318.

[35] D. C. Marquez, H. W. Chen, E. M. Curran, W. V. Welshons, R. J. Pietras, Estrogen receptors in membrane lipid rafts and signal transduction in breast cancer, Mol Cell Endocrinol 246(1-2) (2006) 91-100.
[36] D. C. Marquez, R. J. Pietras, Membrane-associated binding sites for estrogen contribute to growth regulation of human breast cancer cells, Oncogene 20(39) (2001) 5420-5430.
[37] R. J. Pietras, J. Arboleda, D. M. Reese, N. Wongvipat, M. D. Pegram, L. Ramos, C. M. Gorman, M. G. Parker, M. X. Sliwkowski, D. J. Slamon, HER-2 tyrosine kinase pathway targets estrogen receptor and promotes hormone-independent growth in human breast cancer cells, Oncogene 10(12) (1995) 2435-2446.
[38] L. M. Berstein, W. Yue, J. P. Wang, R. J. Santen, Isolated and combined action of tamoxifen and metformin in wild-type, tamoxifen-resistant, and estrogen-deprived MCF-7 cells, Breast Cancer Res Treat 128(1) (2011) 109-117.
[39] J. M. Knowlden, I. R. Hutcheson, H. E. Jones, T. Madden, J. M. Gee, M. E. Harper, D. Barrow, A. E. Wakeling, R. I. Nicholson, Elevated levels of epidermal growth factor receptor/c-erbB2 heterodimers mediate an autocrine growth regulatory pathway in tamoxifen-resistant MCF-7 cells, Endocrinology 144(3) (2003) 1032-1044.
[40] D. Williams, J. Gorski, Preparation and characterization of free cell suspensions from the immature rat uterus, Biochemistry 12(2) (1973) 297-306.
[41] E. K. Shanle, J. R. Hawse, W. Xu, Generation of stable reporter breast cancer cell lines for the identification of E R subtype selective ligands, Biochem Pharmacol 82(12) (2011) 1940-1949.
[42] V. S. Wilson, K. Bobseine, L. E. Gray, Jr., Development and characterization of a cell line that stably expresses an estrogen-responsive luciferase reporter for the detection of estrogen receptor agonist and antagonists, Toxicol Sci 81(1) (2004) 69-77.
[43] O. K. Weinberg, D. C. Marquez-Garban, M. C. Fishbein, L. Goodglick, H. J. Garban, S. M. Dubinett, R. J. Pietras, Aromatase inhibitors in human lung cancer therapy, Cancer Res 65(24) (2005) 11287-11291.
[44] A. K. Kimball, L. M. Oko, B. L. Bullock, R. A. Nemenoff, L. F. van Dyk, E. T. Clambey, A Beginner's Guide to Analyzing and Visualizing Mass Cytometry Data, J Immunol 200(1) (2018) 3-22.
[45] N. Samusik, Z. Good, M. H. Spitzer, K. L. Davis, G. P. Nolan, Automated mapping of phenotype space with single-cell data, Nat Methods 13(6) (2016) 493-496.
[46] H. Chen, M. C. Lau, M. T. Wong, E. W. Newell, M. Poidinger, J. Chen, Cytofkit: A Bioconductor Package for an Integrated Mass Cytometry Data Analysis Pipeline, PLoS Comput Biol 12(9) (2016) e1005112.
[47] S. C. Wei, J. H. Levine, A. P. Cogdill, Y. Zhao, N. A. S. Anang, M. C. Andrews, P. Sharma, J. Wang, J. A. Wargo, D. Pe'er, J. P. Allison, Distinct Cellular Mechanisms Underlie Anti-CTLA-4 and Anti-PD-1 Checkpoint Blockade, Cell 170(6) (2017) 1120-1133 e1117.
[48] B. Comin-Anduix, H. Sazegar, T. Chodon, D. Matsunaga, J. Jalil, E. von Euw, H. Escuin-Ordinas, R. Balderas, B. Chmielowski, J. Gomez-Navarro, R. C. Koya, A. Ribas, Modulation of cell signaling networks after CTLA4 blockade in patients with metastatic melanoma, PLoS One 5(9) (2010) e12711.
[49] S. Hu-Lieskovan, S. Mok, B. Homet Moreno, J. *Tsoi*, L. Robert, L. Goedert, E. M. Pinheiro, R. C. Koya, T. G. Graeber, B. Comin-Anduix, A. Ribas, Improved antitumor activity of immunotherapy with BRAF and MEK inhibitors in BRAF(V600E) melanoma, Sci Transl Med 7(279) (2015) 279ra241.
[50] Bert B, Marquez-Garban D C, Deng G, Diers E, Jung M E, Pietras R J, New Estrogen Receptor Down-regulators to Treat Human Breast Cancer, Proceedings of the American Association for the Advancement of Science, Pacific Division 31 (Part I) (2016) 110.
[51] N. L. Claussner A, Nique F, Philibert D, Teutsch G, Van de Velde P., 11 beta-amidoalkyl estradiols, a new series of pure antiestrogens. J Steroid Biochem Mol Biol 41(3-8) (1992) 609-614.
[52] H. E. Hanson R N, Hendricks J A, Labaree D, Hochberg R B, Synthesis and evaluation of 11β-(4-substituted phenyl) estradiol analogs: transition from estrogen receptor agonists to antagonists, Bioorg Med Chem 20(12) (2012) 3768-3780.
[53] S. Srinivasan, J. C. Nwachukwu, N. E. Bruno, V. Dharmarajan, D. Goswami, I. Kastrati, S. Novick, J. Nowak, V. Cavett, H. B. Zhou, N. Boonmuen, Y. Zhao, J. Min, J. Frasor, B. S. Katzenellenbogen, P. R. Griffin, J. A. Katzenellenbogen, K. W. Nettles, Corrigendum: Full antagonism of the estrogen receptor without a prototypical ligand side chain, Nat Chem Biol 13(6) (2017) 691.
[54] K. T. Nose A, Studies of Reduction with the Sodium Borohydride-Transition Metal Boride System. I.: Reduction of Nitro and the Other Functional Groups with the Sodium Borohydride-Nickel Boride System, Chem. Pharm. Bull(36) (1988) 1529-1533.
[55] G. B. Osby J O, Rapid and efficient reduction of aliphatic nitro compounds to amines, Tetrahedron Lett (26) (1985) 6413-6416.
[56] D. Ostroumov, N. Fekete-Drimusz, M. Saborowski, F. Kuhnel, N. Woller, CD4 and CD8 T lymphocyte interplay in controlling tumor growth, Cell Mol Life Sci 75(4) (2018) 689-713.
[57] M. Binnewies, E. W. Roberts, K. Kersten, V. Chan, D. F. Fearon, M. Merad, L. M. Coussens, D. I. Gabrilovich, S. Ostrand-Rosenberg, C. C. Hedrick, R. H. Vonderheide, M. J. Pittet, R. K. Jain, W. Zou, T. K. Howcroft, E. C. Woodhouse, R A Weinberg, M. F. Krummel, Understanding the tumor immune microenvironment (TIME) for effective therapy, Nat Med 24(5) (2018) 541-550.
[58] M. L. Disis, Immune regulation of cancer, J Clin Oncol 28(29) (2010) 4531-4538.
[59] R. Dai, M. R. Edwards, B. Heid, S. A Ahmed, 17beta-Estradiol and 17alpha-Ethinyl Estradiol Exhibit Immunologic and Epigenetic Regulatory Effects in NZB/WF1 Female Mice, Endocrinology 160(1) (2019) 101-118.
[60] S. Sakaguchi, T. Yamaguchi, T. Nomura, M. Ono, Regulatory T cells and immune tolerance, Cell 133(5) (2008) 775-787.
[61] L. Y. Chang, Y. C. Lin, C. W. Kang, C. Y. Hsu, Y. Y. Chu, C. T. Huang, Y. J. Day, T. C. Chen, C. T. Yeh, C. Y. Lin, The indispensable role of CCR5 for in vivo suppressor function of tumor-derived CD103+ effector/memory regulatory T cells, J Immunol 189(2) (2012) 567-574.
[62] S. V. Schmidt, A. C. Nino-Castro, J. L. Schultze, Regulatory dendritic cells: there is more than just immune activation, Front Immunol 3 (2012) 274.
[63] A. Sica, A Mantovani, Macrophage plasticity and polarization: in vivo veritas, J Clin Invest 122(3) (2012) 787-795.
[64] F. O. Martinez, S. Gordon, The M1 and M2 paradigm of macrophage activation: time for reassessment, F1000Prime Rep 6 (2014) 13.

[65] I. Capone, P. Marchetti, P. A Ascierto, W. Malomi, L. Gabriele, Sexual Dimorphism of Immune Responses: A New Perspective in Cancer Immunotherapy, Front Immunol 9 (2018) 552.
[66] L. Mirandola, R. Wade, R. Verma, C. Pena, N. Hosiriluck, J. A Figueroa, E. Cobos, M. R. Jenkins, M. Chiriva-Intemati, Sex-driven differences in immunological responses: challenges and opportunities for the immunotherapies of the third millennium, Int Rev Immunol 34(2) (2015) 134-142.
[67] A. Hashimoto, C. Gao, J. Mastio, A Kossenkov, S. I. Abrams, A V. Purandare, H. Desilva, S. Wee, J. Hunt, M. Jure-Kunkel, D. I. Gabrilovich, Inhibition of Casein Kinase 2 Disrupts Differentiation of Myeloid Cells in Cancer and Enhances the Efficacy of Immunotherapy in Mice, Cancer Res 78(19) (2018) 5644-5655.
[68] N. Das, N. Datta, U. Chatterjee, M. K. Ghosh, Estrogen receptor alpha transcriptionally activates casein kinase 2 alpha: A pivotal regulator of promyelocytic leukaemia protein (PML) and AKT in oncogenesis, Cell Signal 28(6) (2016) 675-687.
[69] D. H. Hamilton, L. M. Griner, J. M. Keller, X. Hu, N. Southall, J. Marugan, J. M. David, M. Ferrer, C. Palena, Targeting Estrogen Receptor Signaling with Fulvestrant Enhances Immune and Chemotherapy-Mediated Cytotoxicity of Human Lung Cancer, Clin Cancer Res 22(24) (2016) 6204-6216.
[70] S. Ostrand-Rosenberg, P. Sinha, C. Figley, R. Long, D. Park, D. Carter, V. K. Clements, Frontline Science: Myeloid-derived suppressor cells (MDSCs) facilitate maternal-fetal tolerance in mice, J Leukoc Biol 101(5) (2017) 1091-1101.
[71] T. Pan, Y. Liu, L. M. Zhong, M. H. Shi, X. B. Duan, K. Wu, Q. Yang, C. Liu, J. Y. Wei, X. R. Ma, K. Shi, H. Zhang, J. Zhou, Myeloid-derived suppressor cells are essential for maintaining feto-matemal immunotolerance via STAT3 signaling in mice, J Leukoc Biol 100(3) (2016) 499-511.
[72] A. Sanchez-Aguilera, S. Mendez-Ferrer, Regulation of hematopoietic progenitors by estrogens as a basis for new antileukemic strategies, Mol Cell Oncol 3(1) (2016) e1009728.
[73] D. S. Chen, I. Mellman, Oncology meets immunology: the cancer-immunity cycle, Immunity 39(1) (2013) 1-10.
[74] Y. Huang, C. Ma, Q. Zhang, J. Ye, F. Wang, Y. Zhang, P. Hunborg, M. A. Varvares, D. F. Hoft, E. C. Hsueh, G. Peng, $CD4^+$ and $CD8^+$ T cells have opposing roles in breast cancer progression and outcome, Oncotarget 6(19) (2015) 17462-17478.
[75] S. Ostrand-Rosenberg, P. Sinha, D. W. Beury, V. K. Clements, Cross-talk between myeloid-derived suppressor cells (MDSC), macrophages, and dendritic cells enhances tumor-induced immune suppression, Semin Cancer Biol 22(4) (2012) 275-281.
[76] N. A. Rizvi, M. D. Hellmann, A. Snyder, P. Kvistborg, V. Makarov, J. J. Havel, W. Lee, J. Yuan, P. Wong, T. S. Ho, M. L. Miller, N. Rekhtman, A. L. Moreira, F. Ibrahim, C. Bruggeman, B. Gasmi, R. Zappasodi, Y. Maeda, C. Sander, E. B. Garon, T. Merghoub, J. D. Wolchok, T. N. Schumacher, T. A. Chan, Cancer immunology. Mutational landscape determines sensitivity to PD-1 blockade in non-small cell lung cancer, Science 348(6230) (2015) 124-128.
[77] R. Jaini, M. G. Loya, C. Eng, Immunotherapeutic target expression on breast tumors can be amplified by hormone receptor antagonism: a novel strategy for enhancing efficacy of targeted immunotherapy, Oncotarget 8(20) (2017) 32536-32549.
[78] L. Wu, C. Lv, Y. Su, C. Li, H. Zhang, X. Zhao, M. Li, Expression of programed death-1 (PD-1) and its ligand P D-L1 is upregulated in endometriosis and promoted by 17beta-estradiol, Gynecol Endocrinol (2018) 1-6.
[79] L. Yang, F. Huang, J. Mei, X. Wang, Q. Zhang, H. Wang, M. Xi, Z. You, Posttranscriptional Control of P D-L1 Expression by 17beta-Estradiol via PI3K/Akt Signaling Pathway in ERα lpha-Positive Cancer Cell Lines, Int J Gynecol Cancer 27(2) (2017) 196-205.
[80] M. J. Polanczyk, C. Hopke, A. A. Vandenbark, H. Offner, Treg suppressive activity involves estrogen-dependent expression of programmed death-1 (PD-1), Int Immunol 19(3) (2007) 337-343.
[81] Z. Shen, M. Rodriguez-Garcia, M. V. Patel, F. D. Barr, C. R. Wira, Menopausal status influences the expression of programmed death (P D)-1 and its ligand P D-L1 on immune cells from the human female reproductive tract, Am J Reprod Immunol 76(2) (2016) 118-125.
[82] R. Nanda, L. Q. Chow, E. C. Dees, R. Berger, S. Gupta, R. Geva, L. Pusztai, K. Pathiraja, G. Aktan, J. D. Cheng, V. Karantza, L. Buisseret, Pembrolizumab in Patients With Advanced Triple-Negative Breast Cancer: Phase Ib KEYNOTE-012 Study, J Clin Oncol 34(21) (2016) 2460-2467.
[83] S. Kovats, Estrogen receptors regulate innate immune cells and signaling pathways, Cell Immunol 294(2) (2015) 63-69.
[84] F. Conforti, L. Pala, V. Bagnardi, T. De Pas, M. Martinetti, G. Viale, R. D. Gelber, A. Goldhirsch, Cancer immunotherapy efficacy and patients' sex: a systematic review and meta-analysis, Lancet Oncol 19(6) (2018) 737-746.
[85] C. J. D. Wallis, M. Butaney, R. Satkunasivam, S. J. Freedland, S. P. Patel, O. Hamid, S. K. Pal, Z. Klaassen, Association of Patient Sex With Efficacy of Immune Checkpoint Inhibitors and Overall Survival in Advanced Cancers: A Systematic Review and Meta-analysis, JAMA Oncol (2019).
[86] J. L. F. Teh, A. E. Aplin, Arrested Developments: CDK4/6 Inhibitor Resistance and Alterations in the Tumor Immune Microenvironment, Clin Cancer Res (2018).
[87] R. S. Finn, J. Dering, D. Conklin, O. Kalous, D. J. Cohen, A. J. Desai, C. Ginther, M. Atefi, I. Chen, C. Fowst, G. Los, D. J. Slamon, PD 0332991, a selective cyclin D kinase 4/6 inhibitor, preferentially inhibits proliferation of luminal estrogen receptor-positive human breast cancer cell lines in vitro, Breast Cancer Res 11(5) (2009) $R^{77}$.
[88] E. A. Musgrove, R. L. Sutherland, Cell cycle control by steroid hormones, Semin Cancer Biol 5(5) (1994) 381-389.
[89] S. Guo, C. Zhang, M. Bratton, M. Mottamal, J. Liu, P. Ma, S. Zheng, Q. Zhong, L. Yang, T. E. Wiese, Y. Wu, M. J. Ellis, M. Matossian, M. E. Burow, L. Miele, R. Houtman, G. Wang, ZB716, a steroidal selective estrogen receptor degrader (SERD), is orally efficacious in blocking tumor growth in mouse xenograft models, Oncotarget 9(6) (2018) 6924-6937.
[90] S. E. Wardell, M. J. Ellis, H. M. Alley, K. Eisele, T. VanArsdale, S. G. Dann, K T. Amdt, T. Primeau, E. Griffin, J. Shao, R. Crowder, J. P. Lai, J. D. Norris, D. P. McDonnell, S. Li, Efficacy of SERD/SERM Hybrid- CDK4/6 Inhibitor Combinations in Models of Endocrine Therapy-Resistant Breast Cancer, Clin Cancer Res 21(22) (2015) 5121-5130.

[91] L. Zhao, S. Huang, S. Mei, Z. Yang, L. Xu, N. Zhou, Q. Yang, Q. Shen, W. Wang, X. Le, W. B. Lau, B. Lau, X. Wang, T. Yi, X. Zhao, Y. Wei, M. Warner, J. A. Gustafsson, S. Zhou, Pharmacological activation of estrogen receptor beta augments innate immunity to suppress cancer metastasis, Proc Natl Acad Sci USA 115(16) (2018) E3673-E3681.H. M.

[92] Weir, R. H. Bradbury, M. Lawson, A. A. Rabow, D. Buttar, R. J. Callis, J. O. Curwen, C. de Almeida, P. Ballard, M. Hulse, C. S. Donald, L. J. Feron, G. Karoutchi, P. MacFaul, T. Moss, R. A. Norman, S. E. Pearson, M. Tonge, G. Davies, G. E. Walker, Z. Wilson, R. Rowlinson, S. Powell, C. Sadler, G. Richmond, B. Ladd, E. Pazolli, A M. Mazzola, C. D'Cruz, C. De Savi, AZD9496: An Oral Estrogen Receptor Inhibitor That Blocks the Growth of E R-Positive and ESR1-Mutant Breast Tumors in Preclinical Models, Cancer Res 76(11) (2016) 3307-3318.

REFERENCES

1. Ma C, et al. (2009). Oncology 23: 133-142. 2. Hurvitz S, Pietras R (2008). Cancer 113:2385-97. 3. Early Breast Cancer Trialists' Collaborative Group (1998). Lancet 351:1451-67. 4. McGuire W L, Clark G (1992). N. Engl. J. Med., 326: 1756-1762. 5. Ali S, Coombes R (2002). Nature Rev Cancer 21: 101-113. 6. Prat A, Baselga J (2008). Nat Clin Pract Oncol 5: 531-542. 7. Hoffmann J, et al. (2004). J Natl Cancer Inst 96: 210-218. 8. O'Brien J, et al. (2006). J Biol Chem 281: 26683-92. 9. Pietras R J, et al. (2007). Clin Cancer Res 13: 4672-4676. 10. Syed F, et al. (2007). Endocrinology 148:1902-10. 11. Massarweh S, et al. (2008). Cancer Res 68:826-33. 12. Lipton A et al. (2003) J Clin Oncol 21: 1967-1972. 13. Ellis M J et al. (2006) J Clin Oncol 24: 3019-3025. 14. Pietras, R, J et al. (1995). Oncogene 10: 2435-2446. 15. Marquez D C, Pietras R J (2001). Oncogene 20:5420-30. 16. Marquez D C, et al. (2006). Mol Cell Endocrinol. 246:91-100. 17. Mintz P, et al. (2008). Cancer 113: 1489-1495. 18. Madak-Erdogan Z, Kieser K, Kim S et al. (2008). Mol Endocrinol 22: 2116-2127. 19. Hammes S, Levin E (2007). Endocr Rev 28: 726-41. 20. Beug H. and T. Graf (1989). Eur. J. Clin. Invest., 19: 491-501. 21. Slamon D. J., et al. (1987). Science, 235: 177-181. 22. Adnane J, et al. (1989). Oncogene, 4: 1389-1395. 23. Zeillinger R, et al. (1989). Oncogene, 4: 109-113. 24. Read L., D. et al. (1990). Cancer Res., 50: 3947-3955. 25. Nicholson S., et al. (1990). J. Steroid Biochem., 37: 811-818. 26. Reddy, K., et al. (1992). Cancer Res., 52: 3636-3644 27. Benz C., et al. (1993). Breast Cancer Res. Treatment, 24: 85-92. 28. Kato, S., et al. (1995). Science, 270: 1491-1494. 29. Pietras R J, et al. (2005). Steroids 70: 372-381. 30. Liu Y, et al. (1995). Breast Cancer Res Trtmt 34: 97-117. 31. Witters I, et al. (1997). Breast Cancer Res. Trtmt 42: 1-5. 32. Bouras T, et al. (2001). Cancer Res 61: 903-907. 33. Font de Mora J, Brown M (2000). Mol Cell Biol 20: 5041-7. 34. Dowsett M, et al. (2001). Cancer Res 61: 8452-8458. 35. Kurokawa H, et al. (2000). Cancer Res 60: 5887-5894. 36. Marquez, D, Pietras, R J (2001). Oncogene, 20: 5420-5430. 37. Simoncini T, et al. (2000). Nature 407: 538-41. 38. Oh A, et al. (2001). Mol Endocrinol 15: 1344-1359. 39. Marquez, D, et al. (2001). Endocrine 16: 73-81. 40. Chung Y L, et al. (2002). Int. J. Cancer 97: 306-312. 41. Osborne C K, et al. (2003). J Natl Cancer Inst. 95:353-361. 42. De Laurentis M et al, 2005. Clin Cancer Res 11:4741-48. 43. Arpino G, et al. (2005). J Natl Cancer Inst 97: 1254-1239. 44. Yarden Y, Sliwkowski M X (2001). Nat Rev Mol Cell Biol 2: 127-137. 45. Carter P, et al. (1992). Proc Natl Acad Sci USA 89: 4285-4289. 46. Slamon D J, et al. (2001) N Engl J Med 344: 783-792. 47. Weinberg O, et al. (2005). Drug Resistance Updates (in press). 48. Bange J, et al. (2001). Nat Med 7:548-52. 49. Knowlden J, et al. (2003). Endocrinology 144:1032-44. 50. Ciana P, et al. (2003). Nature Med. 9: 82-86. 51. Migliaccio A, et al. (1986). EMBO J. 5: 2867-2872. 52. Weigel N (1996). Biochem J 319: 657-667. 53. Dowsett M (2001). Endocrine-Related Cancer 8: 191-195. 54. Early Breast Cancer Trialists' Collaborative Group (2005). Lancet 365: 1687-1717. 55. Coombes R C et al. (2004) N Engl J Med 350: 1081-1092. 56. The Breast International Group 1-98 Collaborative Group (2005) N Engl J Med 353: 2747-2757. 57. ATAC Trialists' Group (2005). Lancet 365: 60-62. 58. Wakeling A E, et al. (1991). Cancer Res 51:3867-73. 59. Wakeling A, et al. (2001). Clin. Cancer Res. 7: 4350s-4355s. 60. Wijayaratne, A. L. and McDonnell, D. P. (2001) J. Biol. Chem. 276, 35684-356892 61. Robertson J, et al. (2009). J Clin Oncol August 24. 62. Osborne C K, et al. (2002) J Clin Oncol 20: 3386-3395. 63. Haas A, Siepmann T (1997). FASEB J. 11, 1257-1268. 64. Lange, C. A., et al. (2000). Proc. Natl Acad. Sci. 97, 1032-1037. 65. Alarid, E. T., et al. (1999). Mol. Endocrinol. 13, 1522-1534. 66. Nawaz, Z., et al. (1999) Proc. Natl Acad. Sci. USA 96: 1858-1862. 67. Wang Y, et al. (2009). J. Biochem. 145: 331-343. 68. Kim T K, Maniatis T (1996). Science 273, 1717-1719. 69. Ring A, Dowsett M (2004) Endocr Relat Cancer 11: 643-658. 70. Pike A C, et al. 2001 Structure (Camb) 9:145-153. 71. Dauvois S, et al. (1992). Proc. Natl. Acad. Sci. U.S.A. 89: 4037-4041. 72. Knowlden J, et al. (2003). Endocrinology 144:1032-44. 73. Aguilar Z, et al. (1999). Oncogene 18:6050-62. 74. Pietras, R J, et al. (2003). Breast Cancer Res Trtmt 82, Suppl 1:12-13. 75. Pietras R J (2003). Breast Journal 9: 361-373. 76. Konecny G, et al. (2003). J Natl Cancer Inst. 95:142-153. 77. Song R X, et al. (2002). Mol Endocrinol 16: 116-127. 78. Hennessy B, et al. (2005). Mol Cellular Endocrinol 229: 39-47. 79. Ernst M, et al. (1991). Mol Endocrinol 5:1597-606. 80. Lenferink A, et al. (2001). Cancer Res 61: 6583-6591. 81. Thiantanawat A, et al. (2003). Cancer Res 63:8037-50. 82. Teixeira C, et al. (1995). Cancer Res 55:3902-7. 83. Razandi M, et al. (2000). Mol Endocrinol 14:1434-47. 84. Kunisue H, et al. (2000). Brit. J. Cancer 82: 46-51. 85. Wang C-X, et al. (2005). Breast Cancer Res Treatment 92: 251-263. 86. Tran C, et al. (2009). Science 324: 787-790. 87. Stephan E, et al. (1995). Steroids 60, 809-11. 88. Liang C, et al. (1976). Tetrahedron 32, 2067-9. 89. Labaree D, et al. (2003). J Med Chem 46: 1886-1904. 90. Tedesco R, et al. (1995). J Org Chem 60: 5316-18. 91. Hanson J, et al. (1985). J Chem Res (S): 46-7. 92. Murdoch F, et al. (1990). Biochemistry 29: 8377-8385. 93. Pietras R, Szego C (1980). Biochem J 191: 743-760. [PMCID: PMC1 162274] 94. Jones S, et al. (2003). Methods in Enzymology 364: 53-71. 95. Laios I, et al. (2005). J Steroid Biochem Molecular Biol 94: 347-359. 96. Mollerup S, et al. (2002). Lung Cancer 37: 153-159. 97. Brunner N, et al. (1993). Eur. J. Cancer 29A: 562-569. 98. Wu X, J et al. (2009). Cancer Res 69: 1722-7. 99. Dubik D, et al. (1987). Cancer Res. 47, 6517-6521. 100. Navarro F, et al. (2003). Fertility Sterility 79: 1409-1415. 101. Greb R, O. et al. (1997). Hum Reprod 12: 1280-1292. 102. Wu W, et al. (2007). Mol CancerIherap 6: 471-483. 103. Li D, et al. (2002). Oncogene. 21:2805-14. 104. Pegram M, et al. (2004). J Natl Cancer Inst 96:739-49. 105. Pietras R J, Szego C M (1977). Nature 265: 69-72. 106. Pietras R, et al. (1998). Oncogene 17:2235-49. 107. Chou T, Talalay P (1984). Adv Enzyme Regul. 22: 27-55. 108. Pegram, M., et al. (1999). Oncogene, 18: 2241-2251. 109. Verrier F, et al. (2001). J Virol 75: 9177-9186. 110. Chou T C (2002). J Virol 76: 10577; author reply: 10578. 111. Geyer C E, et al. (2006) N Engl J Med 355: 2733-2743. 112. Osborne C, et al. (1995). J Natl Cancer Inst 87: 746-60. 113. Mah V, et al. (2007). Cancer Res 67: 10484-90. 114. Kobayashi N, et al. (2008). Cancer Res 68:3066-73. 115. Reckamp K, et al. (2008). J Thorac Oncol 3: 117-24. 116. Detre S, et al. (2003). Cancer Res 63: 6516-22. 1. Ma C, et al. (2009). Oncology 23: 133-142. 2. Hurvitz S, Pietras R (2008). Cancer 113:2385-97. 3. Early Breast Cancer Trialists' Collaborative Group (1998). Lancet 351:1451-67. 4. McGuire W L, Clark G (1992). N. Engl. J. Med., 326: 1756-1762. 5. Ali S, Coombes R (2002). Nature Rev Cancer 21: 101-113. 6. Prat A, Baselga J (2008). Nat Clin Pract Oncol 5: 531-542. 7. Hoffmann J, et al. (2004). J Natl Cancer Inst 96: 210-218. 8. O'Brien J, et al. (2006). J Biol Chem 281: 26683-92. 9. Pietras R J, et al. (2007). Clin Cancer Res 13: 4672-4676. 10. Syed F, et al. (2007). Endocrinology 148:1902-10. 11. Massarweh S, et al. (2008). Cancer Res 68:826-33. 12. Lipton A et al. (2003) J Clin Oncol 21: 1967-1972. 13. Ellis M J et al. (2006) J Clin Oncol 24: 3019-3025. 14. Pietras, R, et al. (1995). Oncogene 10: 2435-2446. 15. Marquez D C, Pietras R J (2001). Oncogene 20:5420-30. 16. Marquez D C, et al. (2006). Mol Cell Endocrinol. 246:91-100. 17. Mintz P, et al. (2008). Cancer 113: 1489-1495. 18. Madak-Erdogan Z, et al. (2008). Mol Endocrinol 22: 2116-2127. 19. Hammes S, Levin E (2007). Endocr Rev 28: 726-41. 20. Weinberg O, et al. (2005). Drug Resistance Updates 8:219-233. 21. Early Breast Cancer Trialists' Collaborative Group (2005). Lancet 365: 1687-1717. 22. Dowsett M, et al. (2005). Breast Cancer Res Treat. 93 Suppl 1: S11-18. 23. The Breast International Group 1-98 Collaborative Group (2005). N Engl J Med 353: 2747-2757. 24. ATAC Trialists' Group (2005). Lancet 365: 60-62. 25. Wakeling A E, et al. (1991). Cancer Res 51:3867-73. 26. Wakeling A, et al. (2001). Clin. Cancer Res. 7: 4350s-4355s. 27. Wijayaratne, A. L. and McDonnell, D. P. (2001) J. Biol. Chem. 276, 35684-356892 28. Robertson J, et al. (2009). J Clin Oncol 27:4530-5. 29. Osborne C K, et al. (2002) J Clin Oncol 20: 3386-3395. 30. Haas A, Siepmann T (1997). FASEB J. 11, 1257-1268. 31. Lange, C. A., et al. (2000). Proc. Natl Acad. Sci. 97, 1032-1037. 32. Alarid, E. T., et al. (1999). Mol. Endocrinol. 13, 1522-1534. 33. Nawaz, Z., et al. (1999) Proc. Natl Acad. Sci. USA 96: 1858-1862. 34. Wang Y, et al. (2009). J. Biochem. 145: 331-343. 35. Kim T K, Maniatis T (1996). Science 273, 1717-1719. 36. Ring A, Dowsett M (2004) Endocr Relat Cancer 11: 643-658. 37. Pike A C, et al. 2001 Structure (Camb) 9:145-153. 38. Dauvois S, et al. (1992). Proc. Natl. Acad. Sci. U.S.A. 89: 4037-4041. 39. Clemons M J, et al. (2014). Breast Cancer Res Treat. 146:153-62. 40. Di Leo A, et al. (2014). J Natl Cancer Inst 106 337-44. 41. Robertson J F, et al. (2012). Breast Cancer Res Treat. 136:503-11. 42. Estdvez L, et al. (2013). Cancer Treat Rev. 39:136-41. 43. Di Leo A, et al. (2010). J Clin Oncol 28:4594-600. 44. Pietras R J, et al. (2005). Steroids, 70:372-81. 45. Shah K N, Faridi, J S (2011). J Steroid Biochem Mol Biol 125:219-225. 46. Robertson J F R G E, et al. (2004). Breast Cancer Res Treat 88:S236-S7. 47. Wakeling A E, et al. (1991). Cancer Res 51:3867-73. 48. Michel van Kruchten, et al. (2014). Proc American Assoc Clin Oncol Annual Meeting: 588. 1) Laszlo Kurti, et al. Org. Lett., 2008, 10, 5247-5250. 2) Chongsoo Lim, et al. Tetrahedron Lett., 2006, 47, 6417-6420. 3) David C. Labaree, et al. J. Med. Chem. 2003, 46, 1886-1904. 1. http://www.cancer.org/research/cancer-factsstatistics/cancerfactsfigures2014/index (estimate of the American Cancer Society for 2014). 2. D. J. Kojetin, et al. Endocrine-Related Cancer 2008, 15, 851-870. A. K. Shiau, et al. Cell, 1998, 95, 927-937. 3.D. C. Labaree, et al. Med. Chem. 2003, 46, 1886-1904. R. Tedesco, et al. J. Org. Chem. 1995, 60, 5316-5318. 4. Nose, A.; Kudo, T. Chem. Pharm. Bull. 1988, 36, 1529-1533. Osby, J. O.; Ganem, B. Tetrahedron Lett. 1985, 26, 6413-6416. 5. Hammond, et al., Journal of Clinical Oncology, vol. 28, number 16, Jun. 1 2010, 2784-2795. 6. Harvey et al., Journal of Clinical Oncology, Vol 17, No 5 (May), 1999: pp 1474-1481.

Additional references 1. Hurvitz S, Pietras R (2008). Rational management of endocrine resistance in breast cancer: a compre-hensive review of estrogen receptor biology, treatment options and future direction. Cancer 113:2385-97. 2. Early Breast Cancer Trialists' Collaborative Group (1998). Tamoxifen for early breast cancer: an overview of the randomised trials. Lancet 351:1451-67. 3. Ali S, Coombes R (2002). Endocrine-responsive breast cancer and strategies for combating resistance. Nature Rev Cancer 21: 101-113. 4.Prat A, Baselga J (2008). The role of hormonal therapy in the management of hormonal receptor-positive breast cancer with co-expression of HER2. Nat Clin Pract Oncol 5: 531-542. 5.Robertson J F, Lindemann J, Garnett S, Anderson E, Nicholson R I, Kuter I, Gee J M (2014). A Good Drug Made Better: The Fulvestrant Dose-Response Story. Clin Breast Cancer. 14:381-389. 6. van Kruchten M, de Vries E, Glaudemans A et al. Measuring residual estrogen receptor availability during fulvestrant therapy in patients with metastatic breast cancer. Cancer Discov 2014: ii: CD-14-0697. 7. O'Brien J, Peterson T, Tong M et al. (2006). Estrogen-induced proliferation of uterine epithelial cells is independent of ERα binding to classical estrogen response elements. J Biol Chem 281: 26683-92. 8. Pietras R J, Marquez-Garban D C (2007). Membrane-associated estrogen receptor signaling pathways in human cancers. Clin Cancer Res 13: 4672-4676. 9. Syed F, Fraser D, Spelsberg T, Rosen C, Krust A, Chambon P, Jameson J, Khosla S (2007). Effects of loss of classical estrogen response element signaling on bone in male mice. Endocrinology 148:1902-10. 10. Early Breast Cancer Trialists' Collaborative Group (2005). Effects of chemotherapy and hormonal therapy for early breast cancer on recurrence and 15-year survival: an overview of the randomised trials. Lancet 365: 1687-1717. 11. Weinberg O, Marquez D and Pietras R (2005). New approaches to reverse resistance to hormonal therapy in human breast cancer. Drug Resistance Updates 8:219-33. 12. The Breast International Group 1-98 Collaborative Group (2005) A comparison of letrozole and tamoxifen in postmenopausal women with early breast cancer. N Engl J Med 353: 2747-2757. 13. ATAC Trialists' Group (2005). Results of the ATAC (Arimidex, Tamoxifen, Alone or in Combination) trial after completion of 5 years' adjuvant treatment for breast cancer. Lancet 365: 60-62. 14. Massarweh S, Osborne C K, Creighton C et al. (2008). Tamoxifen resistance in breast tumors is driven by growth factor receptor signaling with repression of classic E R genomic function. Cancer Res 68:826-33. 15. Ellis M J et al. (2006) Estrogen-independent proliferation is present in estrogen-receptor HER2-positive primary breast cancer after neoadjuvant letrozole. J Clin Oncol 24: 3019-3025. 16. Johnston S, Pippen J Jr, Pivot X et al. (2009). Lapatinib combined with letrozole versus letrozole and placebo as first-line therapy for postmenopausal hormone receptor-positive metastatic breast cancer. J Clin Oncol. 27:5538-46. 17. Kieser K J, Kim D W, Carlson K E, Katzenellenbogen B S, Katzenellenbogen J A (2010). Characterization of the pharmacophore properties of novel selective estrogen receptor downregulators (SERDs). J Med Chem. 53:3320-9. PMCID: PMC2916745. 18. Fan M, Rickert E, Chen L, Aftab S, Nephew K, Weatherman R V (2007). Characterization of molecular and structural determinants of selective E R downregulators. Breast Cancer Res Treat 103:37-44. 19. Wakeling A E, Dukes M, Bowler J (1991). A potent specific pure antiestrogen with clinical potential. Cancer Res 51:3867-73. 20. Wijayaratne, A. L. and McDonnell, D. P. (2001) the human estrogen receptor-alpha is an ubiquitinated protein whose stability is affected differentially by agonists, antagonists, and selective estrogen receptor modulators. J. Biol. Chem. 276, 35684-356892. 21. Robinson D R, Wu Y M, Vats P et al. (2013). Activating ESR1 mutations in hormone-resistant metastatic breast cancer. Nat Genet 2013, 45:1446-1451.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting breast cancer tumor growth in a patient in need thereof; the method comprising administering to the subject:

(i) a first amount of an anti-PD-L1 inhibitor that is an anti-PD-L1 antibody, and (ii) a second amount of a selective estrogen receptor downregulator or a pharmaceutically acceptable salt thereof, wherein the selective estrogen receptor downregulator has the formula:

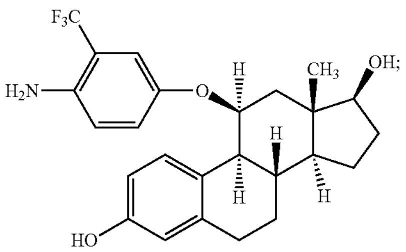

wherein the first amount and the second amount are a combined synergistic amount.

2. The method of claim 1, wherein the anti-PD-L1 antibody is atezolizumab, avelumab, durvalumab, or BMS-9365569.

3. The method of claim 1, wherein the anti-PD-L1 antibody is atezolizumab.

4. The method of claim 1, wherein the anti-PD-L1 antibody is avelumab.

5. The method of claim 1, wherein the anti-PD-L1 antibody is durvalumab.

6. The method of claim 1, wherein the anti-PD-L1 antibody inhibitor is BMS-9365569.

7. The method of claim 1, wherein the breast cancer tumor is a triple-negative breast cancer tumor.

8. The method of claim 1, wherein the breast cancer tumor is an ER-positive breast cancer tumor.

9. The method of claim 1, wherein the breast cancer tumor is an ER-negative breast cancer tumor.

10. The method of claim 1, wherein (i) and (ii) are:

(a) administered to the patient as separate dosage forms; or (b) in the form of a single pharmaceutical composition and administered to the patient as a single dosage form.

11. A method of treating breast cancer in a patient in need thereof; the method comprising administering to the subject:

(i) a first amount of an anti-PD-L1 inhibitor that is an anti-PD-L1 antibody, and (ii) a second amount of a selective estrogen receptor downregulator or a pharmaceutically acceptable salt thereof, wherein the selective estrogen receptor downregulator has the formula:

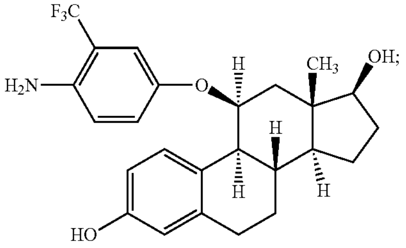

wherein the first amount and the second amount are a combined synergistic amount.

12. The method of claim 11, wherein the anti-PD-L1 antibody is atezolizumab, avelumab, durvalumab, or BMS-9365569.

13. The method of claim 11, wherein the anti-PD-L1 antibody is atezolizumab.

14. The method of claim 11, wherein the anti-PD-L1 antibody is avelumab.

15. The method of claim 11, wherein the anti-PD-L1 antibody is durvalumab.

16. The method of claim 11, wherein the anti-PD-L1 antibody is BMS-9365569.

17. The method of claim 11, wherein the breast cancer is a triple-negative breast cancer.

18. The method of claim 11, wherein the breast cancer is an ER-positive breast cancer.

19. The method of claim 11, wherein the breast cancer is an ER-negative breast cancer.

20. The method of claim 11, wherein (i) and (ii) are:

(a) administered to the patient as separate dosage forms; or (b) in the form of a single pharmaceutical composition and administered to the patient as a single dosage form.

* * * * *